(12) United States Patent
Flotte et al.

(10) Patent No.: US 11,884,926 B2
(45) Date of Patent: Jan. 30, 2024

(54) CAMPAIGN-READY SERIES OF RECOMBINANT ADENO-ASSOCIATED VIRUS (RAAV) COMPLEMENTING PLASMIDS

(71) Applicant: University of Massachusetts, Boston, MA (US)

(72) Inventors: Terence Flotte, Holden, MA (US); Qiushi Tang, Worcester, MA (US); Allison Keeler-Klunk, Sutton, MA (US); Qin Su, Westborough, MA (US)

(73) Assignee: University of Massachusetts, Boston, MA (US)

( * ) Notice: Subject to any disclaimer, the term of this patent is extended or adjusted under 35 U.S.C. 154(b) by 691 days.

(21) Appl. No.: 16/966,504

(22) PCT Filed: Feb. 1, 2019

(86) PCT No.: PCT/US2019/016310
§ 371 (c)(1),
(2) Date: Jul. 31, 2020

(87) PCT Pub. No.: WO2019/152816
PCT Pub. Date: Aug. 8, 2019

(65) Prior Publication Data
US 2021/0047650 A1    Feb. 18, 2021

Related U.S. Application Data

(60) Provisional application No. 62/625,644, filed on Feb. 2, 2018.

(51) Int. Cl.
*C12N 15/70* (2006.01)
*C12N 7/00* (2006.01)

(52) U.S. Cl.
CPC .............. *C12N 15/70* (2013.01); *C12N 7/00* (2013.01); *C12N 2750/14143* (2013.01); *C12N 2750/14151* (2013.01); *C12N 2750/14171* (2013.01)

(58) Field of Classification Search
CPC .......... C12N 15/70; C12N 2750/14143; C12N 2750/14152; C12N 15/86
See application file for complete search history.

(56) References Cited

U.S. PATENT DOCUMENTS

| 6,943,019 | B2 | 9/2005 | Wilson et al. |
|---|---|---|---|
| 2015/0218586 | A1 | 8/2015 | Schleef |
| 2016/0108373 | A1 | 4/2016 | Bennett et al. |
| 2017/0166907 | A1 | 6/2017 | Rey et al. |
| 2017/0369874 | A9 | 12/2017 | Flotte et al. |

FOREIGN PATENT DOCUMENTS

| DE | 102013220859 A1 | 4/2015 |
|---|---|---|
| WO | WO 02/088347 A2 | 11/2002 |
| WO | WO 2012/158757 A1 | 11/2012 |

OTHER PUBLICATIONS

Spratt BG, Hedge PJ, te Heesen S, Edelman A, Broome-Smith JK. Kanamycin-resistant vectors that are analogues of plasmids pUC8, pUC9, pEMBL8 and pEMBL9. Gene. 1986;41(2-3):337-42. (Year: 1986).*
Zolotukhin S, Potter M, Hauswirth WW, Guy J, Muzyczka N. A "humanized" green fluorescent protein cDNA adapted for high-level expression in mammalian cells. J Virol. Jul. 1996;70(7):4646-54. (Year: 1996).*
Extended European Search Report for Application No. 19746791.3, dated Oct. 28, 2021.
Kovesdi et al., Adenoviral producer cells. Viruses. Aug. 2010;2(8):1681-1703. doi: 10.3390/v2081681. Epub Aug. 16, 2010.
Robert et al., Manufacturing of recombinant adeno-associated viruses using mammalian expression platforms. Biotechnol J. Mar. 2017;12(3). doi: 10.1002/biot.201600193. Epub Feb. 8, 2017.
Tang et al., Engraftment of Human Hepatocytes in the PiZ-NSG Mouse Model. Methods Mol Biol. 2020;2164:75-85. doi: 10.1007/978-1-0716-0704-6_9.
International Search Report and Written Opinion for Application No. PCT/2019/016310, dated Apr. 11, 2019.
International Preliminary Report on Patentability for Applicaiton No. PCT/US2019/016310, dated Aug. 13, 2020.
Grimm et al., Helper virus-free, optically controllable, and two-plasmid-based production of adeno-associated virus vectors of serotypes 1 to 6. Mol Ther. Jun. 2003;7(6):839-50. doi: 10.1016/s1525-0016(03)00095-9.
Grimm et al., Novel tools for production and purification of recombinant adenoassociated virus vectors. Hum Gene Ther. Dec. 10, 1998;9(18):2745-60. doi: 10.1089/hum.1998.9.18-2745.
Grimm et al., Progress in adeno-associated virus type 2 vector production: promises and prospects for clinical use. Hum Gene Ther. Oct. 10, 1999;10(15):2445-50. doi: 10.1089/10430349950016799.
Grimm et al., Titration of AAV-2 particles via a novel capsid ELISA: packaging of genomes can limit production of recombinant AAV-2. Gene Ther. Jul. 1999;6(7):1322-30. doi: 10.1038/sj.gt.3300946.
Grimm, Production methods for gene transfer vectors based on adeno-associated virus serotypes. Methods. Oct. 2002;28(2):146-57. doi: 10.1016/s1046-2023(02)00219-0.

* cited by examiner

*Primary Examiner* — Janet L Andres
*Assistant Examiner* — Ruixue Wang
(74) *Attorney, Agent, or Firm* — Wolf, Greenfield & Sacks, P.C.

(57) ABSTRACT

In some aspects, the disclosure relates to compositions and methods for production of recombinant adeno-associated virus (rAAV) particles. The disclosure is based, in part, on isolated nucleic acids and systems that include only two vectors and are suitable for production of multiple different single gene viral vectors in a multiple small-scale campaign mode (e.g., $10^{13}$ to $10^{16}$ viral particles.)

18 Claims, 24 Drawing Sheets
Specification includes a Sequence Listing.

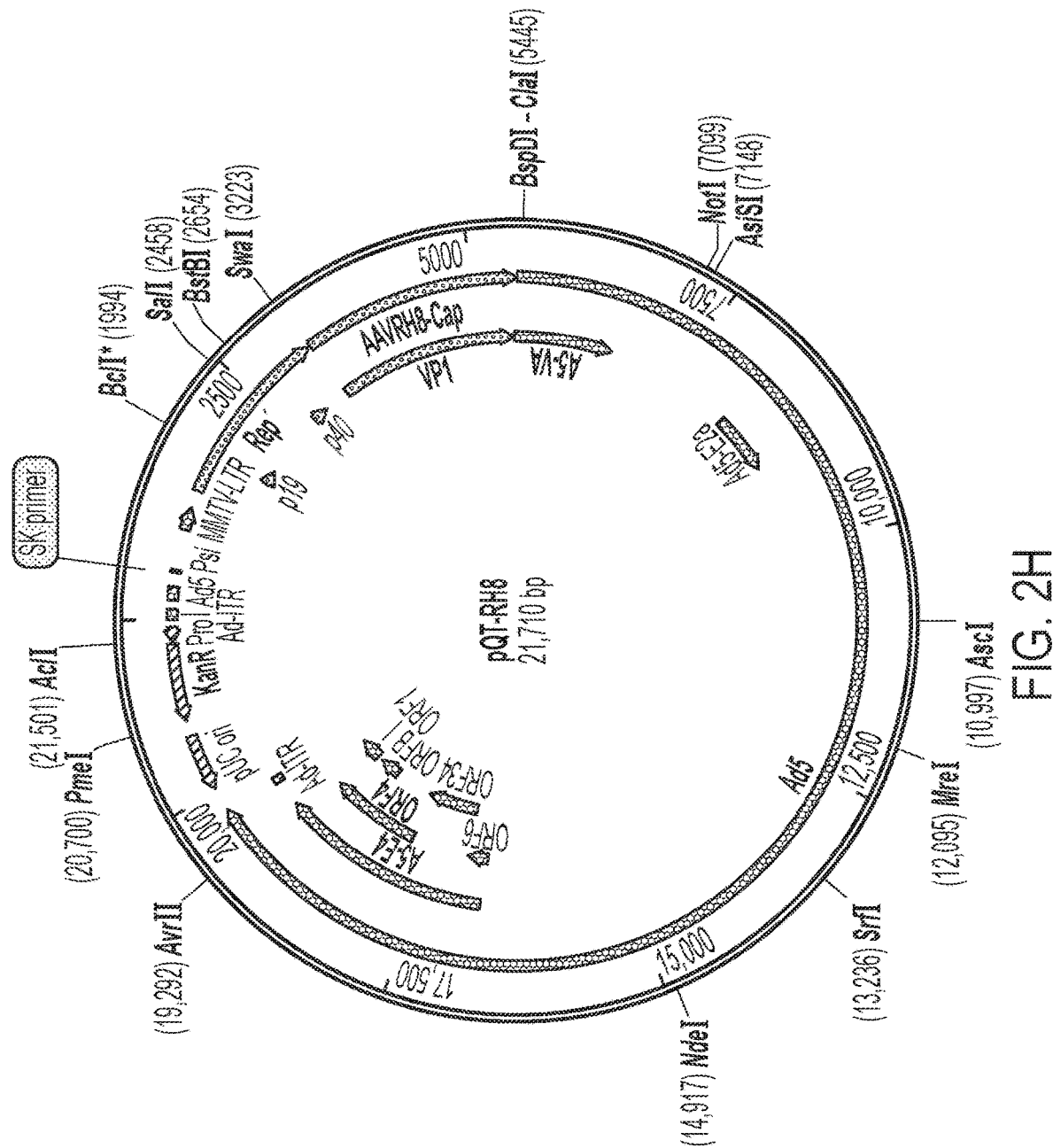

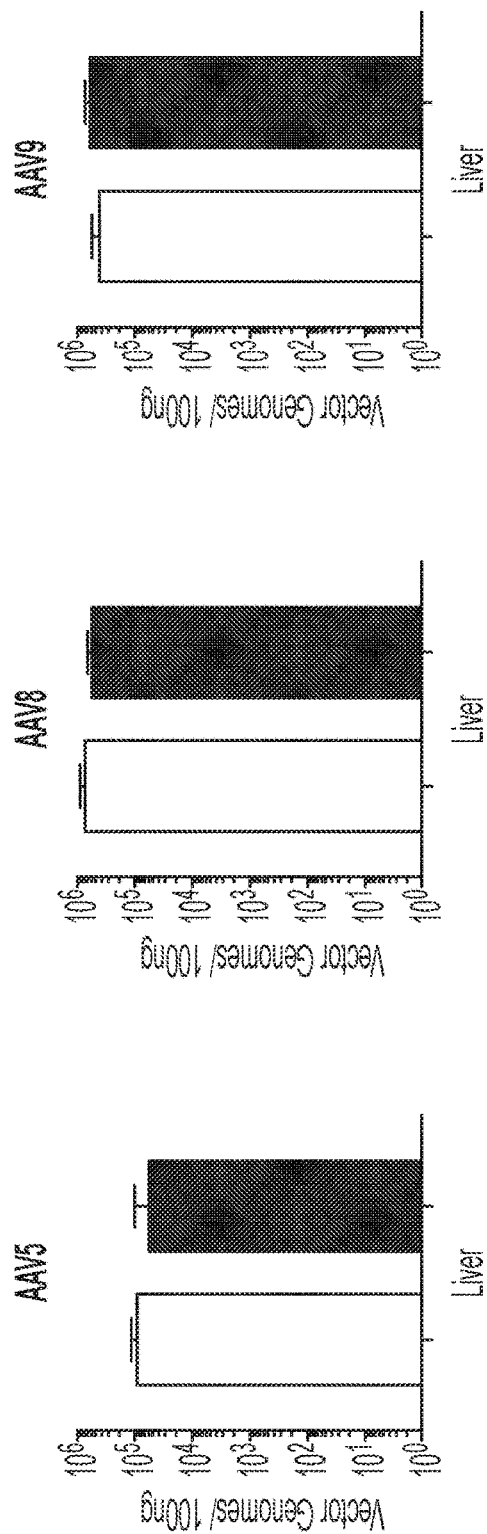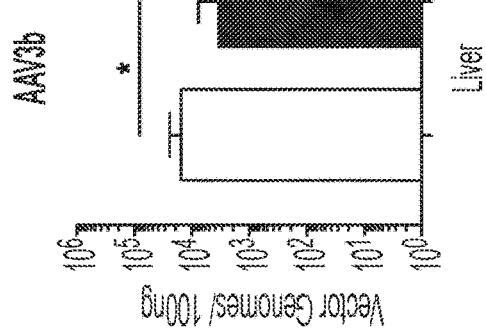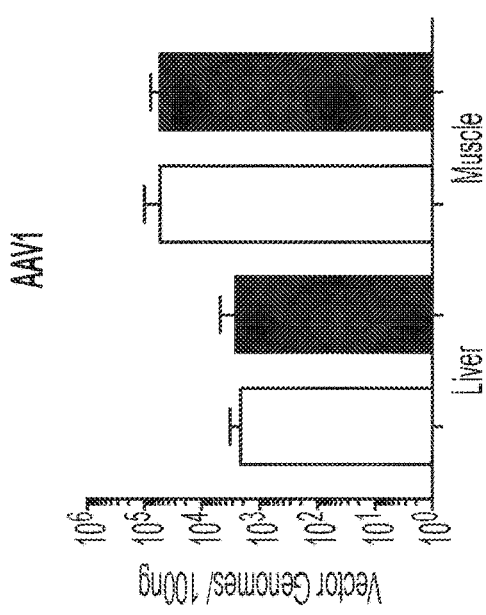
FIG. 13A FIG. 13B FIG. 13C FIG. 13D FIG. 13E

US 11,884,926 B2

CAMPAIGN-READY SERIES OF RECOMBINANT ADENO-ASSOCIATED VIRUS (RAAV) COMPLEMENTING PLASMIDS

RELATED APPLICATIONS

The present application is a national stage filing under 35 U.S.C. § 371 of international PCT application, PCT/US2019/016310, filed Feb. 1, 2019, which claims priority under 35 U.S.C. § 119(e) to U.S. provisional patent application, U.S. Ser. No. 62/625,644, filed Feb. 2, 2018, the entire contents of each of which are incorporated herein by reference.

FEDERALLY SPONSORED RESEARCH

This invention was made with government support under grant numbers HL131471 and DK098252, awarded by the National Institutes of Health. The government has certain rights in the invention.

BACKGROUND

Much emphasis has been placed on developing recombinant adeno-associated virus (rAAV) packaging technologies that can be translated to larger scale at the cGMP level. Examples of packaging platforms suitable for scaling up a single product include the recombinant baculovirus, recombinant HSV, and inducible HeLa cell lines. In contrast, little attention has been devoted to developing rAAV packaging systems into a format suitable for application to multiple different single gene vectors in a multiple small-scale campaign mode.

SUMMARY

Aspects of the disclosure relate to methods and compositions for production of recombinant adeno-associated virus (rAAV) particles. The disclosure is based, in part, on isolated nucleic acids, and systems that include two vectors and are suitable for production of multiple different single gene viral vectors in a multiple small-scale campaign mode (e.g., $10^{10}$ to $10^{16}$ viral particles).

In some aspects, the disclosure provides a recombinant adeno-virus (rAAV) production system comprising a first vector comprising one or more nucleic acids encoding: a non-beta-lactam antibiotic resistance gene, an inducible eukaryotic promoter, an adeno-associated virus (AAV) capsid protein, wherein the nucleic acid encoding the capsid protein is flanked by one or more restriction enzyme recognition sites, and one or more viral helper elements; and a second vector comprising one or more nucleic acids encoding an expression cassette comprising a transgene flanked by adeno-associated virus (AAV) inverted terminal repeat (ITR) sequences.

In some embodiments, a first vector comprises a bacterial plasmid backbone or a bacterial origin of replication (ori). In some embodiments, an origin of replication (ori) is a pUC ori.

In some embodiments, a non-beta-lactam antibiotic resistance gene is a kanamycin resistance (kanR) gene.

In some embodiments, an inducible promoter is a steroid-inducible promoter (e.g., a steroid-inducible eukaryotic promoter). In some embodiments, a steroid-inducible eukaryotic promoter is a Mouse Mammary Tumor Virus Long Terminal Repeat (MMTV-LTR) promoter.

In some embodiments, an AAV capsid protein is selected from an AAV1 capsid protein, AAV2 capsid protein, AAV3B capsid protein, AAV5 capsid protein, AAV7 capsid protein, AAV8 capsid protein, AAV9 capsid protein, AAVrh10 capsid protein, AAVrh8 capsid protein, or AAV-PHP-B capsid protein.

In some embodiments, a restriction enzyme recognition site is cleaved by SwaI or ClaI. In some embodiments, a restriction enzyme recognition site comprises a sequence as set forth in SEQ ID NO: 10 (ATTTAAAT) or 11 (ATCGAT).

In some embodiments, one or more viral helper elements is an Adenovirus (Ad) helper element. In some embodiments, the Adenovirus helper element is an Adenovirus Type 5 (Ad5) helper element. In some embodiments, the one or more viral helper elements is Ad5-VA, Ad5-E2a, Ad5-E2b, or Ad5-E4.

In some embodiments, AAV inverted ITR sequences are AAV2 ITRs.

In some embodiments, a transgene is a protein or an inhibitory nucleic acid. In some embodiments, an inhibitory nucleic acid is dsRNA, siRNA, miRNA, or amiRNA. In some embodiments, a protein is a therapeutic protein.

In some embodiments, an expression cassette further comprises a promoter operably linked to a transgene. In some embodiments, a promoter is a H1, U6, CB, CBA, CB6, Desmin, CMV, AAT, or MHK promoter.

In some embodiments, a first vector is a plasmid or a second vector is a plasmid. In some embodiments, both a first vector and a second vector are each a plasmid. In some embodiments, a first vector comprises the nucleic acid sequence set forth in any one of SEQ ID NOs: 1-9.

In some embodiments, a rAAV production system as described by the disclosure further comprises a host cell. In some embodiments, a host cell is a eukaryotic cell. In some embodiments, a host cell is a mammalian cell. In some embodiments, a mammalian cell is a HEK293 cell, a HEK293T cell, or a Chinese hamster ovary (CHO) cell. In some embodiments, the host cell is a bacterial cell, for example an *E. coli* cell.

In some embodiments, a host cell expresses Adenovirus helper element Ad-E1a.

In some aspects, the disclosure provides a cell (e.g., a host cell) comprising an rAAV production system as described by the disclosure.

In some aspects, the disclosure provides an isolated nucleic acid comprising the sequence set forth in any one of SEQ ID NOs: 1-9.

In some aspects, the disclosure provides a method for producing a recombinant adeno-associated virus (rAAV), the method comprising introducing an rAAV production system as described by the disclosure into a host cell that expresses an Ad-E1a helper function.

In some aspects, the disclosure provides a method for producing a recombinant adeno-associated virus (rAAV), the method comprising introducing an isolated nucleic acid as described by the disclosure into a host cell that expresses an Ad-E1a helper function; and introducing a vector comprising one or more nucleic acids encoding an expression cassette comprising a transgene flanked by adeno-associated virus inverted terminal repeat (ITR) sequences.

In some embodiments, the first vector and second vector of an rAAV production system are introduced into the host cell in a single transfection reaction. In some embodiments, the first vector and second vector of an rAAV production system are introduced into the host cell in separate transfection reactions.

In some embodiments, the isolated nucleic acid and the vector are introduced into the host cell in a single transfection reaction. In some embodiments, the isolated nucleic acid and the vector are introduced into the host cell in separate transfection reactions.

In some embodiments, methods of producing an rAAV described by the disclosure further comprise the step of culturing the cells after introduction of the rAAV production system. In some embodiments, culturing of cells (e.g., host cells comprising an rAAV production system as described herein) occurs in the presence of an antibiotic cognate to the antibiotic-resistance gene of the first vector (e.g., the first vector of the rAAV production system).

In some embodiments, methods of producing an rAAV described by the disclosure further comprise the step of isolating rAAV particles (e.g., rAAV particles comprising the transgene) from the host cells and/or cell culture media.

In some embodiments, a titer of less than $10^{16}$ rAAV particles are produced by rAAV production methods described by the disclosure. In some embodiments, a titer between $10^{10}$ and $10^{16}$ rAAV particles are produced.

The disclosure relates, in part, to cell culture systems comprising rAAV production systems described herein. In some aspects, the disclosure provides an apparatus for production of recombinant adeno-associated virus (rAAV) particles, the apparatus comprising: a container housing an rAAV production system as described herein; and, a population of host cells, wherein the rAAV production system and the host cells are suspended in a cell culture medium.

In some embodiments, the container is a cell culture flask, cell culture plate, a beaker, or a cell culture bag.

In some embodiments, the population of host cells are mammalian cells. In some embodiments, the mammalian cells are HEK293 cells, HEK293T cells or CHO cells. In some embodiments, the population of host cells are bacterial cells. In some embodiments, the bacterial cells are *E. coli* cells.

In some embodiments, the cell culture medium is a bacterial cell culture medium or mammalian cell culture medium.

BRIEF DESCRIPTION OF DRAWINGS

FIGS. 2A-2I show schematics depicting embodiments of a plasmid comprising a combination of AAV protein-encoding genes (e.g., Rep, Cap, etc.) and Adenovirus (Ad) helper genes (e.g., Ad5-VA, Ad5-E2a, E2b, E4, etc.). FIG. 2A depicts a plasmid comprising an AAV7 capsid protein and Adenovirus (Ad) helper genes. FIG. 2B depicts a plasmid comprising an AAV1 capsid protein and Adenovirus (Ad) helper genes. FIG. 2C depicts a plasmid comprising an AAV3B capsid protein and Adenovirus (Ad) helper genes. FIG. 2D depicts a plasmid comprising an AAV5 capsid protein and Adenovirus (Ad) helper genes. FIG. 2E depicts a plasmid comprising an AAV8 capsid protein and Adenovirus (Ad) helper genes. FIG. 2F depicts a plasmid comprising an AAV9 capsid protein and Adenovirus (Ad) helper genes. FIG. 2G depicts a plasmid comprising an AAV-PHP-B capsid protein and Adenovirus (Ad) helper genes. FIG. 2H depicts a plasmid comprising an AAV-RH8 capsid protein and Adenovirus (Ad) helper genes. FIG. 2I depicts a plasmid comprising an AAV-RH10 capsid protein and Adenovirus (Ad) helper genes.

FIG. 4A shows viral titers (VP/ml) and genome copy numbers (GC/ml) measured by silver stain gel, droplet digital PCR (ddPCR), and microscopic analysis. FIG. 4B shows viral band detection in pQT-7, pDG-7 and core low yield samples.

FIGS. 13A-13E show vector genome (vg) quantification after in vivo delivery of different capsid variants. AAV particles were produced by either the traditional triple-plasmid transfection system or pQT transfection. In FIG. 13A, AAV1 particles were intramuscularly injected into either liver or muscle. Tissue was collected from the muscle injection site and liver injection site. FIG. 13B, shows quantification of AAV3b particles from liver. FIG. 13C shows quantification of AAV5 particles from liver. FIG. 13D shows quantification of AAV8 particles from liver. FIG. 13E shows quantification of AAV9 particles from liver. The vg's were measured by qPCR using a primer targeting the polyA tail.

In FIG. 14A, AAV5, AAV8, or AAV9 particles were injected intravenously. Tissue was collected from the liver. In FIG. 14B, AAV1 particles were injected intramuscularly. Tissue was collected from the muscle injection site.

In FIG. 15A, $5 \times 10^{11}$ vg's were injected intravenously (IV) via the tail vein. Blood samples were taken from the mice at 0, 1, 2, 3, 4, 5, 6, 8, and 12 weeks after IV injection. In FIG. 15B, $1 \times 10^{11}$ vg's were injected intramuscularly (IM). Blood samples were taken from the mice at 0, 1, 2, 3, 4, 5, 6, 8, and 10 weeks after IM injection. Asterisks (*) designate statistical significance between pQT8 and AAV8 as measured by 2-way repeated measures ANOVA.

In FIG. 16A, the levels of the AAT protein approximated by measuring the c-myc levels. Blood samples were taken from the mice at 0, 1, 2, 3, 4, 5, 6, and 8 weeks after IV injection. In FIG. 16B, the expression levels of the mutant PiZ mutant protein are measured after blood samples were taken from the mice at 0, 1, 2, 3, 4, 5, 6, and 8 weeks after IV injection.

DETAILED DESCRIPTION

Figure 1:
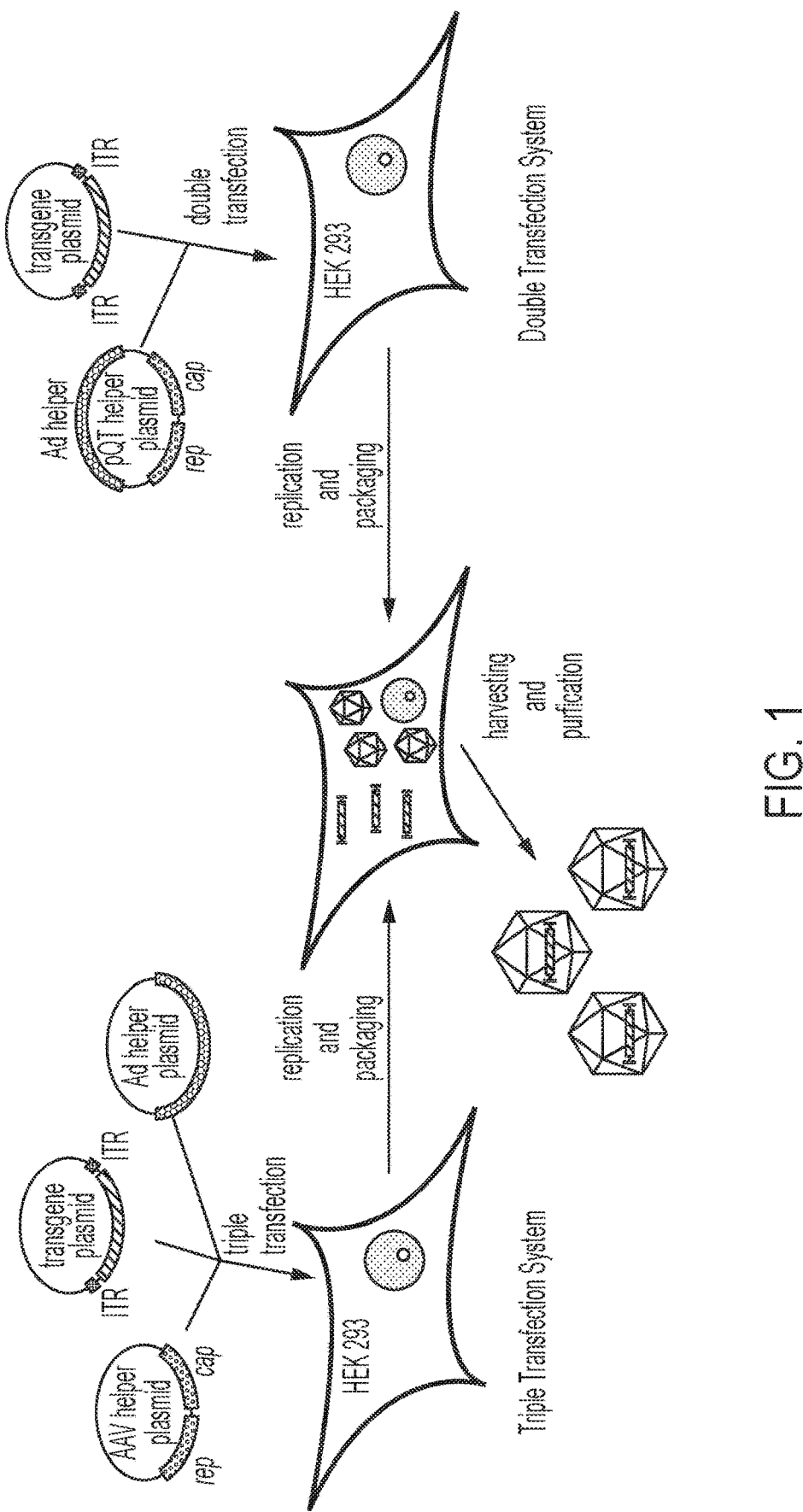
FIG. 1 shows a schematic comparing a triple-plasmid transfection system with one embodiment of a dual-plasmid transfection system as described by the disclosure.
Figure 2A:
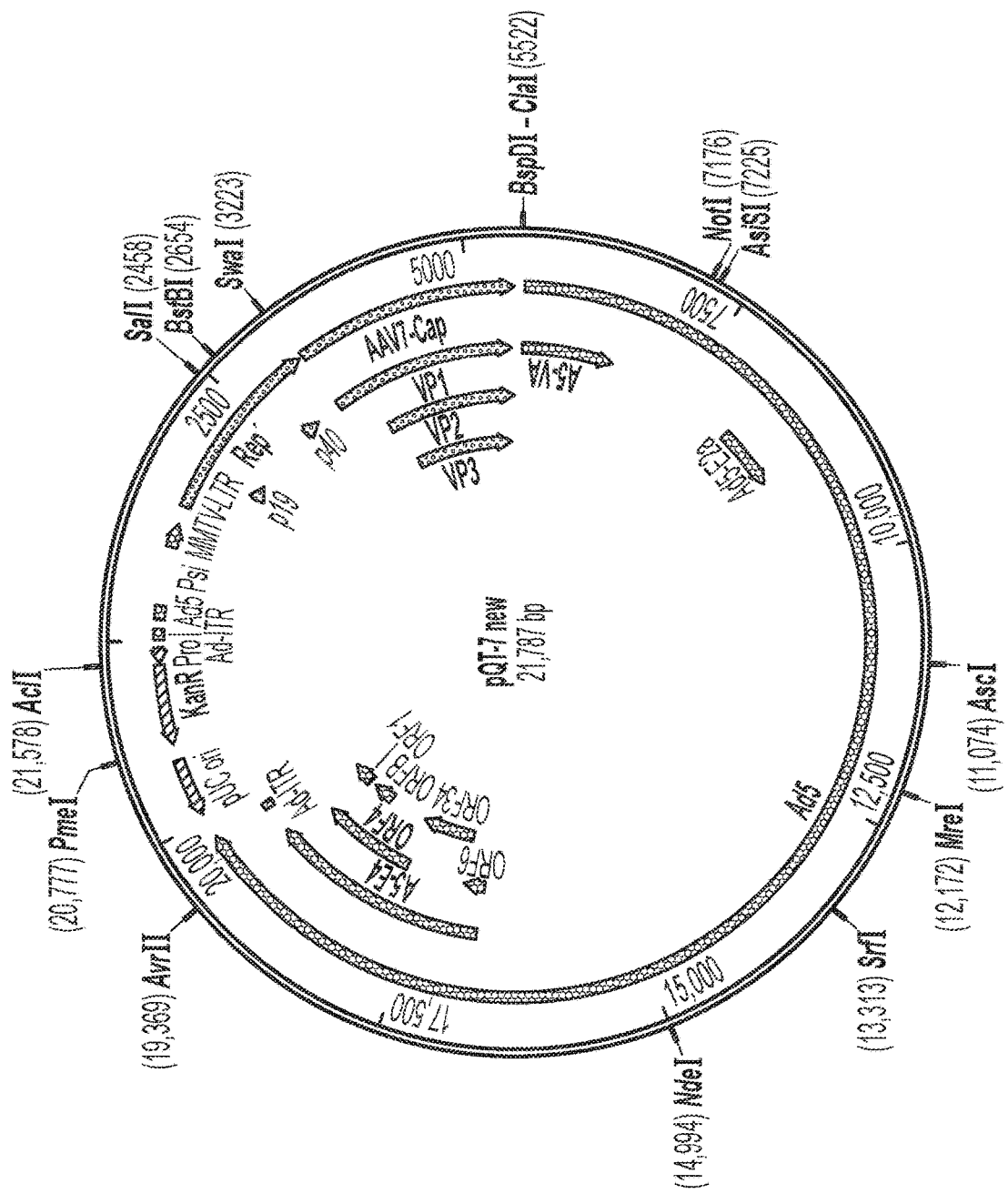
Figure 2B:
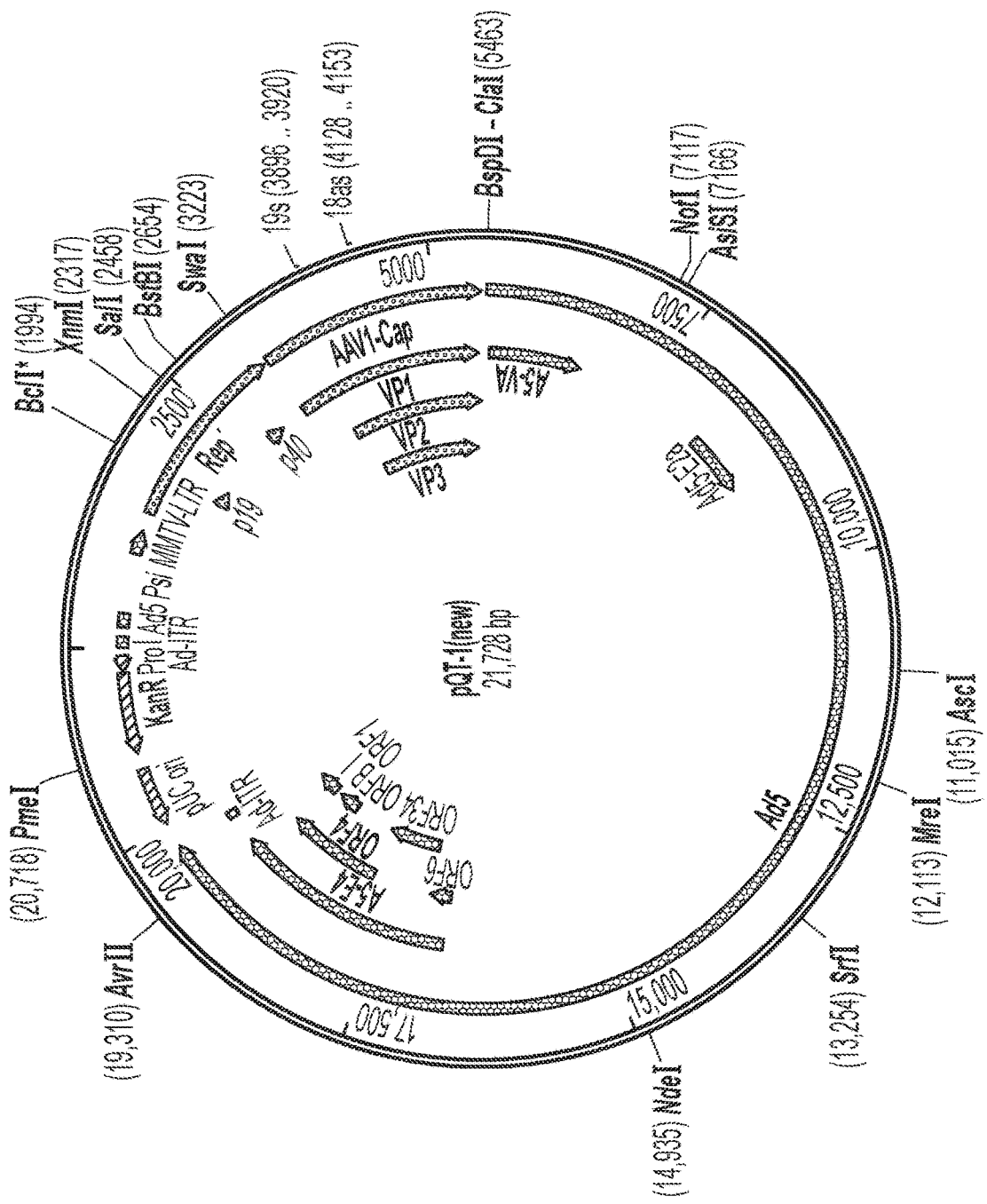
Figure 2C:
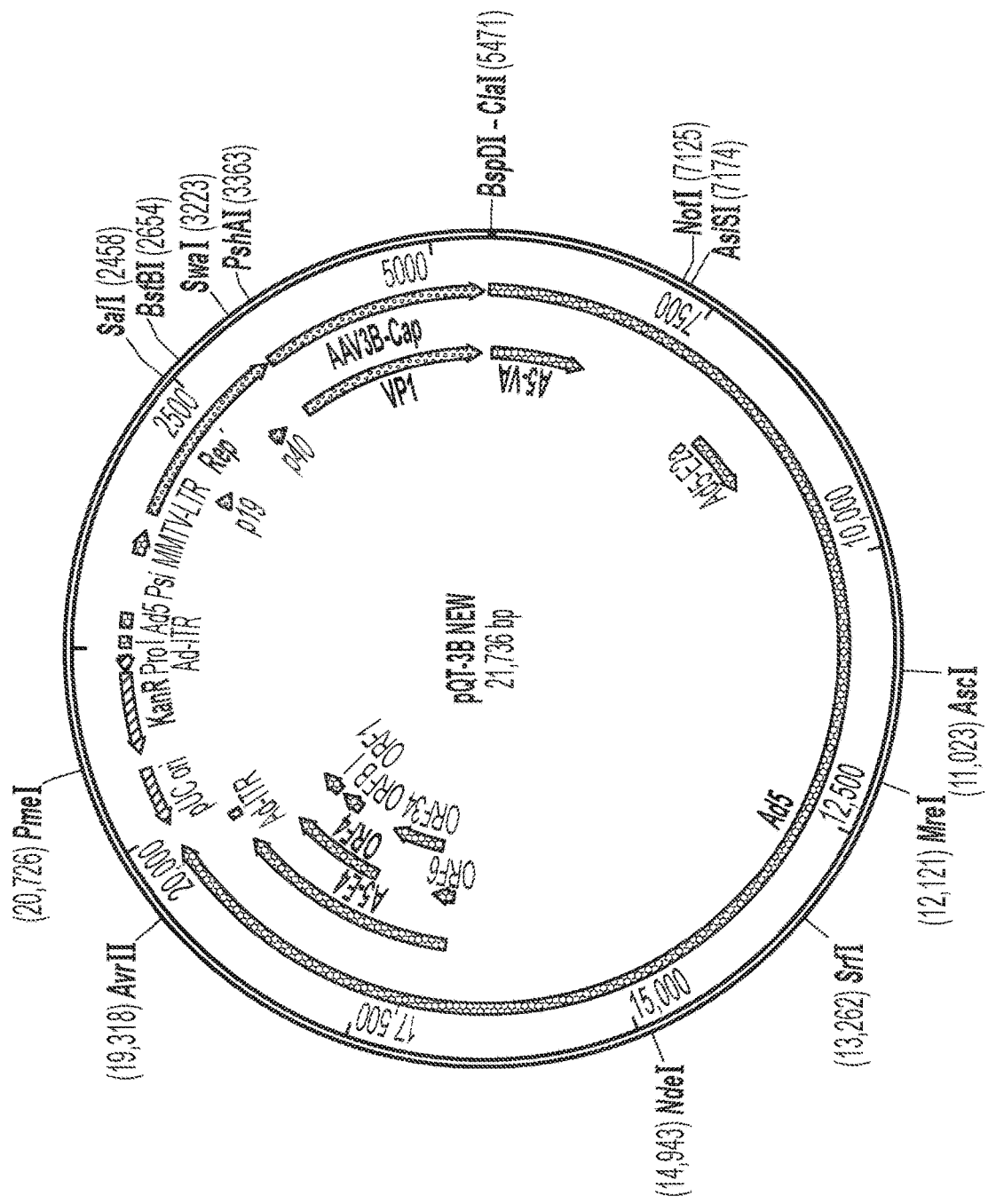
Figure 2D:
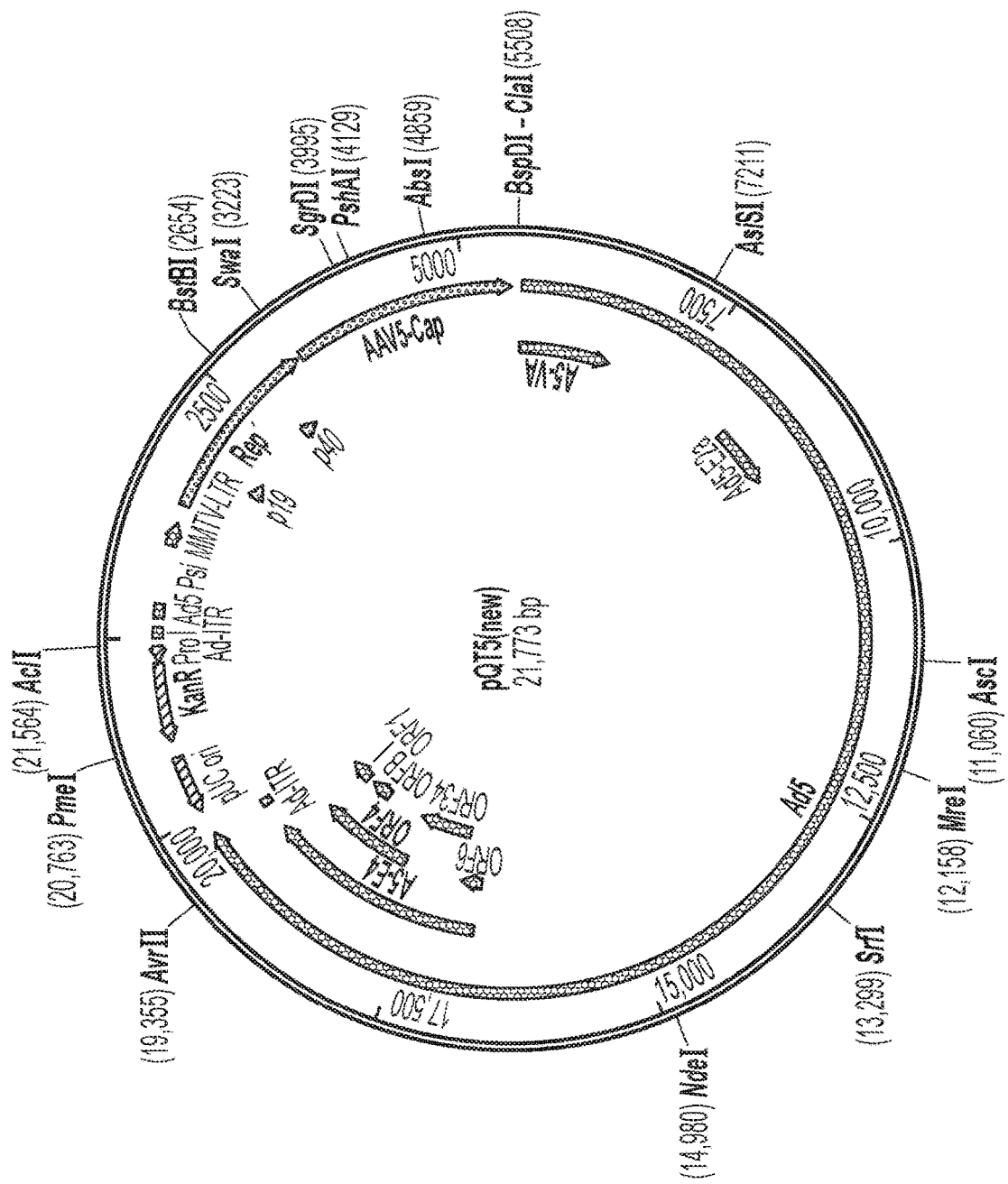
Figure 2E:
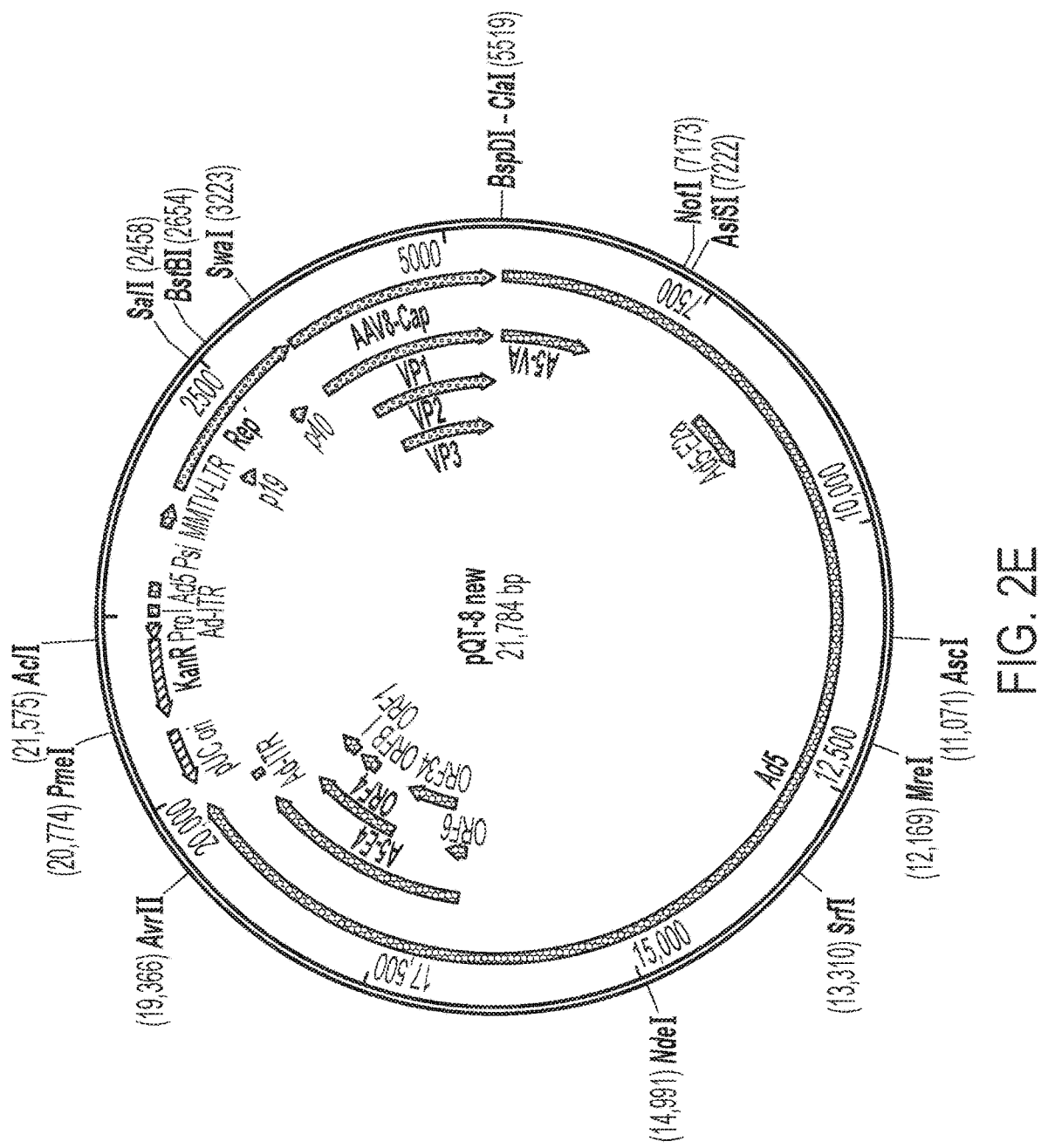
Figure 2F:
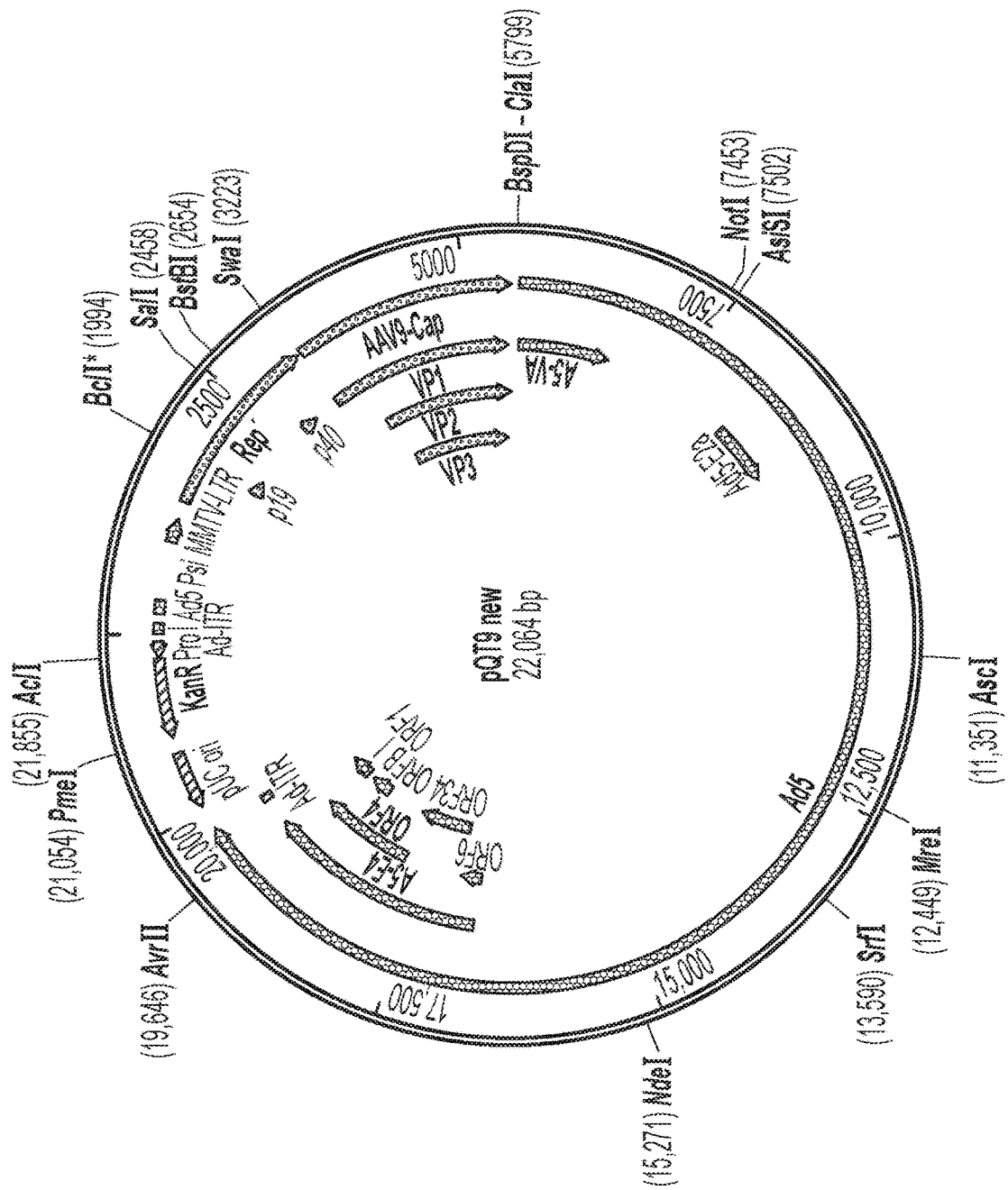
Figure 2G:
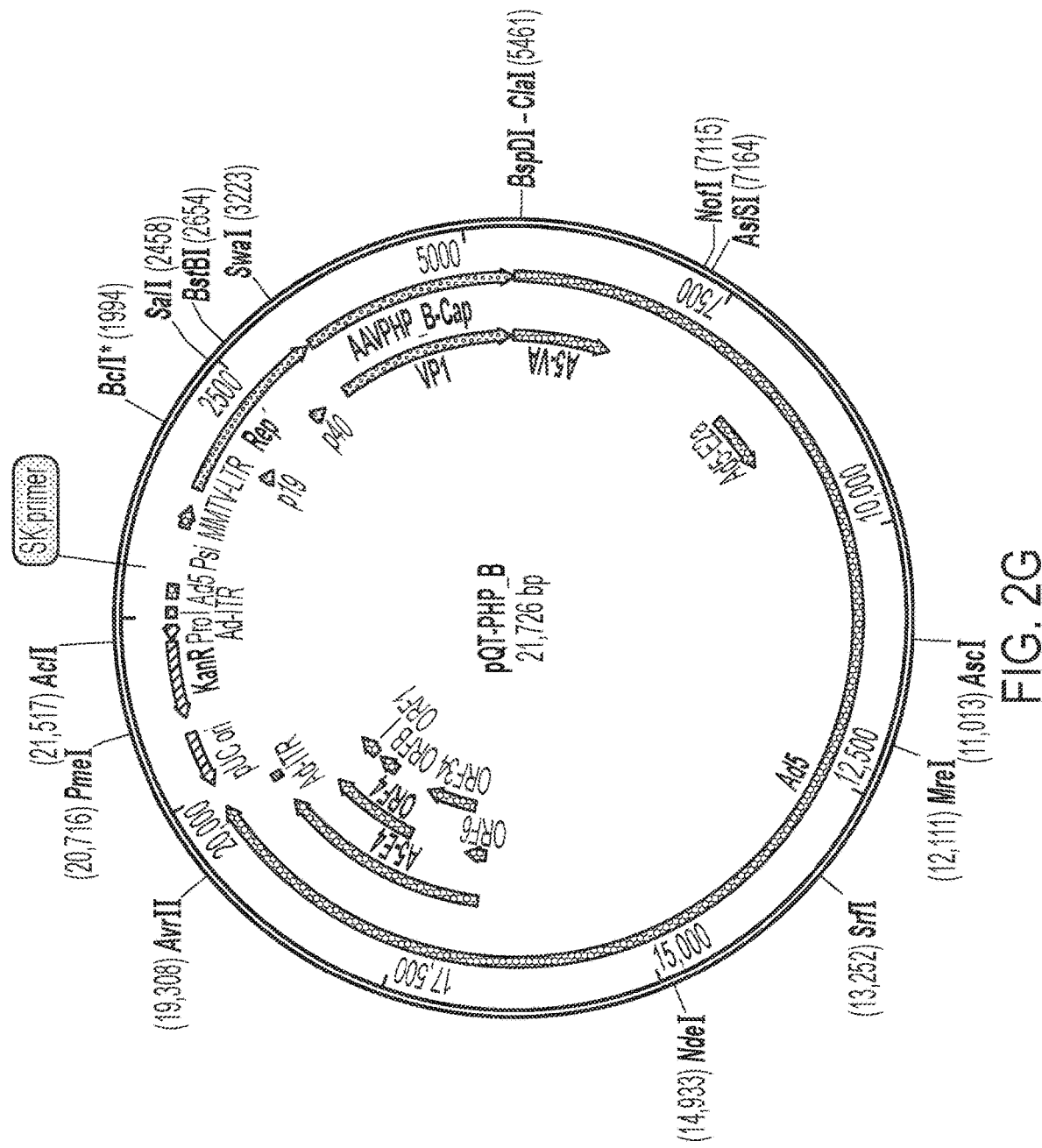
Figure 21:
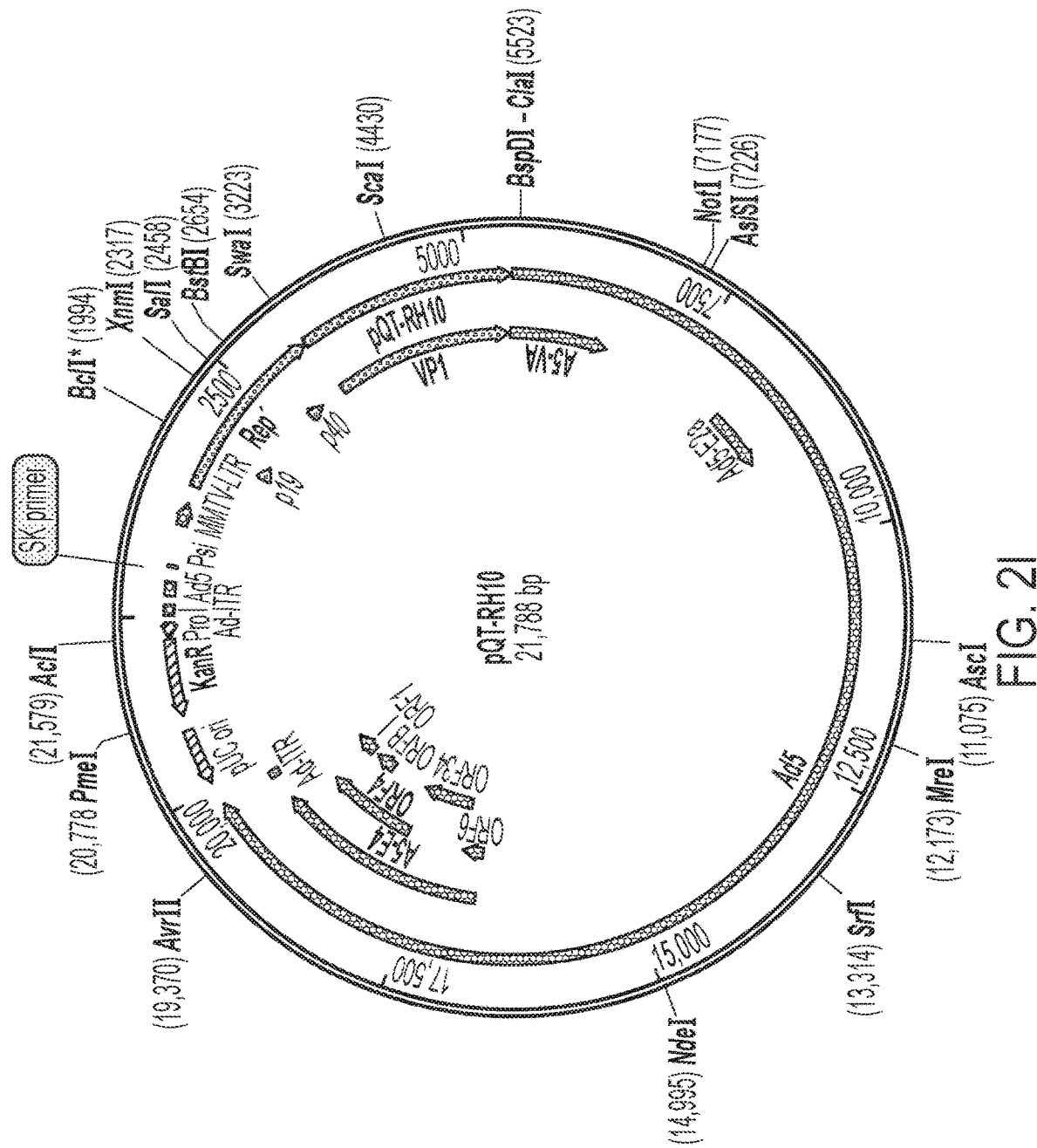

In some aspects, the disclosure relates to methods and systems for production of recombinant adeno-associated virus (rAAV) particles. The disclosure is based, in part, on vector systems comprising a first vector encoding a combination of AAV and viral (e.g., Adenovirus (Ad), etc.) packaging genes and a second vector having a proviral genome (e.g., an isolated nucleic acid encoding an expression construct having a transgene of interest (e.g., a therapeutic protein, interfering RNA, etc.) flanked by AAV inverted terminal repeat sequences). In some embodiments, systems (e.g., rAAV production systems) described herein produce titers of rAAV particles (e.g., titers between $10^{10}$ and $10^{16}$ viral particles) that are efficient, cost-effective and therefore suitable for multiple small-scale clinical trials of gene therapy compositions.

rAAV Production Systems

The disclosure relates, in some embodiments, to isolated nucleic acids (e.g., vectors comprising one or more isolated nucleic acids) that are useful for replication and packaging of rAAVs.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

Furthermore, nucleic acids can be tailored for optimal gene expression based on optimization of nucleotide sequence to reflect the codon bias of a host cell. The skilled artisan appreciates that gene expression may be improved if codon usage is biased towards those codons favored by the host.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

In some aspects, the disclosure provides a recombinant adeno-virus (rAAV) production system comprising a first vector comprising one or more nucleic acids encoding: a non-beta-lactam antibiotic resistance gene, an inducible eukaryotic promoter (e.g., a steroid-inducible eukaryotic promoter), an adeno-associated virus (AAV) capsid protein, wherein the nucleic acid encoding the capsid protein is flanked by one or more restriction enzyme recognition sites, and one or more viral helper elements, for example one or more Adenovirus helper elements selected from Ad-VA, Ad-E2a, Ad-E2b, and Ad-E4.

In some embodiments, a vector as described by the disclosure comprises a nucleic acid sequence encoding one or more antibiotic-resistance genes. An "antibiotic-resistance gene" refers to a nucleic acid that encodes a gene product that enables a cell (e.g., a bacterial cell, a mammalian cell, etc.) to survive in the presence of an antibiotic agent that would otherwise kill the cell and/or kills cells that do not express the antibiotic resistance gene. Examples of antibiotic agents include but are not limited to cytotoxic agents (e.g., antibiotic agents affecting mammalian cells), antifungal agents, antiviral agents, and antibacterial (e.g., bacteriostatic and bactericidal agents). In some embodiments, an antibiotic-resistance gene confers resistance of a cell to an antibacterial agent. Examples of antibacterial agents include but are not limited to kanamycin, spectinomycin, streptomycin, ampicillin, carbenicillin, bleomycin, erythromycin, polymixin B, tetracycline, and chloramphenicol. In some embodiments, an antibiotic agent is a beta-lactam antibiotic (e.g., antibiotic agent having a beta-lactam ring).

Examples of beta-lactam antibiotics include but are not limited to penicillin derivatives (penams, such as benzathine penicillin, benzylpenicillin (penicillin G), phenoxymethylpenicillin (penicillin V), cloxacillin, dicloxacillin, flucloxacillin, methicillin, nafcillin, oxacillin, temocillin, etc.), cephalosporins (cephems, such as cefazolin, cephalexin, cephalosporin C, cephalothin, cefixime, cefotaxime, cefpodoxime, ceftazidime, ceftriaxone, cefepime, cefpirome, etc.), monobactams, carbapenems, ampicillin, amoxicillin, etc. In some embodiments, an antibiotic-resistance gene is not an ampicillin antibiotic resistance gene (e.g., AmpR).

In some embodiments, a vector as described by the disclosure comprises a nucleic acid encoding an antibiotic-resistance gene selected from kanR, bsd (Blasticidin resistance gene), neo (G418/Geneticin resistance gene), hygB (Hygromycin resistance gene), pac (Puromycin resistance gene), and sh bla (Zeocin resistance gene).

In some embodiments, a vector as described by the disclosure comprises a nucleic acid encoding a promoter. In some embodiments, the promoter is an inducible promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter (e.g., MMTV Long Terminal Repeat (MMTV LTR) promoter), the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268: 1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)).

In some embodiments the promoter is a steroid-inducible promoter, for example a promoter comprising a hormone binding domain (HBD) of a glucocorticoid receptor (GR), for example a MMTV LTR promoter. In some embodiments, a steroid-inducible promoter allows for increased expression of AAV Cap proteins relative to AAV Rep proteins (e.g., Rep 78/68 and Rep 52/40).

Still other types of inducible promoters which may be useful in this context are those which are regulated by a specific physiological state, e.g., temperature, acute phase, a particular differentiation state of the cell, or in replicating cells only.

In some embodiments, a vector as described by the disclosure comprises a nucleic acid encoding an adeno-associated virus (AAV) capsid protein. The AAV capsid is an important element in determining tissue-specific targeting capabilities of an rAAV. Thus, an rAAV having a capsid appropriate for the tissue being targeted can be selected. Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments the capsid protein is of a serotype selected from: AAV1, AAV2, AAV3, AAV3B, AAV4, AAV5, AAV6, AAV7, AAV8, AAV9, AAV10, AAV11, AAV12, AAV.rh.10, AAVrh8, AAV-PHP-B and variants of any one of them. Generally, AAV capsid proteins (e.g., VP1, VP2 and VP3 capsid proteins) are encoded by a single Cap gene.

In some aspects, the disclosure relates to vector systems that are configured to allow the capsid protein encoded by the vector to be changed easily (e.g., vectors described by the disclosure allow for a nucleic acid encoding a particular serotype capsid protein to be easily swapped for a nucleic acid sequence encoding a capsid protein having a different serotype). Accordingly, in some embodiments, the nucleic acid encoding the capsid protein is flanked by one or more (e.g., 2, 3, 4, 5, 6, 7, 8, 9, 10, or more) restriction enzyme recognition sites. Examples of restriction enzymes and their recognition sites include SwaI (5'ATTTAAAT3'), ClaI (5'ATCGAT3'), EcoRI (5'GAATTC3'), BamHI (5'GGATCC3'), NotI (5'GCGGCCGC3'), etc.

Further examples of restriction enzymes and their cognate recognition sites are described, for example, by www.neb.com/tools-and-resources/selection-charts/alpha-betized-list-of-recognition-specificities, the entire contents of which are incorporated herein by reference.

In some embodiments, restriction enzyme recognition sites flanking the nucleic acid sequence encoding the capsid protein are cleaved by the same restriction enzyme. In some embodiments, restriction enzyme recognition sites flanking the nucleic acid sequence encoding the capsid protein are cleaved by different (e.g., 2 or more) restriction enzymes.

In some embodiments, a nucleic acid encoding an AAV capsid protein is flanked by two SwaI restriction sites, two ClaI restriction sites, or an SwaI restriction site and a ClaI restriction site. The skilled artisan will recognize that the orientation of the SwaI and ClaI restriction sites may vary with respect to the nucleic acid sequence encoding the capsid protein. For example, in some embodiments, a ClaI restriction site is located 5' to a nucleic acid encoding a capsid protein and a SwaI restriction site is located 3' to the nucleic acid encoding the capsid protein. In some embodiments, an SwaI restriction site is located 5' to a nucleic acid encoding a capsid protein and a ClaI restriction site is located 3' to the nucleic acid encoding the capsid protein.

The disclosure is based, in part, on vectors for rAAV production that comprise a combination of AAV packaging genes and viral helper functions. "Helper functions" generally refers to nucleic acid sequences encoding non-AAV-derived viral and/or cellular functions upon which AAV is dependent for replication (e.g., "accessory functions"). The accessory functions include those functions required for AAV replication, including, without limitation, those moieties involved in activation of AAV gene transcription, stage-specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some embodiments, a vector as described by the disclosure comprises a nucleic acid encoding and one or more viral (e.g., adenovirus (Ad), etc.) helper elements (e.g., accessory functions). Examples of Ad helper elements include but are not limited to Ad-E1a, Ad-VA, Ad-E2a, Ad-E2b, and Ad-E4. The Ad type from which the one or more helper elements are derived can vary. In some embodiments, the one or more helper elements are Ad1, Ad2, Ad3, Ad4, or Ad5 helper elements. In some embodiments, the helper elements are Ad5 helper elements.

In some embodiments, a vector as described by the disclosure comprises a bacterial plasmid backbone or a bacterial origin of replication (ori). Examples of bacterial origins of replication (ori) include but are not limited to pUC (e.g., pMB1), pBR322 (e.g., pMB1), pET (e.g., pBR322), ColE1, R6K, p15A, and pSC101. In some embodiments, an origin of replication (ori) is a pUC ori.

In some embodiments, an rAAV production system comprises a second vector comprising one or more nucleic acids encoding an expression cassette comprising a transgene flanked by adeno-associated virus (AAV) inverted terminal repeat (ITR) sequences (e.g., an rAAV vector).

"Recombinant AAV (rAAV) vectors" are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The instant disclosure provides a vector comprising a single, cis-acting wild-type ITR. In some embodiments, the ITR is a 5' ITR. In some embodiments, the ITR is a 3' ITR Generally, ITR sequences are about 145 bp in length. Preferably, substantially the entire sequences encoding the ITR(s) is used in the molecule, although some degree of minor modification of these sequences is permissible. The ability to modify ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). For example, an ITR may be mutated at its terminal resolution site (TR), which inhibits replication at the vector terminus where the TR has been mutated and results in the formation of a self-complementary AAV. Another example of such a molecule employed in the present disclosure is a "cis-acting" plasmid containing the transgene, in which the selected transgene sequence and associated regulatory elements are flanked by the 5' AAV ITR sequence and a 3' hairpin-forming RNA sequence. AAV ITR sequences may be obtained from any known AAV, including presently identified mammalian AAV types. In some embodiments, an ITR sequence is an AAV2, AAV3, AAV4, AAV5, AAV6, AAV7, AAV8, AAVrh8, AAV9, AAV10, AAV-PHP_B and/or AAVrh10 ITR sequence.

In some embodiments, the rAAVs of the disclosure are pseudotyped rAAVs. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA, miRNA inhibitor).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the (3-actin promoter, the phosphoglycerol kinase (PGK) promoter, and the EF1α promoter [Invitrogen].

In another embodiment, the native promoter for the transgene (e.g., hairpin forming nucleic acid) will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, a promoter is an RNA polymerase II (pol II) promoter or an RNA polymerase III (pol III) promoter. In some embodiments, a promoter is a H1, U6, CB, CBA, CB6, Desmin, CMV, AAT, or MHK promoter The disclosure relates, in some aspects, to isolated nucleic acids and vectors (e.g., rAAV vectors) comprising one or more nucleic acids sequences encoding a transgene. The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

Thus, the disclosure embraces the delivery of vectors encoding one or more peptides, polypeptides, or proteins, which are useful for the treatment or prevention of disease states in a mammalian subject. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16 IL-17, and IL-18.

The vectors disclosed herein may comprise a transgene to be transferred to a subject to treat a disease associated with reduced expression, lack of expression or dysfunction of the native gene. Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase, associated with ornithine transcarbamylase deficiency; argininosuccinic acid synthetase, associated with citrullinemia; low density lipoprotein receptor protein, associated with familial hypercholesterolemia; UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-glucocerebrosidase, associated with Gaucher disease; beta-glucuronidase, associated with Sly syndrome; peroxisome membrane protein 70 kDa, associated with Zellweger syndrome; porphobilinogen deaminase, associated with acute intermittent porphyria; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, antisense to, or a mutant form of, phospholamban, the sarco(endo)plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin for the treatment of diabetes.

The following are further non-limiting examples of proteins that may be encoded by transgenes of the vectors disclosed herein to treat a disease associated with reduced expression, lack of expression or dysfunction of the native gene: a-galactosidase, acid-glucosidase, adiopokines, adiponectin, alglucosidase alfa, anti-thrombin, ApoAV, ApoCII, apolipoprotein A-I (APOA1), arylsulfatase A, arylsulfatase B, ATP-binding cassette transporter A1 (ABCA1), ABCD1, CCR5 receptor, erythropoietin, Factor VIII, Factor VII, Factor IX, Factor V, fetal hemoglobin, beta-globin, GPI-anchored HDL-binding protein (GPI-HBP) I, growth hormone, hepatocyte growth factor, imiglucerase, lecithin-cholesterol acyltransferase (LCAT), leptin, LDL receptor, lipase maturation factor (LMF) 1, lipoprotein lipase, lysozyme, nicotinamide dinucleotide phosphate (NADPH) oxidase, Rab escort protein-1 (REP-1), retinal degeneration slow (RDS), retinal pigment epithelium-specific 65 (RPE65), rhodopsin, T cell receptor alpha or beta chains, thrombopoeitin, tyrosine hydroxylase, VEGF, von heldebrant factor, von willebrand factor, and X-linked inhibitor of apoptosis (XIAP).

In some aspects, the disclosure relates to rAAVs and rAAV vectors comprising a transgene, wherein the transgene is a hairpin-forming RNA. Non-limiting examples of hairpin-forming RNA include short hairpin RNA (shRNA), microRNA (miRNA) and artificial microRNA (AmiRNA). In some embodiments, nucleic acids are provided herein that contain or encode the target recognition and binding sequences (e.g., a seed sequence or a sequence complementary to a target) of any one of the inhibitory RNAs (e.g., shRNA, miRNA, AmiRNA) disclosed herein.

Generally, hairpin-forming RNAs are arranged into a self-complementary "stem-loop" structure that includes a single nucleic acid encoding a stem portion having a duplex comprising a sense strand (e.g., passenger strand) connected to an antisense strand (e.g., guide strand) by a loop sequence. The passenger strand and the guide strand share complementarity. In some embodiments, the passenger strand and guide strand share 100% complementarity. In some embodiments, the passenger strand and guide strand share at least 50%, at least 60%, at least 70%, at least 80%, at least 90%, at least 95%, or at least 99% complementarity. A passenger strand and a guide strand may lack complementarity due to a base-pair mismatch. In some embodiments, the passenger strand and guide strand of a hairpin-forming RNA have at least 1, at least 2, at least 3, at least 4, at least 5, at least 6, at least 7 at least 8, at least 9, or at least 10 mismatches. Generally, the first 2-8 nucleotides of the stem (relative to the loop) are referred to as "seed" residues and play an important role in target recognition and binding. The first residue of the stem (relative to the loop) is referred to as the "anchor" residue. In some embodiments, hairpin-forming RNA have a mismatch at the anchor residue.

Hairpin-forming RNA are useful for translational repression and/or gene silencing via the RNAi pathway. Due to having a common secondary structure, hairpin-forming RNA share the characteristic of being processed by the proteins Drosha and Dicer prior to being loaded into the RNA-induced silencing complex (RISC). Duplex length amongst hairpin-forming RNA can vary. In some embodiments, a duplex is between about 19 nucleotides and about 200 nucleotides in length. In some embodiments, a duplex is between about between about 14 nucleotides to about 35 nucleotides in length. In some embodiments, a duplex is between about 19 and 150 nucleotides in length. In some embodiments, hairpin-forming RNA has a duplex region that is 19, 20, 21, 22, 23, 24, 25, 26, 27, 28, 29, 30, 31, 32, or 33 nucleotides in length. In some embodiments, a duplex is between about 19 nucleotides and 33 nucleotides in length. In some embodiments, a duplex is between about 40 nucleotides and 100 nucleotides in length. In some embodiments, a duplex is between about 60 and about 80 nucleotides in length.

In some embodiments, the hairpin-forming RNA is a microRNA (miRNA), or artificial microRNA (AmiRNA). A microRNA (miRNA) is a small non-coding RNA found in plants and animals and functions in transcriptional and post-translational regulation of gene expression. An artificial microRNA (AmiRNA) is derived by modifying native miRNA to replace natural targeting regions of pre-mRNA with a targeting region of interest. For example, a naturally occurring, expressed miRNA can be used as a scaffold or backbone (e.g., a pri-miRNA scaffold), with the stem sequence replaced by that of an miRNA targeting a gene of interest. An artificial precursor microRNA (pre-amiRNA) is normally processed such that one single stable small RNA is preferentially generated. In some embodiments, scAAV vectors and scAAVs described herein comprise a nucleic acid encoding an AmiRNA. In some embodiments, the pri-miRNA scaffold of the AmiRNA is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

The following non-limiting list of miRNA genes, and their homologues, which are also useful in certain embodiments of the vectors provided herein: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-120'7-3p, hsa-miR-120'7-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-12'7-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-548l, hsa-miR-548m, hsa-miR-548n, hsa-miR-548o, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*. In some embodiments, the above miRNAs may be encoded for in a vector provided herein (e.g., in a hairpin nucleic acid that replaces a mutant ITR). In some embodiments, sequences of the foregoing miRNAs may be useful as scaffolds or as targeting regions (e.g., seed regions of AmiRNA).

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

In some aspects, the disclosure relates to rAAV comprising a combination of hairpin-forming nucleic acid and a protein coding gene. rAAV vectors comprising an interfering nucleic acid and a protein coding gene are useful for simultaneously performing gene silencing and gene substitution. For example, rAAV vectors described herein can be used to silence a defective gene (e.g., mutated SOD1) while simultaneously delivering a non-mutated or functional copy of the defective gene (e.g., wild-type SOD1).

In some embodiments, the disclosure relates to an AAV comprising a nucleic acid encoding a protein or functional RNA useful for the treatment of a condition, disease or disorder associated with the central nervous system (CNS). The following is a non-limiting list of genes associated with CNS disease: DRD2, GRIA1, GRIA2,GRIN1, SLC1A1, SYP, SYT1, CHRNA7, 3Rtau/4rTUS, APP, BAX, BCL-2, GRIK1, GFAP, IL-1, AGER, associated with Alzheimer's Disease; UCH-L1, SKP1, EGLN1, Nurr-1, BDNF, TrkB, gstm1, S106β, associated with Parkinson's Disease; IT15, PRNP, JPH3, TBP, ATXN1, ATXN2, ATXN3, Atrophin 1, FTL, TITF-1, associated with Huntington's Disease; FXN, associated with Freidrich's ataxia; ASPA, associated with Canavan's Disease; DMD, associated with muscular dystrophy; and SMN1, UBE1, DYNC1H1 associated with spinal muscular atrophy. In some embodiments, the disclosure relates to recombinant AAVs comprising nucleic acids that express one or more of the foregoing genes or fragments thereof. In some embodiments, the disclosure relates to recombinant AAVs comprising nucleic acids that express one or more functional RNAs that inhibit expression of one or more of the foregoing genes.

Host Cells

In some embodiments, a rAAV production system as described by the disclosure further comprises a host cell. A "host cell" refers to any cell that harbors, or is capable of harboring, a substance of interest. In some embodiments, a host cell is a eukaryotic cell. In some embodiments, a host cell is a mammalian cell. In some embodiments, a mammalian cell is a HEK293 cell, a HEK293T cell, or a Chinese hamster ovary (CHO) cell. In some embodiments, a host cell is a bacterial cell, for example an *E. coli* cell.

A host cell may be used as a recipient of an isolated nucleic acid or vector as described herein, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

The disclosure is based, in part, on isolated nucleic acids and vectors (e.g., plasmids) that comprise components needed to replicate and package recombinant adeno-associated virus particles. In some embodiments, an isolated nucleic acid or vector as described herein lacks one or more genes required for replication and/or packaging of rAAV. In some embodiments, an isolated nucleic acid or vector as described herein lacks Ad Ela helper element. In some embodiments, a host cell expresses (or is capable of expressing) the one or more helper elements missing from the isolated nucleic acid or vector. For example, in some embodiments, a host cell expresses Adenovirus helper element Ad-E1a. In some embodiments the Ad-E1a is integrated into the genome of the host cell (e.g., HEK293 cells). In some embodiments, the Ad-E1a is introduced into a host cell and/or transiently expressed in a host cell (e.g., CHO cells).

rAAV Production Methods

In some aspects, the disclosure provides methods for producing a recombinant adeno-associated virus (rAAV), comprising the step of introducing an rAAV production system as described by the disclosure into a host cell that expresses an Ad-E1a helper function.

Generally, methods described by the disclosure involve transfecting a population of host cells (e.g., host cells expressing Ad-E1a) with a first vector comprising a combination of rAAV packaging genes (e.g., Rep and Cap genes) and Adenoviral helper elements (e.g., Ad5-VA, Ad5-E2a, Ad5-E2b, or Ad5-E4). The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells. In some embodiments, the first vector and second vector of an rAAV production system are introduced into the host cell in a single transfection reaction. In some embodiments, the first vector and second vector of an rAAV production system are introduced into the host cell in separate transfection reactions.

After transfection with the isolated nucleic acids and/or vectors described herein, the host cells can be cultured in the presence of an antibiotic agent that is cognate to the antibiotic-resistance gene of the first vector (e.g., the first vector of the rAAV production system). For example, in some embodiments, a vector comprises an kanR gene and the transfected host cells are cultured in the presence of kanamycin. The concentration of antibiotic agent present in the culture media can vary. In some embodiments, the concentration of antibiotic agent in the culture media ranges from about 5-100 μg/mL (e.g., any amount between 5 and 100 μg/mL, inclusive).

In some embodiments, methods described by the disclosure further comprise the step of isolating rAAV particles (e.g., rAAV particles comprising the transgene) from the host cells and/or cell culture media. Methods of rAAV purification are known in the art and are described, for example by WO2010148143, WO2016/114992, Potter et al. Mol Ther Methods Clin Dev. 2014; 1: 14034, and Wang et al. Methods Mol Biol. 2011; 807:361-404.

The disclosure relates, in part, to cell culture systems comprising rAAV production systems described herein. In some aspects, the disclosure provides an apparatus for production of recombinant adeno-associated virus (rAAV) particles, the apparatus comprising: a container housing an rAAV production system as described herein; and, a population of host cells, wherein the rAAV production system and the host cells are suspended in a cell culture medium.

In some embodiments, the container is a cell culture flask, cell culture plate, a beaker, or a cell culture bag. In some embodiments, the cell culture medium is a mammalian cell culture medium. Examples of cell culture media are described, for example, by Yao et al. (2017) *Reproductive Medicine and Biology* 16(2): 99-117.

The disclosure is based, in part, on the recognition that transformation of host cells with isolated nucleic acids and vectors (e.g., rAAV production systems) described by the disclosure allow for production of rAAV viral particles that is cost and time-efficient relative to currently available rAAV production methods (e.g., the triple-transfection method). Methods of measuring viral titer (and/or viral genome copy number) are known in the art and include, for example, silver-stain gel analysis, digital droplet (dd) polymerase chain reaction (ddPCR), and microscopic image analysis. In some embodiments, methods as described by the disclosure produce a viral titer of less than $10^{16}$ rAAV particles (e.g., $10^{15}$, $10^{14}$, $10^{13}$, $10^{12}$, $10^{11}$, $10^{10}$, etc.). In some embodiments, a titer between $10^{10}$ and $10^{16}$ (e.g., $10^{15}$, $10^{14}$, $10^{13}$, $10^{12}$, $10^{11}$, $10^{10}$, or any integer therebetween) rAAV particles are produced.

EXAMPLES

Example 1: Vector Systems for rAAV Production

Previously described systems for rAAV production have many challenges. For example, the triple transfection method (e.g., transfection with three plasmids comprising, respectively, an rAAV vector, Rep/Cap functions, and adenoviral helper genes) and generally have limited scalability. In another example, baculovirus helper-based systems require laborious insect cell culture systems, are difficult to optimize across different constructs (e.g., each transgene construct requires separate optimization), may contain non-mammalian glycosylation patterns, and generally result in a practical lot size ranging between $10^{16}$ to $10^{20}$ viral particles. In another example, herpesvirus-based (HSV) vector systems also require three expression constructs, are difficult to optimize across different constructs (e.g., each transgene construct requires separate optimization), and generally result in a practical lot size ranging between $10^{16}$ to $10^{20}$ viral particles.

This example describes systems (e.g., plasmid-based systems) for rAAV production that include only two vectors and are suitable for application to multiple different single gene vectors in a multiple small-scale campaign mode (e.g., $10^{13}$ to $10^{16}$ viral particles.) Dual-vector systems for rAAV production described by the disclosure are generally described and are compared with three-plasmid-based vector systems in FIG. 1.

In some embodiments, elements to the vector systems described herein (e.g., elements encoded by one or more nucleic acids on a plasmid described herein, for example a pQT plasmid) are illustrated in FIGS. 2A-2I. Salient features of the vector described in FIGS. 2A-2I are described below:
1. pUC ori—provides a high copy-number plasmid replication origin for cGMP-compatible plasmid production at a manageable scale of *E. coli* incubation.
2. Kanamycin resistance gene—driven from a bacterial promoter, this gene allows for scaled production in the absence of ampicillin.
3. MMTV LTR promoter—in the absence of any induction, produces a lower proportion of long Rep proteins (Rep78 and Rep68) as compared with short Rep (Rep52, Rep40) and Cap gene products (VP1, VP2, VP3). In some embodiments, a MMTV LTR promoter improves the yield of rAAV on a per cell basis.
4. Cap gene—the AAV capsid gene (e.g., Cap gene) is easily interchangeable in the vector, which allows the vector to support the packaging of viral genomes in a number of different AAV capsid serotypes (e.g., AAV1, AAV2, AAV3, AAV4, AAV5, AAV6, AAV7, AAV8, AAVrh8, AAV9, AAV-PHP-B, AAVrh10, etc., and variants thereof).
5. Adenoviral helper genes (Ad genes)—The Ad genes enable efficient helper function to assist in rAAV replication and packaging. In some embodiments, the vector comprises one or more of Ad5-VA, Ad5-E2a, E2B, or E4 genes.

The vector (e.g., single plasmid) described above, when transfected into HEK-293 or 293-T cells (which express Ad E1a and E1b), is sufficient to support replication and packaging of rAAV vectors. The second component of the vector system, a proviral vector plasmid (e.g., AAV-ITRs flanking an expression cassette with a gene of interest), supplies the viral genome and transgene to be packaged into rAAV viral particles.

Example 2: Packaging of AAV7-Based Vectors

This example describes production of rAAV7-CB-GFP viral particles using a vector system described in Example 1. Briefly, HEK-293 cells in roller bottle suspension were transfected by calcium phosphate transfection with vector plasmid pCB6.PI.EGFP.RBG and a packaging plasmid (e.g., pQT7 plasmid as described in Example 1).

Figure 3:
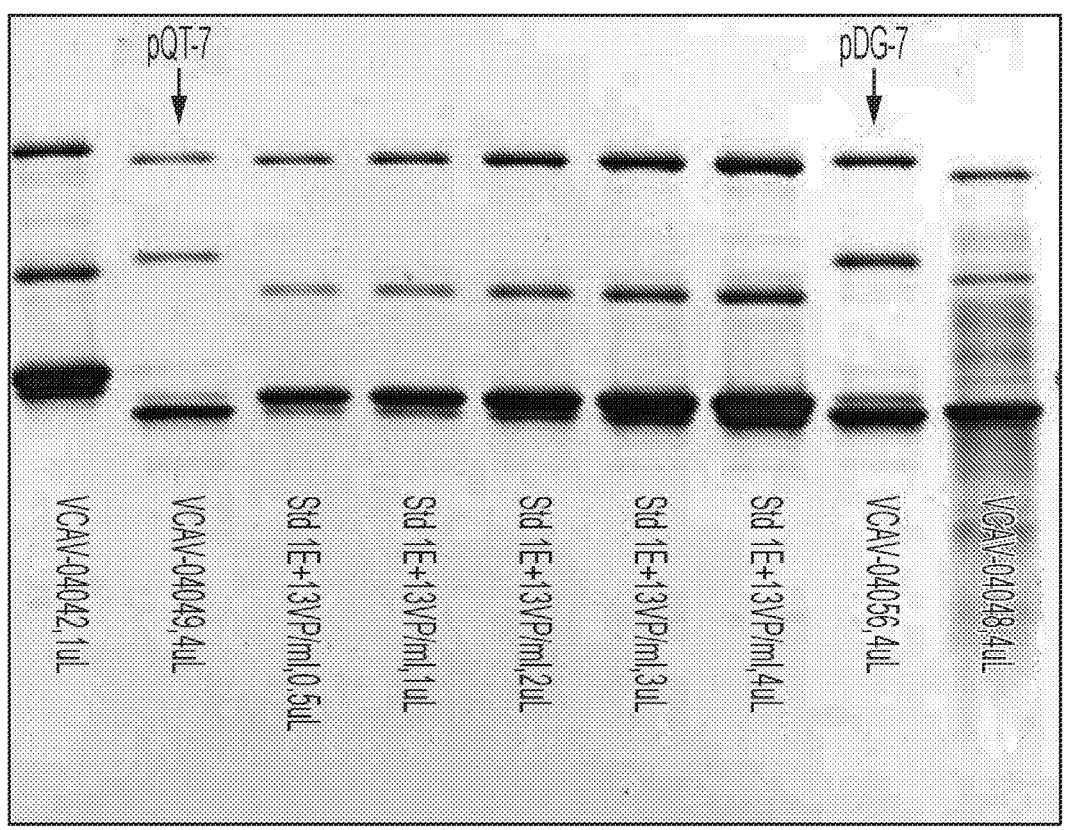
FIG. 3 shows representative data for silver stain gel analysis of estimated viral titers (VP/ml) of rAAVs packaged by an AAV7 capsid protein produced using the pQT-7 plasmid and the previously described pGD-7 plasmid.
Figure 4A:
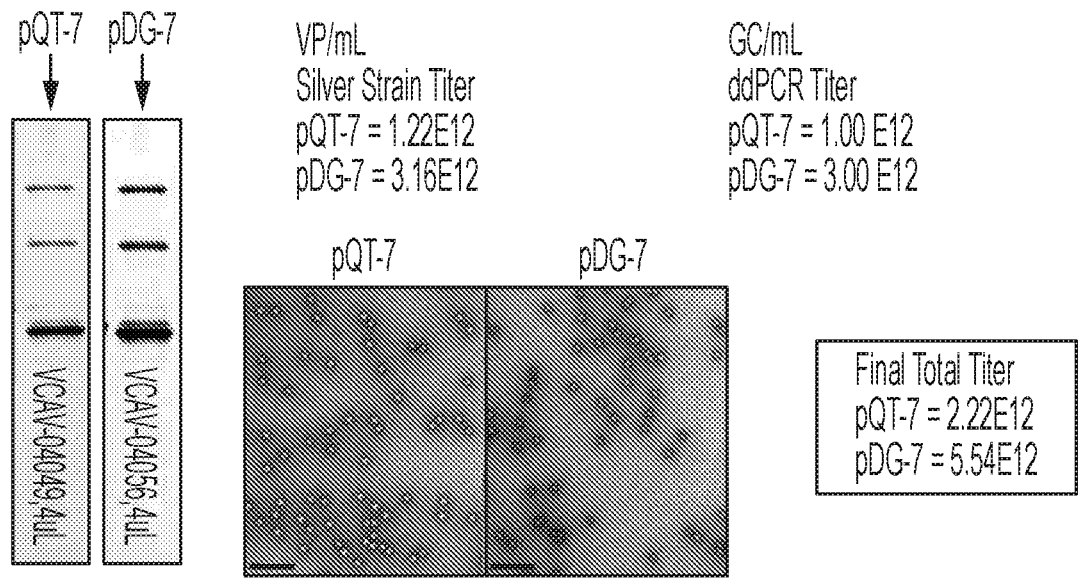
FIGS. 4A-4B show representative data of estimated viral titers of rAAVs packaged by an AAV7 capsid protein produced using the pQT-7 plasmid and the previously described pGD-7 plasmid.
Figure 4B:
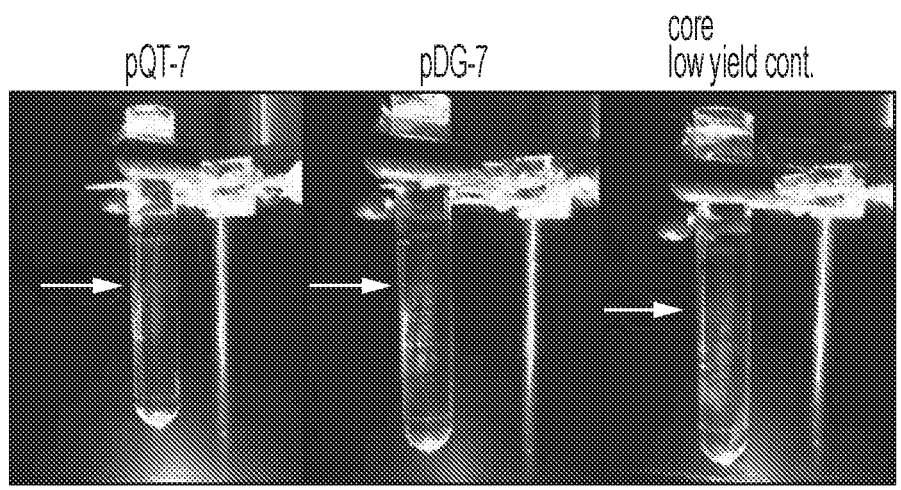

A comparison was made between pQT7 and another complementing plasmid (pDG7). Vector yield characterized by digital droplet (dd)PCR, transmission electron microscopy (EM), and silver-stained gel electrophoresis of the VP1, VP2, VP3 banding pattern. FIG. 3 shows representative data for silver stain gel analysis of estimated viral titers (VP/ml) of rAAVs packaged by an AAV7 capsid protein produced using the pQT-7 plasmid and the previously described pGD-7 plasmid. FIG. 4A shows viral titers (VP/ml) and genome copy numbers (GC/ml) measured by silver stain gel, (ddPCR), and microscopic analysis. FIG. 4B shows viral band detection in pQT-7, pDG-7 and core low yield samples. A comparison of vg titer is shown below in Table 1.

TABLE 1

| Complementing Plasmid | ddPCR vg titer | Silver stain VP titer | Final titer (concentration) |
|---|---|---|---|
| pQT7 | $1.22 \times 10^{12}$/ml | $1.0 \times 10^{12}$/ml | $2.22 \times 10^{12}$/ml |
| pDG7 | $3.16 \times 10^{12}$/ml | $3.0 \times 10^{12}$/ml | $5.54 \times 10^{12}$/ml |

Example 3: Packaging of AAV8-based and AAV9-based Vectors

This example describes a head-to-head comparison of a previously-described triple transfection method of rAAV production with rAAVs produced using dual-vector systems described in Example 1. Transfection conditions were as described as follows. Triple transfection was performed at a weight ratio of 1:1:1 (e.g., Cap: 1.0 mg, ΔF6: 1.0 mg, GFP: 1.0 mg). Dual-vector transfection was performed at a molecular ratio of 1:1 (e.g., a basepair (bp) ratio 1:4.2), using 4.2 mg of pQT plasmid (as described in Example 1) and 1 mg of a rAAV vector encoding a GFP transgene (e.g., a GFP transgene flanked by AAV2 ITRs).

In Table 2 (below), a comparison between the 3-plasmid technique (e.g., triple transfection) commonly for research grade vector production and dual-vector rAAV productions systems described by the disclosure (e.g., using a pQT plasmid described in Example 1) is shown.

GFP: 1.5 mg; 3.35 mg pUC19). Notes three different Cap plasmids were used for triple-transfection (e.g., AAV1 Cap, AAV3B Cap, and AAV5 Cap). Dual-vector transfection was performed at a molecular ratio of 1:1 (e.g., a basepair (bp) ratio 1:4.2), using 6.35 mg of pQT plasmid (as described in Example 1) and 1.5 mg of a rAAV vector encoding a GFP transgene (e.g., a GFP transgene flanked by AAV2 ITRs). Note, three different pQT plasmids were tested, each having a different capsid gene (e.g., AAV1 Cap, AAV3B Cap, and AAV5 Cap).

Figure 6:
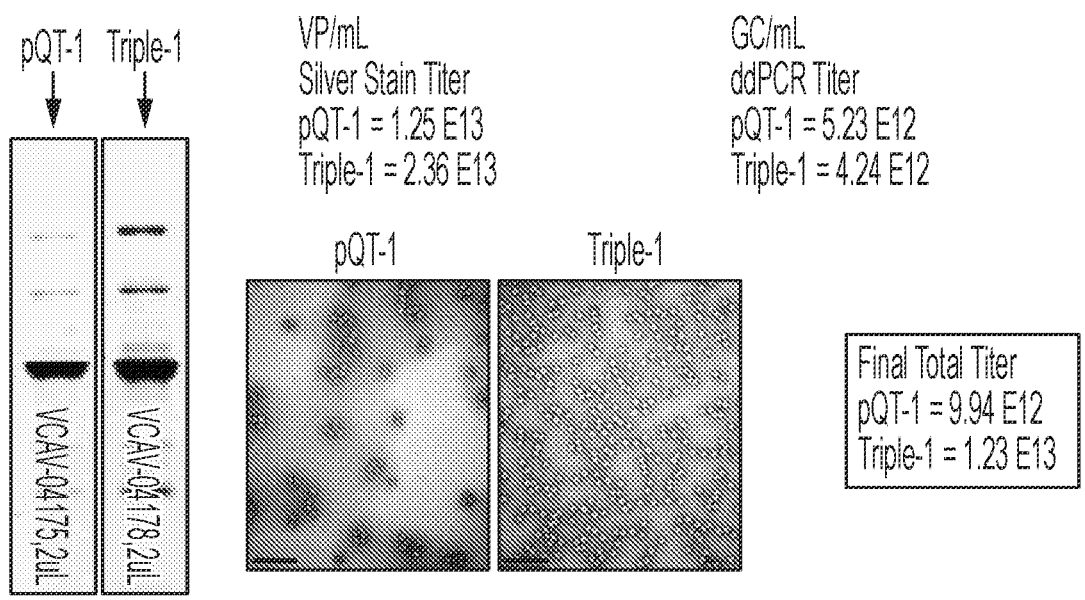
FIG. 6 shows viral titers (VP/ml) and genome copy numbers (GC/ml) of rAAVs packaged by an AAV1 capsid protein produced using the pQT-7 plasmid and the previously described pGD-7 plasmid measured by silver stain gel, droplet digital PCR (ddPCR), and microscopic analysis.

FIG. 6 shows viral titers (VP/ml) and genome copy numbers (GC/ml) of rAAVs packaged by an AAV1 capsid protein produced using the pQT-7 plasmid and the previously described pGD-7 plasmid measured by silver stain gel, droplet digital PCR (ddPCR), and microscopic analysis. The final total titer calculated for the triple-transfection method was $1.23 \times 10^{13}$ and the number of viral particles measured by silver stain was $2.36 \times 10^{13}$. The final total titer calculated for the dual-vector transfection was $9.94 \times 10^{12}$ and the number of viral particles measured by silver stain was $1.25 \times 10^{13}$.

Figure 7:
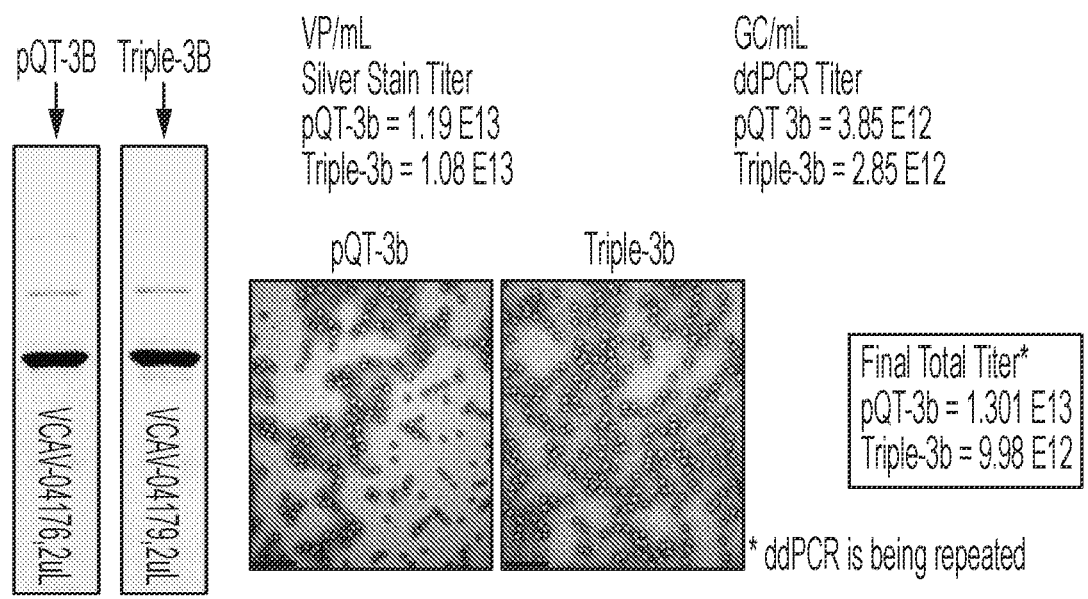
FIG. 7 shows viral titers (VP/ml) and genome copy numbers (GC/ml) of rAAVs packaged by an AAV3B capsid protein produced using the pQT-7 plasmid and the previously described pGD-7 plasmid measured by silver stain gel, droplet digital PCR (ddPCR), and microscopic analysis.

FIG. 7 shows viral titers (VP/ml) and genome copy numbers (GC/ml) of rAAVs packaged by an AAV3B capsid protein produced using the pQT-7 plasmid and the previously described pGD-7 plasmid measured by silver stain gel, droplet digital PCR (ddPCR), and microscopic analysis. The final total titer calculated for the triple-transfection method was $9.98 \times 10^{12}$ and the number of viral particles measured by

TABLE 2

| | AAV1 Triple | AAV1 pQT | AAV3b Triple | AAV3b pQt | AAV5 Triple | AAV5 pQT | AAV8 Triple | AAV8 pQT | AAV9 Triple | AAV9 pQT |
|---|---|---|---|---|---|---|---|---|---|---|
| VP/ml | 2.36E+13 | 1.25E+13 | 1.08E+13 | 1.19E+13 | 1.78E+13 | 2.33E+13 | 1E+13 | 8E+12 | 9E+12 | 5.5E+12 |
| GC/ml | 4.24E+12 | 5.23E+12 | 2.85E+12 | 3.85E+12 | 6.65E+12 | 7.59E+12 | 4.55E+12 | 3.02E+12 | 6.51E+12 | 2.49E+12 |
| Total Volume | 2.9 | 1.9 | 3.5 | 3.4 | 3 | 3.2 | 2 | 3 | 2 | 3 |
| Total Titer | 1.2296E+13 | 9.937E+12 | 9.975E+12 | 1.309E+13 | 1.995E+13 | 2.43E+13 | 1.46E+13 | 1.65E+13 | 1.55E+13 | 1.2E+13 |

Figure 9:
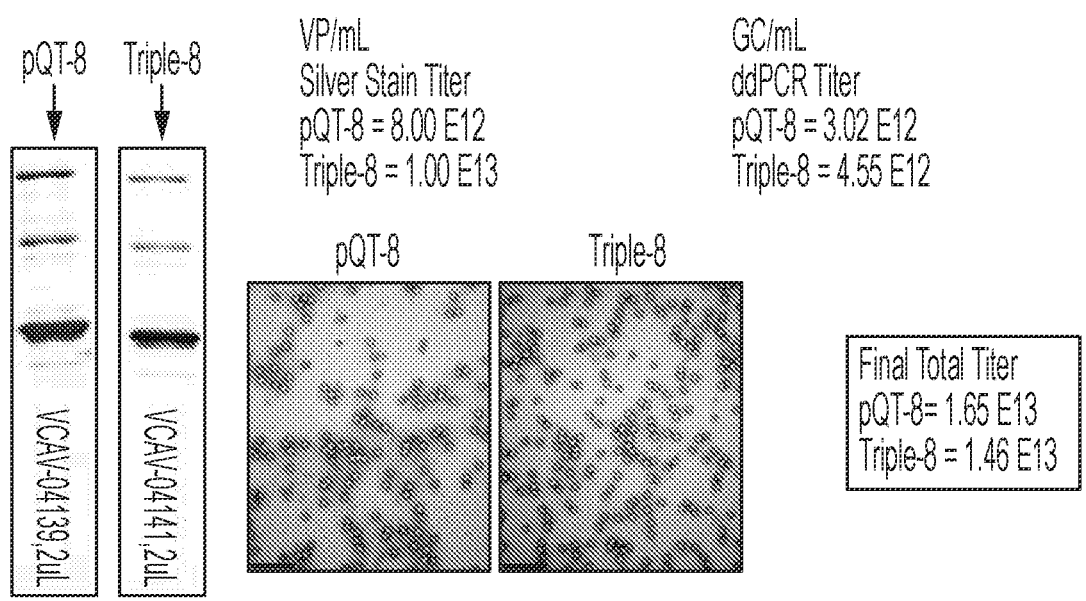
FIG. 9 shows viral titers (VP/ml) and genome copy numbers (GC/ml) of rAAVs packaged by an AAV8 capsid protein produced using the pQT-7 plasmid and the previously described pGD-7 plasmid measured by silver stain gel, droplet digital PCR (ddPCR), and microscopic analysis.

FIG. 9 shows viral titers (VP/ml) and genome copy numbers (GC/ml) of rAAVs packaged by an AAV8 capsid protein produced using the pQT-7 plasmid and the previously described pGD-7 plasmid measured by silver stain gel, droplet digital PCR (ddPCR), and microscopic analysis.

Figure 5:
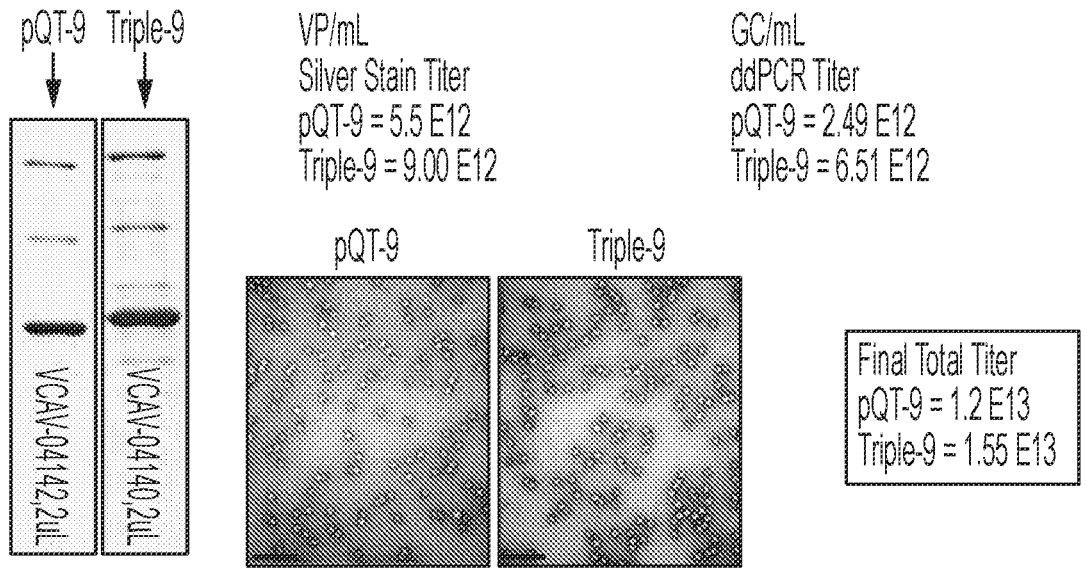
FIG. 5 shows viral titers (VP/ml) and genome copy numbers (GC/ml) of rAAVs packaged by an AAV9 capsid protein produced using the pQT-7 plasmid and the previously described pGD-7 plasmid measured by silver stain gel, droplet digital PCR (ddPCR), and microscopic analysis.

FIG. 5 shows viral titers (VP/ml) and genome copy numbers (GC/ml) of rAAVs packaged by an AAV9 capsid protein produced using the pQT-7 plasmid and the previously described pGD-7 plasmid measured by silver stain gel, droplet digital PCR (ddPCR), and microscopic analysis.

Figure 11:
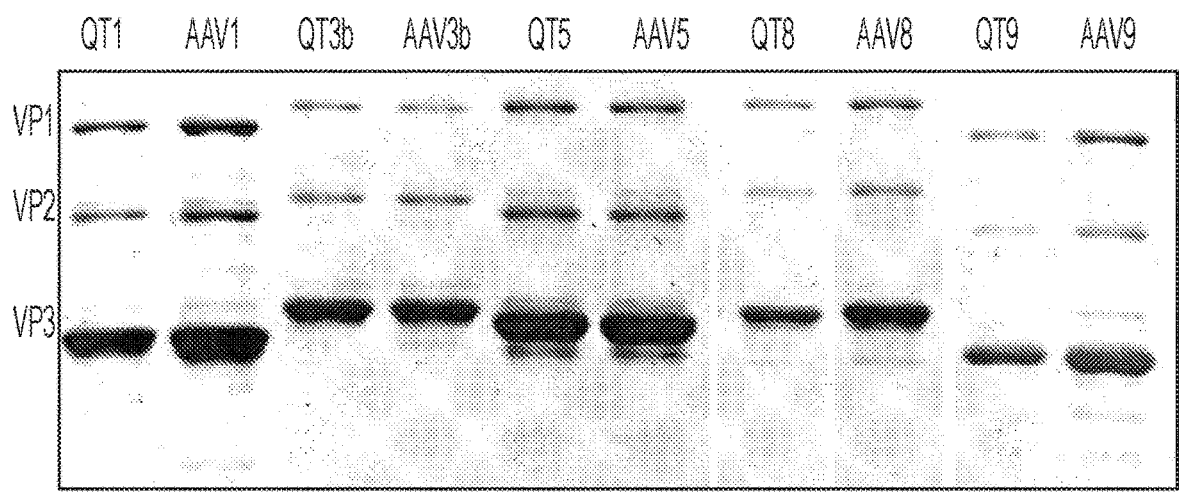
FIG. 11 shows a silver-stained protein gel of AAV VP1, VP2, and VP3 viral capsid proteins from multiple capsid variants. pQT viral capsid proteins are produced by one embodiment of the dual-transfection procedure as described by the disclosure. AAV plasmids are produced by the triple-plasmid transfection procedure as described herein. After purification of AAV particles, 5 µl of virus were run on a SDS-PAGE gel.

FIG. 11 shows a silver stain of VP1, VP1, and VP3 AAV capsid proteins from AAV1, AAV3b, AAV5, AAV8, and AAV9 serotypes produced by the triple-transfection protocol and the pQT-transfection protocol.

Figure 12:
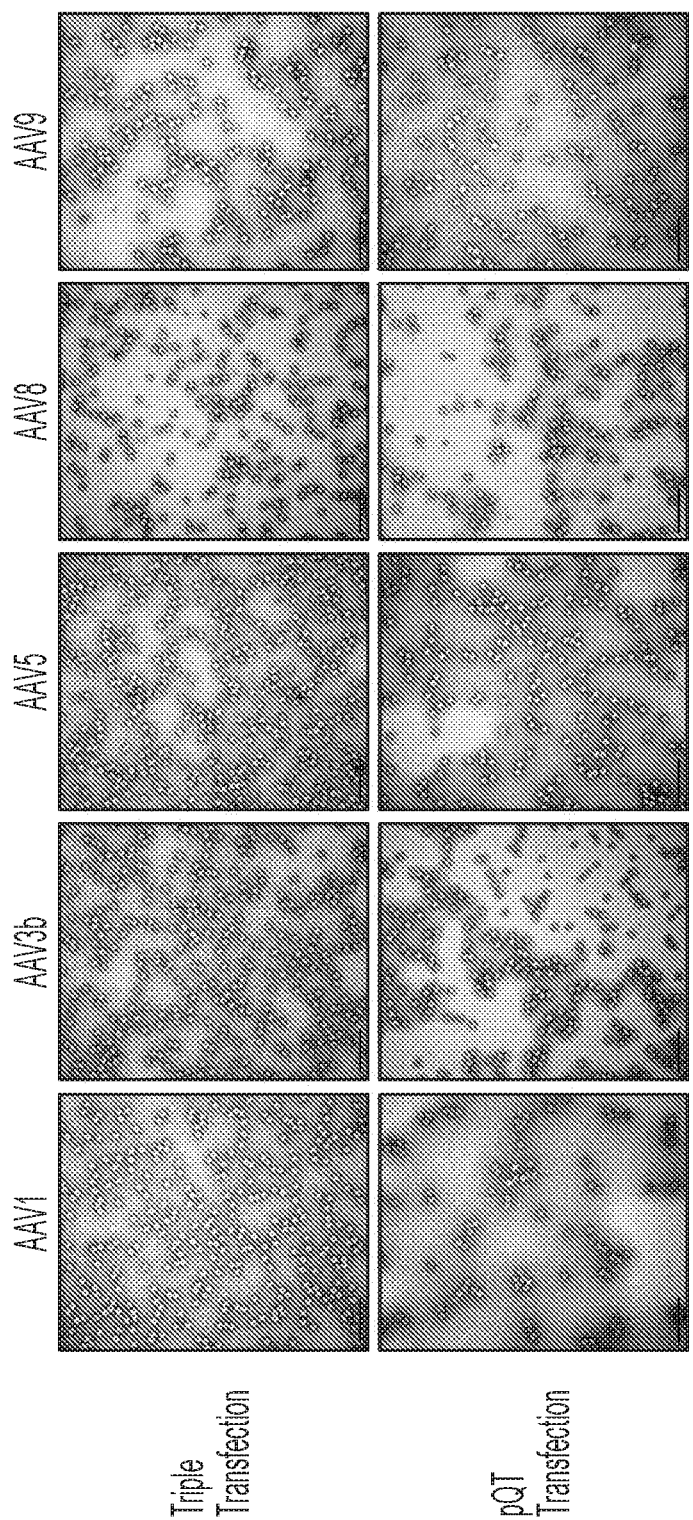
FIG. 12 shows an electron micrograph of multiple AAV variants. After purification of AAV particles by either the traditional triple transfection system or pQT transfection, the lysates were imaged by electron microscopy to assess the purity of viral preparations. Low numbers of empty capsids were observed in both triple transfection and pQT transfection systems. The scale bar represents 200 nm.

FIG. 12 shows electron micrographs of AAV1. AAV3b, AAV5, AAV8, and AAV9 capsid particles produced by the triple-transfection protocol and the pQT-transfection protocol.

Example 4: Packaging of AAV1, AAV3B and AAV5-based Vectors

This example describes a head-to-head comparison of a previously-described triple transfection method of rAAV production with rAAVs produced using dual-vector systems described in Example 1. Transfection conditions were as described as follows. Triple transfection was performed at a weight ratio of 1.5:1.5:1.5 (e.g., Cap: 1.5 mg, ΔF6: 1.5 mg, silver stain was $1.08 \times 10^{13}$. The final total titer calculated for the dual-vector transfection was $1.301 \times 10^{13}$ and the number of viral particles measured by silver stain was $1.19 \times 10^{13}$.

Figure 8:
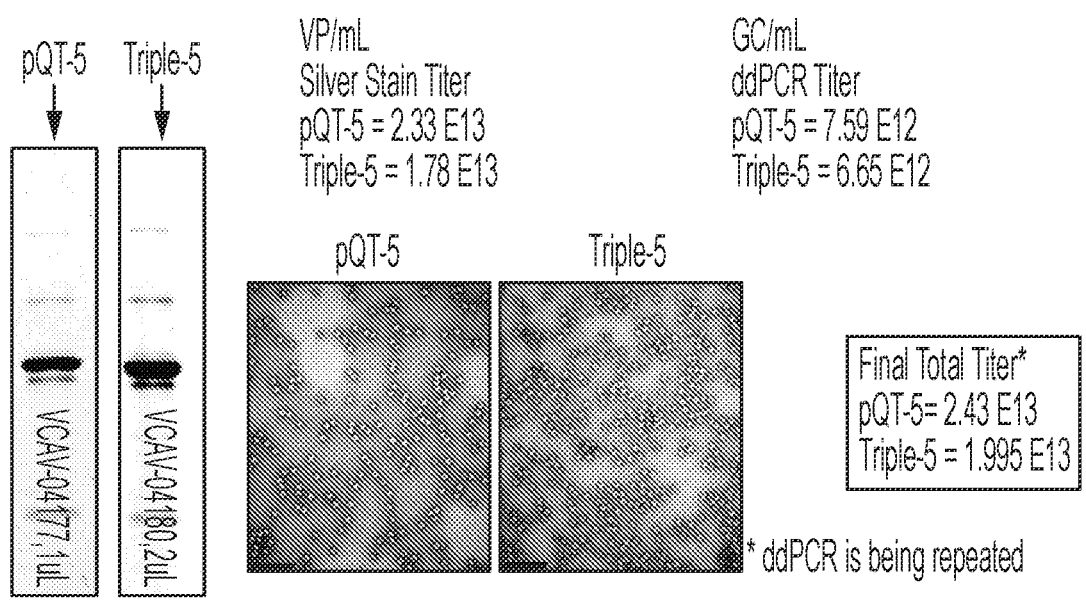
FIG. 8 shows viral titers (VP/ml) and genome copy numbers (GC/ml) of rAAVs packaged by an AAV5 capsid protein produced using the pQT-7 plasmid and the previously described pGD-7 plasmid measured by silver stain gel, droplet digital PCR (ddPCR), and microscopic analysis.

FIG. 8 shows viral titers (VP/ml) and genome copy numbers (GC/ml) of rAAVs packaged by an AAV5 capsid protein produced using the pQT-7 plasmid and the previously described pGD-7 plasmid measured by silver stain gel, droplet digital PCR (ddPCR), and microscopic analysis. The final total titer calculated for the triple-transfection method was $1.995 \times 10^{13}$ and the number of viral particles measured by silver stain was $1.78 \times 10^{13}$. The final total titer calculated for the dual-vector transfection was $2.43 \times 10^{13}$ and the number of viral particles measured by silver stain was $2.33 \times 10^{13}$.

Figure 10:
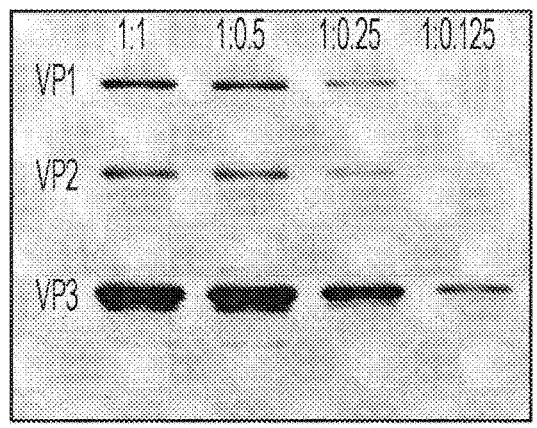
FIG. 10 shows viral titers (VP/ml) and genome copy numbers (GC/ml) of rAAVs packaged by an AAV8 capsid viral protein 1 (VP1), viral protein 2 (VP2), and viral protein 3 (VP3) proteins produced using the pQT-8 plasmid as measured by silver stain gel. The ratio of transgene plasmid:pQT packaging plasmid was 1:1, 1:0.5, 1:0.25, 1:0.125.

FIG. 11 shows viral titers (VP/ml) and genome copy numbers (GC/ml) of rAAVs packaged by an AAV8 capsid protein produced using the pQT-8 plasmid measured by silver stain gel (FIG. 10). Different ratios of transgene plasmid: packaging plasmid (1:1, 1:0.5, 1:0.25, 1:0.125) were used to package the pQT-8 virus. The final total titer calculated for the 1:1 plasmid ratio was $3.8 \times 10^{12}$ and the number of viral particles measured by silver stain was $5.0 \times 10^{11}$. The final total titer calculated for the 1:0.5 plasmid ratio was $4.5 \times 10^{12}$ and the number of viral particles measured by silver stain was $1.0 \times 10^{12}$. The final total titer calculated for the 1:0.25 plasmid ratio was $1.7 \times 10^{12}$ and the number of viral particles measured by silver stain was $1.0 \times 10^{12}$. The final total titer calculated for the 1:0.125 plasmid ratio was $2.0 \times 10^{11}$ and the number of viral particles measured by silver stain was $1.0 \times 10^{11}$.

Comparative data are summarized in Table 2 above.

Example 5: In Vivo Studies

This example describes an in vivo side by side comparison of triple and double transfection-produced (pQT) vectors were performed by intravenous injection via the tail vein for AAV3b, AAV5, AAV8 and AAV9, and intramuscular injection for AAV1 into C57/B16 mice.

Figure 14A:
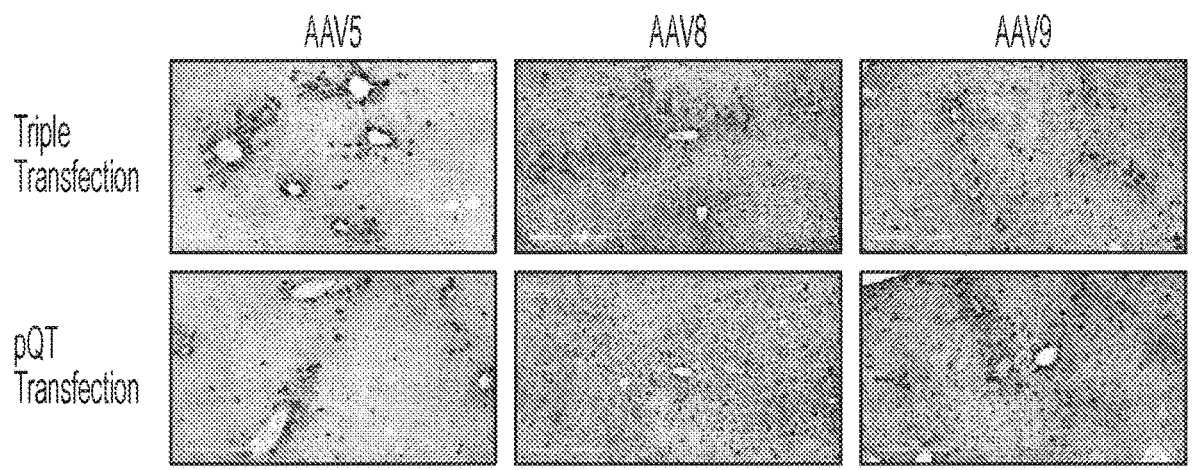
FIGS. 14A-14B show immunohistochemical detection of GFP expression in liver and muscle after in vivo AAV administration of multiple capsid variants. AAV particles were produced by either the traditional triple-plasmid transfection system or pQT transfection. GFP expression was visualized by 3,3'-diaminobenzidine (DAB) staining.
Figure 14B:
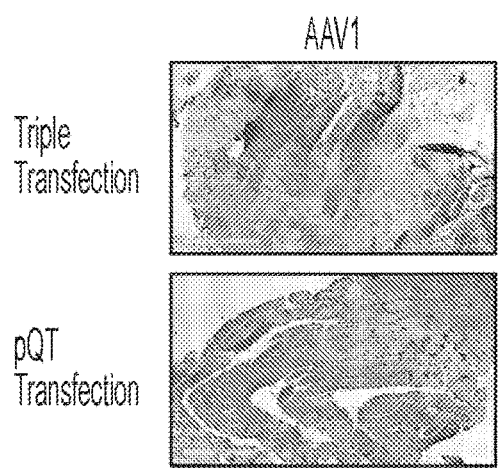

The efficiency of expression and transduction of the triple-transfection produced AAV capsids and pQT-produced AAV capsids. FIGS. 13A-13E show the vector genomes in muscle and liver four weeks after intramuscular or intravenous injection. FIGS. 14A-14B show the immunohistochemistry of GFP staining. Most of the pQT-produced AAV capsids are transduced (FIGS. 13A-13E) and expressed as efficiently in liver and muscle tissue (FIGS. 14A-14B) compared to triple-transfection-produced AAV capsids.

Figure 15A:
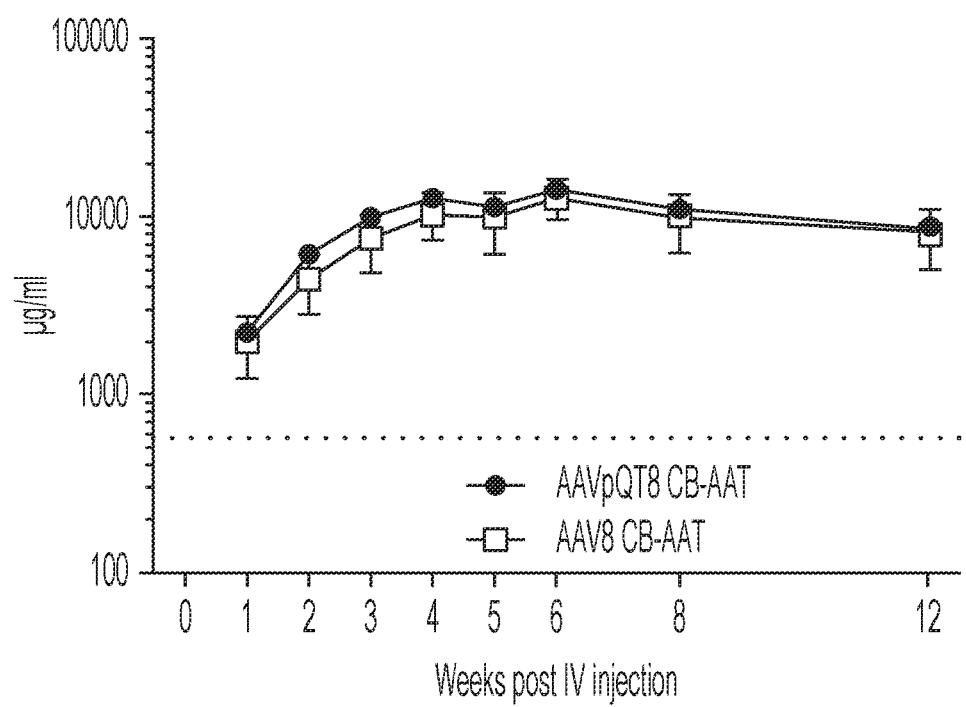
FIGS. 15A-15B show total serum Alpha-1-Antitrypsin (AAT) as measured by ELISA after delivery of pQT8 or AAV8 expressing AAT in $Rag^{-/-}$ mice. AAV particles were produced by either the traditional triple-plasmid transfection system (squares) or pQT transfection (circles).
Figure 15B:
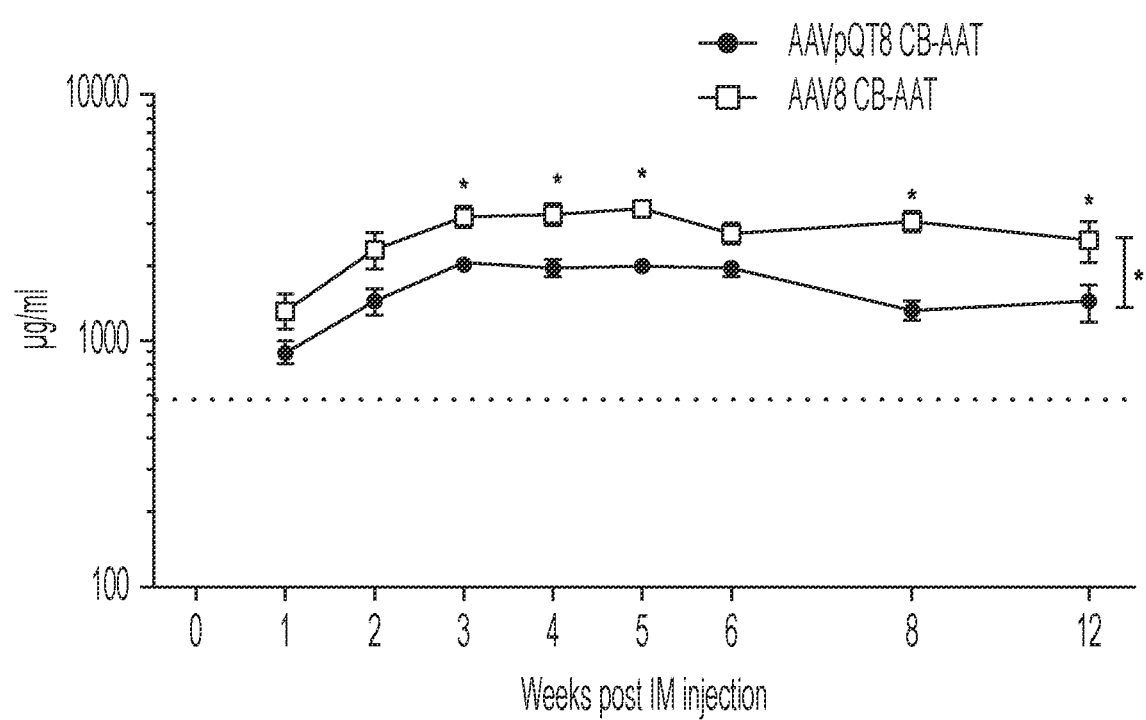

A dual-vector transfection packaging system was created from two different packaging plasmids having a different transgene insert, human Alpha-1-antitrypsin (AAT) gene. Rag−/− mice, which lack B-cells and T-cells, were examined for the bioactivity of vectors by assaying AAT expression in the serum of mice injected intravenously in the tail vein with $5 \times 10^{11}$ vg AAV8 vectors packaged by triple-transfection (AAV8-AAT) or pQT-transfection (pQT8-AAV8-AAT) (FIG. 15A). AAT expression levels are similar in Rag−/− mice injection with both AAV8-AAT vectors and pQT8-AAV8-AAT vectors. Rag−/− mice were also injected intramuscularly with $1 \times 10^{11}$ vg with AAV8-AAT or pQT-AAV8-AAT vectors. AAT expression levels were statistically lower in Rag−/− mice injected with pQT8-AAV8 vectors compared with AAV8-AAT vectors (FIG. 15B).

Figure 16A:
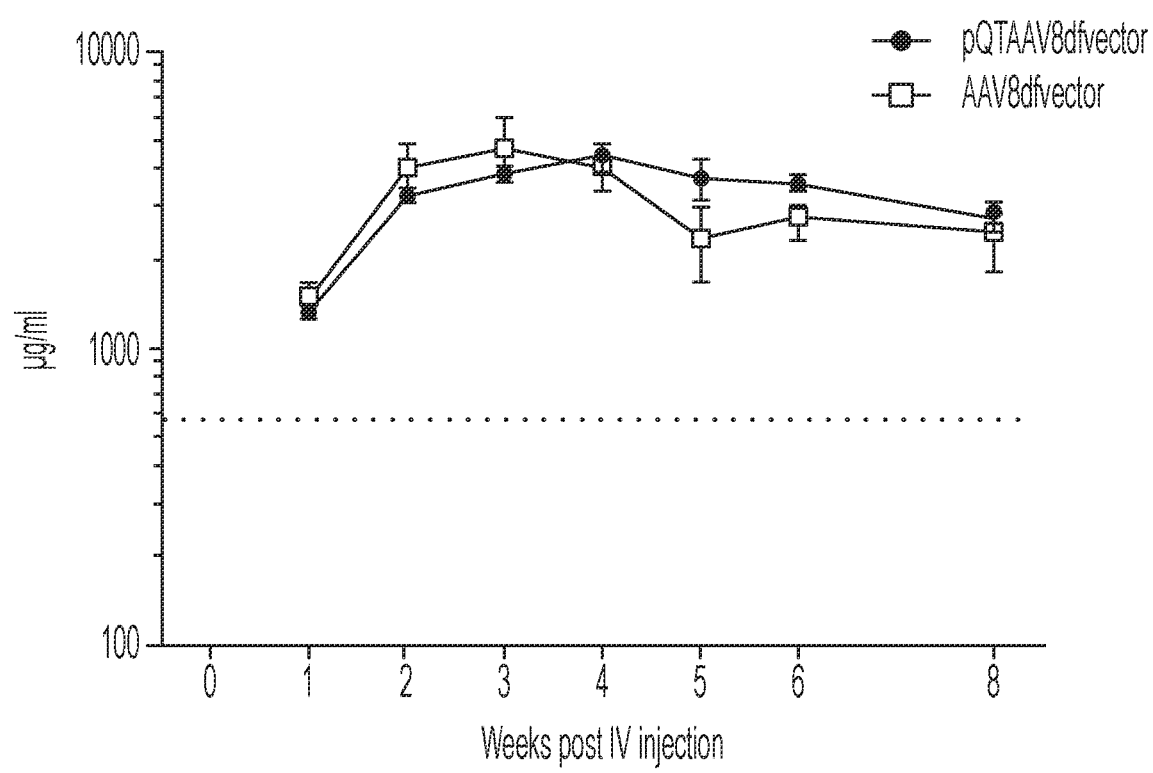
FIGS. 16A-16B show AAT expression and knock-down of a mutant Alpha-1 Antitrypsin Z (PiZ) protein after intravenous injection of a pQT8 or AAV8 dual function vector. AAV particles were produced by either the traditional triple-plasmid transfection system or pQT transfection. A dual-function vector containing an AAT gene operably linked to a c-myc tag and a microRNA targeting a mutant PiZ gene allele. Transgenic mice expressing the mutant PiZ gene allele were injected with $5 \times 10^{11}$ vg via the tail vein with the dual function vector packed by either the pQT transfection method (circles) or triple-transfection (squares).
Figure 16B:
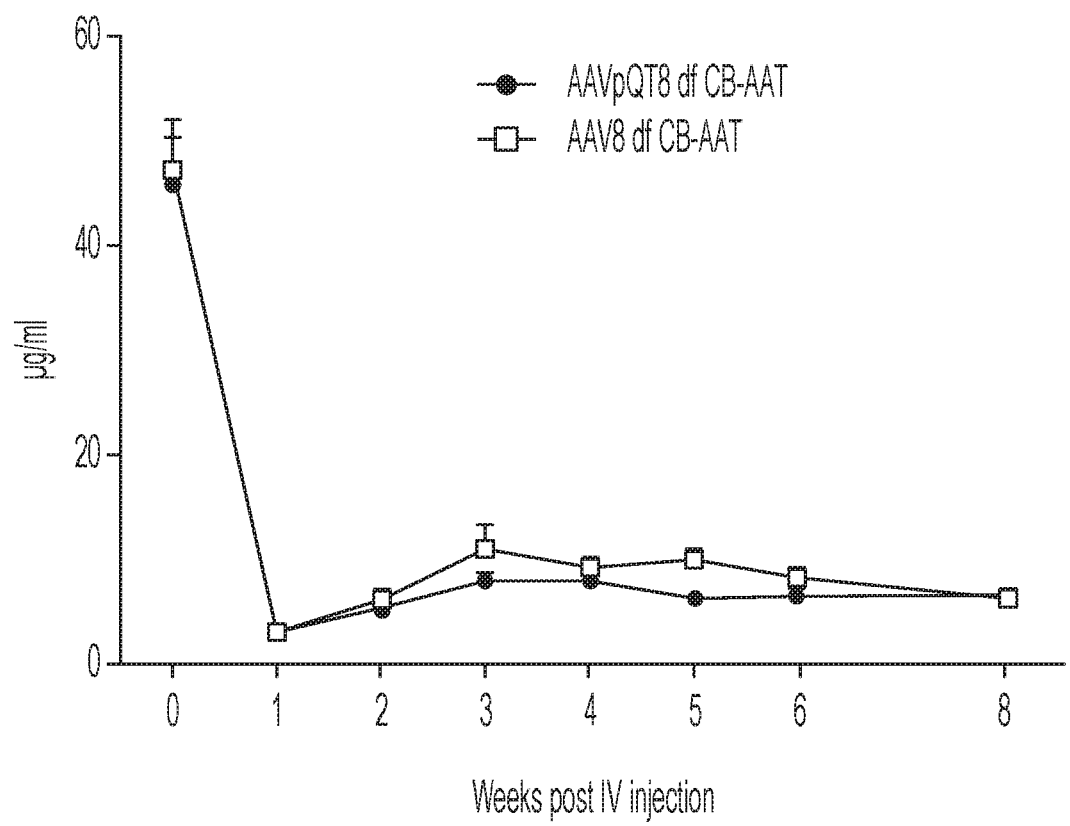

Dual function vectors were created to simultaneously express a human AAT transgene operably linked to a c-myc tag and a microRNA targeting a mutant Alpha-1 Antitrypsin Z protein (PiZ) allele. Transgenic mice expressing the mutant PiZ allele (PiZ*) were injected with $5 \times 10^{11}$ vg AAV8 vectors packaged triple-transfection (AAV8-dfAAT) or pQT-transfection (pQT8-AAV8-dfAAT). Human AAT expression levels are similar in PiZ* mice injected with both AAV8-dfAAT and pQT-AAV8-dfAAT vectors (FIG. 16A). The expression of the mutant PiZ allele is decreased to similar levels in PiZ* mice injected with both AAV8-dfAAT and pQT-AAV8-dfAAT vectors (FIG. 16B).

In summary, this data describes compositions useful for production of mid-range ($10^{12}$-$10^{16}$) campaign-ready packaging of AAV vectors such as AAV1, AAV3b, AAV5, AAV8 and AAV9. These AAV vectors efficiently drive transgene expression and decrease target endogenous gene expression in vivo.

What is claimed is:

1. A recombinant adeno-associated virus (rAAV) production system comprising:
   (i) a first vector comprising the nucleic acid sequence set forth in any one of SEQ ID NOs: 1-9; and,
   (ii) a second vector comprising one or more nucleic acids encoding an expression cassette comprising a transgene flanked by adeno-associated virus inverted terminal repeat (ITR) sequences.

2. The rAAV production system of claim 1, wherein the adeno-associated virus inverted terminal repeat (ITR) sequences are AAV2 ITRs.

3. The rAAV production system of claim 1, wherein the transgene is a protein or an inhibitory nucleic acid, optionally wherein the inhibitory nucleic acid is dsRNA, siRNA, miRNA, or amiRNA.

4. The rAAV production system of claim 1, wherein the expression cassette further comprises a promoter operably linked to the transgene, optionally wherein the promoter is a H1, U6, CB, CBA, CB6, Desmin, CMV, AAT, or MHK promoter.

5. The rAAV production system of claim 1, further comprising a host cell.

6. An isolated nucleic acid comprising the sequence set forth in any one of SEQ ID NOs: 1-9.

7. A method for producing a recombinant adeno-associated virus (rAAV), the method comprising introducing the rAAV production system of claim 1 into a host cell that expresses an Ad-E1a helper function.

8. The method of claim 7, wherein the first vector and second vector of the rAAV production system are introduced into the host cell in (i) a single transfection reaction or (ii) separate transfection reactions.

9. The method of claim 7, further comprising the step of culturing the cells after introduction of the rAAV production system.

10. A method for producing a recombinant adeno-associated virus (rAAV), the method comprising:
    (i) introducing the isolated nucleic acid of claim 6 into a host cell that expresses an Ad-E1a helper function; and
    (ii) introducing a vector comprising one or more nucleic acids encoding an expression cassette comprising a transgene flanked by adeno-associated virus inverted terminal repeat (ITR) sequences.

11. The method of claim 10, wherein the host cell is a mammalian cell.

12. The method of claim 10, wherein the isolated nucleic acid and the vector are introduced into the host cell in (i) a single transfection reaction or (ii) separate transfection reactions.

13. The method of claim 10, further comprising the step of culturing the cells after the introduction of the nucleic acid and the vector.

14. An apparatus for production of recombinant adeno-associated virus (rAAV) particles, the apparatus comprising:

(i) a container housing the rAAV production system of claim 1; and,
(ii) a population of host cells,
wherein the rAAV production system and the host cells are suspended in a cell culture medium.

15. The rAAV production system of claim 5, wherein the host cell is a mammalian cell.

16. The method of claim 9, wherein the culturing occurs in the presence of an antibiotic cognate to the antibiotic-resistance gene of the first vector.

17. The method of claim 10, wherein the mammalian cell is a HEK293 cell, HEK293T cell, or a CHO cell.

18. The method of claim 13, wherein the culturing occurs in the presence of an antibiotic cognate to the antibiotic-resistance gene of the first vector.

* * * * *

SEQUENCE LISTING

```
<160> NUMBER OF SEQ ID NOS: 9

<210> SEQ ID NO 1
<211> LENGTH: 21728
<212> TYPE: DNA
<213> ORGANISM: Artificial Sequence
<220> FEATURE:
<223> OTHER INFORMATION: SYNTHETIC POLYNUCLEOTIDE

<400> SEQUENCE: 1
gaattggatc cgaattctta attaacatca tcaataatat accttatttt ggattgaagc      60
caatatgata atgaggggt ggagtttgtg acgtggcgcg gggcgtggga acggggcggg     120
tgacgtagta gtgtggcgga agtgtgatgt tgcaagtgtg gcggaacaca tgtaagcgac     180 ggatgtgca aaagtgacgt ttttggtgtg cgccggtgta cacaggaagt gacaattttc     240
gcgcggtttt aggcggatgt tgtagtaaat ttgggcgtaa ccgagtaaga tttggccatt     300
ttcgcgggaa aactgaataa gaggaagtga aatctgaata attttgtgtt actcatagcg     360
cgtaatattt gtctagggcc gcggggactt tgaccgttta cgtggagact cgcccaggtg     420
tttttctcag gtgtttccg cgttccgggt caaagttggc gttttattat tatagtcagg     480
gggatcctct agaactagtg gatccgtccc tcaggcctag aagtaaaaaa gggaaaaaag     540
agtgtgtttg tcaaaatagg agacaggtgg tggcaaccaa ggacttatag gggaccttac     600
atctacagac caacagatgc ccccttacca tatacaggaa gatatgactt aaattgggat     660
aggtgggtca caatcaacgg ctataaagtg ttatacagat ccctcccctc ccctttcgtg     720
aaagactcgc cagagctaga cctccttggt gtatgctaac tgagaagaga aagacgacat     780
gaaacaacag gtacatgatt atatttatct aggaacagga atgcactttt ggggaaaggt     840
tttccatacc aaggaagggg cagtggctgg actgataaga cattattctg caaaaactta     900
tggtatgagt tattatgatt agcctttatt tgcccaacct tgcggttccc agggtttaaa     960
```

```
taagtttatg gttacaaact gttcttaaaa cgaggatgtg agacaagtgg tttcctgact    1020
tggtttggta atcaaatgtt ctgatctgag ctcttagtgt tctattttcc tatgttcttt    1080
tggaatctat ccaagtctta tgtaaatgct tatgtaaacc ataatataaa agagtgctga    1140
ttttttgagt aaacttgcaa cagtcctaac attcttctct cgtgtgtttg tgtctgttcg    1200
ccatcccgtc tccgctcgtc acttatcctt cacttttcag agggtccccc cgcagatccc    1260
ggtcaccctc aggtcgggac ctgcagaaga cgcccgagtg agcacgcagg gtctccattt    1320
tgaagcggga ggtttgaacg cgcagccgcc atgccggggt tttacgagat tgtgattaag    1380
gtccccagcg accttgacgg gcatctgccc ggcatttctg acagctttgt gaactgggtg    1440
gccgagaagg aatgggagtt gccgccagat tctgacatgg atctgaatct gattgagcag    1500
gcacccctga ccgtggccga aagctgcag cgcgactttc tgacggaatg cgccgtgtg     1560 agtaaggccc cggaggccct tttctttgtg caatttgaga agggagagag ctacttccac    1620
atgcacgtgc tcgtggaaac caccggggtg aaatccatgg ttttgggacg tttcctgagt    1680
cagattcgcg aaaaactgat tcagagaatt taccgcggga tcgagccgac tttgccaaac    1740
tggttcgcgg tcacaaagac cagaaatggc gccggaggcg ggaacaaggt ggtggatgag    1800
tgctacatcc ccaattactt gctccccaaa acccagcctg agctccagtg ggcgtggact    1860
aatatggaac agtatttaag cgcctgtttg aatctcacgg agcgtaaacg gttggtggcg    1920
cagcatctga cgcacgtgtc gcagacgcag gagcagaaca aagagaatca gaatcccaat    1980
tctgatgcgc cggtgatcag atcaaaaact tcagccaggt acatggagct ggtcgggtgg    2040
ctcgtggaca aggggattac ctcggagaag cagtggatcc aggaggacca ggcctcatac    2100
atctccttca atgcggcctc caactcgcgg tcccaaatca aggctgcctt ggacaatgcg    2160
ggaaagatta tgagcctgac taaaaccgcc cccgactacc tggtgggcca gcagcccgtg    2220
gaggacattt ccagcaatcg gatttataaa attttggaac taaacgggta cgatccccaa    2280
tatgcggctt ccgtctttct gggatgggcc acgaaaaagt tcggcaagag gaacaccatc    2340
tggctgtttg ggcctgcaac taccgggaag accaacatcg cggaggccat agcccacact    2400
gtgcccttct acgggtgcgt aaactggacc aatgagaact ttcccttcaa cgactgtgtc    2460
gacaagatgg tgatctggtg ggaggagggg aagatgaccg ccaaggtcgt ggagtcggcc    2520
aaagccattc tcggaggaag caaggtgcgc gtggaccaga atgcaagtc ctcggcccag     2580 atagacccga ctcccgtgat cgtcacctcc aacaccaaca tgtgcgccgt gattgacggg    2640
aactcaacga ccttcgaaca ccagcagccg ttgcaagacc ggatgttcaa atttgaactc    2700
acccgccgtc tggatcatga ctttgggaag gtcaccaagc aggaagtcaa agacttttc     2760 cggtgggcaa aggatcacgt ggttgaggtg agcatgaat tctacgtcaa aaagggtgga     2820
gccaagaaaa gacccgcccc cagtgacgca gatataagtg agcccaaacg ggtgcgcgag    2880
tcagttgcgc agccatcgac gtcagacgcg aagcttcga tcaactacgc agacaggtac     2940
caaaacaaat gttctcgtca cgtgggcatg aatctgatgc tgtttccctg cagacaatgc    3000
gagagaatga atcagaattc aaatatctgc ttcactcacg gacagaaaga ctgtttagag    3060
tgctttcccg tgtcagaatc tcaacccgtt tctgtcgtca aaaaggcgta tcagaaactg    3120
tgctacattc atcatatcat gggaaaggtg ccagacgctt gcactgcctg cgatctggtc    3180
aatgtggatt tggatgactg catctttgaa caataaatga tttaaatcag gtatggctgc    3240
cgatggttat cttccagatt ggctcgagga caacctctct gagggcattc gcgagtggtg    3300
```

```
ggacttgaaa cctggagccc cgaagcccaa agccaaccag caaaagcagg acgacggccg    3360
gggtctggtg cttcctggct acaagtacct cggacccttc aacggactcg acaaggggga    3420
gcccgtcaac gcggcggacg cagcggccct cgagcacgac aaggcctacg accagcagct    3480
caaagcgggt gacaatccgt acctgcggta taaccacgcc gacgccgagt ttcaggagcg    3540
tctgcaagaa gatacgtctt ttgggggcaa cctcgggcga gcagtcttcc aggccaagaa    3600
gcgggttctc gaacctctcg gtctggttga ggaaggcgct aagacggctc ctggaaagaa    3660
acgtccggta gagcagtcgc cacaagagcc agactcctcc tcgggcatcg gcaagacagg    3720
ccagcagccc gctaaaaaga gactcaattt tggtcagact ggcgactcag agtcagtccc    3780
cgatccacaa cctctcggag aacctccagc aaccccgct gctgtgggac ctactacaat    3840
ggcttcaggc ggtggcgcac caatggcaga caataacgaa ggcgccgacg gagtgggtaa    3900
tgcctcagga aattggcatt gcgattccac atggctgggc gacagagtca tcaccaccag    3960
cacccgcacc tgggccttgc ccacctacaa taaccacctc tacaagcaaa tctccagtgc    4020
ttcaacgggg gccagcaacg acaaccacta cttcggctac agcaccccct gggggtattt    4080
tgatttcaac agattccact gccactttc accacgtgac tggcagcgac tcatcaacaa    4140
caattgggga ttccggccca agagactcaa cttcaaactc ttcaacatcc aagtcaagga    4200
ggtcacgacg aatgatggcg tcacaaccat cgctaataac cttaccagca cggttcaagt    4260
cttctcggac tcggagtacc agcttccgta cgtcctcggc tctgcgcacc agggctgcct    4320
ccctccgttc ccggcggacg tgttcatgat tccgcaatac ggctacctga cgctcaacaa    4380
tggcagccaa gccgtgggac gttcatcctt ttactgcctg gaatatttcc cttctcagat    4440
gctgagaacg ggcaacaact ttaccttcag ctacacctt gaggaagtgc ctttccacag    4500
cagctacgcg cacagccaga gcctggaccg gctgatgaat cctctcatcg accaatacct    4560
gtattacctg aacagaactc aaaatcagtc cggaagtgcc caaacaagg acttgctgtt    4620 tagccgtggg tctccagctg gcatgtctgt tcagcccaaa aactggctac ctggaccctg    4680
ttatcggcag cagcgcgttt ctaaaacaaa aacagacaac aacaacagca tttttacctg    4740
gactggtgct tcaaaatata acctcaatgg gcgtgaatcc atcatcaacc ctggcactgc    4800
tatggcctca cacaaagacg acgaagacaa gttcttccc atgagcggtg tcatgatttt    4860
tggaaaagag agcgccggag cttcaaacac tgcattggac aatgtcatga ttacagacga    4920
agaggaaatt aaagccacta accctgtggc caccgaaaga tttgggaccg tggcagtcaa    4980
tttccagagc agcagcacag accctgcgac cggagatgtg catgctatgg agcattacc    5040 tggcatggtg tggcaagata gagacgtgta cctgcagggt cccatttggg ccaaaattcc    5100
tcacacagat ggcacttttc acccgtctcc tcttatgggc ggctttgac tcaagaaccc    5160 gcctcctcag atcctcatca aaaacacgcc tgttcctgcg aatcctccgg cggagttttc    5220
agctacaaag tttgcttcat tcatcaccca atactccaca ggacaagtga gtgtggaaat    5280
tgaatgggag ctgcagaaag aaaacagcaa gcgctggaat cccgaagtgc agtacacatc    5340
caattatgca aaatctgcca acgttgattt tactgtggac aacaatggac tttatactga    5400
gcctcgcccc attggcaccc gttaccttac ccgtccctg taattacgtg ttaatcaata    5460
aatcgatgca tgtccttggg tccggcctgc tgaatgcgca ggcggtcggc catgccccag    5520
gcttcgtttt gacatcggcg caggtctttg tagtagtctt gcatgagcct ttctaccggc    5580
acttcttctt ctccttcctc ttgtcctgca tctcttgcat ctatcgctgc ggcggcggcg    5640
gagtttggcc gtaggtggcg ccctcttcct cccatcgtgt gaccccgaag cccctcatcg    5700
```

```
gctgaagcag ggctaggtcg gcgacaacgc gctcggctaa tatggcctgc tgcacctgcg    5760
tgagggtaga ctggaagtca tccatgtcca caaagcggtg gtatgcgccc gtgttgatgg    5820
tgtaagtgca gttggccata acggaccagt taacggtctg gtgacccggc tgcgagagct    5880
cggtgtacct gagacgcgag taagccctcg agtcaaatac gtagtcgtta caagtccgca    5940
ccaggtactg gtatcccacc aaaaagtgcg gcggcggctg gcggtagagg ggccagcgta    6000
gggtggccgg ggctccgggg gcgagatctt ccaacataag gcgatgatat ccgtagatgt    6060
acctggacat ccaggtgatg ccggcggcgg tggtggaggc gcgcggaaag tcgcggacgc    6120
ggttccagat gttgcgcagc ggcaaaaagt gctccatggt cgggacgctc tggccggtca    6180
ggcgcgcgca atcgttgacg ctctagaccg tgcaaaagga gagcctgtaa gcgggcactc    6240
ttccgtggtc tggtggataa attcgcaagg gtatcatggc ggacgaccgg ggttcgagcc    6300
ccgtatccgg ccgtccgccg tgatccatgc ggttaccgcc cgcgtgtcga acccaggtgt    6360
gcgacgtcag acaacggggg agtgctcctt ttggcttcct tccaggcgcg gcggctgctg    6420
cgctagcttt tttggccact ggccgcgcgc agcgtaagcg gttaggctgg aaagcgaaag    6480
cattaagtgg ctcgctccct gtagccgagg ggttattttc caagggttga gtcgcgggac    6540
ccccggttcg agtctcggac cggccggact gcggcgaacg ggggtttgtc tccccgtcat    6600
gcaagacccc gcttgcaaat tcctccggaa acagggacga gccccttttt tgcttttccc    6660
agatgcatcc ggtgctgcgg cagatgcgcc ccctcctca gcagcggcaa gagcaagagc    6720
agcggcagac atgcagggca ccctcccctc ctcctaccgc gtcaggaggg gcgacatccg    6780
cggttgacgc ggcagcagat ggtgattacg aaccccgcg gcgccgggcc cggcactacc    6840
tggacttgga ggagggcgag ggcctggcgc ggctaggagc gccctctcct gagcggcacc    6900
caagggtgca gctgaagcgt gatacgcgtg aggcgtacgt gccgcggcag aacctgtttc    6960
gcgaccgcga gggagaggag cccgaggaga tgcgggatcg aaagttccac gcagggcgcg    7020
agctgcggca tggcctgaat cgcgagcggt tgctgcgcga ggaggacttt gagcccgacg    7080
cgcgaaccgg gattagtccc gcgcgcgcac acgtggcggc cgccgacctg gtaaccgcat    7140
acgagcagac ggtgaaccag ggcgatcgca cccttttggcg catcccattc tccagtaact    7200
ttatgtccat gggcgcactc acagacctgg gccaaaacct tctctacgcc aactccgccc    7260
acgcgctaga catgactttt gaggtggatc ccatggacga gccaccctt ctttatgttt    7320 tgtttgaagt ctttgacgtg gtccgtgtgc accggccgca ccgcggcgtc atcgaaaccg    7380
tgtacctgcg cacgcccttc tcggccggca acgccacaac ataaagaagc aagcaacatc    7440
aacaacagct gccgccatgg gctccagtga gcaggaactg aaagccattg tcaaagatct    7500
tggttgtggg ccatattttt tgggcaccta tgacaagcgc tttccaggct ttgtttctcc    7560
acacaagctc gcctgcgcca tagtcaatac ggccggtcgc gagactgggg gcgtacactg    7620
gatggccttt gcctggaacc cgcactcaaa aacatgctac ctctttgagc cctttggctt    7680
ttctgaccag cgactcaagc aggtttacca gtttgagtac gagtcactcc tgcgccgtag    7740
cgccattgct tcttcccccg accgctgtat aacgctggaa aagtccaccc aaagcgtaca    7800
ggggcccaac tcggccgcct gtggactatt ctgctgcatg tttctccacg cctttgccaa    7860
ctggccccaa actcccatgg atcacaaccc caccatgaac cttattaccg gggtacccaa    7920
ctccatgctc aacagtcccc aggtacagcc caccctgcgt cgcaaccagg aacagctcta    7980
cagcttcctg gagcgccact cgccctactt ccgcagccac agtgcgcaga ttaggagcgc    8040
```

-continued

```
cacttctttt tgtcacttga aaaacatgta aaaataatgt actagagaca ctttcaataa    8100
aggcaaatgc ttttatttgt acactctcgg gtgattattt accccaccc ttgccgtctg    8160
cgccgtttaa aaatcaaagg ggttctgccg cgcatcgcta tgcgccactg gcagggacac    8220
gttgcgatac tggtgtttag tgctccactt aaactcaggc acaaccatcc gcggcagctc    8280
ggtgaagttt tcactccaca ggctgcgcac catcaccaac gcgtttagca ggtcgggcgc    8340
cgatatcttg aagtcgcagt tggggcctcc gccctgcgcg cgcgagttgc gatacacagg    8400
gttgcagcac tggaacacta tcagcgccgg gtggtgcacg ctggccagca cgctcttgtc    8460
ggagatcaga tccgcgtcca ggtcctccgc gttgctcagg gcgaacggag tcaactttgg    8520
tagctgcctt cccaaaaagg gcgcgtgccc aggctttgag ttgcactcgc accgtagtgg    8580
catcaaaagg tgaccgtgcc cggtctgggc gttaggatac agcgcctgca taaaagcctt    8640
gatctgctta aaagccacct gagcctttgc gccttcagag aagaacatgc cgcaagactt    8700
gccgaaaaac tgattggccg gacaggccgc gtcgtgcacg cagcaccttg cgtcggtgtt    8760
ggagatctgc accacatttc ggccccaccg gttcttcacg atcttggcct tgctagactg    8820
ctccttcagc gcgcgctgcc cgttttcgct cgtcacatcc atttcaatca cgtgctcctt    8880
atttatcata atgcttccgt gtagacactt aagctcgcct tcgatctcag cgcagcggtg    8940
cagccacaac gcgcagcccg tgggctcgtg atgcttgtag gtcacctctg caaacgactg    9000
caggtacgcc tgcaggaatc gccccatcat cgtcacaaag gtcttgttgc tggtgaaggt    9060
cagctgcaac ccgcggtgct cctcgttcag ccaggtcttg catacggccg ccagagcttc    9120
cacttggtca ggcagtagtt tgaagttcgc ctttagatcg ttatccacgt ggtacttgtc    9180
catcagcgcg cgcgcagcct ccatgcccctt ctcccacgca gacacgatcg gcacactcag    9240
cgggttcatc accgtaattt cactttccgc ttcgctgggc tcttcctctt cctcttgcgt    9300
ccgcatacca cgcgccactg ggtcgtcttc attcagccgc cgcactgtgc gcttacctcc    9360
tttgccatgc ttgattagca ccggtgggtt gctgaaaccc accatttgta gcgccacatc    9420
ttctctttct tcctcgctgt ccacgattac ctctggtgat ggcgggcgct cgggcttggg    9480
agaagggcgc ttcttttttct tcttgggcgc aatggccaaa tccgccgccg aggtcgatgg    9540
ccgcgggctg ggtgtgcgcg gcaccagcgc gtcttgtgat gagtcttcct cgtcctcgga    9600
ctcgatacgc cgcctcatcc gcttttttgg gggcgcccgg ggaggcggcg gcgacgggga    9660
cggggacgac acgtcctcca tggttggggg acgtcgcgcc gcaccgcgtc gcgctcggg    9720
ggtggtttcg cgctgctcct cttcccgact ggccatttcc ttctcctata ggcagaaaaa    9780
gatcatggag tcagtcgaga agaaggacag cctaaccgcc ccctctgagt tcgccaccac    9840
cgcctccacc gatgccgcca acgcgcctac caccttcccc gtcgaggcac cccgcttga    9900
ggaggaggaa gtgattatcg agcaggaccc aggttttgta agcgaagacg acgaggaccg    9960
ctcagtacca acagaggata aaaagcaaga ccaggacaac gcagaggcaa acgaggaaca   10020
agtcgggcgg ggggacgaaa ggcatggcga ctacctagat gtgggagacg acgtgctgtt   10080
gaagcatctg cagcgccagt gcgccattat ctgcgacgcg ttgcaagagc gcagcgatgt   10140
gcccctcgcc atagcggatg tcagccttgc ctacgaacgc cacctattct caccgcgcgt   10200
accccccaaa cgccaagaaa acggcacatg cgagcccaac ccgcgcctca acttctaccc   10260
cgtatttgcc gtgccagagg tgcttgccac ctatcacatc ttttttccaaa actgcaagat   10320
accccctatc tgccgtgcca accgcagccg agcggacaag cagctggcct tgcggcaggg   10380
cgctgtcata cctgatatcg cctcgctcaa cgaagtgcca aaaatctttg agggtcttgg   10440
```

```
acgcgacgag aagcgcgcgg caaacgctct gcaacaggaa acagcgaaaa atgaaagtca   10500
ctctggagtg ttggtggaac tcgagggtga caacgcgcgc ctagccgtac taaaacgcag   10560
catcgaggtc acccactttg cctacccggc acttaaccta ccccccaagg tcatgagcac   10620
agtcatgagt gagctgatcg tgcgccgtgc gcagcccctg agagggatg caaatttgca    10680 agaacaaaca gaggagggcc tacccgcagt tggcgacgag cagctagcgc gctggcttca   10740
aacgcgcgag cctgccgact tggaggagcg acgcaaacta atgatggccg cagtgctcgt   10800
taccgtggag cttgagtgca tgcagcggtt ctttgctgac ccggagatgc agcgcaagct   10860
agaggaaaca ttgcactaca cctttcgaca gggctacgta cgccaggcct gcaagatctc   10920
caacgtggag ctctgcaacc tggtctccta ccttggaatt ttgcacgaaa accgccttgg   10980
gcaaaacgtg cttcattcca cgctcaaggg cgaggcgcgc cgcgactacg tccgcgactc   11040
cgtttactta tttctatgct acacctggca gacggccatg ggcgtttggc agcagtgctt   11100
ggaggagtgc aacctcaagg agctgcagaa actgctaaag caaaacttga aggacctatg   11160
gacggccttc aacgagcgct ccgtggccgc gcacctggcg gacatcattt tccccgaacg   11220
cctgcttaaa accctgcaac agggtctgcc agacttcacc agtcaaagca tgttgcagaa   11280
ctttaggaac tttatcctag agcgctcagg aatcttgccc gccacctgct gtgcacttcc   11340
tagcgacttt gtgcccatta agtaccgcga atgccctccg ccgctttggg gccactgcta   11400
ccttctgcag ctagccaact accttgccta ccactctgac ataatggaag acgtgagcgg   11460
tgacggtcta ctggagtgtc actgtcgctg caacctatgc ccccgcacc gctccctggt    11520 ttgcaattcg cagctgctta acgaaagtca aattatcggt acctttgagc tgcagggtcc   11580
ctcgcctgac gaaaagtccg cggctccggg gttgaaactc actccggggc tgtgacgtc    11640 ggcttacctt cgcaaatttg tacctgagga ctaccacgcc cacgagatta ggttctacga   11700
agaccaatcc cgcccgccaa atgcggagct taccgcctgc gtcattaccc agggccacat   11760
tcttggccaa ttgcaagcca tcaacaaagc ccgccaagag tttctgctac gaaagggacg   11820
gggggtttac ttggaccccc agtccggcga ggagctcaac ccaatccccc cgccgccgca   11880
gccctatcag cagcagccgc gggccctttgc ttcccaggat ggcacccaaa aagaagctgc   11940
agctgccgcc gccacccacg gacgaggagg aatactggga cagtcaggca gaggaggttt   12000
tggacgagga ggaggaggac atgatggaag actgggagag cctagacgag gaagcttccg   12060
aggtcgaaga ggtgtcagac gaaacaccgt caccctcggt cgcattcccc tcgccggcgc   12120
cccagaaatc ggcaaccggt tccagcatgg ctacaacctc cgctcctcag gcgccgccgg   12180
cactgcccgt tcgccgaccc aaccgtagat gggacaccac tggaaccagg gccggtaagt   12240
ccaagcagcc gccgccgtta gcccaagagc aacaacagcg ccaaggctac cgctcatggc   12300
gcgggcacaa gaacgccata gttgcttgct tgcaagactg tggggcaac atctccttcg     12360 cccgccgctt tcttctctac catcacgcg tggccttccc ccgtaacatc ctgcattact    12420
accgtcatct ctacagccca tactgcaccg gcggcagcgg cagcggcagc aacagcagcg   12480
gccacacaga agcaaaggcg accggatagc aagactctga caaagcccaa gaaatccaca   12540
gcggcggcag cagcaggagg aggagcgctg cgtctggcgc ccaacgaacc cgtatcgacc   12600
cgcgagctta gaaacaggat ttttcccact ctgtatgcta tatttcaaca gagcaggggc   12660
caagaacaag agctgaaaat aaaaaacagg tctctgcgat ccctcacccg cagctgcctg   12720
tatcacaaaa gcgaagatca gcttcggcgc acgctggaag acgcggaggc tctcttcagt   12780
```

-continued

```
aaatactgcg cgctgactct taaggactag tttcgcgccc tttctcaaat ttaagcgcga    12840
aaactacgtc atctccagcg gccacacccg gcgccagcac ctgtcgtcag cgccattatg    12900
agcaaggaaa ttcccacgcc ctacatgtgg agttaccagc cacaaatggg acttgcggct    12960
ggagctgccc aagactactc aacccgaata aactacatga gcgcgggacc ccacatgata    13020
tcccgggtca acggaatccg cgcccaccga aaccgaattc tcttggaaca ggcggctatt    13080
accaccacac ctcgtaataa ccttaatccc cgtagttggc ccgctgccct ggtgtaccag    13140
gaaagtcccg ctcccaccac tgtggtactt cccagagacg cccaggccga agttcagatg    13200
actaactcag gggcgcagct tgcgggcggc tttcgtcaca gggtgcggtc gcccgggcag    13260
ggtataactc acctgacaat cagagggcga ggtattcagc tcaacgacga gtcggtgagc    13320
tcctcgcttg gtctccgtcc ggacgggaca tttcagatcg gcggcgccgg ccgctcttca    13380
ttcacgcctc gtcaggcaat cctaactctg cagacctcgt cctctgagcc gcgctctgga    13440
ggcattggaa ctctgcaatt tattgaggag tttgtgccat cggtctactt taacccttc     13500
tcgggacctc ccgccactta tccggatcaa tttattccta actttgacgc ggtaaaggac    13560
tcggcggatg gctacgactg aatgttaagt ggagaggcag agcaactgcg cctgaaacac    13620
ctggtccact gtcgccgcca caagtgcttt gcccgcgact ccggtgagtt ttgctacttt    13680
gaattgcccg aggatcatat cgagggcccg gcgcacggcg tccggcttac cgcccaggga    13740
gagcttgccc gtagcctgat tcgggagttt acccagcgcc cctgctagt tgagcggac     13800
aggggaccct gtgttctcac tgtgatttgc aactgtccta accctggatt acatcaagat    13860
cttttgttgcc atctctgtgc tgagtataat aaatacagaa attaaatat actgggctc     13920
ctatcgccat cctgtaaacg ccaccgtctt caccccgccca agcaaaccaa ggcgaacctt    13980
acctggtact tttaacatct ctccctctgt gatttacaac agtttcaacc cagacggagt    14040
gagtctacga gagaacctct ccgagctcag ctactccatc agaaaaaaca ccaccctcct    14100
tacctgccgg gaacgtacga gtgcgtcacc ggccgctgca ccacacctac cgcctgaccg    14160
taaaccagac ttttttccgga cagacctcaa taactctgtt taccagaaca ggaggtgagc    14220
ttagaaaacc cttagggtat taggccaaag gcgcagctac tgtggggttt atgaacaatt    14280
caagcaactc tacgggctat tctaattcag gtttctctag aaatggacgg aattattaca    14340
gagcagcgcc tgctagaaag acgcagggca gcggccgagc aacagcgcat gaatcaagag    14400
ctccaagaca tggttaactt gcaccagtgc aaaaggggta tctttttgtct ggtaaagcag    14460
gccaaagtca cctacgacag taataccacc ggacaccgcc ttagctacaa gttgccaacc    14520
aagcgtcaga aattggtggt catggtggga gaaaagccca ttaccataac tcagcactcg    14580
gtagaaaccg aaggctgcat tcactcacct tgtcaaggac ctgaggatct ctgcaccctt    14640
attaagaccc tgtgcggtct caaagatctt attcccttta actaataaaa aaaaataata    14700
aagcatcact tacttaaaat cagttagcaa atttctgtcc agtttattca gcagcacctc    14760
cttgccctcc tcccagctct ggtattgcag cttcctcctg gctgcaaact ttctccacaa    14820
tctaaatgga atgtcagttt cctcctgttc ctgtccatcc gcacccacta tcttcatgtt    14880
gttgcagatg aagcgcgcaa gaccgtctga agataccttc aaccccgtgt atccatga     14940
cacggaaacc ggtcctccaa ctgtgccttt tcttactcct cccttttgtat ccccaatgg    15000
gtttcaagag agtccccctg gggtactctc tttgcgccta tccgaacctc tagttacctc    15060
caatggcatg cttgcgctca aaatgggcaa cggcctctct ctggacgagg ccggcaacct    15120
tacctcccaa aatgtaacca ctgtgagccc acctctcaaa aaaaccaagt caaacataaa    15180
```

-continued

```
cctggaaata tctgcacccc tcacagttac ctcagaagcc ctaactgtgg ctgccgccgc    15240
acctctaatg gtcgcgggca acacactcac catgcaatca caggccccgc taaccgtgca    15300
cgactccaaa cttagcattg ccacccaagg accccctcaca gtgtcagaag gaaagctagc   15360
cctgcaaaca tcaggccccc tcaccaccac cgatagcagt acccttacta tcactgcctc    15420
accccctcta actactgcca ctggtagctt gggcattgac ttgaaagagc ccatttatac    15480
acaaaatgga aaactaggac taaagtacgg ggctcctttg catgtaacag acgacctaaa    15540
cactttgacc gtagcaactg gtccaggtgt gactattaat aatacttcct tgcaaactaa    15600
agttactgga gccttgggtt ttgattcaca aggcaatatg caacttaatg tagcaggagg    15660
actaaggatt gattctcaaa acagacgcct tatacttgat gttagttatc cgtttgatgc    15720
tcaaaaccaa ctaaatctaa gactaggaca gggccctctt tttataaact cagcccacaa    15780
cttggatatt aactacaaca aaggccttta cttgtttaca gcttcaaaca attccaaaaa    15840
gcttgaggtt aacctaagca ctgccaaggg gttgatgttt gacgctacag ccatagccat    15900
taatgcagga gatgggcttg aatttggttc acctaatgca ccaaacacaa atcccctcaa    15960
aacaaaaatt ggccatggcc tagaatttga ttcaaacaag gctatggttc ctaaactagg    16020
aactggcctt agttttgaca gcacaggtgc cattacagta ggaaacaaaa ataatgataa    16080
gctaactttg tggaccacac cagctccatc tcctaactgt agactaaatg cagagaaaga    16140
tgctaaactc actttggtct taacaaaatg tggcagtcaa atacttgcta cagtttcagt    16200
tttggctgtt aaaggcagtt tggctccaat atctggaaca gttcaaagtg ctcatcttat    16260
tataagattt gacgaaaatg gagtgctact aaacaattcc ttcctggacc cagaatattg    16320
gaactttaga aatggagatc ttactgaagg cacagcctat acaaacgctg ttggatttat    16380
gcctaaccta tcagcttatc caaaatctca cggtaaaact gccaaaagta acattgtcag    16440
tcaagtttac ttaaacggag acaaaactaa acctgtaaca ctaaccatta cactaaacgg    16500
tacacaggaa acaggagaca caactccaag tgcatactct atgtcatttt catgggactg    16560
gtctggccac aactcattaa tgaaatatt tgccacatcc tcttacactt tttcatacat    16620
tgcccaagaa taaagaatcg tttgtgttat gtttcaacgt gtttattttt caattgcaga    16680
aaatttcaag tcatttttca ttcagtagta tagccccacc accacatagc ttatacagat    16740
caccgtacct taatcaaact cacagaaccc tagtattcaa cctgccacct ccctcccaac    16800
acacagagta cacagtcctt tctccccggc tggccttaaa aagcatcata tcatgggtaa    16860
cagacatatt cttaggtgtt atattccaca cggtttcctg tcgagccaaa cgctcatcag    16920
tgatattaat aaactccccg ggcagctcac ttaagttcat gtcgctgtcc agctgctgag    16980
ccacaggctg ctgtccaact tgcggttgct taacgggcgg cgaaggagaa gtccacgcct    17040 acatggggt agagtcataa tcgtgcatca ggatagggcg gtggtgctgc agcagcgcgc     17100
gaataaactg ctgccgccgc cgctccgtcc tgcaggaata caacatggca gtggtctcct    17160
cagcgatgat tcgcaccgcc cgcagcataa ggcgccttgt cctccgggca cagcagcgca    17220
ccctgatctc acttaaatca gcacagtaac tgcagcacag caccacaata ttgttcaaaa    17280
tcccacagtg caaggcgctg tatccaaagc tcatggcggg gaccacagaa cccacgtggc    17340
catcatacca caagcgcagg tagattaagt ggcgaccct cataaacacg ctggacataa     17400
acattacctc ttttggcatg ttgtaattca ccacctcccg gtaccatata aacctctgat    17460
taaacatggc gccatccacc accatcctaa accagctggc caaaacctgc ccgccggcta    17520
```

```
tacactgcag ggaaccggga ctggaacaat gacagtggag agcccaggac tcgtaaccat    17580
ggatcatcat gctcgtcatg atatcaatgt tggcacaaca caggcacacg tgcatacact    17640
tcctcaggat tacaagctcc tcccgcgtta gaaccatatc ccagggaaca acccattcct    17700
gaatcagcgt aaatcccaca ctgcagggaa gacctcgcac gtaactcacg ttgtgcattg    17760
tcaaagtgtt acattcgggc agcagcggat gatcctccag tatggtagcg cgggtttctg    17820
tctcaaaagg aggtagacga tccctactgt acggagtgcg ccgagacaac cgagatcgtg    17880
ttggtcgtag tgtcatgcca aatggaacgc cggacgtagt catatttcct gaagcaaaac    17940
caggtgcggg cgtgacaaac agatctgcgt ctccggtctc gccgcttaga tcgctctgtg    18000
tagtagttgt agtatatcca ctctctcaaa gcatccaggc gcccctggc ttcgggttct     18060 atgtaaactc cttcatgcgc cgctgccctg ataacatcca ccaccgcaga ataagccaca    18120
cccagccaac ctacacattc gttctgcgag tcacacacgg gaggagcggg aagagctgga    18180
agaaccatgt tttttttttt attccaaaag attatccaaa acctcaaaat gaagatctat    18240
taagtgaacg cgctcccctc cggtggcgtg gtcaaactct acagcaaag aacagataat      18300 ggcatttgta agatgttgca caatggcttc caaaaggcaa acggccctca cgtccaagtg    18360
gacgtaaagg ctaaacccct tcagggtgaat ctcctctata aacattccag cacctttcaac  18420 catgcccaaa taattctcat ctcgccacct tctcaatata tctctaagca aatcccgaat    18480
attaagtccg gccattgtaa aaatctgctc cagagcgccc tccaccttca gcctcaagca    18540
gcgaatcatg attgcaaaaa ttcaggttcc tcacagacct gtataagatt caaaagcgga    18600
acattaacaa aaataccgcg atcccgtagg tccttcgca gggccagctg aacataatcg     18660
tgcaggtctg cacggaccag cgcggccact tccccgccag gaaccatgac aaaagaaccc    18720
acactgatta tgacacgcat actcggagct atgctaacca gcgtagcccc gatgtaagct    18780
tgttgcatgg gcggcgatat aaaatgcaag gtgctgctca aaaaatcagg caaagcctcg    18840
cgcaaaaaag aaagcacatc gtagtcatgc tcatgcagat aaaggcaggt aagctccgga    18900
accaccacag aaaaagacac cattttctc tcaaacatgt ctgcgggttt ctgcataaac     18960
acaaaataaa ataacaaaaa acatttaaa cattagaagc ctgtcttaca acaggaaaaa     19020
caacccttat aagcataaga cggactacgg ccatgccggc gtgaccgtaa aaaaactggt    19080
caccgtgatt aaaaagcacc accgacagct cctcggtcat gtccggagtc ataatgtaag    19140
actcggtaaa cacatcaggt tgattcacat cggtcagtgc taaaaagcga ccgaaatagc    19200 ccggggggaat acatacccgc aggcgtagag acaacattac agcccccata ggaggtataa   19260
caaaattaat aggagagaaa aacacataaa cacctgaaaa accctcctgc ctaggcaaaa    19320
tagcaccctc ccgctccaga acaacataca gcgcttccac agcggcagcc ataacagtca   19380
gccttaccag taaaaagaa aacctattaa aaaaacacca ctcgacacgg caccagctca    19440
atcagtcaca gtgtaaaaaa gggccaagtg cagagcgagt atatatagga ctaaaaaatg   19500
acgtaacggt taaagtccac aaaaaacacc cagaaaaccg cacgcgaacc tacgcccaga    19560
aacgaaagcc aaaaaaccca caacttcctc aaatcgtcac ttccgttttc ccacgttacg    19620
tcacttccca ttttaagaaa actacaattc ccaacacata caagttactc cgccctaaaa    19680
cctacgtcac ccgccccgtt cccacgcccc gcgccacgtc acaaactcca cccctcatt    19740 atcatattgg cttcaatcca aaataaggta tattattgat gatgttaatt aagaattcgg    19800
atctgcgacg cgaggctgga tggccttccc cattatgatt cttctcgctt ccggcggcat    19860
cgggatgccc gcgttgcagg ccatgctgtc caggcaggta gatgacgacc atcagggaca    19920
```
gcttcaaggc cagcaaaagg ccaggaaccg taaaaaggcc gcgttgctgg cgttttttcca   19980 taggctccgc cccctgacg agcatcacaa aaatcgacgc tcaagtcaga ggtggcgaaa   20040
cccgacagga ctataaagat accaggcgtt tccccctgga agctccctcg tgcgctctcc   20100
tgttccgacc ctgccgctta ccggatacct gtccgccttt ctcccttcgg gaagcgtggc   20160
gctttctcat agctcacgct gtaggtatct cagttcggtg taggtcgttc gctccaagct   20220
gggctgtgtg cacgaacccc ccgttcagcc cgaccgctgc gccttatccg gtaactatcg   20280
tcttgagtcc aacccggtaa gacacgactt atcgccactg gcagcagcca ctggtaacag   20340
gattagcaga gcgaggtatg taggcggtgc tacagagttc ttgaagtggt ggcctaacta   20400
cggctacact agaaggacag tatttggtat ctgcgctctg ctgaagccag ttaccttcgg   20460
aaaaagagtt ggtagctctt gatccggcaa acaaaccacc gctggtagcg gtggtttttt   20520
tgtttgcaag cagcagatta cgcgcagaaa aaaggatct caagaagatc ctttgatctt   20580
ttctacgggg tctgacgctc agtggaacga aaactcacgt taagggattt tggtcatgag   20640
attatcaaaa aggatcttca cctagatcct tttaaatcaa tctaaagtat atatgagtaa   20700
acttggtctg acagttttaa actcagaaga actcgtcaag aaggcgatag aaggcgatgc   20760
gctgcgaatc gggagcggcg ataccgtaaa gcacgaggaa gcggtcagcc cattcgccgc   20820
caagctcttc agcaatatca cgggtagcca acgctatgtc ctgatagcgg tccgccacac   20880
ccagccggcc acagtcgatg aatccagaaa agcggccatt ttccaccatg atattcggca   20940
agcaggcatc gccatgggtc acgacgagat cctcgccgtc gggcatgctc gccttgagcc   21000
tggcgaacag ttcggctggc gcgagcccct gatgctcttc gtccagatca tcctgatcga   21060
caagaccggc ttccatccga gtacgtgctc gctcgatgcg atgtttcgct tggtggtcga   21120
atgggcaggt agccggatca agcgtatgca gccgccgcat tgcatcagcc atgatggata   21180
ctttctcggc aggagcaagg tgagatgaca ggagatcctg ccccggcact cgcccaata   21240 gcagccagtc ccttcccgct tcagtgacaa cgtcgagcac agctgcgcaa ggaacgcccg   21300
tcgtggccag ccacgatagc cgcgctgcct cgtcttgcag ttcattcagg gcaccggaca   21360
ggtcggtctt gacaaaaaga accgggcgcc cctgcgctga cagccggaac acggcggcat   21420
cagagcagcc gattgtctgt tgtgcccagt catagccgaa tagcctctcc acccaagcgg   21480
ccggagaacc tgcgtgcaat ccatcttgtt caatcataac gttactcttc ctttttcaat   21540
attattgaag catttatcag ggttattgtc tcatgagcgg atacatattt gaatgtattt   21600
agaaaaataa acaaataggg gttccgcgca catttccccg aaaagtgcca cctgacgtct   21660
aagaaaccat tattatcatg acattaacct ataaaaatag gcgtatcacg aggccctttc   21720
gtcttcaa                                                            21728

<210> SEQ ID NO 2
<211> LENGTH: 21736
<212> TYPE: DNA
<213> ORGANISM: Artificial Sequence
<220> FEATURE:
<223> OTHER INFORMATION: SYNTHETIC POLYNUCLEOTIDE

<400> SEQUENCE: 2
gaattggatc cgaattctta attaacatca tcaataatat accttatttt ggattgaagc     60
caatatgata atgagggggt ggagtttgtg acgtggcgcg gggcgtggga acggggcggg    120
tgacgtagta gtgtggcgga agtgtgatgt tgcaagtgtg gcggaacaca tgtaagcgac    180

```
ggatgtggca aaagtgacgt ttttggtgtg cgccggtgta cacaggaagt gacaattttc      240
gcgcggtttt aggcggatgt tgtagtaaat ttgggcgtaa ccgagtaaga tttggccatt      300
ttcgcgggaa aactgaataa gaggaagtga aatctgaata attttgtgtt actcatagcg      360
cgtaatattt gtctagggcc gcggggactt tgaccgttta cgtggagact cgcccaggtg      420 ttttctcag gtgttttccg cgttccgggt caaagttggc gttttattat tatagtcagg       480
gggatcctct agaactagtg gatccgtccc tcaggcctag aagtaaaaaa gggaaaaaag      540
agtgtgtttg tcaaaatagg agacaggtgg tggcaaccaa ggacttatag gggaccttac      600
atctacagac caacagatgc ccccttacca tatacaggaa gatatgactt aaattgggat      660
aggtgggtca caatcaacgg ctataaagtg ttatacagat ccctcccctc cctttcgtg       720 aaagactcgc cagagctaga cctccttggt gtatgctaac tgagaagaga aagacgacat      780
gaaacaacag gtacatgatt atatttatct aggaacagga atgcactttt ggggaaaggt      840
tttccatacc aaggaagggg cagtggctgg actgatagaa cattattctg caaaaactta      900
tggtatgagt tattatgatt agcctttatt tgcccaacct tgcggttccc agggtttaaa      960
taagtttatg gttacaaact gttcttaaaa cgaggatgtg agacaagtgg tttcctgact     1020
tggtttggta atcaaatgtt ctgatctgag ctcttagtgt tctatttcc tatgttcttt      1080 tggaatctat ccaagtctta tgtaaatgct tatgtaaacc ataatataaa agagtgctga     1140
ttttttgagt aaacttgcaa cagtcctaac attcttctct cgtgtgtttg tgtctgttcg     1200
ccatcccgtc tccgctcgtc acttatcctt cacttttcag agggtcccc cgcagatccc      1260 ggtcaccctc aggtcgggac ctgcagaaga cgcccgagtg agcacgcagg gtctccattt     1320
tgaagcggga ggtttgaacg cgcagccgcc atgccggggt tttacgagat tgtgattaag     1380
gtccccagcg accttgacgg gcatctgccc ggcatttctg acagctttgt gaactgggtg     1440
gccgagaagg aatgggagtt gccgccagat tctgacatgg atctgaatct gattgagcag     1500
gcacccctga ccgtggccga aagctgcag cgcgactttc tgacggaatg gcgccgtgtg     1560
agtaaggccc cggaggccct tttctttgtg caatttgaga agggagagag ctacttccac     1620
atgcacgtgc tcgtggaaac caccggggtg aaatccatgg ttttgggacg tttcctgagt     1680
cagattcgcg aaaaactgat tcagagaatt taccgcggga tcgagccgac tttgccaaac     1740
tggttcgcgc tcacaaagac cagaaatggc gccggaggcg ggaacaaggt ggtgatgag     1800 tgctacatcc ccaattactt gctccccaaa acccagcctg agctccagtg ggcgtggact     1860
aatatggaac agtatttaag cgcctgtttg aatctcacgg agcgtaaacg gttggtggcg    1920
cagcatctga cgcacgtgtc gcagacgcag gagcagaaca aagagaatca gaatcccaat     1980
tctgatgcgc cggtgatcag atcaaaaact tcagccaggt acatggagct ggtcgggtgg    2040
ctcgtggaca aggggattac ctcggagaag cagtggatcc aggaggacca ggcctcatac    2100
atctccttca tgcggcctc caactcgcgg tcccaaatca aggctgcctt ggacaatgcg    2160
ggaaagatta tgagcctgac taaaaccgcc ccgactaccc tggtgggcca gcagcccgtg    2220
gaggacattt ccagcaatcg gatttataaa attttggaac taaacgggta cgatccccaa     2280
tatgcggctt ccgtctttct gggatgggcc acgaaaaagt tcggcaagag gaacaccatc     2340
tggctgtttg ggcctgcaac taccgggaag accaacatcg cggaggccat agcccacact    2400
gtgcccttct acgggtgcgt aaactggacc aatgagaact ttcccttcaa cgactgtgtc    2460
gacaagatgg tgatctggtg ggaggagggg aagatgaccg ccaaggtcgt ggagtcggcc    2520
aaagccattc tcggaggaag caaggtgcgc gtggaccaga aatgcaagtc ctcggcccag    2580
```

```
atagacccga ctcccgtgat cgtcacctcc aacaccaaca tgtgcgccgt gattgacggg   2640
aactcaacga ccttcgaaca ccagcagccg ttgcaagacc ggatgttcaa atttgaactc   2700
acccgccgtc tggatcatga cttggggaag gtcaccaagc aggaagtcaa agactttttc   2760
cggtgggcaa aggatcacgt ggttgaggtg gagcatgaat tctacgtcaa aaagggtgga   2820
gccaagaaaa gacccgcccc cagtgacgca gatataagtg agcccaaacg ggtgcgcgag   2880
tcagttgcgc agccatcgac gtcagacgcg gaagcttcga tcaactacgc agacaggtac   2940
caaaacaaat gttctcgtca cgtgggcatg aatctgatgc tgtttccctg cagacaatgc   3000
gagagaatga atcagaattc aaatatctgc ttcactcacg gacagaaaga ctgtttagag   3060
tgctttcccg tgtcagaatc tcaacccgtt tctgtcgtca aaaggcgta tcagaaactg    3120 tgctacattc atcatatcat gggaaaggtg ccagacgctt gcactgcctg cgatctggtc   3180
aatgtggatt tggatgactg catctttgaa caataaatga tttaaatgac ttaaaccagg   3240
tatggctgct gacggttatc ttccagattg gctcgaggac aacctttctg aaggcattcg   3300
tgagtggtgg gctctgaaac ctggagtccc tcaacccaaa gcgaaccaac aacaccagga   3360
caaccgtcgg ggtcttgtgc ttccgggtta caaatacctc ggacccggta acggactcga   3420
caaaggagag ccggtcaacg aggcggacgc ggcagccctc gaacacgaca agcttacga    3480 ccagcagctc aaggccggtg acaacccgta cctcaagtac aaccacgccg acgccgagtt   3540
tcaggagcgt cttcaagaag atacgtcttt tgggggcaac cttggcagag cagtcttcca   3600
ggccaaaaag aggatccttg agcctcttgg tctggttgag gaagcagcta aaacggctcc   3660
tggaaagaag aggcctgtag atcagtctcc tcaggaaccg gactcatcat ctggtgttgg   3720
caaatcgggc aaacagcctg ccagaaaaag actaaatttc ggtcagactg gcgactcaga   3780
gtcagtccca gaccctcaac ctctcggaga accaccagca gcccccacaa gtttgggatc   3840
taatacaatg gcttcaggcg gtggcgcacc aatggcagac aataacgagg gtgccgatgg   3900
agtgggtaat tcctcaggaa attggcattg cgattcccaa tggctgggcg acagagtcat   3960
caccaccagc accagaacct gggccctgcc cacttacaac aaccatctct acaagcaaat   4020
ctccagccaa tcaggagctt caaacgacaa ccactacttt ggctacagca ccccttgggg   4080
gtattttgac tttaacagat tccactgcca cttctcacca cgtgactggc agcgactcat   4140
taacaacaac tggggattcc ggcccaagaa actcagcttc aagctcttca acatccaagt   4200
taaagaggtc acgcagaacg atggcacgac gactattgcc aataacctta ccagcacggt   4260
tcaagtgttt acggactcgg agtatcagct cccgtacgtg ctcgggtcgg cgcaccaagg   4320
ctgtctcccg ccgtttccag cggacgtctt catggtccct cagtatggat acctcaccct   4380
gaacaacgga agtcaagcgg tgggacgctc atccttttac tgcctggagt acttcccttc   4440
gcagatgcta aggactggaa ataacttcca attcagctat accttcgagg atgtaccttt   4500
tcacagcagc tacgctcaca gccagagttt ggatcgcttg atgaatcctc ttattgatca   4560
gtatctgtac tacctgaaca gaacgcaagg aacaacctct ggaacaacca accaatcacg   4620
gctgcttttt agccaggctg ggcctcagtc tatgtctttg caggccagaa attggctacc   4680
tgggccctgc taccggcaac agagacttc aaagactgct aacgacaaca acaacagtaa   4740
ctttccttgg acagcggcca gcaaatatca tctcaatggc cgcgactcgc tggtgaatcc   4800
aggaccagct atgccagtc acaaggacga tgaagaaaaa ttttcccta tgcacggcaa    4860 tctaatattt ggcaaagaag ggacaacggc aagtaacgca gaattagata atgtaatgat   4920
```

```
tacggatgaa gaagagattc gtaccaccaa tcctgtggca acagagcagt atggaactgt      4980
ggcaaataac ttgcagagct caaatacagc tcccacgact agaactgtca atgatcaggg      5040
ggccttacct ggcatggtgt ggcaagatcg tgacgtgtac cttcaaggac ctatctgggc      5100
aaagattcct cacacggatg gacactttca tccttctcct ctgatgggag gctttggact      5160
gaaacatccg cctcctcaaa tcatgatcaa aaatactccg gtaccggcaa atcctccgac      5220
gactttcagc ccggccaagt ttgcttcatt tatcactcag tactccactg gacaggtcag      5280
cgtggaaatt gagtgggagc tacagaaaga aaacagcaaa cgttggaatc cagagattca      5340
gtacacttcc aactacaaca agtctgttaa tgtggacttt actgtagaca ctaatggtgt      5400
ttatagtgaa cctcgcccta ttggaacccg gtatctcaca cgaaacttgt aatcctggtt      5460
aatcaataaa tcgatgcatg tccttgggtc cggcctgctg aatgcgcagg cggtcggcca      5520
tgccccaggc ttcgttttga catcggcgca ggtctttgta gtagtcttgc atgagccttt      5580
ctaccggcac ttcttcttct ccttcctctt gtcctgcatc tcttgcatct atcgctgcgg      5640
cggcggcgga gtttggccgt aggtggcgcc ctcttcctcc catcgtgtga ccccgaagcc      5700
cctcatcggc tgaagcaggg ctaggtcggc gacaacgcgc tcggctaata tggcctgctg      5760
cacctgcgtg agggtagact ggaagtcatc catgtccaca aagcggtggt atgcgcccgt      5820
gttgatggtg taagtgcagt tggccataac ggaccagtta acggtctggt gacccggctg      5880
cgagagctcg gtgtacctga gacgcgagta agccctcgag tcaaatacgt agtcgttaca      5940
agtccgcacc aggtactggt atcccaccaa aaagtgcggc ggcggctggc ggtagagggg      6000
ccagcgtagg gtggccgggg ctccggggc gagatcttcc aacataaggc gatgatatcc       6060
gtagatgtac ctggacatcc aggtgatgcc ggcggcggtg gtggaggcgc gcggaaagtc      6120 gcggacgcg ttccagatgt tgcgcagcgg caaaaagtgc tccatggtcg ggacgctctg       6180
gccggtcagg cgcgcgcaat cgttgacgct ctagaccgtg caaaaggaga gcctgtaagc      6240
gggcactctt ccgtggtctg gtggataaat tcgcaagggt atcatggcgg acgaccgggg      6300
ttcgagcccc gtatccggcc gtccgccgtg atccatgcgg ttaccgcccg cgtgtcgaac      6360
ccaggtgtgc gacgtcagac aacgggggag tgctccttt ggcttccttc caggcgcggc       6420
ggctgctgcg ctagcttttt tggccactgg ccgcgcgcag cgtaagcggt taggctggaa      6480
agcgaaagca ttaagtggct cgctcccgt agcggaggg ttatttcca agggttgagt        6540 cgcgggaccc ccggttcgag tctcggaccg gccggactgc ggcgaacggg ggtttgtctc      6600
cccgtcatgc aagaccccgc ttgcaaattc ctccggaaac agggacgagc ccctttttg       6660 cttttcccag atgcatccgg tgctgcggca gatgcgcccc cctcctcagc agcggcaaga      6720
gcaagagcag cggcagacat gcagggcacc ctcccctcct cctaccgcgt caggaggggc      6780
gacatccgcg gttgacgcgg cagcagatgg tgattacgaa cccccgcggc gccgggcccg      6840
gcactacctg gacttggagg agggcgaggg cctggcgcgg ctaggagcgc cctctcctga      6900
gcggcaccca agggtgcagc tgaagcgtga tacgcgtgag gcgtacgtgc gcggcagaa       6960 cctgtttcgc gaccgcgagg gagaggagcc cgaggagatg cgggatcgaa agttccacgc      7020
agggcgcgag ctgcggcatg gcctgaatcg cgagcggttg ctgcgcgagg aggactttga      7080
gcccgacgcg cgaaccggga ttagtcccgc gcgcgcacac gtggcggccg ccgacctggt      7140
aaccgcatac gagcagacgg tgaaccaggg cgatcgcacc ctttggcgca tcccattctc      7200
cagtaacttt atgtccatgg gcgcactcac agacctgggc caaaaccttc tctacgccaa      7260
ctccgcccac gcgctagaca tgactttga ggtggatccc atggacgagc ccacccttct       7320
```

-continued

```
ttatgttttg tttgaagtct ttgacgtggt ccgtgtgcac cggccgcacc gcggcgtcat    7380
cgaaaccgtg tacctgcgca cgcccttctc ggccggcaac gccacaacat aaagaagcaa    7440
gcaacatcaa caacagctgc cgccatgggc tccagtgagc aggaactgaa agccattgtc    7500
aaagatcttg gttgtgggcc atatttttg ggcacctatg acaagcgctt tccaggcttt    7560
gtttctccac acaagctcgc ctgcgccata gtcaatacgg ccggtcgcga ctgggggc     7620
gtacactgga tggcctttgc ctggaacccg cactcaaaaa catgctacct ctttgagccc    7680
tttggctttt ctgaccagcg actcaagcag gtttaccagt ttgagtacga gtcactcctg    7740
cgccgtagcg ccattgcttc ttcccccgac cgctgtataa cgctggaaaa gtccacccaa    7800
agcgtacagg ggcccaactc ggccgcctgt ggactattct gctgcatgtt tctccacgcc    7860
tttgccaact ggccccaaac tcccatggat cacaacccca ccatgaacct tattaccggg    7920
gtacccaact ccatgctcaa cagtccccag gtacagccca cctgcgtcg caaccaggaa     7980
cagctctaca gcttcctgga gcgccactcg ccctacttcc gcagccacag tgcgcagatt    8040
aggagcgcca cttcttttg tcacttgaaa acatgtaaa aataatgtac tagagacact      8100
ttcaataaag gcaaatgctt ttatttgtac actctcgggt gattatttac ccccacccct    8160
gccgtctgcg ccgtttaaaa atcaaagggg ttctgccgcg catcgctatg cgccactggc    8220
agggacacgt tgcgatactg gtgtttagtg ctccacttaa actcaggcac aaccatccgc    8280
ggcagctcgg tgaagttttc actccacagg ctgcgcacca tcaccaacgc gtttagcagg    8340
tcgggcgccg atatcttgaa gtcgcagttg gggcctccgc cctgcgcgcg cgagttgcga    8400
tacacagggt tgcagcactg gaacactatc agcgccgggt ggtgcacgct ggccagcacg    8460
ctcttgtcgg agatcagatc cgcgtccagg tcctccgcgt tgctcagggc gaacggagtc    8520
aactttggta gctgccttcc caaaagggc gcgtgcccag gctttgagtt gcactcgcac     8580
cgtagtggca tcaaaggtg accgtgcccg gtctgggcgt taggatacag cgcctgcata    8640
aaagccttga tctgcttaaa agccacctga gcctttgcgc cttcagagaa gaacatgccg    8700
caagacttgc cggaaaactg attggccgga caggccgcgt cgtgcacgca gcaccttgcg    8760
tcggtgttgg agatctgcac cacatttcgg ccccaccggt tcttcacgat cttggccttg    8820
ctagactgct ccttcagcgc gcgctgcccg ttttcgctcg tcacatccat ttcaatcacg    8880
tgctccttat ttatcataat gcttccgtgt agacacttaa gctcgccttc gatctcagcg    8940
cagcggtgca gccacaacgc gcagcccgtg ggctcgtgat gcttgtaggt cacctctgca    9000
aacgactgca ggtacgcctg caggaatcgc cccatcatcg tcacaaaggt cttgttgctg    9060
gtgaaggtca gctgcaaccc gcggtgctcc tcgttcagcc aggtcttgca tacggccgcc    9120
agagcttcca cttggtcagg cagtagtttg aagttcgcct ttagatcgtt atccacgtgg    9180
tacttgtcca tcagcgcgcg cgcagcctcc atgcccttct cccacgcaga cacgatcggc    9240
acactcagcg ggttcatcac cgtaatttca ctttccgctt cgctgggctc ttcctcttcc    9300
tcttgcgtcc gcataccacg cgccactggg tcgtcttcat tcagccgccg cactgtgcgc    9360
ttacctcctt tgccatgctt gattagcacc ggtgggttgc tgaaacccac catttgtagc    9420
gccacatctt ctctttcttc ctcgctgtcc acgattacct ctggtgatgg cgggcgctcg    9480
ggcttgggag aagggcgctt cttttcttc ttgggcgcaa tggccaaatc cgccgccgag    9540
gtcgatggcc gcgggctggg tgtgcgcggc accagcgcgt cttgtgatga gtcttcctcg    9600
tcctcggact cgatacgccg cctcatccgc ttttttgggg gcgcccgggg aggcggcggc    9660
```

-continued

```
gacggggacg gggacgacac gtcctccatg gttggggac gtcgcgccgc accgcgtccg    9720
cgctcggggg tggtttcgcg ctgctcctct tcccgactgg ccatttcctt ctcctatagg    9780
cagaaaaaga tcatggagtc agtcgagaag aaggacagcc taaccgcccc ctctgagttc    9840
gccaccaccg cctccaccga tgccgccaac gcgcctacca ccttcccgt cgaggcaccc     9900 ccgcttgagg aggaggaagt gattatcgag caggacccag gttttgtaag cgaagacgac    9960
gaggaccgct cagtaccaac agaggataaa aagcaagacc aggacaacgc agaggcaaac   10020
gaggaacaag tcgggcgggg ggacgaaagg catggcgact acctagatgt gggagacgac   10080
gtgctgttga agcatctgca gcgccagtgc gccattatct gcgacgcgtt gcaagagcgc   10140
agcgatgtgc ccctcgccat agcggatgtc agccttgcct acgaacgcca cctattctca   10200
ccgcgcgtac cccccaaacg ccaagaaaac ggcacatgcg agcccaaccc gcgcctcaac   10260
ttctaccccg tatttgccgt gccagaggtg cttgccacct atcacatctt tttccaaaac   10320
tgcaagatac ccctatcctg ccgtgccaac cgcagccgag cggacaagca gctggccttg   10380
cggcagggcg ctgtcatacc tgatatcgcc tcgctcaacg aagtgccaaa aatctttgag   10440
ggtcttggac gcgacgagaa gcgcgcggca aacgctctgc aacaggaaaa cagcgaaaat   10500
gaaagtcact ctggagtgtt ggtggaactc gagggtgaca acgcgcgcct agccgtacta   10560
aaacgcagca tcgaggtcac ccactttgcc tacccggcac ttaacctacc ccccaaggtc   10620
atgagcacag tcatgagtga gctgatcgtg cgccgtgcgc agcccctgga gagggatgca   10680
aatttgcaag aacaaacaga ggagggccta cccgcagttg gcgacgagca gctagcgcgc   10740
tggcttcaaa cgcgcgagcc tgccgacttg gaggagcgac gcaaactaat gatgccgca    10800 gtgctcgtta ccgtggagct tgagtgcatg cagcggttct ttgctgaccc ggagatgcag   10860
cgcaagctag aggaaacatt gcactacacc tttcgacagg gctacgtacg ccaggcctgc   10920
aagatctcca acgtggagct ctgcaacctg gtctcctacc ttggaatttt gcacgaaaac   10980
cgccttgggc aaaacgtgct tcattccacg ctcaagggcg aggcgcgccg cgactacgtc   11040
cgcgactgcg tttacttatt tctatgctac acctggcaga cggccatggg cgtttggcag   11100
cagtgcttgg aggagtgcaa cctcaaggag ctgcagaaac tgctaaagca aaacttgaag   11160
gacctatgga cggccttcaa cgagcgctcc gtggccgcgc acctggcgga catcattttc   11220
cccgaacgcc tgcttaaaac cctgcaacag ggtctgccag acttcaccag tcaaagcatg   11280
ttgcagaact ttaggaactt tatcctagag cgctcaggaa tcttgccgc cacctgctgt    11340 gcacttccta gcgactttgt gcccattaag taccgcgaat gccctccgcc gctttggggc   11400
cactgctacc ttctgcagct agccaactac cttgcctacc actctgacat aatggaagac   11460
gtgagcggtg acggtctact ggagtgtcac tgtcgctgca acctatgcac cccgcaccgc   11520
tccctggttt gcaattcgca gctgcttaac gaaagtcaaa ttatcggtac ctttgagctg   11580
cagggtccct cgcctgacga aaagtccgcg gctccggggt tgaaactcac tccggggctg   11640
tggacgtcgg cttaccttcg caaatttgta cctgaggact accacgccca cgagattagg   11700
ttctacgaag accaatcccg cccgccaaat gcggagctta ccgcctgcgt cattacccag   11760
ggccacattc ttggccaatt gcaagccatc aacaaagccc gccaagagtt tctgctacga   11820
aagggacggg gggtttactt ggaccccag tccggcgagg agctcaaccc aatcccccg     11880 ccgccgcagc cctatcagca gcagccgcgg gcccttgctt cccaggatgg cacccaaaaa   11940
gaagctgcag ctgccgccgc cacccacgga cgaggaggaa tactgggaca gtcaggcaga   12000
ggaggttttg gacgaggagg aggaggacat gatggaagac tgggagagcc tagacgagga   12060
```

```
agcttccgag gtcgaagagg tgtcagacga acaccgtca ccctcggtcg cattcccctc   12120
gccggcgccc cagaaatcgg caaccggttc cagcatggct acaacctccg ctcctcaggc   12180
gccgccggca ctgcccgttc gccgacccaa ccgtagatgg gacaccactg gaaccagggc   12240
cggtaagtcc aagcagccgc cgccgttagc ccaagagcaa caacagcgcc aaggctaccg   12300
ctcatggcgc gggcacaaga acgccatagt tgcttgcttg caagactgtg ggggcaacat   12360
ctccttcgcc cgccgctttc ttctctacca tcacggcgtg gccttccccc gtaacatcct   12420
gcattactac cgtcatctct acagcccata ctgcaccggc ggcagcggca gcggcagcaa   12480
cagcagcggc cacacagaag caaaggcgac cggatagcaa gactctgaca agcccaaga    12540
aatccacagc ggcggcagca gcaggaggag gagcgctgcg tctggcgccc aacgaacccg   12600
tatcgacccg cgagcttaga aacaggattt ttcccactct gtatgctata tttcaacaga   12660
gcagggcca agaacaagag ctgaaaataa aaaacaggtc tctgcgatcc ctcacccgca    12720
gctgcctgta tcacaaaagc gaagatcagc ttcggcgcac gctggaagac gcggaggctc   12780
tcttcagtaa atactgcgcg ctgactctta aggactagtt tcgcgccctt tctcaaattt   12840
aagcgcgaaa actacgtcat ctccagcggc cacaccccgc gccagcacct gtcgtcagcg   12900
ccattatgag caaggaaatt cccacgccct acatgtggag ttaccagcca caaatgggac   12960
ttgcggctgg agctgcccaa gactactcaa cccgaataaa ctacatgagc gcggaccccc   13020
acatgatatc ccgggtcaac ggaatccgcg cccaccgaaa ccgaattctc ttggaacagg   13080
cggctattac caccacacct cgtaataacc ttaatcccg tagttggccc gctgccctgg    13140
tgtaccagga aagtcccgct cccaccactg tggtacttcc cagagacgcc caggccgaag   13200
ttcagatgac taactcaggg gcgcagcttg cgggcggctt tcgtcacagg gtgcggtcgc   13260
ccgggcaggg tataactcac ctgacaatca gagggcgagg tattcagctc aacgacgagt   13320
cggtgagctc ctcgcttggt ctccgtccgg acgggacatt tcagatcgg ggcgccggcc     13380
gctcttcatt cacgcctcgt caggcaatcc taactctgca gacctcgtcc tctgagccgc   13440
gctctggagg cattggaact ctgcaattta ttgaggagtt tgtgccatcg gtctacttta   13500
accccttctc gggacctccc ggccactatc cggatcaatt tattcctaac tttgacgcgg   13560
taaaggactc ggcggatggc tacgactgaa tgttaagtgg agaggcagag caactgcgcc   13620
tgaaacacct ggtccactgt cgccgccaca agtgctttgc ccgcgactcc ggtgagtttt   13680
gctactttga attgcccgag gatcatatcg agggcccggc gcacggcgtc cggcttaccg   13740
cccagggaga gcttgcccgt agcctgattc gggagtttac ccagcgcccc ctgctagttg   13800
agcgggacag gggaccctgt gttctcactg tgatttgcaa ctgtcctaac cctggattac   13860
atcaagatct ttgttgccat ctctgtgctg agtataataa atacagaaat taaaatatac   13920
tggggctcct atcgccatcc tgtaaacgcc accgtcttca cccgcccaag caaaccaagg   13980
cgaaccttac ctggtacttt taacatctct ccctctgtga tttacaacag tttcaaccca   14040
gacggagtga gtctacgaga gaacctctcc gagctcagct actccatcag aaaaaacacc   14100
accctcctta cctgccggga acgtacgagt gcgtcaccgg ccgctgcacc acacctaccg   14160
cctgaccgta aaccagactt tttccggaca gacctcaata actctgttta ccagaacagg   14220
aggtgagctt agaaaaccct agggtatta ggccaaaggc gcagctactg tggggtttat     14280
gaacaattca agcaactcta cgggctattc taattcaggt ttctctagaa atggacggaa   14340
ttattacaga gcagcgcctg ctagaaagac gcagggcagc ggccgagcaa cagcgcatga   14400
```

```
atcaagagct ccaagacatg gttaacttgc accagtgcaa aaggggtatc ttttgtctgg   14460
taaagcaggc caaagtcacc tacgacagta ataccaccgg acaccgcctt agctacaagt   14520
tgccaaccaa gcgtcagaaa ttggtggtca tggtgggaga aaagcccatt accataactc   14580
agcactcggt agaaaccgaa ggctgcattc actcaccttg tcaaggacct gaggatctct   14640
gcacccttat taagaccctg tgcggtctca aagatcttat tccctttaac taataaaaaa   14700
aaataataaa gcatcactta cttaaaatca gttagcaaat ttctgtccag tttattcagc   14760
agcacctcct tgccctcctc ccagctctgg tattgcagct tcctcctggc tgcaaacttt   14820
ctccacaatc taaatggaat gtcagtttcc tcctgttcct gtccatccgc acccactatc   14880
ttcatgttgt tgcagatgaa gcgcgcaaga ccgtctgaag ataccttcaa ccccgtgtat   14940
ccatatgaca cggaaaccgg tcctccaact gtgccttttc ttactcctcc ctttgtatcc   15000
cccaatgggt ttcaagagag tccccctggg gtactctctt tgcgcctatc cgaacctcta   15060
gttacctcca atggcatgct tgcgctcaaa atgggcaacg gcctctctct ggacgaggcc   15120
ggcaaccttt acctcccaaaa tgtaaccact gtgagcccac ctctcaaaaa aaccaagtca   15180
aacataaacc tggaaatatc tgcacccctc acagttacct cagaagccct aactgtggct   15240
gccgccgcac ctctaatggt cgcgggcaac acactcacca tgcaatcaca ggccccgcta   15300
accgtgcacg actccaaaact tagcattgcc acccaaggac ccctcacagt gtcagaagga   15360
aagctagccc tgcaaacatc aggccccctc accaccaccg atagcagtac ccttactatc   15420
actgcctcac cccctctaac tactgccact ggtagcttgg gcattgactt gaaagagccc   15480
atttatacac aaaatggaaa actaggacta aagtacgggg ctccttttgca tgtaacagac   15540 gacctaaaca ctttgaccgt agcaactggt ccaggtgtga ctattaataa tacttccttg   15600
caaactaaag ttactggagc cttgggtttt gattcacaag gcaatatgca acttaatgta   15660
gcaggaggac taaggattga ttctcaaaac agacgcctta tacttgatgt tagttatccg   15720
tttgatgctc aaaaccaact aaatctaaga ctaggacagg gccctctttt tataaactca   15780
gcccacaact tggatattaa ctacaacaaa ggcctttact tgtttacagc ttcaaacaat   15840
tccaaaaagc ttgaggttaa cctaagcact gccaaggggt tgatgtttga cgctacagcc   15900
atagccatta atgcaggaga tgggcttgaa tttggttcac ctaatgcacc aaacacaaat   15960
cccctcaaaa caaaaattgg ccatggccta gaatttgatt caaacaaggc tatggttcct   16020
aaactaggaa ctggccttag ttttgacagc acaggtgcca ttacagtagg aaacaaaaat   16080
aatgataagc taactttgtg gaccacacca gctccatctc ctaactgtag actaaatgca   16140
gagaaagatg ctaaactcac tttggtctta acaaaatgtg gcagtcaaat acttgctaca   16200
gtttcagttt tggctgttaa aggcagtttg gctccaatat ctggaacagt tcaaagtgct   16260
catcttatta taagatttga cgaaaatgga gtgctactaa caattccttt cctgacccca   16320
gaatattgga acttttagaaa tggagatctt actgaaggca cagcctatac aaacgctgtt   16380
ggatttatgc ctaacctatc agcttatcca aaatctcacg gtaaaactgc caaaagtaac   16440
attgtcagtc aagtttactt aaacggagac aaaactaaac ctgtaacact aaccattaca   16500
ctaaacggta cacaggaaac aggagacaca actccaagtg catactctat gtcattttca   16560
tgggactggt ctggccacaa ctacattaat gaaatatttg ccacatcctc ttacactttt   16620
tcatacattg cccaagaata aagaatcgtt tgtgttatgt ttcaacgtgt ttatttttca   16680
attgcagaaa atttcaagtc attttttcatt cagtagtata gccccaccac cacatagctt   16740
atacagatca ccgtacctta atcaaactca cagaaccccta gtattcaacc tgccacctcc   16800
```

```
ctcccaacac acagagtaca cagtcctttc tccccggctg gccttaaaaa gcatcatatc   16860
atgggtaaca gacatattct taggtgttat attccacacg gtttcctgtc gagccaaacg   16920
ctcatcagtg atattaataa actccccggg cagctcactt aagttcatgt cgctgtccag   16980
ctgctgagcc acaggctgct gtccaacttg cggttgctta acgggcggcg aaggagaagt   17040
ccacgcctac atgggggtag agtcataatc gtgcatcagg atagggcggt ggtgctgcag   17100
cagcgcgcga ataaactgct gccgccgccg ctccgtcctg caggaataca acatggcagt   17160
ggtctcctca gcgatgattc gcaccgcccg cagcataagg cgccttgtcc tccgggcaca   17220
gcagcgcacc ctgatctcac ttaaatcagc acagtaactg cagcacagca ccacaatatt   17280
gttcaaaatc ccacagtgca aggcgctgta tccaaagctc atggcgggga ccacagaacc   17340
cacgtggcca tcataccaca agcgcaggta gattaagtgg cgacccctca taaacacgct   17400
ggacataaac attacctctt ttggcatgtt gtaattcacc acctcccggt accatataaa   17460
cctctgatta aacatggcgc catccaccac catcctaaac cagctggcca aaacctgccc   17520
gccggctata cactgcaggg aaccgggact ggaacaatga cagtggagag cccaggactc   17580
gtaaccatgg atcatcatgc tcgtcatgat atcaatgttg gcacaacaca ggcacacgtg   17640
catacacttc ctcaggatta caagctcctc ccgcgttaga accatatccc agggaacaac   17700
ccattcctga atcagcgtaa atcccacact gcagggaaga cctcgcacgt aactcacgtt   17760
gtgcattgtc aaagtgttac attcgggcag cagcggatga tcctccagta tggtagcgcg   17820
ggtttctgtc tcaaaaggag gtagacgatc cctactgtac ggagtgcgcc gagacaaccg   17880
agatcgtgtt ggtcgtagtg tcatgccaaa tggaacgccg gacgtagtca tatttcctga   17940
agcaaaacca ggtgcgggcg tgacaaacag atctgcgtct ccggtctcgc cgcttagatc   18000
gctctgtgta gtagttgtag tatatccact ctctcaaagc atccaggcgc ccctggctt   18060 cgggttctat gtaaactcct tcatgcgccg ctgccctgat aacatccacc accgcagaat   18120
aagccacacc cagccaacct acacattcgt tctgcgagtc acacacggga ggagcgggaa   18180
gagctggaag aaccatgttt tttttttat tccaaaagat tatccaaaac ctcaaaatga   18240
agatctatta agtgaacgcg ctcccctccg gtggcgtggt caaactctac agccaaagaa   18300
cagataatgg catttgtaag atgttgcaca atggcttcca aaaggcaaac ggccctcacg   18360
tccaagtgga cgtaaaggct aaaccccttca gggtgaatct cctctataaa cattccagca   18420
ccttcaacca tgcccaaata attctcatct cgccaccttc tcaatatatc tctaagcaaa   18480
tcccgaatat taagtccggc cattgtaaaa atctgctcca gagcgccctc caccttcagc   18540
ctcaagcagc gaatcatgat tgcaaaaatt caggttcctc acagacctgt ataagattca   18600
aaagcggaac attaacaaaa ataccgcgat cccgtaggtc ccttcgcagg ccagctgaa   18660 cataatcgtg caggtctgca cggaccagcg cggccacttc cccgccagga accatgacaa   18720
aagaacccac actgattatg acacgcatac tcggagctat gctaaccagc gtagccccga   18780
tgtaagcttg ttgcatgggc ggcgatataa aatgcaaggt gctgctcaaa aaatcaggca   18840
aagcctcgcg caaaaaagaa agcacatcgt agtcatgctc atgcagataa aggcaggtaa   18900
gctccggaac caccacagaa aaagacacca ttttctctc aaacatgtct gcgggtttct   18960
gcataaacac aaaataaaat aacaaaaaaa catttaaaca ttagaagcct gtcttacaac   19020
aggaaaaaca acccttataa gcataagacg gactacggcc atgccggcgt gaccgtaaaa   19080
aaactggtca ccgtgattaa aaagcaccac cgacagctcc tcggtcatgt ccggagtcat   19140
```

```
aatgtaagac tcggtaaaca catcaggttg attcacatcg gtcagtgcta aaaagcgacc   19200
gaaatagccc gggggaatac atacccgcag gcgtagagac aacattacag cccccatagg   19260
aggtataaca aaattaatag gagagaaaaa cacataaaca cctgaaaaac cctcctgcct   19320
aggcaaaata gcaccctccc gctccagaac aacatacagc gcttccacag cggcagccat   19380
aacagtcagc cttaccagta aaaagaaaa cctattaaaa aaacaccact cgacacggca    19440
ccagctcaat cagtcacagt gtaaaaaagg gccaagtgca gagcgagtat atataggact   19500
aaaaaatgac gtaacggtta aagtccacaa aaacaccca gaaaaccgca cgcgaaccta    19560
cgcccagaaa cgaaagccaa aaacccaca acttcctcaa atcgtcactt ccgttttccc    19620
acgttacgtc acttcccatt ttaagaaaac tacaattccc aacacataca agttactccg   19680
ccctaaaacc tacgtcaccc gccccgttcc cacgccccgc gccacgtcac aaactccacc   19740
ccctcattat catattggct tcaatccaaa ataaggtata ttattgatga tgttaattaa   19800
gaattcggat ctgcgacgcg aggctggatg gccttcccca ttatgattct tctcgcttcc   19860
ggcggcatcg ggatgcccgc gttgcaggcc atgctgtcca ggcaggtaga tgacgaccat   19920
cagggacagc ttcaaggcca gcaaaaggcc aggaaccgta aaaaggccgc gttgctggcg   19980 ttttttccata ggctccgccc ccctgacgag catcacaaaa atcgacgctc aagtcagagg   20040
tggcgaaacc cgacaggact ataaagatac caggcgtttc cccctggaag ctccctcgtg   20100
cgctctcctg ttccgaccct gccgcttacc ggatacctgt ccgcctttct cccttcggga   20160
agcgtggcgc tttctcatag ctcacgctgt aggtatctca gttcggtgta ggtcgttcgc   20220
tccaagctgg gctgtgtgca cgaaccccc gttcagcccg accgctgcgc cttatccggt    20280
aactatcgtc ttgagtccaa cccggtaaga cacgacttat cgccactggc agcagccact   20340
ggtaacagga ttagcagagc gaggtatgta ggcggtgcta cagagttctt gaagtggtgg   20400
cctaactacg gctacactag aaggacagta tttggtatct gcgctctgct gaagccagtt   20460
accttcggaa aaagagttgg tagctcttga tccggcaaac aaaccaccgc tggtagcggt   20520
ggtttttttg tttgcaagca gcagattacg cgcagaaaaa aaggatctca agaagatcct   20580
ttgatctttt ctacggggtc tgacgctcag tggaacgaaa actcacgtta agggattttg   20640
gtcatgagat tatcaaaaag gatcttcacc tagatccttt taaatcaatc taaagtatat   20700
atgagtaaac ttggtctgac agttttaaac tcagaagaac tcgtcaagaa ggcgatagaa   20760
ggcgatgcgc tgcgaatcgg gagcggcgat accgtaaagc acgaggaagc ggtcagccca   20820
ttcgccgcca agctcttcag caatatcacg ggtagccaac gctatgtcct gatagcggtc   20880
cgccacaccc agccggccac agtcgatgaa tccagaaaag cggccatttt ccaccatgat   20940
attcggcaag caggcatcgc catgggtcac gacgagatcc tcgccgtcgg gcatgctcgc   21000
cttgagcctg gcgaacagtt cggctggcgc gagcccctga tgctcttcgt ccagatcatc   21060
ctgatcgaca agaccggctt ccatccgagt acgtgctcgc tcgatgcgat gtttcgcttg   21120
gtggtcgaat gggcaggtag ccggatcaag cgtatgcagc cgccgcattg catcagccat   21180
gatggatact ttctcggcag gagcaaggtg agatgacagg agatcctgcc ccggcacttc   21240
gcccaatagc agccagtccc ttcccgcttc agtgacaacg tcgagcacag ctgcgcaagg   21300
aacgcccgtc gtggccagcc acgatagccg cgctgcctcg tcttgcagtt cattcagggc   21360
accggacagg tcggtcttga caaaaagaac cgggcgcccc tgcgctgaca gccggaacac   21420
ggcggcatca gagcagccga ttgtctgttg tgcccagtca tagccgaata gcctctccac   21480
ccaagcggcc ggagaacctg cgtgcaatcc atcttgttca atcataacgt tactcttcct   21540
```

```
ttttcaatat tattgaagca tttatcaggg ttattgtctc atgagcggat acatatttga   21600
atgtatttag aaaaataaac aaataggggt tccgcgcaca tttccccgaa aagtgccacc   21660
tgacgtctaa gaaaccatta ttatcatgac attaacctat aaaaataggc gtatcacgag   21720 gcccttttcgt cttcaa                                                  21736

<210> SEQ ID NO 3
<211> LENGTH: 21773
<212> TYPE: DNA
<213> ORGANISM: Artificial Sequence
<220> FEATURE:
<223> OTHER INFORMATION: SYNTHETIC POLYNUCLEOTIDE

<400> SEQUENCE: 3
gaattggatc cgaattctta attaacatca tcaataatat accttatttt ggattgaagc     60
caatatgata atgagggggt ggagtttgtg acgtggcgcg gggcgtggga acggggcggg    120
tgacgtagta gtgtggcgga agtgtgatgt tgcaagtgtg gcggaacaca tgtaagcgac    180
ggatgtggca aaagtgacgt ttttggtgtg cgccggtgta cacaggaagt gacaattttc    240
gcgcggtttt aggcggatgt tgtagtaaat ttgggcgtaa ccgagtaaga tttggccatt    300
ttcgcgggaa aactgaataa gaggaagtga aatctgaata attttgtgtt actcatagcg    360
cgtaatattt gtctagggcc gcggggactt tgaccgttta cgtggagact cgcccaggtg    420
tttttctcag gtgttttccg cgttccgggt caaagttggc gttttattat tatagtcagg    480
gggatcctct agaactagtg gatccgtccc tcaggcctag aagtaaaaaa gggaaaaaag    540
agtgtgtttg tcaaaatagg agacaggtgg tggcaaccaa ggacttatag gggaccttac    600
atctacagac caacagatgc ccccttacca tatacaggaa gatatgactt aaattgggat    660
aggtgggtca caatcaacgg ctataaagtg ttatacagat ccctcccctc cccttttcgtg    720 aaagactcgc cagagctaga cctccttggt gtatgctaac tgagaagaga aagacgacat    780
gaaacaacag gtacatgatt atatttatct aggaacagga atgcactttt ggggaaaggt    840
tttccatacc aaggaagggg cagtggctgg actgatagaa cattattctg caaaaactta    900
tggtatgagt tattatgatt agcctttatt tgcccaacct tgcggttccc agggtttaaa    960
taagtttatg gttacaaact gttcttaaaa cgaggatgtg agacaagtgg tttcctgact   1020
tggtttggta atcaaatgtt ctgatctgag ctcttagtgt tctatttcc tatgttcttt    1080 tggaatctat ccaagtctta tgtaaatgct tatgtaaacc ataatataaa agagtgctga   1140
ttttttgagt aaacttgcaa cagtcctaac attcttctct cgtgtgtttg tgtctgttcg   1200
ccatcccgtc tccgctcgtc acttatcctt cactttttcag agggtccccc cgcagatccc   1260
ggtcaccctc aggtcgggac ctgcagaaga cgcccgagtg agcacgcagg gtctccattt   1320
tgaagcggga ggtttgaacg cgcagccgcc atgccggggt tttacgagat tgtgattaag   1380
gtccccagcg accttgacgg gcatctgccc ggcatttctg acagctttgt gaactgggtg   1440
gccgagaagg aatgggagtt gccgccagat tctgacatgg atctgaatct gattgagcag   1500 gcaccccctga ccgtggccga aagctgcag cgcgactttc tgacggaatg gcgccgtgtg   1560
agtaaggccc cggaggccct tttctttgtg caatttgaga aggagagag ctacttccac   1620 atgcacgtgc tcgtggaaac caccggggtg aaatccatgg ttttgggacg tttcctgagt   1680
cagattcgcg aaaaactgat tcagagaatt taccgcggga tcgagccgac tttgccaaac   1740
tggttcgcgg tcacaaagac cagaaatggc gccggaggcg ggaacaaggt ggtggatgag   1800
```

```
tgctacatcc ccaattactt gctccccaaa acccagcctg agctccagtg ggcgtggact    1860
aatatggaac agtatttaag cgcctgtttg aatctcacgg agcgtaaacg gttggtggcg    1920
cagcatctga cgcacgtgtc gcagacgcag gagcagaaca aagagaatca gaatcccaat    1980
tctgatgcgc cggtgatcag atcaaaaact tcagccaggt acatggagct ggtcgggtgg    2040
ctcgtggaca aggggattac ctcggagaag cagtggatcc aggaggacca ggcctcatac    2100
atctccttca atgcggcctc caactcgcgg tcccaaatca aggctgcctt ggacaatgcg    2160
ggaaagatta tgagcctgac taaaaccgcc cccgactacc tggtgggcca gcagcccgtg    2220
gaggacattt ccagcaatcg gatttataaa attttggaac taaacgggta cgatccccaa    2280
tatgcggctt ccgtctttct gggatgggcc acgaaaaagt tcggcaagag gaacaccatc    2340
tggctgtttg ggcctgcaac taccgggaag accaacatcg cggaggccat agcccacact    2400
gtgcccttct acgggtgcgt aaactggacc aatgagaact ttcccttcaa cgactgtgtc    2460
gacaagatgg tgatctggtg ggaggagggg aagatgaccg ccaaggtcgt ggagtcggcc    2520
aaagccattc tcggaggaag caaggtgcgc gtggaccaga aatgcaagtc ctcggcccag    2580
atagacccga ctcccgtgat cgtcacctcc aacaccaaca tgtgcgccgt gattgacggg    2640
aactcaacga ccttcgaaca ccagcagccg ttgcaagacc ggatgttcaa atttgaactc    2700
acccgccgtc tggatcatga cttttgggaag gtcaccaagc aggaagtcaa agacttttc    2760 cggtgggcaa aggatcacgt ggttgaggtg gagcatgaat tctacgtcaa aaagggtgga    2820
gccaagaaaa gacccgcccc cagtgacgca gatataagtg agcccaaacg ggtgcgcgag    2880
tcagttgcgc agccatcgac gtcagacgcg gaagcttcga tcaactacgc agacaggtac    2940
caaaacaaat gttctcgtca cgtgggcatg aatctgatgc tgtttccctg cagacaatgc    3000
gagagaatga atcagaattc aaatatctgc ttcactcacg gacagaaaga ctgtttagag    3060
tgctttcccg tgtcagaatc tcaacccgtt tctgtcgtca aaaagcgta tcagaaactg    3120 tgctacattc atcatatcat gggaaaggtg ccagacgctt gcactgcctg cgatctggtc    3180
aatgtggatt tggatgactg catctttgaa caataaatga tttaaatcag gtatgtcttt    3240
tgttgatcac cctccagatt ggttggaaga agttggtgaa ggtcttcgcg agttttttggg    3300 ccttgaagcg ggcccaccga aaccaaaacc caatcagcag catcaagatc aagcccgtgg    3360
tcttgtgctg cctggttata actatctcgg acccggaaac ggtctcgatc gaggagagcc    3420
tgtcaacagg gcagacgagg tcgcgcgaga gcacgacatc tcgtacaacg agcagcttga    3480
ggcgggagaa aacccctacc tcaagtacaa ccacgcggac gccgagtttc aggagaagct    3540
cgccgacgac acatccttcg ggggaaacct cggaaaggca gtctttcagg ccaagaaaag    3600
ggttctcgaa ccttttggcc tggttgaaga gggtgctaag acggcccta ccggaaagcg    3660 gatagacgac cactttccaa aaagaaagaa ggcccggacc gaagaggact ccaagccttc    3720
cacctcgtca gacgccgaag ctggaccag cggatcccag cagctgcaaa tcccagccca    3780
accagcctca gtttgggag ctgatacaat gtctgcggga ggtggcggcc cattgggcga    3840
caataaccaa ggtgccgatg gagtgggcaa tgcctcggga gattggcatt gcgattccac    3900
gtggatgggg gacagagtcg tcaccaagtc caccgaacc tgggtgctgc ccagctacaa    3960
caaccaccag taccgagaga tcaaaagcgg ctccgtcgac ggaagcaacg ccaacgccta    4020
ctttggatac agcaccccct gggggtactt tgactttaac cgcttccaca gccactggag    4080
cccccgagac tggcaaagac tcatcaacaa ctactgggg ttcagacccc ggtccctcag    4140
agtcaaaatc ttcaacattc aagtcaaaga ggtcacggtg caggactcca ccaccaccat    4200
```

```
cgccaacaac ctcacctcca ccgtccaagt gtttacggac gacgactacc agctgccta    4260 cgtcgtcggc aacgggaccg agggatgcct gccggccttc cctccgcagg tctttacgct    4320
gccgcagtac ggttacgcga cgctgaaccg cgacaacaca gaaaatccca ccgagaggag    4380
cagcttcttc tgcctagagt actttcccag caagatgctg agaacgggca caactttga    4440 gtttacctac aactttgagg aggtgccctt ccactccagc ttcgctccca gtcagaacct    4500
cttcaagctg gccaacccgc tggtggacca gtacttgtac cgcttcgtga gcacaaataa    4560
cactggcgga gtccagttca caagaacct ggccgggaga tacgccaaca cctacaaaaa     4620
ctggttcccg gggcccatgg gccgaaccca gggctgaac ctgggctccg ggtcaaccg      4680 cgccagtgtc agcgccttcg ccacgaccaa taggatggag ctcgagggcg cgagttacca    4740
ggtgcccccg cagccgaacg gcatgaccaa caacctccag ggcagcaaca cctatgccct    4800
ggagaacact atgatcttca cagccagcc ggcgaacccg gcaccaccg ccacgtacct      4860 cgagggcaac atgctcatca ccagcgagag cgagacgcag ccggtgaacc gcgtggcgta    4920
caacgtcggc gggcagatgg ccaccaacaa ccagagctcc accactgccc ccgcgaccgg    4980
cacgtacaac ctccaggaaa tcgtgcccgg cagcgtgtgg atggagaggg acgtgtacct    5040
ccaaggaccc atctgggcca agatcccaga gacggggcg cactttcacc cctctccggc     5100
catgggcgga ttcggactca aacacccacc gcccatgatg ctcatcaaga acacgcctgt    5160
gcccggaaat atcaccagct ctcggacgt gcccgtcagc agcttcatca cccagtacag     5220
caccgggcag gtcaccgtgg agatggagtg ggagctcaag aaggaaaact ccaagaggtg    5280
gaacccagag atccagtaca caacaacta caacgacccc cagtttgtgg actttgcccc    5340
ggacagcacc ggggaataca gaaccaccag acctatcgga acccgatacc ttacccgacc    5400
cctttaattg cttgttaatc aataaaccgt ttaattcgtt tcagttgaac tttggtctct    5460
gcgtatttct ttcttatcta gtttccatgc tctagagcgg ccgccaatcg atgcatgtcc    5520
ttgggtccgg cctgctgaat gcgcaggcgg tcggccatgc cccaggcttc gttttgacat    5580
cggcgcaggt ctttgtagta gtcttgcatg agccttcta ccggcacttc ttcttctcct     5640
tcctcttgtc ctgcatctct tgcatctatc gctgcgcgg cggcggagtt tggccgtagg    5700
tggcgccctc ttcctcccat cgtgtgaccc cgaagcccct catcggctga agcagggcta    5760
ggtcggcgac aacgcgctcg gctaatatgg cctgctgcac ctgcgtgagg gtagactgga    5820
agtcatccat gtccacaaag cggtggtatg cgccgtgtt gatggtgtaa gtgcagttgg     5880
ccataacgga ccagttaacg gtctggtgac ccggctgcga gagctcggtg tacctgagac    5940
gcgagtaagc cctcgagtca aatacgtagt cgttacaagt ccgcaccagg tactggtatc    6000
ccaccaaaaa gtgcggcggc ggctggcggt agaggggcca gcgtagggtg gccgggctc    6060 cgggggcgag atcttccaac ataaggcgat gatatccgta gatgtacctg gacatccagg    6120
tgatgccggc ggcggtggtg gaggcgcgcg gaaagtcgcg gacgcggttc agatgttgc     6180 gcagcggcaa aaagtgctcc atggtcggga cgctctggcc ggtcaggcgc gcgcaatcgt    6240
tgacgctcta gaccgtgcaa aaggagagcc tgtaagcggg cactcttccg tggtctggtg    6300
gataaattcg caagggtatc atggcggacg accggggttc gagccccgta tccggccgtc    6360
cgccgtgatc catgcggtta ccgcccgcgt gtcgaaccca ggtgtgcgac gtcagacaac    6420
gggggagtgc tccttttggc ttccttccag gcgcggcggc tgctgcgcta gctttttgg     6480 ccactggccg cgcgcagcgt aagcggttag gctggaaagc gaaagcatta agtggctcgc    6540
```

```
tccctgtagc cggagggtta ttttccaagg gttgagtcgc gggaccccccg gttcgagtct    6600
cggaccggcc ggactgcggc gaacgggggt ttgtctcccc gtcatgcaag accccgcttg    6660
caaattcctc cggaaacagg gacgagcccc tttttgctt ttcccagatg catccggtgc     6720
tgcggcagat gcgccccct cctcagcagc ggcaagagca agagcagcgg cagacatgca     6780
gggcaccctc ccctcctcct accgcgtcag gaggggcgac atccgcggtt gacgcggcag    6840
cagatggtga ttacgaaccc ccgcggcgcc gggcccggca ctacctggac ttggaggagg    6900
gcgagggcct ggcgcggcta ggagcgccct ctcctgagcg gcacccaagg gtgcagctga    6960
agcgtgatac gcgtgaggcg tacgtgccgc ggcagaacct gtttcgcgac cgcgagggag    7020
aggagcccga ggagatgcgg gatcgaaagt tccacgcagg gcgcgagctg cggcatggcc    7080
tgaatcgcga gcggttgctg cgcgaggagg actttgagcc cgacgcgcga accgggatta    7140
gtcccgcgcg cgcacacgtg gcggccgccg acctggtaac cgcatacgag cagacggtga    7200
accagggcga tcgcacccttt tggcgcatcc cattctccag taactttatg tccatgggcg    7260
cactcacaga cctgggccaa aaccttctct acgccaactc cgcccacgcg ctagacatga    7320
cttttgaggt ggatcccatg gacgagccca cccttctta tgttttgttt gaagtctttg     7380
acgtggtccg tgtgcaccgg ccgcaccgcg gcgtcatcga aaccgtgtac ctgcgcacgc    7440
ccttctcggc cggcaacgcc acaacataaa gaagcaagca acatcaacaa cagctgccgc    7500
catgggctcc agtgagcagg aactgaaagc cattgtcaaa gatcttggtt gtgggccata    7560
ttttttgggc acctatgaca agcgcttttcc aggctttgtt tctccacaca agctcgcctg    7620
cgccatagtc aatacggccg gtcgcgagac tgggggcgta cactggatgg cctttgcctg    7680
gaacccgcac tcaaaaacat gctacctctt tgagcccttt ggcttttctg accagcgact    7740
caagcaggtt taccagtttg agtacagatc actcctgcgc cgtagcgcca ttgcttcttc    7800
ccccgaccgc tgtataacgc tggaaaagtc caccccaaagc gtacaggggc ccaactcggc    7860
cgcctgtgga ctattctgct gcatgttcct ccacgccttt gccaactggc cccaaactcc    7920
catggatcac aacccccacca tgaaccttat taccgggggta cccaactcca tgctcaacag    7980
tccccaggta cagcccaccc tgcgtcgcaa ccaggaacag ctctacagct tcctggagcg    8040
ccactcgccc tacttccgca gccacagtgc gcagattagg agcgccactt ctttttgtca    8100
cttgaaaaac atgtaaaaat aatgtactag agacactttc aataaaggca aatgctttta    8160
tttgtacact ctcggtgat tatttacccc cacccttgcc gtctgcgccg tttaaaaatc     8220
aaaggggttc tgccgcgcat cgctatgcgc cactggcagg gacacgttgc gatactggtg    8280
tttagtgctc cacttaaact caggcacaac catccgcggc agctcggtga agttttcact    8340
ccacaggctg cgcaccatca ccaacgcgtt tagcaggtcg ggcgccgata tcttgaagtc    8400
gcagttgggg cctccgccct gcgcgcgcga gttgcgatac acagggttgc agcactggaa    8460
cactatcagc gccgggtggt gcacgctggc cagcacgctc ttgtcggaga tcagatccgc    8520
gtccaggtcc tcccgcgttgc tcagggcgaa cggagtcaac tttggtagct gccttcccaa    8580
aaagggcgcg tgcccaggct ttgagttgca ctcgcaccgt agtggcatca aaggtgacc     8640
gtgcccggtc tgggcgttag gatacagcgc ctgcataaaa gccttgatct gcttaaaagc    8700
cacctgagcc tttgcgcctt cagagaagaa catgccgcaa gacttgccgg aaaactgatt    8760
ggccggacag gccgcgtcgt gcacgcagca ccttgcgtcg gtgttggaga tctgcaccac    8820
atttcggccc caccgttct tcacgatctt ggccttgcta gactgctcct tcagcgcgcg    8880
ctgcccgttt tcgctcgtca catccatttc aatcacgtgc tccttattta tcataatgct    8940
```

```
tccgtgtaga cacttaagct cgccttcgat ctcagcgcag cggtgcagcc acaacgcgca   9000
gcccgtgggc tcgtgatgct tgtaggtcac ctctgcaaac gactgcaggt acgcctgcag   9060
gaatcgcccc atcatcgtca caaaggtctt gttgctggtg aaggtcagct gcaacccgcg   9120
gtgctcctcg ttcagccagg tcttgcatac ggccgccaga gcttccactt ggtcaggcag   9180
tagtttgaag ttcgccttta gatcgttatc cacgtggtac ttgtccatca gcgcgcgcgc   9240
agcctccatg cccttctccc acgcagacac gatcggcaca ctcagcgggt tcatcaccgt   9300
aatttcactt tccgcttcgc tgggctcttc ctcttcctct tgcgtccgca taccacgcgc   9360
cactgggtcg tcttcattca gccgccgcac tgtgcgctta cctcctttgc catgcttgat   9420
tagcaccggt gggttgctga aacccaccat tgtagcgcc  acatcttctc tttcttcctc   9480
gctgtccacg attacctctg gtgatggcgg gcgctcgggc ttgggagaag gcgcttctt    9540
tttcttcttg ggcgcaatgg ccaaatccgc cgccgaggtc gatggccgcg ggctgggtgt   9600
gcgcggcacc agcgcgtctt gtgatgagtc ttcctcgtcc tcggactcga tacgccgcct   9660
catccgcttt tttgggggcg cccggggagg cggcggcgac ggggacgggg acgacacgtc   9720
ctccatggtt gggggacgtc gcgccgcacc gcgtccgcgc tcgggggtgg tttcgcgctg   9780
ctcctcttcc cgactggcca tttccttctc ctataggcag aaaaagatca tggagtcagt   9840
cgagaagaag gacagcctaa ccgccccctc tgagttcgcc accaccgcct ccaccgatgc   9900
cgccaacgcg cctaccacct tccccgtcga ggcacccccg cttgaggagg aggaagtgat   9960
tatcgagcag gacccaggtt ttgtaagcga agacgacgag gaccgctcag taccaacaga  10020
ggataaaaag caagaccagg acaacgcaga ggcaaacgag gaacaagtcg ggcgggggga  10080
cgaaaggcat ggcgactacc tagatgtggg agacgacgtg ctgttgaagc atctgcagcg  10140
ccagtgcgcc attatctgcg acgcgttgca agagcgcagc gatgtgcccc tcgccatagc  10200
ggatgtcagc cttgcctacg aacgccacct attctcaccg cgcgtacccc ccaaacgcca  10260
agaaaacggc acatgcgagc ccaacccgcg cctcaacttc taccccgtat ttgccgtgcc  10320
agaggtgctt gccacctatc acatcttttt ccaaaactgc aagataccccc tatcctgccg  10380
tgccaaccgc agccgagcgg acaagcagct ggccttgcgg cagggcgctg tcatacctga  10440
tatcgcctcg ctcaacgaag tgccaaaaat ctttgagggt cttggacgcg acgagaagcg  10500
cgcggcaaac gctctgcaac aggaaaacag cgaaaatgaa agtcactctg gagtgttggt  10560
ggaactcgag ggtgacaacg cgcgcctagc cgtactaaaa cgcagcatcg aggtcaccca  10620
cttttgcctac ccggcactta acctaccccc caaggtcatg agcacagtca tgagtgagct  10680
gatcgtgcgc cgtgcgcagc ccctggagag ggatgcaaat ttgcaagaac aaacagagga  10740
gggcctaccc gcagttggcg acgagcagct agcgcgctgg cttcaaacgc gcgagcctgc  10800
cgacttggag gagcgacgca aactaatgat ggccgcagtg ctcgttaccg tggagcttga  10860
gtgcatgcag cggttctttg ctgacccgga tgcagcgc aagctagagg aaacattgca   10920
ctacacctt  cgacagggct acgtacgcca ggcctgcaag atctccaacg tggagctctg  10980
caacctggtc tcctaccttg gaattttgca cgaaaccgc cttgggcaaa acgtgcttca   11040
ttccacgctc aagggcgagg cgcgccgcga ctacgtccgc gactgcgttt acttatttct  11100
atgctacacc tggcagacgg ccatgggcgt ttggcagcag tgcttggagg agtgcaacct  11160
caaggagctg cagaaactgc taagcaaaa  cttgaaggac ctatgacgg ccttcaacga   11220
gcgctccgtg gccgcgcacc tggcggacat cattttcccc gaacgcctgc ttaaaaccct  11280
```

```
gcaacagggt ctgccagact tcaccagtca aagcatgttg cagaacttta ggaactttat    11340
cctagagcgc tcaggaatct tgcccgccac ctgctgtgca cttcctagcg actttgtgcc    11400
cattaagtac cgcgaatgcc ctccgccgct ttggggccac tgctaccttc tgcagctagc    11460
caactacctt gcctaccact ctgacataat ggaagacgtg agcggtgacg gtctactgga    11520
gtgtcactgt cgctgcaacc tatgcacccc gcaccgctcc ctggtttgca attcgcagct    11580
gcttaacgaa agtcaaatta tcggtacctt tgagctgcag ggtccctcgc ctgacgaaaa    11640
gtccgcggct ccggggttga aactcactcc ggggctgtgg acgtcggctt accttcgcaa    11700
atttgtacct gaggactacc acgcccacga gattaggttc tacgaagacc aatcccgccc    11760
gccaaatgcg gagcttaccg cctgcgtcat tacccagggc cacattcttg gccaattgca    11820
agccatcaac aaagcccgcc aagagtttct gctacgaaag gacgggggg tttacttgga    11880 ccccccagtcc ggcgaggagc tcaacccaat ccccccgccg ccgcagccct atcagcagca    11940
gccgcgggcc cttgcttccc aggatggcac ccaaaaagaa gctgcagctg ccgccgccac    12000
ccacggacga ggaggaatac tgggacagtc aggcagagga ggttttggac gaggaggagg    12060
aggacatgat ggaagactgg gagagcctag acgaggaagc ttccgaggtc gaagaggtgt    12120
cagacgaaac accgtcaccc tcggtcgcat tcccctcgcc ggcgcccag aaatcggcaa    12180 ccggttccag catggctaca acctccgctc ctcaggcgcc gccggcactg cccgttcgcc    12240
gacccaaccg tagatgggac accactggaa ccagggccgg taagtccaag cagccgccgc    12300
cgttagccca agagcaacaa cagcgccaag gctaccgctc atggcgcggg cacaagaacg    12360
ccatagttgc ttgcttgcaa gactgtgggg gcaacatctc cttcgcccgc cgctttcttc    12420
tctaccatca cggcgtggcc ttcccccgta acatcctgca ttactaccgt catctctaca    12480
gcccatactg caccggcggc agcggcagcg gcagcaacag cagcgccac acagaagcaa    12540 aggcgaccgg atagcaagac tctgacaaag cccaagaaat ccacagcggc ggcagcagca    12600
ggaggaggag cgctgcgtct ggcgcccaac gaacccgtat cgaccccgcga gcttagaaac    12660 aggattttc ccactctgta tgctatattt caacagagca ggggccaaga acaagagctg    12720
aaaataaaaa acaggtctct gcgatccctc acccgcagct gcctgtatca caaaagcgaa    12780
gatcagcttc ggcgcacgct ggaagacgcg gaggctctct tcagtaaata ctgcgcgctg    12840
actcttaagg actagtttcg cgccctttct caaatttaag cgcgaaaact acgtcatctc    12900
cagcggccac accggcgcc agcacctgtc gtcagcgcca ttatgagcaa ggaaattccc    12960
acgccctaca tgtggagtta ccagccacaa atgggacttg cggctggagc tgcccaagac    13020
tactcaaccc gaataaacta catgagcgcg ggaccccaca tgatatcccg ggtcaacgga    13080
atccgcgccc accgaaaccg aattctcttg gaacaggcgg ctattaccac cacacctcgt    13140
aataacctta atccccgtag ttggcccgct gccctggtgt accaggaaag tcccgctccc    13200
accactgtgg tacttcccag agacgcccag gccgaagttc agatgactaa ctcaggggcg    13260
cagcttgcgg gcggctttcg tcacagggtg cggtcgcccg gcagggtat aactcacctg    13320 acaatcagag ggcgaggtat tcagctcaac gacgagtcgg tgagctcctc gcttggtctc    13380
cgtccggacg ggacatttca gatcggcggc gccggccgct cttcattcac gcctcgtcag    13440
gcaatcctaa ctctgcagac ctcgtcctct gagccgcgct ctggaggcat tggaactctg    13500
caatttattg aggagtttgt gccatcggtc tactttaacc ccttctcggg acctccggc    13560 cactatccgg atcaatttat tcctaacttt gacgcggtaa aggactcggc ggatggctac    13620
gactgaatgt taagtggaga ggcagagcaa ctgcgcctga aacacctggt ccactgtcgc    13680
```

```
cgccacaagt gctttgcccg cgactccggt gagttttgct actttgaatt gcccgaggat   13740
catatcgagg gcccggcgca cggcgtccgg cttaccgccc agggagagct tgcccgtagc   13800
ctgattcggg agtttaccca gcgcccctg ctagttgagc gggacagggg accctgtgtt    13860
ctcactgtga tttgcaactg tcctaaccct ggattacatc aagatctttg ttgccatctc   13920
tgtgctgagt ataataaata cagaaattaa aatatactgg ggctcctatc gccatcctgt   13980
aaacgccacc gtcttcaccc gcccaagcaa accaaggcga accttacctg gtacttttaa   14040
catctctccc tctgtgattt acaacagttt caacccagac ggagtgagtc tacgagagaa   14100
cctctccgag ctcagctact ccatcagaaa aaacaccacc ctccttacct gccgggaacg   14160
tacgagtgcg tcaccggccg ctgcaccaca cctaccgcct gaccgtaaac cagactttt    14220 ccggacagac ctcaataact ctgtttacca gaacaggagg tgagcttaga aaacccttag   14280
ggtattaggc caaaggcgca gctactgtgg ggtttatgaa caattcaagc aactctacgg   14340
gctattctaa ttcaggtttc tctagaaatg gacggaatta ttacagagca gcgcctgcta   14400
gaaagacgca gggcagcggc cgagcaacag cgcatgaatc aagagctcca agacatggtt   14460
aacttgcacc agtgcaaaag gggtatcttt tgtctggtaa agcaggccaa agtcacctac   14520
gacagtaata ccaccggaca ccgccttagc tacaagttgc caaccaagcg tcagaaattg   14580
gtggtcatgg tgggagaaaa gcccattacc ataactcagc actcggtaga accgaaggc    14640 tgcattcact caccttgtca aggacctgag gatctctgca cccttattaa gaccctgtgc   14700
ggtctcaaag atcttattcc ctttaactaa taaaaaaaa taataaagca tcacttactt    14760
aaaatcagtt agcaaatttc tgtccagttt attcagcagc acctccttgc cctcctccca   14820
gctctggtat tgcagcttcc tcctggctgc aaactttctc cacaatctaa atggaatgtc   14880
agtttcctcc tgttcctgtc catccgcacc cactatcttc atgttgttgc agatgaagcg   14940
cgcaagaccg tctgaagata ccttcaaccc cgtgtatcca tatgacacgg aaaccggtcc    15000
tccaactgtg ccttttctta ctcctccctt tgtatccccc aatgggtttc aagagagtcc    15060
ccctggggta ctctctttgc gcctatccga acctctagtt acctccaatg gcatgcttgc   15120
gctcaaaatg ggcaacggcc tctctctgga cgaggccggc aaccttacct cccaaaatgt   15180
aaccactgtg agcccacctc tcaaaaaaac caagtcaaac ataaacctgg aaatatctgc   15240 accctcaca gttacctcag aagccctaac tgtggctgcc gccgcacctc taatggtcgc    15300
gggcaacaca ctcaccatgc aatcacaggc cccgctaacc gtgcacgact ccaaacttag   15360
cattgccacc caaggacccc tcacagtgtc agaaggaaag ctagccctgc aaacatcagg   15420 cccccctcacc accaccgata gcagtaccct tactatcact gcctcacccc ctctaactac   15480
tgccactggt agcttgggca ttgacttgaa agagcccatt tatacacaaa atggaaaact   15540
aggactaaag tacggggctc ctttgcatgt aacagacgac ctaaacactt tgaccgtagc   15600
aactggtcca ggtgtgacta ttaataatac ttccttgcaa actaaagtta ctggagcctt   15660
gggttttgat tcacaaggca atatgcaact taatgtagca ggaggactaa ggattgattc   15720
tcaaaacaga cgccttatac ttgatgttag ttatccgttt gatgctcaaa accaactaaa   15780
tctaagacta ggacagggcc ctctttttat aaactcagcc cacaacttgg atattaacta   15840
caacaaaggc ctttacttgt ttacagcttc aaacaattcc aaaaagcttg aggttaacct   15900
aagcactgcc aagggttgaa tgtttgacgc tacagccata gccattaatg caggagatgg   15960
gcttgaattt ggttcaccta atgcaccaaa cacaaatccc ctcaaaacaa aaattggcca   16020
```

```
tggcctagaa tttgattcaa acaaggctat ggttcctaaa ctaggaactg gccttagttt    16080
tgacagcaca ggtgccatta cagtaggaaa caaaaataat gataagctaa ctttgtggac    16140
cacaccagct ccatctccta actgtagact aaatgcagag aaagatgcta aactcacttt    16200
ggtcttaaca aaatgtggca gtcaaatact tgctacagtt tcagttttgg ctgttaaagg    16260
cagtttggct ccaatatctg gaacagttca aagtgctcat cttattataa gatttgacga    16320
aaatggagtg ctactaaaca attccttcct ggacccagaa tattggaact ttagaaatgg    16380
agatcttact gaaggcacag cctatacaaa cgctgttgga tttatgccta acctatcagc    16440
ttatccaaaa tctcacggta aaactgccaa aagtaacatt gtcagtcaag tttacttaaa    16500
cggagacaaa actaaacctg taacactaac cattacacta aacggtacac aggaaacagg    16560
agacacaact ccaagtgcat actctatgtc attttcatgg gactggtctg cccacaacta    16620
cattaatgaa atatttgcca catcctctta cacttttttca tacattgccc aagaataaag    16680
aatcgtttgt gttatgtttc aacgtgttta tttttcaatt gcagaaaatt tcaagtcatt    16740
tttcattcag tagtatagcc ccaccaccac atagcttata cagatcaccg taccttaatc    16800
aaactcacag aacccctagta ttcaacctgc caccctccctc ccaacacaca gagtacacag    16860 tccttttctcc ccggctggcc ttaaaaagca tcatatcatg ggtaacagac atattcttag    16920
gtgttatatt ccacacggtt tcctgtcgag ccaaacgctc atcagtgata ttaataaact    16980 cccccgggcag ctcacttaag ttcatgtcgc tgtccagctg ctgagccaca ggctgctgtc    17040
caacttgcgg ttgcttaacg ggcggcgaag gagaagtcca cgcctacatg ggggtagagt    17100
cataatcgtg catcaggata gggcggtggt gctgcagcag cgcgcgaata aactgctgcc    17160
gccgccgctc cgtcctgcag gaatacaaca tggcagtggt ctcctcagcg atgattcgca    17220
ccgcccgcag cataaggcgc cttgtcctcc gggcacagca gcgcaccctg atctcactta    17280
aatcagcaca gtaactgcag cacagcacca caatattgtt caaaatccca cagtgcaagg    17340
cgctgtatcc aaagctcatg gcggggacca cagaacccac gtggccatca taccacaagc    17400
gcaggtagat taagtggcga cccctcataa acacgctgga cataaacatt acctcttttg    17460
gcatgttgta attcaccacc tcccggtacc atataaacct ctgattaaac atggcgccat    17520
ccaccaccat cctaaaccag ctggccaaaa cctgcccgcc ggctatacac tgcagggaac    17580
cgggactgga acaatgacag tggagagccc aggactcgta accatggatc atcatgctcg    17640
tcatgatatc aatgttggca caacacaggc acacgtgcat acacttcctc aggattacaa    17700
gctcctcccg cgttagaacc atatcccagg gaacaaccca ttcctgaatc agcgtaaatc    17760
ccacactgca gggaagacct cgcacgtaac tcacgttgtg cattgtcaaa gtgttacatt    17820
cgggcagcag cggatgatcc tccagtatgg tagcgcgggt ttctgtctca aaaggaggta    17880
gacgatccct actgtacgga gtgcgccgag acaaccgaga tcgtgttggt cgtagtgtca    17940
tgccaaatgg aacgccggac gtagtcatat ttcctgaagc aaaaccaggt gcgggcgtga    18000
caaacagatc tgcgtctccg gtctcgccgc ttagatcgct ctgtgtagta gttgtagtat    18060
atccactctc tcaaagcatc caggcgcccc ctggcttcgg gttctatgta aactccttca    18120
tgcgccgctg ccctgataac atccaccacc gcagaataag ccacacccag ccaacctaca    18180
cattcgttct gcgagtcaca cacgggagga gcgggaagag ctggaagaac catgtttttt    18240
tttttattcc aaaagattat ccaaaacctc aaaatgaaga tctattaagt gaacgcgctc    18300
ccctccggtg gcgtggtcaa actctacagc caaagaacag ataatggcat ttgtaagatg    18360
ttgcacaatg gcttccaaaa ggcaaacggc cctcacgtcc aagtggacgt aaaggctaaa    18420
```

```
cccttcaggg tgaatctcct ctataaacat tccagcacct tcaaccatgc ccaaataatt   18480
ctcatctcgc caccttctca atatatctct aagcaaatcc cgaatattaa gtccggccat   18540
tgtaaaaatc tgctccagag cgccctccac cttcagcctc aagcagcgaa tcatgattgc   18600
aaaaattcag gttcctcaca gacctgtata agattcaaaa gcggaacatt aacaaaaata   18660
ccgcgatccc gtaggtccct tcgcagggcc agctgaacat aatcgtgcag gtctgcacgg   18720
accagcgcgg ccacttcccc gccaggaacc atgacaaaag aacccacact gattatgaca   18780
cgcatactcg gagctatgct aaccagcgta gccccgatgt aagcttgttg catgggcggc   18840
gatataaaat gcaaggtgct gctcaaaaaa tcaggcaaag cctcgcgcaa aaagaaagc    18900 acatcgtagt catgctcatg cagataaagg caggtaagct ccggaaccac cacagaaaaa   18960
gacaccattt ttctctcaaa catgtctgcg ggtttctgca taaacacaaa ataaaataac   19020
aaaaaaacat ttaaacatta gaagcctgtc ttacaacagg aaaaacaacc cttataagca   19080
taagacggac tacggccatg ccggcgtgac cgtaaaaaaa ctggtcaccg tgattaaaaa   19140
gcaccaccga cagctcctcg gtcatgtccg gagtcataat gtaagactcg gtaaacacat   19200
caggttgatt cacatcggtc agtgctaaaa agcgaccgaa atagcccggg ggaatacata   19260
cccgcaggcg tagagacaac attacagccc ccataggagg tataacaaaa ttaataggag   19320
agaaaaacac ataaacacct gaaaaaccct cctgcctagg caaaatagca ccctcccgct   19380
ccagaacaac atacagcgct tccacagcgg cagccataac agtcagcctt accagtaaaa   19440
aagaaaacct attaaaaaaa caccactcga cacggcacca gctcaatcag tcacagtgta   19500
aaaaagggcc aagtgcagag cgagtatata taggactaaa aaatgacgta acggttaaag   19560
tccacaaaaa acacccagaa aaccgcacgc gaacctacgc ccagaaacga agccaaaaa    19620 acccacaact tcctcaaatc gtcacttccg ttttcccacg ttacgtcact tcccatttta   19680
agaaaactac aattcccaac acatacaagt tactccgccc taaaacctac gtcacccgcc   19740
ccgttcccac gccccgcgcc acgtcacaaa ctccaccccc tcattatcat attggcttca   19800
atccaaaata aggtatatta ttgatgatgt taattaagaa ttcggatctg cgacgcgagg   19860
ctggatggcc ttccccatta tgattcttct cgcttccggc ggcatcggga tgcccgcgtt   19920
gcaggccatg ctgtccaggc aggtagatga cgaccatcag ggacagcttc aaggccagca   19980
aaaggccagg aaccgtaaaa aggccgcgtt gctggcgttt ttccataggc tccgcccccc   20040
tgacgagcat cacaaaaatc gacgctcaag tcagaggtgg cgaaacccga caggactata   20100
aagataccag gcgtttcccc ctggaagctc cctcgtgcgc tctcctgttc cgaccctgcc   20160
gcttaccgga tacctgtccg cctttctccc ttcgggaagc gtggcgcttt ctcatagctc   20220
acgctgtagg tatctcagtt cggtgtaggt cgttcgctcc aagctgggct gtgtgcacga   20280
accccccgtt cagcccgacc gctgcgcctt atccggtaac tatcgtcttg agtccaaccc   20340
ggtaagacac gacttatcgc cactggcagc agccactggt aacaggatta gcagagcgag   20400
gtatgtaggc ggtgctacag agttcttgaa gtggtggcct aactacggct acactagaag   20460
gacagtattt ggtatctgcg ctctgctgaa gccagttacc ttcggaaaaa gagttggtag   20520
ctcttgatcc ggcaaacaaa ccaccgctgg tagcggtggt ttttttgttt gcaagcagca   20580
gattacgcgc agaaaaaaag gatctcaaga agatcctttg atcttttcta cggggtctga   20640
cgctcagtgg aacgaaaact cacgttaagg gattttggtc atgagattat caaaaaggat   20700
cttcacctag atccttttaa atcaatctaa agtatatatg agtaaacttg gtctgacagg   20760
```

```
tttaaactca gaagaactcg tcaagaaggc gatagaaggc gatgcgctgc gaatcgggag   20820
cggcgatacc gtaaagcacg aggaagcggt cagcccattc gccgccaagc tcttcagcaa   20880
tatcacgggt agccaacgct atgtcctgat agcggtccgc cacacccagc cggccacagt   20940
cgatgaatcc agaaaagcgg ccattttcca ccatgatatt cggcaagcag gcatcgccat   21000
gggtcacgac gagatcctcg ccgtcgggca tgctcgcctt gagcctggcg aacagttcgg   21060
ctggcgcgag cccctgatgc tcttcgtcca gatcatcctg atcgacaaga ccggcttcca   21120
tccgagtacg tgctcgctcg atgcgatgtt tcgcttggtg gtcgaatggg caggtagccg   21180
gatcaagcgt atgcagccgc cgcattgcat cagccatgat ggatactttc tcggcaggag   21240
caaggtgaga tgacaggaga tcctgccccg gcacttcgcc aatagcagc cagtcccttc    21300
ccgcttcagt gacaacgtcg agcacagctg cgcaaggaac gcccgtcgtg gccagccacg   21360
atagccgcgc tgcctcgtct tgcagttcat tcagggcacc ggacaggtcg gtcttgacaa   21420
aaagaaccgg gcgcccctgc gctgacagcc ggaacacggc ggcatcagag cagccgattg   21480
tctgttgtgc ccagtcatag ccgaatagcc tctccaccca gcggccgga gaacctgcgt    21540
gcaatccatc ttgttcaatc ataacgttac tcttcctttt tcaatattat tgaagcattt   21600
atcagggtta ttgtctcatg agcggataca tatttgaatg tatttagaaa aataaacaaa   21660
taggggttcc gcgcacattt ccccgaaaag tgccacctga cgtctaagaa accattatta   21720
tcatgacatt aacctataaa aataggcgta tcacgaggcc ctttcgtctt caa           21773

<210> SEQ ID NO 4
<211> LENGTH: 21787
<212> TYPE: DNA
<213> ORGANISM: Artificial Sequence
<220> FEATURE:
<223> OTHER INFORMATION: SYNTHETIC POLYNUCLEOTIDE

<400> SEQUENCE: 4
gaattggatc cgaattctta attaacatca tcaataatat accttatttt ggattgaagc     60
caatatgata atgagggggt ggagtttgtg acgtggcgcg gggcgtggga acggggcggg    120
tgacgtagta gtgtggcgga agtgtgatgt tgcaagtgtg gcggaacaca tgtaagcgac    180
ggatgtggca aaagtgacgt ttttggtgtg cgccggtgta cacaggaagt gacaattttc    240
gcgcggtttt aggcggatgt tgtagtaaat ttgggcgtaa ccgagtaaga tttggccatt    300
ttcgcgggaa aactgaataa gaggaagtga atctgaata attttgtgtt actcatagcg     360
cgtaatattt gtctagggcc gcggggactt tgaccgttta cgtggagact cgcccaggtg    420
ttttttctcag gtgttttccg cgttccgggt caaagttggc gttttattat tatagtcagg   480
gggatcctct agaactagtg gatccgtccc tcaggcctag aagtaaaaaa gggaaaaaag    540
agtgtgtttg tcaaaatagg agacaggtgg tgcaaccaa ggacttatag gggaccttac     600
atctacagac caacagatgc ccccttacca tatacaggaa gatatgactt aaattgggat    660
aggtgggtca caatcaacgg ctataaagtg ttatacagat ccctcccctc ccctttcgtg    720
aaagactcgc cagagctaga cctccttggt gtatgctaac tgagaagaga aagacgacat    780
gaaacaacag gtacatgatt atatttatct aggaacagga atgcacttt ggggaaaggt     840
tttccatacc aaggaagggg cagtggctgg actgatagaa cattattctg caaaaactta    900
tggtatgagt tattatgatt agcctttatt tgcccaacct tgcggttccc agggtttaaa    960
taagtttatg gttacaaact gttcttaaaa cgaggatgtg agacaagtgg tttcctgact   1020
tggtttggta atcaaatgtt ctgatctgag ctcttagtgt tctatttccc tatgttcttt   1080
```

```
tggaatctat ccaagtctta tgtaaatgct tatgtaaacc ataatataaa agagtgctga    1140
ttttttgagt aaacttgcaa cagtcctaac attcttctct cgtgtgtttg tgtctgttcg    1200
ccatcccgtc tccgctcgtc acttatcctt cacttttcag agggtccccc cgcagatccc    1260
ggtcaccctc aggtcgggac ctgcagaaga cgcccgagtg agcacgcagg gtctccattt    1320
tgaagcggga ggtttgaacg cgcagccgcc atgccggggt tttacgagat tgtgattaag    1380
gtccccagcg accttgacgg gcatctgccc ggcattctg acagctttgt gaactgggtg     1440
gccgagaagg aatgggagtt gccgccagat tctgacatgg atctgaatct gattgagcag    1500
gcaccgctga ccgtggccga aagctgcag cgcgactttc tgacggaatg gcgccgtgtg     1560
agtaaggccc cggaggccct tttctttgtg caatttgaga agggagagag ctacttccac    1620
atgcacgtgc tcgtggaaac caccggggtg aaatccatgg ttttgggacg tttcctgagt    1680
cagattcgcg aaaaactgat tcagagaatt taccgcggga tcgagccgac tttgccaaac    1740
tggttcgcgg tcacaaagac cagaaatggc gccggaggcg ggaacaaggt ggtggatgag    1800
tgctacatcc ccaattactt gctccccaaa acccagcctg agctccagtg ggcgtggact    1860
aatatggaac agtatttaag cgcctgtttg aatctcacgg agcgtaaacg gttggtggcg    1920
cagcatctga cgcacgtgtc gcagacgcag gagcagaaca aagagaatca gaatcccaat    1980
tctgatgcgc cggtgatcag atcaaaaact tcagccaggt acatggagct ggtcgggtgg    2040
ctcgtggaca aggggattac ctcggagaag cagtggatcc aggaggacca ggcctcatac    2100
atctccttca atgcggcctc caactcgcgg tcccaaatca aggctgcctt ggacaatgcg    2160
ggaaagatta tgagcctgac taaaaccgcc cccgactacc tggtgggcca gcagcccgtg    2220
gaggacattt ccagcaatcg gatttataaa attttggaac taaacgggta cgatccccaa    2280
tatgcggctt ccgtctttct gggatgggcc acgaaaaagt tcggcaagag gaacaccatc    2340
tggctgtttg ggcctgcaac taccgggaag accaacatcg cggaggccat agcccacact    2400
gtgccctcct acgggtgcgt aaactggacc aatgagaact ttcccttcaa cgactgtgtc    2460
gacaagatgg tgatctggtg ggaggagggg aagatgaccg ccaaggtcgt ggagtcggcc    2520
aaagccattc tcggaggaag caaggtgcgc gtggaccaga aatgcaagtc ctcggcccag    2580
atagacccga ctcccgtgat cgtcacctcc aacaccaaca tgtgcgccgt gattgacggg    2640
aactcaacga ccttcgaaca ccagcagccg ttgcaagacc ggatgttcaa atttgaactc    2700
acccgccgtc tggatcatga ctttgggaag gtcaccaagc aggaagtcaa agactttttc    2760
cggtgggcaa aggatcacgt ggttgaggtg gagcatgaat tctacgtcaa aaagggtgga    2820
gccaagaaaa gacccgcccc cagtgacgca gatataagtg agcccaaacg ggtgcgcgag    2880
tcagttgcgc agccatcgac gtcagacgcg gaagcttcga tcaactacgc agacaggtac    2940
caaaacaaat gttctcgtca cgtgggcatg aatctgatgc tgtttccctg cagacaatgc    3000
gagagaatga atcagaattc aaatatctgc ttcactcacg acagaaaga ctgtttagag     3060 tgctttcccg tgtcagaatc tcaacccgtt tctgtcgtca aaaaggcgta tcagaaactg    3120
tgctacattc atcatatcat gggaaaggtg ccagacgctt gcactgcctg cgatctggtc    3180
aatgtggatt tggatgactg catctttgaa caataaatga tttaaatcag gtatggctgc    3240
cgatggttat cttccagatt ggctcgagga caacctctct gagggcattc gcgagtggtg    3300
ggacctgaaa cctggagccc cgaaacccaa agccaaccag caaaagcagg acaacggccg    3360
gggtctggtg cttcctggct acaagtacct cggacccttc aacggactcg acaaggggga    3420
```

```
gcccgtcaac gcggcggacg cagcggccct cgagcacgac aaggcctacg accagcagct   3480
caaagcgggt gacaatccgt acctgcggta taaccacgcc gacgccgagt ttcaggagcg   3540
tctgcaagaa gatacgtcat ttgggggcaa cctcgggcga gcagtcttcc aggccaagaa   3600
gcgggttctc gaacctctcg gtctggttga ggaaggcgct aagacggctc ctgcaaagaa   3660
gagaccggta gagccgtcac ctcagcgttc ccccgactcc tccacgggca tcggcaagaa   3720
aggccagcag cccgccagaa agagactcaa tttcggtcag actggcgact cagagtcagt   3780
ccccgaccct caacctctcg gagaacctcc agcagcgccc tctagtgtgg gatctggtac   3840
agtggctgca gcggtggcg caccaatggc agacaataac gaaggtgccg acggagtggg   3900
taatgcctca ggaaattggc attgcgattc cacatggctg ggcgacagag tcattaccac   3960
cagcacccga acctgggccc tgcccaccta caacaaccac ctctacaagc aaatctccag   4020
tgaaactgca ggtagtacca acgacaacac ctacttcggc tacagcaccc cctgggggta   4080
ttttgacttt aacagattcc actgccactt ctcaccacgt gactggcagc gactcatcaa   4140
caacaactgg ggattccggc caagaagct gcggttcaag ctcttcaaca tccaggtcaa   4200
ggaggtcacg acgaatgacg gcgttacgac catcgctaat aaccttacca gcacgattca   4260
ggtattctcg gactcggaat accagctgcc gtacgtcctc ggctctgcgc accagggctg   4320
cctgcctccg ttcccggcgg acgtcttcat gattcctcag tacggctacc tgactctcaa   4380
caatggcagt cagtctgtgg gacgttcctc cttctactgc ctggagtact cccctctca   4440
gatgctgaga cgggcaaca ctttgagtt cagctacagc ttcgaggacg tgccttttcca  4500
cagcagctac gcacacagcc agagcctgga ccggctgatg aatcccctca tcgaccagta   4560
cttgtactac ctggccagaa cacagagtaa cccaggaggc acagctggca atcgggaact   4620
gcagttttac cagggcgggc cttcaactat ggccgaacaa gccaagaatt ggttacctgg   4680
accttgcttc cggcaacaaa gagtctccaa aacgctggat caaaacaaca acagcaactt   4740
tgcttggact ggtgccacca atatcaccct gaacggcaga aactcgttgg ttaatcccgg   4800
cgtcgccatg gcaactcaca aggacgacga ggaccgcttt ttcccatcca gcggagtcct   4860
gattttgga aaaactggag caactaacaa aactacattg gaaaatgtgt taatgacaaa   4920
tgaagaagaa attcgtccta ctaatcctgt agccacggaa gaatacggga tagtcagcag   4980
caacttacaa gcggctaata ctgcagccca gacacaagtt gtcaacaacc agggagcctt   5040
acctggcatg gtctggcaga accgggacgt gtacctgcag ggtcccatct gggccaagat   5100
tcctcacacg gatggcaact ttcacccgtc tccttttgatg gcggctttg gacttaaaca   5160
tccgcctcct cagatcctga tcaagaacac tcccgttccc gctaatcctc cggaggtgtt   5220
tactcctgcc aagtttgctt cgttcatcac acagtacagc accggacaag tcagcgtgga   5280
aatcgagtgg gagctgcaga aggaaaacag caagcgctgg aacccggaga ttcagtacac   5340
ctccaacttt gaaaagcaga ctggtgtgga ctttgccgtt gacagccagg tgtttactc   5400
tgagcctcgc cctattggca ctcgttacct cacccgtaat ctgtaattgc atgttaatca   5460
ataaaccggt tgattcgttt cagttgaact ttggtctctg cgaagggcga attcgtttcc   5520
atcgatgcat gtccttgggt ccggcctgct gaatgcgcag gcggtcggcc atgccccagg   5580
cttcgttttg acatcggcgc aggtctttgt agtagtcttg catgagcctt tctaccggca   5640
cttcttcttc tccttcctct tgtcctgcat ctccttgcatc tatcgctgcg gcggcggcgg   5700
agtttggccc taggtggcgc cctcttcctc ccatcgtgtg accccgaagc ccctcatcgg   5760
ctgaagcagg gctaggtcgg cgacaacgcg ctcggctaat atggcctgct gcacctgcgt   5820
```

```
gagggtagac tggaagtcat ccatgtccac aaagcggtgg tatgcgcccg tgttgatggt   5880
gtaagtgcag ttggccataa cggaccagtt aacggtctgg tgacccggct gcagagagctc  5940 ggtgtacctg agacgcgagt aagccctcga gtcaaatacg tagtcgttac aagtccgcac   6000
caggtactgg tatcccacca aaaagtgcgg cggcggctgg cggtagaggg gccagcgtag   6060
ggtggccggg gctccggggg cgagatcttc aacataagg cgatgatatc cgtagatgta    6120
cctggacatc caggtgatgc cggcggcggt ggtggaggcg cgcggaaagt cgcggacgcg    6180
gttccagatg ttgcgcagcg gcaaaaagtg ctccatggtc gggacgctct ggccggtcag   6240
gcgcgcgcaa tcgttgacgc tctagaccgt gcaaaggag agcctgtaag cgggcactct    6300
tccgtggtct ggtggataaa ttcgcaaggg tatcatggcg gacgaccggg gttcgagccc   6360
cgtatccggc cgtccgccgt gatccatgcg gttaccgccc gcgtgtcgaa cccaggtgtg   6420
cgacgtcaga caacggggga gtgctccttt tggcttcctt ccaggcgcgg cggctgctgc   6480
gctagctttt ttggccactg gccgcgcgca gcgtaagcgg ttaggctgga aagcgaaagc    6540
attaagtggc tcgctccctg tagccggagg gttattttcc aagggttgag tcgcgggacc    6600
cccggttcga gtctcggacc ggccggactg cggcgaacgg gggtttgtct ccccgtcatg    6660
caagaccccg cttgcaaatt cctccggaaa cagggacgag ccccttttt gcttttccca     6720 gatgcatccg gtgctgcggc agatgcgccc ccctcctcag cagcggcaag agcaagagca    6780
gcggcagaca tgcagggcac cctcccctcc tcctaccgcg tcaggagggg cgacatccgc    6840
ggttgacgcg gcagcagatg gtgattacga accccgcgg gcgcgggccc ggcactacct     6900
ggacttggag gagggcgagg gcctggcgcg gctaggagcg ccctctcctg agcggcaccc    6960
aagggtgcag ctgaagcgtg atacgcgtga ggcgtacgtg ccgcggcaga acctgtttcg    7020
cgaccgcgag ggagaggagc ccgaggagat gcgggatcga aagttccacg cagggcgcga    7080
gctgcggcat ggcctgaatc gcgagcggtt gctgcgcgag gaggactttg agcccgacgc    7140
gcgaaccggg attagtcccg cgcgcgcaca cgtggcggcc gccgacctgg taaccgcata    7200
cgagcagacg gtgaaccagg gcgatcgcac cctttggcgc atcccattct ccagtaactt    7260
tatgtccatg ggcgcactca cagacctggg ccaaaacctt ctctacgcca actccgccca    7320
cgcgctagac atgacttttg aggtggatcc catggacgag cccacccttc tttatgtttt    7380
gtttgaagtc tttgacgtgg tccgtgtgca ccggccgcac cgcggcgtca tcgaaaccgt    7440
gtacctgcgc acgcccttct cggccggcaa cgccacaaca taaagaagca agcaacatca    7500
acaacagctg ccgccatggg ctccagtgag caggaactga aagccattgt caaagatctt    7560
ggttgtgggc catatttttt gggcacctat gacaagcgct ttccaggctt tgtttctcca    7620
cacaagctcg cctgcgccat agtcaatacg gccggtcgcg agactggggg cgtacactgg    7680
atggcctttg cctggaaccc gcactcaaaa acatgctacc tctttgagcc ctttggcttt    7740
tctgaccagc gactcaagca ggtttaccag tttgagtacg agtcactcct cgccgtagc     7800 gccattgctt cttccccga ccgctgtata acgctggaaa agtccaccca aagcgtacag     7860
gggcccaact cggccgcctg tggactattc tgctgcatgt ttctccacgc ctttgccaac    7920 tggcccaaa ctcccatgga tcacaacccc accatgaacc ttattaccgg ggtacccaac     7980
tccatgctca acagtcccca ggtacagccc accctgcgtc gcaaccagga acagctctac    8040
agcttcctgg agcgccactc gccctacttc cgcagccaca gtgcgcagat taggagcgcc    8100
acttcttttt gtcacttgaa aaacatgtaa aaataatgta ctagagacac tttcaataaa    8160
```

```
ggcaaatgct tttatttgta cactctcggg tgattattta cccccacccct tgccgtctgc   8220
gccgtttaaa aatcaaaggg gttctgccgc gcatcgctat gcgccactgg cagggacacg   8280
ttgcgatact ggtgtttagt gctccactta aactcaggca caaccatccg cggcagctcg   8340
gtgaagtttt cactccacag gctgcgcacc atcaccaacg cgtttagcag gtcgggcgcc   8400
gatatcttga agtcgcagtt ggggcctccg ccctgcgcgc gcgagttgcg atacacaggg   8460
ttgcagcact ggaacactat cagcgccggg tggtgcacgc tggccagcac gctcttgtcg   8520
gagatcagat ccgcgtccag gtcctccgcg ttgctcaggg cgaacggagt caactttggt   8580
agctgccttc ccaaaaaggg cgcgtgccca ggctttgagt tgcactcgca ccgtagtggc   8640
atcaaaaggt gaccgtgccc ggtctgggcg ttaggataca gcgcctgcat aaaagccttg   8700
atctgcttaa aagccacctg agcctttgcg ccttcagaga agaacatgcc gcaagacttg   8760
ccggaaaact gattggccgg acaggccgcg tcgtgcacgc agcaccttgc gtcggtgttg   8820
gagatctgca ccacatttcg gccccaccgg ttcttcacga tcttggcctt gctagactgc   8880
tccttcagcg cgcgctgccc gttttcgctc gtcacatcca tttcaatcac gtgctcctta   8940
tttatcataa tgcttccgtg tagacactta agctcgcctt cgatctcagc gcagcggtgc   9000
agccacaacg cgcagcccgt gggctcgtga tgcttgtagg tcacctctgc aaacgactgc   9060
aggtacgcct gcaggaatcg ccccatcatc gtcacaaagg tcttgttgct ggtgaaggtc   9120
agctgcaacc cgcggtgctc ctcgttcagc caggtcttgc atacggccgc cagagcttcc   9180
acttggtcag gcagtagttt gaagttcgcc tttagatcgt tatccacgtg gtacttgtcc   9240
atcagcgcgc gcgcagcctc catgcccttc tcccacgcag acacgatcgg cacactcagc   9300
gggttcatca ccgtaatttc actttccgct tcgctgggct cttcctcttc ctcttgcgtc   9360
cgcataccac gcgccactgg gtcgtcttca ttcagccgcc gcactgtgcg cttacctcct   9420
ttgccatgct tgattagcac cggtgggttg ctgaaaccca ccatttgtag cgccacatct   9480
tctctttctt cctcgctgtc cacgattacc tctggtgatg gcgggcgctc gggcttggga   9540
gaagggcgct tcttttttctt cttgggcgca atggccaaat ccgccgccga ggtcgatggc   9600
cgcgggctgg gtgtgcgcgg caccagcgcg tcttgtgatg agtcttcctc gtcctcggac   9660
tcgatacgcc gcctcatccg cttttttggg ggcgcccggg gaggcggcgg cgacggggac   9720
ggggacgaca cgtcctccat ggttggggga cgtcgcgccg caccgcgtcc gcgctcgggg   9780
gtggtttcgc gctgctcctc ttcccgactg gccatttcct tctcctatag gcagaaaaag   9840
atcatggagt cagtcgagaa gaaggacagc ctaaccgccc cctctgagtt cgccaccacc   9900
gcctccaccg atgccgccaa cgcgcctacc accttccccg tcgaggcacc cccgcttgag   9960
gaggaggaag tgattatcga gcaggaccca ggttttgtaa gcgaagacga cgaggaccgc  10020
tcagtaccaa cagaggataa aaagcaagac caggacaacg cagaggcaaa cgaggaacaa  10080
gtcgggcggg gggacgaaag gcatggcgac tacctagatg tgggagacga cgtgctgttg  10140
aagcatctgc agcgccagtg cgccattatc tgcgacgcgt tgcaagagcg cagcgatgtg  10200
cccctcgcca tagcggatgt cagccttgcc tacgaacgcc acctattctc accgcgcgta  10260
cccccccaaac gccaagaaaa cggcacatgc gagcccaacc cgcgcctcaa cttctacccc  10320
gtatttgccg tgccagaggt gcttgccacc tatcacatct tttccaaaaa ctgcaagata  10380
cccctatcct gccgtgccaa ccgcagccga gcggacaagc agctggcctt gcggcagggc  10440
gctgtcatac ctgatatcgc ctcgctcaac gaagtgccaa aaatctttga gggtcttgga  10500
cgcgacgaga agcgcgcggc aaacgctctg caacaggaaa acagcgaaaa tgaaagtcac  10560
```

```
tctggagtgt tggtggaact cgagggtgac aacgcgcgcc tagccgtact aaaacgcagc    10620
atcgaggtca cccactttgc ctacccggca cttaacctac cccccaaggt catgagcaca    10680
gtcatgagtg agctgatcgt gcgccgtgcg cagcccctgg agagggatgc aaatttgcaa    10740
gaacaaacag aggagggcct acccgcagtt ggcgacgagc agctagcgcg ctggcttcaa    10800
acgcgcgagc ctgccgactt ggaggagcga cgcaaactaa tgatggccgc agtgctcgtt    10860
accgtggagc ttgagtgcat gcagcggttc tttgctgacc cggagatgca cgcaagcta    10920
gaggaaacat tgcactacac ctttcgacag ggctacgtac gccaggcctg caagatctcc    10980
aacgtggagc tctgcaacct ggtctcctac cttggaattt tgcacgaaaa ccgccttggg    11040
caaaacgtgc ttcattccac gctcaagggc gaggcgcgcc gcgactacgt ccgcgactgc    11100
gtttacttat ttctatgcta cacctggcag acggccatgg gcgtttggca gcagtgcttg    11160
gaggagtgca acctcaagga gctgcagaaa ctgctaaagc aaaacttgaa ggacctatgg    11220
acggccttca cgagcgctc cgtggccgcg cacctggcgg acatcatttt ccccgaacgc    11280
ctgcttaaaa ccctgcaaca gggtctgcca gacttcacca gtcaaagcat gttgcagaac    11340
tttaggaact ttatcctaga gcgctcagga atcttgcccg ccacctgctg tgcacttcct    11400
agcgactttg tgcccattaa gtaccgcgaa tgccctccgc cgctttgggg ccactgctac    11460
cttctgcagc tagccaacta ccttgcctac cactctgaca taatgaaaga cgtgagcggt    11520
gacggtctac tggagtgtca ctgtcgctgc aacctatgca ccccgcaccg ctccctggtt    11580
tgcaattcgc agctgcttaa cgaaagtcaa attatcggta cctttgagct gcagggtccc    11640
tcgcctgacg aaaagtccgc ggctccgggg ttgaaactca ctccggggct gtggacgtcg    11700
gcttaccttc gcaaatttgt acctgaggac taccacgccc acgagattag gttctacgaa    11760
gaccaatccc gcccgccaaa tgcggagctt accgcctgcg tcattaccca gggccacatt    11820
cttggccaat tgcaagccat caacaaagcc cgccaagagt ttctgctacg aaagggacgg    11880
ggggtttact tggaccccca gtccggcgag gagctcaacc caatcccccc gccgccgcag    11940
ccctatcagc agcagccgcg ggcccttgct tcccaggatg gcacccaaaa agaagctgca    12000
gctgccgccg ccacccacgg acgaggagga atactggaca gtcaggcag aggaggtttt    12060
ggacgaggag gaggaggaca tgatggaaga ctgggagagc ctagacgagg aagcttccga    12120
ggtcgaagag gtgtcagacg aaacaccgtc accctcggtc gcattcccct cgccggcgcc    12180
ccagaaatcg gcaaccggtt ccagcatggc tacaacctcc gctcctcagg cgccgccggc    12240
actgccgtt cgccgaccca accgtagatg ggacaccact ggaaccaggg ccggtaagtc    12300
caagcagccg ccgccgttag cccaagagca acaacagcgc caaggctacc gctcatggcg    12360
cgggcacaag aacgccatag ttgcttgctt gcaagactgt gggggcaaca tctccttcgc    12420
ccgccgcttt cttctctacc atcacggcgt ggccttcccc cgtaacatcc tgcattacta    12480
ccgtcatctc tacagcccat actgcaccgg cggcagcggc agcggcagca acagcagcgg    12540
ccacacagaa gcaaaggcga ccggatagca agactctgac aaagcccaag aaatccacag    12600
cggcggcagc agcaggagga ggagcgctgc gtctggcgcc caacgaaccc gtatcgaccc    12660
gcgagcttag aaacaggatt tttcccactc tgtatgctat atttcaacag gcagggcc    12720
aagaacaaga gctgaaaata aaaaacaggt ctctgcgatc cctcacccgc agctgcctgt    12780
atcacaaaag cgaagatcag cttcggcgca cgctggaaga gcggaggct ctcttcagta    12840
aatactgcgc gctgactctt aaggactagt ttcgcgccct ttctcaaatt taagcgcgaa    12900
```

```
aactacgtca tctccagcgg ccacacccgg cgccagcacc tgtcgtcagc gccattatga    12960
gcaaggaaat tcccacgccc tacatgtgga gttaccagcc acaaatggga cttgcggctg    13020
gagctgccca agactactca acccgaataa actacatgag cgcgggaccc cacatgatat    13080
cccgggtcaa cggaatccgc gcccaccgaa accgaattct cttggaacag gcggctatta    13140
ccaccacacc tcgtaataac cttaatcccc gtagttggcc cgctgccctg tgtaccagg     13200 aaagtcccgc tcccaccact gtggtacttc ccagagacgc ccaggccgaa gttcagatga    13260
ctaactcagg ggcgcagctt gcgggcggct ttcgtcacag ggtgcggtcg cccgggcagg    13320
gtataactca cctgacaatc agagggcgag gtattcagct caacgacgag tcggtgagct    13380
cctcgcttgg tctccgtccg gacgggacat tcagatcgg cggcgccggc cgctcttcat     13440
tcacgcctcg tcaggcaatc ctaactctgc agacctcgtc ctctgagccg cgctctggag    13500
gcattggaac tctgcaattt attgaggagt ttgtgccatc ggtctacttt aaccccttct    13560
cgggacctcc cggccactat ccggatcaat ttattcctaa cttttgacgcg gtaaaggact    13620 cggcggatgg ctacgactga atgttaagtg gagaggcaga gcaactgcgc ctgaaacacc    13680
tggtccactg tcgccgccac aagtgctttg cccgcgactc cggtgagttt tgctactttg    13740
aattgcccga ggatcatatc gagggcccgg cgcacgcgt ccggcttacc gcccaggag      13800 agcttgcccg tagcctgatt cgggagttta cccagcgccc cctgctagtt gagcgggaca    13860
ggggaccctg tgttctcact gtgatttgca actgtcctaa ccctggatta catcaagatc    13920
tttgttgcca tctctgtgct gagtataata aatacagaaa ttaaaatata ctggggctcc    13980
tatcgccatc ctgtaaacgc caccgtcttc acccgcccaa gcaaaccaag gcgaaccttta   14040 cctggtactt ttaacatctc tccctctgtg atttacaaca gtttcaaccc agacggagtg    14100
agtctacgag agaacctctc cgagctcagc tactccatca gaaaaaacac caccctcctt    14160
acctgccggg aacgtacgag tgcgtcaccg gccgctgcac cacacctacc gcctgaccgt    14220
aaaccagact ttttccggac agacctcaat aactctgttt accagaacag gaggtgagct    14280
tagaaaaccc ttagggtatt aggccaaagg cgcagctact gtggggttta tgaacaattc    14340
aagcaactct acgggctatt ctaattcagg tttctctaga aatggacgga attattacag    14400
agcagcgcct gctagaaaga cgcagggcag cggccgagca acagcgcatg aatcaagagc    14460
tccaagacat ggttaacttg caccagtgca aaagggtat cttttgtctg gtaaagcagg      14520
ccaaagtcac ctacgacagt aataccaccg gacaccgcct tagctacaag ttgccaacca    14580
agcgtcagaa attggtggtc atggtgggag aaaagcccat taccataact cagcactcgg    14640
tagaaaccga aggctgcatt cactcacctt gtcaaggacc tgaggatctc tgcaccctta    14700
ttaagcccct gtgcggtctc aaagatctta ttccctttaa ctaataaaaa aaaataataa    14760
agcatcactt acttaaaatc agttagcaaa tttctgtcca gtttattcag cagcacctcc    14820
ttgccctcct cccagctctg gtattgcagc ttcctcctgg ctgcaaactt tctccacaat    14880
ctaaatggaa tgtcagtttc ctcctgttcc tgtccatccg cacccactat cttcatgttg    14940
ttgcagatga agcgcgcaag accgtctgaa gataccttca accccgtgta tccatatgac    15000
acggaaaccg gtcctccaac tgtgcctttt cttactcctc cctttgtatc ccccaatggg    15060
tttcaagaga gtcccctgg ggtactctct ttgcgcctat ccgaacctct agttacctcc      15120
aatggcatgc ttgcgctcaa aatgggcaac ggcctctctc tggacgaggc cggcaacctt    15180
acctcccaaa atgtaaccac tgtgagccca cctctcaaaa aaaccaagtc aaacataaac    15240
ctggaaatat ctgcaccccct cacagttacc tcagaagccc taactgtggc tgccgccgca    15300
```

```
cctctaatgg tcgcgggcaa cacactcacc atgcaatcac aggccccgct aaccgtgcac   15360
gactccaaac ttagcattgc cacccaagga ccctcacag tgtcagaagg aaagctagcc    15420
ctgcaaacat caggccccct caccaccacc gatagcagta cccttactat cactgcctca   15480 cccctctaa ctactgccac tggtagcttg ggcattgact tgaaagagcc catttataca    15540
caaaatggaa aactaggact aaagtacggg gctcctttgc atgtaacaga cgacctaaac   15600
actttgaccg tagcaactgg tccaggtgtg actattaata atacttcctt gcaaactaaa   15660
gttactggag ccttgggttt tgattcacaa ggcaatatgc aacttaatgt agcaggagga   15720
ctaaggattg attctcaaaa cagacgcctt atacttgatg ttagttatcc gtttgatgct   15780
caaaaccaac taaatctaag actaggacag ggccctcttt ttataaactc agcccacaac   15840
ttggatatta actacaacaa aggcctttac ttgtttacag cttcaaacaa ttccaaaaag   15900
cttgaggtta acctaagcac tgccaagggg ttgatgtttg acgctacagc catagccatt   15960
aatgcaggag atgggcttga atttggttca cctaatgcac caaacacaaa tcccctcaaa   16020
acaaaaattg gccatggcct agaatttgat tcaaacaagg ctatggttcc taaactagga   16080
actgccctta gttttgacag cacaggtgcc attacagtag gaaacaaaaa taatgataag   16140
ctaactttgt ggaccacacc agctccatct cctaactgta gactaaatgc agagaaagat   16200
gctaaactca ctttggtctt aacaaaatgt ggcagtcaaa tacttgctac agtttcagtt   16260
ttggctgtta aaggcagttt ggctccaata tctggaacag ttcaaagtgc tcatcttatt   16320
ataagatttg acgaaaatgg agtgctacta aacaattcct tcctggaccc agaatattgg   16380
aactttagaa atggagatct tactgaaggc acagcctata caaacgctgt tggatttatg   16440
cctaacctat cagcttatcc aaaatctcac ggtaaaactg ccaaaagtaa cattgtcagt   16500
caagtttact taaacggaga caaaactaaa cctgtaacac taaccattac actaaacggt   16560
acacaggaaa caggagacac aactccaagt gcatactcta tgtcattttc atgggactgg   16620
tctggccaca actacattaa tgaaatattt gccacatcct cttacacttt ttcatacatt   16680
gcccaagaat aaagaatcgt tgtgttatg tttcaacgtg tttatttttc aattgcagaa    16740
aatttcaagt cattttcat tcagtagtat agccccacca ccacatagct tatacagatc    16800
accgtacctt aatcaaactc acagaaccct agtattcaac ctgccacctc cctcccaaca   16860
cacagagtac acagtccttt ctccccggct ggccttaaaa agcatcatat catgggtaac   16920
agacatattc ttaggtgtta tattccacac ggtttcctgt cgagccaaac gctcatcagt   16980
gatattaata aactccccgg gcagctcact taagttcatg tcgctgtcca gctgctgagc   17040
cacaggctgc tgtccaactt gcggttgctt aacgggcggc gaaggagaag tccacgccta   17100 catggggta gagtcataat cgtgcatcag gataggcgg tggtgctgca gcagcgcgcg     17160
aataaactgc tgccgccgcc gctccgtcct gcaggaatac aacatggcag tggtctcctc   17220
agcgatgatt cgcaccgccc gcagcataag gcgccttgtc ctccgggcac agcagcgcac   17280
cctgatctca cttaaatcag cacagtaact gcagcacagc accacaatat tgttcaaaat   17340
cccacagtgc aaggcgctgt atccaaagct catggcgggg accacagaac ccacgtggcc   17400
atcataccac aagcgcaggt agattaagtg gcgacccctc ataaacacgc tggacataaa   17460
cattacctct tttggcatgt tgtaattcac cacctcccgg taccatataa acctctgatt   17520
aaacatggcg ccatccacca ccatcctaaa ccagctggcc aaaacctgcc cgccggctat   17580
acactgcagg gaaccgggac tggaacaatg acagtggaga gcccaggact cgtaaccatg   17640
```

```
gatcatcatg ctcgtcatga tatcaatgtt ggcacaacac aggcacacgt gcatacactt    17700
cctcaggatt acaagctcct cccgcgttag aaccatatcc cagggaacaa cccattcctg    17760
aatcagcgta aatcccacac tgcagggaag acctcgcacg taactcacgt tgtgcattgt    17820
caaagtgtta cattcgggca gcagcggatg atcctccagt atggtagcgc gggtttctgt    17880
ctcaaaagga ggtagacgat ccctactgta cggagtgcgc cgagacaacc gagatcgtgt    17940
tggtcgtagt gtcatgccaa atggaacgcc ggacgtagtc atatttcctg aagcaaaacc    18000
aggtgcgggc gtgacaaaca gatctgcgtc tccggtctcg ccgcttagat cgctctgtgt    18060
agtagttgta gtatatccac tctctcaaag catccaggcg cccctggct tcgggttcta    18120 tgtaaactcc ttcatgcgcc gctgccctga taacatccac caccgcagaa taagccacac    18180
ccagccaacc tacacattcg ttctgcgagt cacacgggg aggagcggga agagctggaa    18240
gaaccatgtt ttttttttta ttccaaaaga ttatccaaaa cctcaaaatg aagatctatt    18300
aagtgaacgc gctcccctcc ggtggcgtgg tcaaactcta cagccaaaga acagataatg    18360
gcatttgtaa gatgttgcac aatggcttcc aaaaggcaaa cggccctcac gtccaagtgg    18420
acgtaaaggc taaaccccttc agggtgaatc tcctctataa acattccagc accttcaacc    18480
atgcccaaat aattctcatc tcgccacctt ctcaatatat ctctaagcaa atcccgaata    18540
ttaagtccgg ccattgtaaa aatctgctcc agagcgccct ccaccttcag cctcaagcag    18600
cgaatcatga ttgcaaaaat tcaggttcct cacagacctg tataagattc aaaagcggaa    18660
cattaacaaa aataccgcga tcccgtaggt cccttcgcag ggccagctga acataatcgt    18720
gcaggtctgc acgaccagc gcggccactt ccccgccagg aaccatgaca aaagaaccca    18780
cactgattat gacacgcata ctcggagcta tgctaaccag cgtagccccg atgtaagctt    18840
gttgcatggg cggcgatata aaatgcaagg tgctgctcaa aaaatcaggc aaagcctcgc    18900
gcaaaaaaga aagcacatcg tagtcatgct catgcagata aaggcaggta agctccggaa    18960
ccaccacaga aaaagacacc atttttctct caaacatgtc tgcgggtttc tgcataaaca    19020
caaaataaaa taacaaaaaa acatttaaac attagaagcc tgtcttacaa caggaaaaac    19080
aacccttata agcataagac ggactacggc catgccggcg tgaccgtaaa aaaactggtc    19140
accgtgatta aaaagcacca ccgacagctc ctcggtcatg tccggagtca taatgtaaga    19200
ctcggtaaac acatcaggtt gattcacatc ggtcagtgct aaaaagcgac cgaaatagcc    19260
cgggggaata catacccgca ggcgtagaga caacattaca gccccatag gaggtataac    19320 aaaattaata ggagagaaaa acacataaac acctgaaaaa ccctcctgcc taggcaaaat    19380
agcaccctcc cgctccagaa caacatacag cgcttccaca gcggcagcca taacagtcag    19440
ccttaccagt aaaaagaaa acctattaaa aaaacaccac tcgacacggc accagctcaa    19500
tcagtcacag tgtaaaaaag ggccaagtgc agagcgagta tatataggac taaaaaatga    19560
cgtaacggtt aaagtccaca aaaaacaccc agaaaccgc acgcgaacct acgcccagaa    19620
acgaaagcca aaaaacccac aacttcctca aatcgtcact tccgtttttcc cacgttacgt    19680 cacttcccat tttaagaaaa ctacaattcc caacacatac aagttactcc gccctaaaac    19740
ctacgtcacc cgccccgttc ccacgccccg cgccacgtca caaactccac cccctcatta    19800
tcatattggc ttcaatccaa aataaggtat attattgatg atgttaatta agaattcgga    19860
tctgcgacgc gaggctggat ggccttcccc attatgattc ttctcgcttc cggcggcatc    19920
gggatgcccg cgttgcaggc catgctgtcc aggcaggtag atgacgacca tcagggacag    19980
cttcaaggcc agcaaaaggc caggaaccgt aaaaaggccg cgttgctggc gttttttccat    20040
```

```
aggctccgcc ccctgacga gcatcacaaa atcgacgct caagtcagag gtggcgaaac    20100
ccgacaggac tataaagata ccaggcgttt ccccctggaa gctccctcgt gcgctctcct    20160
gttccgaccc tgccgcttac cggatacctg tccgcctttc tcccttcggg aagcgtggcg    20220
ctttctcata gctcacgctg taggtatctc agttcggtgt aggtcgttcg ctccaagctg    20280
ggctgtgtgc acgaaccccc cgttcagccc gaccgctgcg ccttatccgg taactatcgt    20340
cttgagtcca acccggtaag acacgactta tcgccactgg cagcagccac tggtaacagg    20400
attagcagag cgaggtatgt aggcggtgct acagagttct tgaagtggtg gcctaactac    20460
ggctacacta aaggacagt atttggtatc tgcgctctgc tgaagccagt taccttcgga    20520
aaaagagttg gtagctcttg atccggcaaa caaaccaccg ctggtagcgg tggttttttt    20580
gtttgcaagc agcagattac gcgcagaaaa aaaggatctc aagaagatcc tttgatcttt    20640
tctacggggt ctgacgctca gtggaacgaa aactcacgtt aagggatttt ggtcatgaga    20700
ttatcaaaaa ggatcttcac ctagatcctt ttaaatcaat ctaaagtata tatgagtaaa    20760
cttggtctga caggtttaaa ctcagaagaa ctcgtcaaga aggcgataga aggcgatgcg    20820
ctgcgaatcg ggagcggcga taccgtaaag cacgaggaag cggtcagccc attcgccgcc    20880
aagctcttca gcaatatcac gggtagccaa cgctatgtcc tgatagcggt ccgccacacc    20940
cagccggcca cagtcgatga atccagaaaa gcggccattt tccaccatga tattcggcaa    21000
gcaggcatcg ccatgggtca cgacgagatc ctcgccgtcg gcatgctcg ccttgagcct    21060
ggcgaacagt tcggctggcg cgagcccctg atgctcttcg tccagatcat cctgatcgac    21120
aagaccggct tccatccgag tacgtgctcg ctcgatgcga tgtttcgctt ggtggtcgaa    21180
tgggcaggta ccggatcaa gcgtatgcag ccgccgcatt gcatcagcca tgatggatac    21240
tttctcggca ggagcaaggt gagatgacag gagatcctgc cccggcactt cgcccaatag    21300
cagccagtcc cttcccgctt cagtgacaac gtcgagcaca gctgcgcaag gaacgcccgt    21360
cgtggccagc cacgatagcc gcgctgcctc gtcttgcagt tcattcaggg caccggacag    21420
gtcggtcttg acaaaaagaa ccgggcgccc ctgcgctgac agccggaaca cggcggcatc    21480
agagcagccg attgtctgtt gtgcccagtc atagccgaat agcctctcca cccaagcggc    21540
cggagaacct gcgtgcaatc catcttgttc aatcataacg ttactcttcc tttttcaata    21600
ttattgaagc atttatcagg gttattgtct catgagcgga tacatatttg aatgtattta    21660
gaaaaataaa caaatagggg ttccgcgcac atttccccga aaagtgccac ctgacgtcta    21720
agaaaccatt attatcatga cattaaccta taaaaatagg cgtatcacga ggccctttcg    21780
tcttcaa                                                              21787
```

<210> SEQ ID NO 5
<211> LENGTH: 21784
<212> TYPE: DNA
<213> ORGANISM: Artificial Sequence
<220> FEATURE:
<223> OTHER INFORMATION: SYNTHETIC POLYNUCLEOTIDE

<400> SEQUENCE: 5

```
gaattggatc cgaattctta attaacatca tcaataatat accttatttt ggattgaagc      60
caatatgata atgaggggt ggagtttgtg acgtggcgcg gggcgtggga acggggcggg     120
tgacgtagta gtgtggcgga agtgtgatgt tgcaagtgtg gcggaacaca tgtaagcgac     180
ggatgtggca aaagtgacgt ttttggtgtg cgccggtgta cacaggaagt gacaatttc     240
```

-continued

```
gcgcggtttt aggcggatgt tgtagtaaat ttgggcgtaa ccgagtaaga tttggccatt    300
ttcgcgggaa aactgaataa gaggaagtga aatctgaata attttgtgtt actcatagcg    360
cgtaatattt gtctagggcc gcggggactt tgaccgttta cgtggagact cgcccaggtg    420
ttttttctcag gtgttttccg cgttccgggt caaagttggc gttttattat tatagtcagg    480
gggatcctct agaactagtg gatccgtccc tcaggcctag aagtaaaaaa gggaaaaaag    540
agtgtgtttg tcaaaatagg agacaggtgg tggcaaccaa ggactatag gggaccttac     600
atctacagac caacagatgc ccccttacca tatacaggaa gatatgactt aaattgggat    660
aggtgggtca caatcaacgg ctataaagtg ttatacagat ccctcccctc cccttttcgtg   720
aaagactcgc cagagctaga cctccttggt gtatgctaac tgagaagaga aagacgacat    780
gaaacaacag gtacatgatt atatttatct aggaacagga atgcactttt ggggaaaggt    840
tttccatacc aaggaagggg cagtggctgg actgatagaa cattattctg caaaaactta    900
tggtatgagt tattatgatt agcctttatt tgcccaacct tgcggttccc agggtttaaa    960
taagtttatg gttacaaact gttcttaaaa cgaggatgtg agacaagtgg tttcctgact   1020
tggtttggta atcaaatgtt ctgatctgag ctcttagtgt tctatttttcc tatgttcttt   1080
tggaatctat ccaagtctta tgtaaatgct tatgtaaacc ataatataaa agagtgctga   1140
ttttttgagt aaacttgcaa cagtcctaac attcttctct cgtgtgtttg tgtctgttcg   1200
ccatcccgtc tccgctcgtc acttatcctt cacttttcag agggtccccc cgcagatccc   1260
ggtcaccctc aggtcgggac ctgcagaaga cgcccgagtg agcacgcagg gtctccattt   1320
tgaagcggga ggtttgaacg cgcagccgcc atgccggggt tttacgagat tgtgattaag   1380
gtccccagcg accttgacgg gcatctgccc ggcatttctg acagctttgt gaactgggtg   1440
gccgagaagg aatgggagtt gccgccagat tctgacatgg atctgaatct gattgagcag   1500
gcacccctga ccgtggccga aagctgcag gcgactttc tgacggaatg gcgccgtgtg   1560
agtaaggccc cggaggccct tttctttgtg caatttgaga agggagagag ctacttccac   1620
atgcacgtgc tcgtggaaac caccggggtg aaatccatgg ttttgggacg tttcctgagt   1680
cagattcgcg aaaaactgat tcagagaatt taccgcggga tcgagccgac tttgccaaac   1740
tggttcgcgg tcacaaagac cagaaatggc gccggaggcg gaacaaggt ggtggatgag    1800
tgctacatcc ccaattactt gctccccaaa acccagcctg agctccagtg ggcgtggact   1860
aatatggaac agtatttaag cgcctgtttg aatctcacgg agcgtaaacg gttggtggcg   1920
cagcatctga cgcacgtgtc gcagacgcag gagcagaaca aagagaatca gaatcccaat   1980
tctgatgcgc cggtgatcag atcaaaaact tcagccaggt acatggagct ggtcgggtgg   2040
ctcgtggaca aggggattac ctcggagaag cagtggatcc aggaggacca ggcctcatac   2100
atctccttca atgcggcctc caactcgcgg tcccaaatca aggctgcctt ggacaatgcg   2160
ggaaagatta tgagcctgac taaaaccgcc ccgactacc tggtgggcca gcagcccgtg   2220
gaggacattt ccagcaatcg gatttataaa attttggaac taaacgggta cgatcccaa    2280
tatgcggctt ccgtctttct gggatgggcc acgaaaaagt tcggcaagag gaacaccatc   2340
tggctgtttg gcctgcaac taccgggaag accaacatcg cggaggccat agcccacact   2400
gtgcccttct acgggtgcgt aaactggacc aatgagaact ttcccttcaa cgactgtgtc   2460
gacaagatgg tgatctggtg ggaggagggg aagatgaccg ccaaggtcgt ggagtcggcc   2520
aaagccattc tcggaggaag caaggtgcgc gtggaccaga atgcaagtc ctcggcccag    2580
atagacccga ctcccgtgat cgtcacctcc aacaccaaca tgtgcgccgt gattgacggg   2640
```

```
aactcaacga ccttcgaaca ccagcagccg ttgcaagacc ggatgttcaa atttgaactc   2700
acccgccgtc tggatcatga ctttgggaag gtcaccaagc aggaagtcaa agactttttc   2760
cggtgggcaa aggatcacgt ggttgaggtg gagcatgaat tctacgtcaa aaagggtgga   2820
gccaagaaaa gacccgcccc cagtgacgca gatataagtg agcccaaacg ggtgcgcgag   2880
tcagttgcgc agccatcgac gtcagacgcg gaagcttcga tcaactacgc agacaggtac   2940
caaaacaaat gttctcgtca cgtgggcatg aatctgatgc tgtttccctg cagcaatgc    3000 gagagaatga atcagaattc aaatatctgc ttcactcacg gacagaaaga ctgtttagag   3060
tgctttcccg tgtcagaatc tcaacccgtt tctgtcgtca aaaaggcgta tcagaaactg   3120
tgctacattc atcatatcat gggaaaggtg ccagacgctt gcactgcctg cgatctggtc   3180
aatgtggatt tggatgactg catctttgaa caataaatga tttaaatcag gtatggctgc   3240
cgatggttat cttccagatt ggctcgagga caacctctct gagggcattc gcgagtggtg   3300
ggcgctgaaa cctggagccc cgaagcccaa agccaaccag caaaagcagg acgacggccg   3360
gggtctggtg cttcctggct acaagtacct cggacccttc aacggactcg acaaggggga   3420
gcccgtcaac gcggcggacg cagcggccct cgagcacgac aaggcctacg accagcagct   3480
gcaggcgggt gacaatccgt acctgcggta taaccacgcc gacgccgagt ttcaggagcg   3540
tctgcaagaa gatacgtctt tgggggcaa cctcggcga gcagtcttcc aggccaagaa    3600
gcgggttctc gaacctctcg gtctggttga ggaaggcgct aagacggctc ctggaaagaa   3660
gagaccggta gagccatcac cccagcgttc tccagactcc tctacgggca tcggcaagaa   3720
aggccaacag cccgccagaa aaagactcaa ttttggtcag actggcgact cagagtcagt   3780
tccagaccct caacctctcg gagaacctcc agcagcgccc tctggtgtgg gacctaatac   3840
aatggctgca ggcggtggcg caccaatggc agacaataac gaaggcgccg acggagtggg   3900
tagttcctcg ggaaattggc attgcgattc cacatggctg ggcgacagag tcatcaccac   3960
cagcacccga acctgggccc tgcccaccta caacaaccac ctctacaagc aaatctccaa   4020
cgggacatcg ggaggagcca ccaacgacaa cacctacttc ggctacagca cccccctgggg  4080 gtattttgac tttaacagat ccactgccca cttttcacca cgtgactggc agcgactcat   4140
caacaacaac tggggattcc ggcccaagag actcagcttc aagctcttca acatccaggt   4200
caaggaggtc acgcagaatg aaggcaccaa gaccatcgcc aataacctca ccagcaccat   4260
ccaggtgttt acggactcgg agtaccagct gccgtacgtt ctcggctctg cccaccaggg   4320
ctgcctgcct ccgttcccgg cggacgtgtt catgattccc cagtacggct acctaacact   4380
caacaacggt agtcaggccg tgggacgctc ctccttctac tgcctggaat actttccttc   4440
gcagatgctg agaaccggca caacttcca gtttacttac accttcgagg acgtgccttt    4500
ccacagcagc tacgcccaca gccagagctt ggaccggctg atgaatcctc tgattgacca   4560
gtacctgtac tacttgtctc ggactcaaac aacaggagc acggcaaata cgcagactct    4620
gggcttcagc caaggtgggc ctaatacaat ggccaatcag gcaaagaact ggctgccagg   4680
accctgttac cgccaacaac gcgtctcaac gacaaccggg caaaacaaca atagcaactt   4740
tgcctggact gctgggacca ataccatct gaatggaaga aattcattgg ctaatcctgg    4800
catcgctatg gcaacacaca aagacgacga ggagcgtttt tttcccagta acgggatcct   4860 gattttggc aaacaaaatg ctgccagaga caatgcggat tacagcgatg tcatgctcac    4920
cagcgaggaa gaaatcaaaa ccactaaccc tgtggctaca gaggaatacg gtatcgtggc   4980
```

```
agataacttg cagcagcaaa acacggctcc tcaaattgga actgtcaaca gccagggggc    5040
cttacccggt atggtctggc agaaccggga cgtgtacctg cagggtccca tctgggccaa    5100
gattcctcac acggacggca acttccaccc gtctccgctg atgggcggct ttggcctgaa    5160
acatcctccg cctcagatcc tgatcaagaa cacgcctgta cctgcggatc ctccgaccac    5220
cttcaaccag tcaaagctga actctttcat cacgcaatac agcaccggac aggtcagcgt    5280
ggaaattgaa tgggagctgc agaaggaaaa cagcaagcgc tggaaccccg agatccagta    5340
cacctccaac tactacaaat ctacaagtgt ggactttgct gttaatacag aaggcgtgta    5400
ctctgaaccc cgcccattg gcacccgtta cctcacccgt aatctgtaat tgcctgttaa    5460
tcaataaacc ggttgattcg tttcagttga actttggtct ctgcgaaggg cgaattcatc    5520
gatgcatgtc cttgggtccg gcctgctgaa tgcgcaggcg gtcggccatg ccccaggctt    5580
cgttttgaca tcggcgcagg tctttgtagt agtcttgcat gagcctttct accggcactt    5640
cttcttctcc ttcctcttgt cctgcatctc ttgcatctat cgctgcggcg gcggcggagt    5700
ttggccgtag gtggcgccct cttcctccca tcgtgtgacc ccgaagcccc tcatcggctg    5760
aagcagggct aggtcggcga caacgcgctc ggctaatatg gcctgctgca cctgcgtgag    5820
ggtagactgg aagtcatcca tgtccacaaa gcggtggtat cgcccgtgt tgatggtgta    5880 agtgcagttg gccataacgg accagttaac ggtctggtga cccggctgcg agagctcggt    5940
gtacctgaga cgcgagtaag ccctcgagtc aaatacgtag tcgttacaag tccgcaccag    6000
gtactggtat cccaccaaaa agtgcggcgg cggctggcgg tagaggggcc agcgtagggt    6060
ggccggggct ccgggggcga gatcttccaa cataaggcga tgatatccgt agatgtacct    6120
ggacatccag gtgatgccgg cggcggtggt ggaggcgcgc ggaaagtcgc ggacgcggtt    6180
ccagatgttg cgcagcggca aaagtgctc catggtcggg acgctctggc cggtcaggcg    6240
cgcgcaatcg ttgacgctct agaccgtgca aaaggagagc ctgtaagcgg gcactcttcc    6300
gtggtctggt ggataaattc gcaagggtat catggcggac gacgggggtt cgagcccgt    6360 atccggccgt ccgccgtgat ccatgcggtt accgcccgcg tgtcgaaccc aggtgtgcga    6420
cgtcagacaa cggggagtg ctcctttgg cttccttcca ggcgcggcgg ctgctgcgct    6480 agctttttg gccactggcc gcgcgcagcg taagcggtta ggctggaaag cgaaagcatt    6540
aagtggctcg ctccctgtag ccggagggtt attttccaag ggttgagtcg cgggaccccc    6600
ggttcgagtc tcggaccggc cggactgcgg cgaacggggg tttgtctccc cgtcatgcaa    6660
gaccccgctt gcaaattcct ccggaaacag ggacgagccc cttttttgct tttcccagat    6720
gcatccggtg ctgcggcaga tgcgcccccc tcctcagcag cggcaagagc aagagcagcg    6780
gcagacatgc agggcaccct cccctcctcc taccgcgtca ggaggggcga catccgcggt    6840
tgacgcggca gcagatggtg attacgaacc cccgcggcgc cgggcccggc actacctgga    6900
cttggaggag ggcgagggcc tggcgcggct aggagcgccc tctcctgagc ggcacccaag    6960
ggtgcagctg aagcgtgata cgcgtgaggc gtacgtgccg cggcagaacc tgtttcgcga    7020
ccgcgaggga gaggagcccg aggagatgcg ggatcgaaag ttccacgcag ggcgcgagct    7080
gcggcatggc ctgaatcgcg agcggttgct gcgcgaggag gactttgagc ccgacgcgcg    7140
aaccgggatt agtcccgcgc gcgcacacgt ggcggccgcc gacctggtaa ccgcatacga    7200
gcagacggtg aaccagggcg atcgcaccct ttggcgcatc ccattctcca gtaactttat    7260
gtccatgggc gcactcacag acctgggcca aaaccttctc tacgccaact ccgcccacgc    7320
gctagacatg acttttgagg tggatcccat ggacgagccc acccttcttt atgttttgtt    7380
```

```
tgaagtctttt gacgtggtcc gtgtgcaccg gccgcaccgc ggcgtcatcg aaaccgtgta    7440
cctgcgcacg cccttctcgg ccggcaacgc cacaacataa agaagcaagc aacatcaaca    7500
acagctgccg ccatgggctc cagtgagcag gaactgaaag ccattgtcaa agatcttggt    7560
tgtgggccat attttttggg cacctatgac aagcgctttc caggctttgt ttctccacac    7620
aagctcgcct gcgccatagt caatacggcc ggtcgcgaga ctgggggcgt acactggatg    7680
gcctttgcct ggaacccgca ctcaaaaaca tgctacctct ttgagccctt tggcttttct    7740
gaccagcgac tcaagcaggt ttaccagttt gagtacgagt cactcctgcg ccgtagcgcc    7800
attgcttctt cccccgaccg ctgtataacg ctggaaaagt ccacccaaag cgtacagggg    7860
cccaactcgg ccgcctgtgg actattctgc tgcatgtttc tccacgcctt tgccaactgg    7920
ccccaaactc ccatggatca aaccccacc atgaacctta ttaccggggt acccaactcc    7980
atgctcaaca gtccccaggt acagcccacc ctgcgtcgca accaggaaca gctctacagc    8040
ttcctggagc gccactcgcc ctacttccgc agccacagtg cgcagattag gagcgccact    8100
tcttttgtc acttgaaaaa catgtaaaaa taatgtacta gagacacttt caataaaggc    8160
aaatgctttt atttgtacac tctcgggtga ttatttaccc ccacccttgc cgtctgcgcc    8220
gtttaaaaat caaggggtt ctgccgcgca tcgctatgcg ccactggcag ggacacgttg    8280
cgatactggt gtttagtgct ccacttaaac tcaggcacaa ccatccgcgg cagctcggtg    8340
aagttttcac tccacaggct gcgcaccatc accaacgcgt ttagcaggtc gggcgccgat    8400
atcttgaagt cgcagttggg gcctccgccc tgcgcgcgcg agttgcgata cacagggttg    8460
cagcactgga acactatcag cgccgggtgg tgcacgctgg ccagcacgct cttgtcggag    8520
atcagatccg cgtccaggtc ctccgcgttg ctcaggcgga acggagtcaa ctttggtagc    8580
tgccttccca aaagggcgc gtgcccaggc tttgagttgc actcgcaccg tagtggcatc    8640
aaaaggtgac cgtgcccggt ctgggcgtta ggatacagcg cctgcataaa agccttgatc    8700
tgcttaaaag ccacctgagc ctttgcgcct tcagagaaga acatgccgca agacttgccg    8760
gaaaactgat tggccggaca ggccgcgtcg tgcacgcagc accttgcgtc ggtgttggag    8820
atctgcacca catttcggcc ccaccggttc ttcacgatct tggccttgct agactgctcc    8880
ttcagcgcgc gctgcccgtt ttcgctcgtc acatccattt caatcacgtg ctccttattt    8940
atcataatgc ttccgtgtag acacttaagc tcgccttcga tctcagcgca gcggtgcagc    9000
cacaacgcgc agcccgtggg ctcgtgatgc ttgtaggtca cctctgcaaa cgactgcagg    9060
tacgcctgca ggaatcgccc catcatcgtc acaaaggtct tgttgctggt gaaggtcagc    9120
tgcaacccgc ggtgctcctc gttcagccag gtcttgcata cggccgccag agcttccact    9180
tggtcaggca gtagtttgaa gttcgccttt agatcgttat ccacgtggta cttgtccatc    9240
agcgcgcgcg cagcctccat gcccttctcc cacgcagaca cgatcggcac actcagcggg    9300
ttcatcaccg taatttcact ttccgcttcg ctgggctctt cctcttcctc ttgcgtccgc    9360
ataccacgcg ccactgggtc gtcttcattc agccgccgca ctgtgcgctt acctcctttg    9420
ccatgcttga ttagcaccgg tgggttgctg aaacccacca tttgtagcgc cacatcttct    9480
ctttcttcct cgctgtccac gattacctct ggtgatggcg ggcgctcggg cttgggagaa    9540
gggcgcttct ttttcttctt gggcgcaatg gccaaatccg ccgccgaggt cgatggccgc    9600
gggctgggtg tgcgcggcac cagcgcgtct tgtgatgagt cttcctcgtc ctcggactcg    9660
atacgccgcc tcatccgctt ttttgggggc gcccggggag gcggcggcga cggggacggg    9720
```

```
gacgacacgt cctccatggt tgggggacgt cgcgccgcac cgcgtccgcg ctcggggtg    9780 gtttcgcgct gctcctcttc ccgactggcc atttccttct cctataggca gaaaaagatc   9840
atggagtcag tcgagaagaa ggacagccta accgccccct ctgagttcgc caccaccgcc   9900
tccaccgatg ccgccaacgc gcctaccacc ttccccgtcg aggcaccccc gcttgaggag   9960
gaggaagtga ttatcgagca ggacccaggt tttgtaagcg aagacgacga ggaccgctca  10020
gtaccaacag aggataaaaa gcaagaccag gacaacgcag aggcaaacga ggaacaagtc  10080
gggcgggggg acgaaaggca tggcgactac ctagatgtgg gagacgacgt gctgttgaag  10140
catctgcagc gccagtgcgc cattatctgc gacgcgttgc aagagcgcag cgatgtgccc  10200
ctcgccatag cggatgtcag ccttgcctac gaacgccacc tattctcacc gcgcgtaccc  10260
cccaaacgcc aagaaaacgg cacatgcgag cccaacccgc gcctcaactt ctaccccgta  10320
tttgccgtgc cagaggtgct tgccacctat cacatctttt tccaaaactg caagataccc  10380
ctatcctgcc gtgccaaccg cagccgagcg gacaagcagc tggccttgcg gcagggcgct  10440
gtcatacctg atatcgcctc gctcaacgaa gtgccaaaaa tctttgaggg tcttggacgc  10500
gacgagaagc gcgcggcaaa cgctctgcaa caggaaaaca gcgaaaatga aagtcactct  10560
ggagtgttgg tggaactcga gggtgacaac gcgcgcctag ccgtactaaa acgcagcatc  10620
gaggtcaccc actttgccta cccggcactt aacctacccc ccaaggtcat gagcacagtc  10680
atgagtgagc tgatcgtgcg ccgtgcgcag cccctggaga gggatgcaaa tttgcaagaa  10740
caaacagagg agggcctacc cgcagttggc gacgagcagc tagcgcgctg gcttcaaacg  10800
cgcgagcctg ccgacttgga ggagcgacgc aaactaatga tggccgcagt gctcgttacc  10860
gtggagcttg agtgcatgca gcggttcttt gctgacccgg agatgcagcg caagctagag  10920
gaaacattgc actacacctt tcgacagggc tacgtacgcc aggcctgcaa gatctccaac  10980
gtggagctct gcaacctggt ctcctacctt ggaattttgc acgaaaaccg ccttgggcaa  11040
aacgtgcttc attccacgct caagggcgag gcgcgccgcg actacgtccg cgactgcgtt  11100
tacttatttc tatgctacac ctggcagacg gccatgggcg tttggcagca gtgcttggag  11160
gagtgcaacc tcaaggagct gcagaaactg ctaaagcaaa acttgaagga cctatggacg  11220
gccttcaacg agcgctccgt ggccgcgcac ctggcggaca tcatttttccc cgaacgcctg  11280 cttaaaaccc tgcaacaggg tctgccagac ttcaccagtc aaagcatgtt gcagaacttt  11340 aggaactttta tcctagagcg ctcaggaatc ttgcccgcca cctgctgtgc acttcctagc  11400
gactttgtgc ccattaagta ccgcgaatgc cctccgccgc tttggggcca ctgctacctt  11460
ctgcagctag ccaactacct tgcctaccac tctgacataa tggaagacgt gagcggtgac  11520
ggtctactgg agtgtcactg tcgctgcaac ctatgcaccc cgcaccgctc cctggtttgc  11580
aattcgcagc tgcttaacga aagtcaaatt atcggtacct tgagctgca gggtccctcg  11640 cctgacgaaa agtccgcggc tccggggttg aaactcactc cggggctgtg gacgtcggct  11700
taccttcgca aatttgtacc tgaggactac cacgcccacg agattaggtt ctacgaagac  11760
caatcccgcc cgccaaatgc ggagcttacc gcctgcgtca ttacccaggg ccacattctt  11820
ggccaattgc aagccatcaa caaagcccgc caagagtttc tgctacgaaa gggacggggg  11880
gtttacttgg accccagtc cggcgaggag ctcaacccaa tcccccgcc gccgcagccc  11940 tatcagcagc agccgcgggc ccttgcttcc caggatggca cccaaaaaga agctgcagct  12000
gccgccgcca cccacggacg aggaggaata ctggacagt caggcagagg aggttttgga  12060
cgaggaggag gaggacatga tggaagactg ggagagccta gacgaggaag cttccgaggt  12120
```

```
cgaagaggtg tcagacgaaa caccgtcacc ctcggtcgca ttcccctcgc cggcgcccca   12180
gaaatcggca accggttcca gcatggctac aacctccgct cctcaggcgc cgccggcact   12240
gcccgttcgc cgacccaacc gtagatggga caccactgga accagggccg gtaagtccaa   12300
gcagccgccg ccgttagccc aagagcaaca acagcgccaa ggctaccgct catggcgcgg   12360
gcacaagaac gccatagttg cttgcttgca agactgtggg ggcaacatct ccttcgcccg   12420
ccgctttctt ctctaccatc acggcgtggc cttcccccgt aacatcctgc attactaccg   12480
tcatctctac agcccatact gcaccggcgg cagcggcagc ggcagcaaca gcagcggcca   12540
cacagaagca aaggcgaccg gatagcaaga ctctgacaaa gcccaagaaa tccacagcgg   12600
cggcagcagc aggaggagga gcgctgcgtc tggcgcccaa cgaacccgta tcgacccgcg   12660
agcttagaaa caggattttt cccactctgt atgctatatt caacagagc aggggccaag   12720 aacaagagct gaaaataaaa aacaggtctc tgcgatccct cacccgcagc tgcctgtatc   12780
acaaaagcga agatcagctt cggcgcacgc tggaagacgc ggaggctctc ttcagtaaat   12840
actgcgcgct gactcttaag gactagtttc gcgccctttc tcaaatttaa gcgcgaaaac   12900
tacgtcatct ccagcggcca cacccggcgc cagcacctgt cgtcagcgcc attatgagca   12960
aggaaattcc cacgccctac atgtggagtt accagccaca aatgggactt gcggctggag   13020
ctgcccaaga ctactcaacc cgaataaact acatgagcgc gggaccccac atgatatccc   13080
gggtcaacgg aatccgcgcc caccgaaacc gaattctctt ggaacaggcg gctattacca   13140
ccacacctcg taataacctt aatccccgta gttggcccgc tgccctggtg taccaggaaa   13200
gtcccgctcc caccactgtg gtacttccca gagacgccca ggccgaagtt cagatgacta   13260
actcaggggc gcagcttgcg gcggcttttc gtcacagggt gcggtcgccc gggcagggta   13320
taactcacct gacaatcaga gggcgaggta ttcagctcaa cgacgagtcg gtgagctcct   13380
cgcttggtct ccgtccggac gggacatttc agatcggcgg cgccggccgc tcttcattca   13440
cgcctcgtca ggcaatccta actctgcaga cctcgtcctc tgagccgcgc tctggaggca   13500
ttggaactct gcaatttatt gaggagtttg tgccatcggt ctactttaac cccttctcgg   13560
gacctcccgg ccactatccg gatcaattta ttcctaactt tgacgcggta aaggactcgg   13620
cggatggcta cgactgaatg ttaagtggag aggcagagca actgcgcctg aaacacctgg   13680
tccactgtcg ccgccacaag tgctttgccc gcgactccgg tgagttttgc tactttgaat   13740
tgcccgagga tcatatcgag ggcccggcgc acggcgtccg gcttaccgcc cagggagagc   13800
ttgcccgtag cctgattcgg gagtttaccc agcgcccct gctagttgag cgggacaggg   13860
gaccctgtgt tctcactgtg atttgcaact gtcctaaccc tggattacat caagatcttt   13920
gttgccatct ctgtgctgag tataataaat acagaaatta aaatatactg gggctcctat   13980
cgccatcctg taaacgccac cgtcttcacc cgcccaagca aaccaaggcg aaccttacct   14040 ggtacttta acatctctcc ctctgtgatt tacaacagtt tcaacccaga cggagtgagt   14100
ctacgagaga acctctccga gctcagctac tccatcagaa aaacaccac cctccttacc   14160 tgccgggaac gtacgagtgc gtcaccggcc gctgcaccac acctaccgcc tgaccgtaaa   14220
ccagactttt tccggacaga cctcaataac tctgtttacc agaacaggag gtgagcttag   14280
aaaaccctta gggtattagg ccaaaggcgc agctactgtg gggtttatga acaattcaag   14340
caactctacg ggctattcta attcaggttt ctctagaaat ggacggaatt attacagagc   14400
agcgcctgct agaaagacgc agggcagcgg ccgagcaaca gcgcatgaat caagagctcc   14460
```

```
aagacatggt taacttgcac cagtgcaaaa ggggtatctt ttgtctggta aagcaggcca   14520
aagtcaccta cgacagtaat accaccggac accgccttag ctacaagttg ccaaccaagc   14580
gtcagaaatt ggtggtcatg gtgggagaaa agcccattac cataactcag cactcggtag   14640
aaaccgaagg ctgcattcac tcaccttgtc aaggacctga ggatctctgc acccttatta   14700
agaccctgtg cggtctcaaa gatcttattc cctttaacta ataaaaaaaa ataataaagc   14760
atcacttact taaaatcagt tagcaaattt ctgtccagtt tattcagcag cacctccttg   14820
ccctcctccc agctctggta ttgcagcttc ctcctggctg caaactttct ccacaatcta   14880 aatgaatgt cagtttcctc ctgttcctgt ccatccgcac ccactatctt catgttgttg   14940
cagatgaagc gcgcaagacc gtctgaagat accttcaacc ccgtgtatcc atatgacacg   15000
gaaaccggtc ctccaactgt gccttttctt actcctccct ttgtatcccc caatgggttt   15060
caagagagtc ccctgggggt actctctttg cgcctatccg aacctctagt tacctccaat   15120
ggcatgcttg cgctcaaaat gggcaacggc ctctctctgg acgaggccgg caaccttacc   15180
tcccaaaatg taaccactgt gagcccacct ctcaaaaaaa ccaagtcaaa cataaacctg   15240
gaaatatctg caccccctcac agttacctca gaagccctaa ctgtggctgc cgccgcacct   15300
ctaatggtcg cgggcaacac actcaccatg caatcacagg ccccgctaac cgtgcacgac   15360
tccaaactta gcattgccac ccaaggaccc ctcacagtgt cagaaggaaa gctagccctg   15420
caaacatcag gcccctcac caccaccgat agcagtaccc ttactatcac tgcctcaccc   15480
cctctaacta ctgccactgg tagcttgggc attgacttga agagcccat ttatacacaa   15540 aatgaaaac taggactaaa gtacggggct cctttgcatg taacagacga cctaaacact   15600
ttgaccgtag caactggtcc aggtgtgact attaataata cttccttgca aactaaagtt   15660
actggagcct tgggttttga ttcacaaggc aatatgcaac ttaatgtagc aggaggacta   15720
aggattgatt ctcaaaacag acgccttata cttgatgtta gttatccgtt tgatgctcaa   15780
aaccaactaa atctaagact aggacagggc cctcttttta taaactcagc ccacaacttg   15840
gatattaact acaacaaagg cctttacttg tttacagctt caaacaattc caaaagctt   15900 gaggttaacc taagcactgc caagggggttg atgtttgacg ctacagccat agccattaat   15960
gcaggagatg ggcttgaatt tggttcacct aatgcaccaa acacaaatcc cctcaaaaca   16020
aaaattggcc atggcctaga atttgattca aacaaggcta tggttcctaa actaggaact   16080
ggccttagtt ttgacagcac aggtgccatt acagtaggaa acaaaaataa tgataagcta   16140
actttgtgga ccacaccagc tccatctcct aactgtagac taaatgcaga gaaagatgct   16200
aaactcactt tggtcttaac aaaatgtggc agtcaaatac ttgctacagt ttcagttttg   16260
gctgttaaag gcagttttggc tccaatatct ggaacagttc aaagtgctca tcttattata   16320
agatttgacg aaaatggagt gctactaaac aattccttcc tggacccaga atattggaac   16380
tttagaaatg gagatcttac tgaaggcaca gcctatacaa acgctgttgg atttatgcct   16440
aacctatcag cttatccaaa atctcacggt aaaactgcca aaagtaacat tgtcagtcaa   16500
gtttacttaa acggagacaa aactaaacct gtaacactaa ccattacact aaacggtaca   16560
caggaaacag gagacacaac tccagtgcaa tactctatgt cattttcatg ggactggtct   16620
ggccacaact acattaatga aatatttgcc acatcctctt acacttttttc atacattgcc   16680 caagaataaa gaatcgtttg tgttatgttt caacgtgttt attttttcaat tgcagaaaat   16740 ttcaagtcat ttttcattca gtagtataagc cccaccacca catagcttat acagatcacc   16800
gtaccttaat caaactcaca gaaccctagt attcaacctg ccacctccct cccaacacac   16860
```

```
agagtacaca gtcctttctc cccggctggc cttaaaaagc atcatatcat gggtaacaga   16920
catattctta ggtgttatat tccacacggt ttcctgtcga gccaaacgct catcagtgat   16980
attaataaac tccccgggca gctcacttaa gttcatgtcg ctgtccagct gctgagccac   17040
aggctgctgt ccaacttgcg gttgcttaac gggcggcgaa ggagaagtcc acgcctacat   17100
gggggtagag tcataatcgt gcatcaggat agggcggtgg tgctgcagca gcgcgcgaat   17160
aaactgctgc cgccgccgct ccgtcctgca ggaatacaac atggcagtgg tctcctcagc   17220
gatgattcgc accgcccgca gcataaggcg ccttgtcctc cgggcacagc agcgcaccct   17280
gatctcactt aaatcagcac agtaactgca gcacagcacc acaatattgt tcaaaatccc   17340
acagtgcaag gcgctgtatc caaagctcat ggcggggacc acagaaccca cgtggccatc   17400
ataccacaag cgcaggtaga ttaagtggcg acccctcata acacgctggg acataaacat   17460
tacctctttt ggcatgttgt aattcaccac ctcccggtac catataaacc tctgattaaa   17520
catggcgcca tccaccacca tcctaaacca gctggccaaa acctgcccgc cggctataca   17580
ctgcagggaa ccgggactgg aacaatgaca gtggagagcc caggactcgt aaccatggat   17640
catcatgctc gtcatgatat caatgttggc acaacacagg cacacgtgca tacacttcct   17700
caggattaca agctcctccc gcgttagaac catatcccag ggaacaaccc attcctgaat   17760
cagcgtaaat cccacactgc agggaagacc tcgcacgtaa ctcacgttgt gcattgtcaa   17820
agtgttacat tcgggcagca gcggatgatc ctccagtatg gtagcgcggg tttctgtctc   17880
aaaaggaggt agacgatccc tactgtacgg agtgcgccga gacaaccgag atcgtgttgg   17940
tcgtagtgtc atgccaaatg gaacgccgga cgtagtcata tttcctgaag caaaaccagg   18000
tgcgggcgtg acaaacagat ctgcgtctcc ggtctcgccg cttagatcgc tctgtgtagt   18060
agttgtagta tatccactct ctcaaagcat ccaggcgccc cctggcttcg ggttctatgt   18120
aaactccttc atgcgccgct gccctgataa catccaccac cgcagaataa gccacaccca   18180
gccaacctac acattcgttc tgcgagtcac acacgggagg agcgggaaga gctggaagaa   18240
ccatgttttt ttttttattc caaaagatta tccaaaacct caaaatgaag atctattaag   18300
tgaacgcgct cccctccggt ggcgtggtca aactctacag ccaaagaaca gataatggca   18360
tttgtaagat gttgcacaat ggcttccaaa aggcaaacgg ccctcacgtc caagtggacg   18420
taaaggctaa acccttcagg gtgaatctcc tctataaaca ttccagcacc ttcaaccatg   18480
cccaaataat tctcatctcg ccaccttctc aatatatctc taagcaaatc ccgaatatta   18540
agtccggcca ttgtaaaaat ctgctccaga gcgccctcca ccttcagcct caagcagcga   18600
atcatgattg caaaaattca ggttcctcac agacctgtat aagattcaaa agcggaacat   18660
taacaaaaat accgcgatcc cgtaggtccc ttcgcagggc cagctgaaca taatcgtgca   18720
ggtctgcacg gaccagcgcg gccacttccc cgccaggaac catgacaaaa gaacccacac   18780
tgattatgac acgcatactc ggagctatgc taaccagcgt agccccgatg taagcttgtt   18840
gcatgggcgg cgatataaaa tgcaaggtgc tgctcaaaaa atcaggcaaa gcctcgcgca   18900
aaaaagaaag cacatcgtag tcatgctcat gcagataaag gcaggtaagc tccggaacca   18960
ccacagaaaa agacaccatt tttctctcaa acatgtctgc gggtttctgc ataaacacaa   19020
aataaaataa caaaaaaaca tttaaacatt agaagcctgt cttacaacag gaaaaacaac   19080
ccttataagc ataagacgga ctacggccat gccggcgtga ccgtaaaaaa actggtcacc   19140
gtgattaaaa agcaccaccg acagctcctc ggtcatgtcc ggagtcataa tgtaagactc   19200
```

```
ggtaaacaca tcaggttgat tcacatcggt cagtgctaaa aagcgaccga aatagcccgg   19260
gggaatacat acccgcaggc gtagagacaa cattacagcc cccataggag gtataacaaa   19320
attaatagga gagaaaaaca cataaacacc tgaaaaaccc tcctgcctag gcaaaatagc   19380
accctcccgc tccagaacaa catacagcgc ttccacagcg gcagccataa cagtcagcct   19440
taccagtaaa aagaaaaacc tattaaaaaa acaccactcg acacggcacc agctcaatca   19500
gtcacagtgt aaaaagggc caagtgcaga gcgagtatat ataggactaa aaaatgacgt   19560
aacggttaaa gtccacaaaa aacacccaga aaaccgcacg cgaacctacg cccagaaacg   19620
aaagccaaaa aacccacaac ttcctcaaat cgtcacttcc gttttcccac gttacgtcac   19680
ttcccatttt aagaaaacta caattcccaa cacatacaag ttactccgcc ctaaaaccta   19740
cgtcacccgc cccgttccca cgccccgcgc cacgtcacaa actccacccc ctcattatca   19800
tattggcttc aatccaaaat aaggtatatt attgatgatg ttaattaaga attcggatct   19860
gcgacgcgag gctggatggc cttccccatt atgattcttc tcgcttccgg cggcatcggg   19920
atgcccgcgt tgcaggccat gctgtccagg caggtagatg acgaccatca gggacagctt   19980
caaggccagc aaaaggccag gaaccgtaaa aaggccgcgt tgctggcgtt tttccatagg   20040
ctccgccccc ctgacgagca tcacaaaaat cgacgctcaa gtcagaggtg gcgaaacccg   20100
acaggactat aaagatacca ggcgtttccc cctggaagct ccctcgtgcg ctctcctgtt   20160
ccgaccctgc cgcttaccgg atacctgtcc gcctttctcc cttcgggaag cgtggcgctt   20220
tctcatagct cacgctgtag gtatctcagt tcggtgtagg tcgttcgctc caagctgggc   20280
tgtgtgcacg aaccccccgt tcagcccgac cgctgcgcct tatccggtaa ctatcgtctt   20340
gagtccaacc cggtaagaca cgacttatcg ccactggcag cagccactgg taacaggatt   20400
agcagagcga ggtatgtagg cggtgctaca gagttcttga agtggtggcc taactacggc   20460
tacactagaa ggacagtatt tggtatctgc gctctgctga agccagttac cttcggaaaa   20520
agagttggta gctcttgatc cggcaaacaa accaccgctg gtagcggtgg tttttttgtt   20580
tgcaagcagc agattacgcg cagaaaaaaa ggatctcaag aagatccttt gatcttttct   20640
acggggtctg acgctcagtg gaacgaaaac tcacgttaag ggattttggt catgagatta   20700
tcaaaaagga tcttcaccta gatcctttta aatcaatcta agtatatat gagtaaactt   20760
ggtctgacag gtttaaactc agaagaactc gtcaagaagg cgatagaagg cgatgcgctg   20820
cgaatcggga gcggcgatac cgtaaagcac gaggaagcgg tcagcccatt cgccgccaag   20880
ctcttcagca atatcacggg tagccaacgc tatgtcctga tagcggtccg ccacacccag   20940
ccggccacag tcgatgaatc cagaaaagcg gccattttcc accatgatat tcggcaagca   21000
ggcatcgcca tgggtcacga cgagatcctc gccgtcgggc atgctcgcct tgagcctggc   21060
gaacagttcg gctggcgcga gcccctgatg ctcttcgtcc agatcatcct gatcgacaag   21120
accggcttcc atccgagtac gtgctcgctc gatgcgatgt ttcgcttggt ggtcgaatgg   21180
gcaggtagcc ggatcaagcg tatgcagccg ccgcattgca tcagccatga tggatacttt   21240
ctcggcagga gcaaggtgag atgacaggag atcctgcccc ggcacttcgc ccaatagcag   21300
ccagtccctt cccgcttcag tgacaacgtc gagcacagct gcgcaaggaa cgcccgtcgt   21360
ggccagccac gatagccgcg ctgcctcgtc ttgcagttca ttcagggcac cggacaggtc   21420
ggtcttgaca aaaagaaccg ggcgcccctg cgctgacagc cggaacacgg cggcatcaga   21480
gcagccgatt gtctgttgtg cccagtcata gccgaatagc ctctccaccc aagcggccgg   21540
agaacctgcg tgcaatccat cttgttcaat cataacgtta ctcttccttt ttcaatatta   21600
```

-continued

| | |
|---|---|
| ttgaagcatt tatcagggtt attgtctcat gagcggatac atatttgaat gtatttagaa | 21660 |
| aaataaacaa atagggggttc cgcgcacatt tccccgaaaa gtgccacctg acgtctaaga | 21720 |
| aaccattatt atcatgacat taacctataa aaataggcgt atcacgaggc cctttcgtct | 21780 |
| tcaa | 21784 |

<210> SEQ ID NO 6
<211> LENGTH: 22064
<212> TYPE: DNA
<213> ORGANISM: Artificial Sequence
<220> FEATURE:
<223> OTHER INFORMATION: SYNTHETIC POLYNUCLEOTIDE

<400> SEQUENCE: 6

| | |
|---|---|
| gaattggatc cgaattctta attaacatca tcaataatat accttatttt ggattgaagc | 60 |
| caatatgata atgaggggt ggagtttgtg acgtggcgcg gggcgtggga acggggcggg | 120 |
| tgacgtagta gtgtggcgga agtgtgatgt tgcaagtgtg gcggaacaca tgtaagcgac | 180 |
| ggatgtggca aaagtgacgt ttttggtgtg cgccggtgta cacaggaagt gacaattttc | 240 |
| gcgcggtttt aggcggatgt tgtagtaaat ttgggcgtaa ccgagtaaga tttggccatt | 300 |
| ttcgcgggaa aactgaataa gaggaagtga aatctgaata attttgtgtt actcatagcg | 360 |
| cgtaatattt gtctagggcc gcggggactt tgaccgttta cgtggagact cgcccaggtg | 420 |
| tttttctcag gtgttttccg cgttccgggt caaagttggc gttttattat tatagtcagg | 480 |
| gggatcctct agaactagtg gatccgtccc tcaggcctag aagtaaaaaa gggaaaaaag | 540 |
| agtgtgtttg tcaaaatagg agacaggtgg tgcaaccaa ggacttatag gggaccttac | 600 |
| atctacagac caacagatgc ccccttacca tatacaggaa gatatgactt aaattgggat | 660 |
| aggtgggtca caatcaacgg ctataaagtg ttatacagat ccctcccctc cccttttcgtg | 720 |
| aaagactcgc cagagctaga cctccttggt gtatgctaac tgagaagaga aagacgacat | 780 |
| gaaacaacag gtacatgatt atatttatct aggaacagga atgcacttt ggggaaaggt | 840 |
| tttccatacc aaggaagggg cagtggctgg actgatagaa cattattctg caaaaactta | 900 |
| tggtatgagt tattatgatt agcctttatt tgcccaacct tgcggttccc agggtttaaa | 960 |
| taagtttatg gttacaaact gttcttaaaa cgaggatgtg agacaagtgg tttcctgact | 1020 |
| tggtttggta atcaaatgtt ctgatctgag ctcttagtgt tctatttttcc tatgttcttt | 1080 |
| tggaatctat ccaagtctta tgtaaatgct tatgtaaacc ataatataaa agagtgctga | 1140 |
| tttttttgagt aaacttgcaa cagtcctaac attcttctct cgtgtgtttg tgtctgttcg | 1200 |
| ccatcccgtc tccgctcgtc acttatcctt cacttttcag agggtccccc cgcagatccc | 1260 |
| ggtcaccctc aggtcgggac ctgcagaaga cgcccgagtg agcacgcagg gtctccattt | 1320 |
| tgaagcggga ggtttgaacg cgcagccgcc atgccggggt tttacgagat tgtgattaag | 1380 |
| gtccccagcg accttgacgg gcatctgccc ggcatttctg acagctttgt gaactgggtg | 1440 |
| gccgagaagg aatgggagtt gccgccagat tctgacatgg atctgaatct gattgagcag | 1500 |
| gcaccccctga ccgtggccga aagctgcag cgcgactttc tgacggaatg gcgccgtgtg | 1560 |
| agtaaggccc cggaggccct tttctttgtg caatttgaga agggagagag ctacttccac | 1620 |
| atgcacgtgc tcgtggaaac caccggggtg aaatccatgg ttttgggacg tttcctgagt | 1680 |
| cagattcgcg aaaaactgat tcagagaatt taccgcggga tcgagccgac tttgccaaac | 1740 |
| tggttcgcgg tcacaaagac cagaaatggc gccggaggcg gaacaaggt ggtggatgag | 1800 |

-continued

```
tgctacatcc ccaattactt gctccccaaa acccagcctg agctccagtg ggcgtggact    1860
aatatggaac agtatttaag cgcctgtttg aatctcacgg agcgtaaacg gttggtggcg    1920
cagcatctga cgcacgtgtc gcagacgcag gagcagaaca aagagaatca gaatcccaat    1980
tctgatgcgc cggtgatcag atcaaaaact tcagccaggt acatggagct ggtcgggtgg    2040
ctcgtggaca agggggattac ctcggagaag cagtggatcc aggaggacca ggcctcatac    2100
atctccttca atgcggcctc caactcgcgg tcccaaatca aggctgcctt ggacaatgcg    2160
ggaaagatta tgagcctgac taaaaccgcc cccgactacc tggtgggcca gcagcccgtg    2220
gaggacattt ccagcaatcg gatttataaa attttggaac taaacgggta cgatccccaa    2280
tatgcggctt ccgtctttct gggatgggcc acgaaaaagt tcggcaagag gaacaccatc    2340
tggctgtttg ggcctgcaac taccgggaag accaacatcg cggaggccat agcccacact    2400
gtgcccttct acgggtgcgt aaactggacc aatgagaact ttcccttcaa cgactgtgtc    2460
gacaagatgg tgatctggtg ggaggagggg aagatgaccg ccaaggtcgt ggagtcggcc    2520
aaagccattc tcggaggaag caaggtgcgc gtggaccaga aatgcaagtc ctcggcccag    2580
atagacccga ctcccgtgat cgtcacctcc aacaccaaca tgtgcgccgt gattgacggg    2640
aactcaacga ccttcgaaca ccagcagccg ttgcaagacc ggatgttcaa atttgaactc    2700
acccgccgtc tggatcatga ctttgggaag gtcaccaagc aggaagtcaa agactttttc    2760
cggtgggcaa aggatcacgt ggttgaggtg gagcatgaat tctacgtcaa aaagggtgga    2820
gccaagaaaa gacccgcccc cagtgacgca gatataagtg agcccaaacg ggtgcgcgag    2880
tcagttgcgc agccatcgac gtcagacgcg gaagcttcga tcaactacgc agacaggtac    2940
caaaacaaat gttctcgtca cgtgggcatg aatctgatgc tgtttccctg cagacaatgc    3000
gagagaatga atcagaattc aaatatctgc ttcactcacg gacagaaaga ctgtttagag    3060
tgctttcccg tgtcagaatc tcaacccgtt tctgtcgtca aaaaggcgta tcagaaactg    3120
tgctacattc atcatatcat gggaaaggtg ccagacgctt gcactgcctg cgatctggtc    3180
aatgtggatt tggatgactg catctttgaa caataaatga tttaaataaa acaaatgttc    3240
tcgtcacgtg ggcatgaatc tgatgctgtt tccctgcaga caatgcgaga gactgaatca    3300
gaattcaaat atctgcttca ctcacggtgt caaagactgt ttagagtgct ttcccgtgtc    3360
agaatctcaa cccgtttctg tcgtcaaaaa ggcgtatcag aaactgtgct acattcatca    3420
catcatggga aaggtgccag acgcttgcac tgcttgcgac ctggtcaatg tggacttgga    3480
tgactgtgtt tctgaacaat aaatgactta aaccaggtat ggctgccgat ggttatcttc    3540
cagattggct cgaggacaac cttagtgaag gaattcgcga gtggtgggct ttgaaacctg    3600
gagcccctca acccaaggca aatcaacaac atcaagacaa cgctcgaggt cttgtgcttc    3660
cgggttacaa ataccttgga cccggcaacg gactcgacaa gggggagccg gtcaacgcag    3720
cagacgcggc ggccctcgag cacgacaagg cctacgacca gcagctcaag gccgagaca    3780 acccgtacct caagtacaac cacgccgacg ccgagttcca ggagcggctc aaagaagata    3840
cgtcttttgg gggcaaccct gggcgagcag tcttccaggc caaaaagagg cttcttgaac    3900
ctcttggtct ggttgaggaa gcggctaaga cggctcctgg aaagaagagg cctgtagagc    3960
agtctcctca ggaaccggac tcctccgcgg gtattggcaa atcgggtgca cagcccgcta    4020
aaaagagact caatttcggt cagactggcg acacagagtc agtcccagac cctcaaccaa    4080
tcggagaacc tcccgcagcc ccctcaggtg tgggatctct acaatggct tcaggtggtg    4140 gcgcaccagt ggcagacaat aacgaaggtg ccgatggagt gggtagttcc tcgggaaatt    4200
```

```
ggcattgcga ttcccaatgg ctgggggaca gagtcatcac caccagcacc cgaacctggg    4260
ccctgcccac ctacaacaat cacctctaca agcaaatctc caacagcaca tctggaggat    4320
cttcaaatga caacgcctac ttcggctaca gcacccsctg ggggtatttt gacttcaaca    4380
gattccactg ccacttctca ccacgtgact ggcagcgact catcaacaac aactggggat    4440
tccggcctaa gcgactcaac ttcaagctct caacattca ggtcaaagag gttacggaca    4500
acaatggagt caagaccatc gccaataacc ttaccagcac ggtccaggtc ttcacggact    4560
cagactatca gctcccgtac gtgctcgggt cggctcacga gggctgcctc ccgccgttcc    4620
cagcggacgt tttcatgatt cctcagtacg ggtatctgac gcttaatgat ggaagccagg    4680
ccgtgggtcg ttcgtccttt tactgcctgg aatatttccc gtcgcaaatg ctaagaacgg    4740
gtaacaactt ccagttcagc tacgagtttg agaacgtacc tttccatagc agctacgctc    4800
acagccaaag cctggaccga ctaatgaatc cactcatcga ccaatacttg tactatctct    4860
caaagactat taacggttct ggacagaatc aacaaacgct aaaattcagt gtggccggac    4920
ccagcaacat ggctgtccag ggaagaaact acatacctgg acccagctac cgacaacaac    4980
gtgtctcaac cactgtgact caaaacaaca acagcgaatt tgcttggcct ggagcttctt    5040
cttgggctct caatggacgt aatagcttga tgaatcctgg acctgctatg ccagccaca    5100 aagaaggaga ggaccgtttc tttcctttgt ctggatcttt aattttggc aaacaaggaa    5160 ctggaagaga caacgtggat gcggacaaag tcatgataac caacgaagaa gaaattaaaa    5220
ctactaaccc ggtagcaacg gagtcctatg gacaagtggc cacaaaccac cagagtgccc    5280
aagcacaggc gcagaccggc tgggttcaaa accaaggaat acttccgggt atggtttggc    5340
aggacagaga tgtgtacctg caaggaccca tttgggccaa aattcctcac acggacggca    5400
actttcaccc ttctccgctg atgggagggt ttggaatgaa gcacccgcct cctcagatcc    5460
tcatcaaaaa cacacctgta cctgcggatc ctccaacggc cttcaacaag gacaagctga    5520
actctttcat cacccagtat tctactggcc aagtcagcgt ggagatcgag tgggagctgc    5580
agaaggaaaa cagcaagcgc tggaacccgg agatccagta cacttccaac tattacaagt    5640
ctaataatgt tgaatttgct gttaatactg aaggtgtata tagtgaaccc cgccccattg    5700
gcaccagata cctgactcgt aatctgtaat tgcttgttaa tcaataaacc gtttaattcg    5760
tttcagttga actttggtct ctgcgaaggg cgaattcatc gatgcatgtc cttgggtccg    5820
gcctgctgaa tgcgcaggcg gtcggccatg ccccaggctt cgttttgaca tcggcgcagg    5880
tctttgtagt agtcttgcat gagcctttct accggcactt cttcttctcc ttcctcttgt    5940
cctgcatctc ttgcatctat cgctgcggcg gcggcggagt ttggccgtag gtggcgccct    6000
cttcctccca tcgtgtgacc ccgaagcccc tcatcggctg aagcagggct aggtcggcga    6060
caacgcgctc ggctaatatg gcctgctgca cctgcgtgag ggtagactgg aagtcatcca    6120
tgtccacaaa gcgtggtat gcgcccgtgt tgatggtgta agtgcagttg gccataacgg    6180
accagttaac ggtctggtga cccggctgcg agagctcggt gtacctgaga cgcgagtaag    6240
ccctcgagtc aaatacgtag tcgttacaag tccgcaccag gtactggtat cccaccaaaa    6300
agtgcggcgc cggctggcgg tagagggggcc agcgtagggt ggccgggggct ccggggcga    6360 gatcttccaa cataaggcga tgatatccgt agatgtacct ggacatccag gtgatgccgg    6420
cggcggtggt ggaggcgcgc ggaaagtcgc ggacgcggtt ccagatgttg cgcagcggca    6480
aaaagtgctc catggtcggg acgctctggc cggtcaggcg cgcgcaatcg ttgacgctct    6540
```

```
agaccgtgca aaaggagagc ctgtaagcgg gcactcttcc gtggtctggt ggataaattc    6600
gcaagggtat catggcggac gaccgggggtt cgagccccgt atccggccgt ccgccgtgat   6660
ccatgcggtt accgcccgcg tgtcgaaccc aggtgtgcga cgtcagacaa cgggggagtg    6720
ctccttttgg cttccttcca ggcgcggcgg ctgctgcgct agcttttttg gccactggcc    6780
gcgcgcagcg taagcggtta ggctggaaag cgaaagcatt aagtggctcg ctccctgtag    6840
ccggagggtt attttccaag ggttgagtcg cgggacccccc ggttcgagtc tcggaccggc   6900
cggactgcgg cgaacggggg tttgtctccc cgtcatgcaa gaccccgctt gcaaattcct    6960
ccggaaacag ggacgagccc ctttttttgct tttcccagat gcatccggtg ctgcggcaga   7020
tgcgcccccc tcctcagcag cggcaagagc aagagcagcg gcagacatgc agggcaccct    7080
cccctcctcc taccgcgtca ggaggggcga catccgcggt tgacgcggca gcagatggtg    7140
attacgaacc cccgcggcgc cgggcccggc actacctgga cttggaggag ggcgagggcc    7200
tggcgcggct aggagcgccc tctcctgagc ggcacccaag ggtgcagctg aagcgtgata    7260
cgcgtgaggc gtacgtgccg cggcagaacc tgtttcgcga ccgcgaggga gaggagcccg    7320
aggagatgcg ggatcgaaag ttccacgcag ggcgcgagct gcggcatggc ctgaatcgcg    7380
agcggttgct gcgcgaggag gactttgagc ccgacgcgcg aaccgggatt agtcccgcgc    7440
gcgcacacgt ggcggccgcc gacctggtaa ccgcatacga gcagacggtg aaccagggcg    7500
atcgcaccct ttggcgcatc ccattctcca gtaactttat gtccatgggc gcactcacag    7560
acctgggcca aaaccttctc tacgccaact ccgcccacgc gctagacatg acttttgagg    7620
tggatcccat ggacgagccc acccttcttt atgttttgtt tgaagtcttt gacgtggtcc    7680
gtgtgcaccg gccgcaccgc ggcgtcatcg aaaccgtgta cctgcgcacg cccttctcgg    7740
ccggcaacgc cacaacataa agaagcaagc aacatcaaca acagctgccg ccatgggctc    7800
cagtgagcag gaactgaaag ccattgtcaa agatcttggt tgtgggccat attttttggg    7860
cacctatgac aagcgctttc caggctttgt ttctccacac aagctcgcct gcgccatagt    7920
caatacggcc ggtcgcgaga ctgggggcgt acactggatg gcctttgcct ggaacccgca    7980
ctcaaaaaca tgctacctct ttgagcccctt tggcttttct gaccagcgac tcaagcaggt   8040
ttaccagttt gagtacgagt cactcctgcg ccgtagcgcc attgcttctt cccccgaccg    8100
ctgtataacg ctggaaaagt ccacccaaag cgtacagggg cccaactcgg ccgcctgtgg    8160
actattctgc tgcatgtttc tccacgcctt tgccaactgg ccccaaactc ccatggatca    8220
caaccccacc atgaacctta ttaccgggggt acccaactcc atgctcaaca gtccccaggt    8280
acagcccacc ctgcgtcgca accaggaaca gctctacagc ttcctggagc gccactcgcc    8340
ctacttccgc agccacagtg cgcagattag gagcgccact tctttttgtc acttgaaaaa    8400
catgtaaaaa taatgtacta gagacacttt caataaaggc aaatgctttt atttgtacac    8460
tctcgggtga ttatttaccc ccaccccttgc cgtctgcgcc gtttaaaaat caaagggggtt   8520
ctgccgcgca tcgctatgcg ccactggcag ggacacgttg cgatactggt gtttagtgct    8580
ccacttaaac tcaggcacaa ccatccgcgg cagctcggtg aagttttcac tccacaggct    8640
gcgcaccatc accaacgcgt ttagcaggtc gggcgccgat atcttgaagt cgcagttggg    8700
gcctccgccc tgcgcgcgcg agttgcgata cacagggttg cagcactgga acactatcag    8760
cgccgggtgg tgcacgctgg ccagcacgct cttgtcggag atcagatccg cgtccaggtc    8820
ctccgcgttg ctcagggcga acggagtcaa ctttggtagc tgccttccca aaaagggcgc    8880
gtgcccaggc tttgagttgc actcgcaccg tagtggcatc aaaaggtgac cgtgcccggt    8940
```

```
ctgggcgtta ggatacagcg cctgcataaa agccttgatc tgcttaaaag ccacctgagc   9000
ctttgcgcct tcagagaaga acatgccgca agacttgccg gaaaactgat tggccggaca   9060
ggccgcgtcg tgcacgcagc accttgcgtc ggtgttggag atctgcacca catttcggcc   9120
ccaccggttc ttcacgatct tggccttgct agactgctcc ttcagcgcgc gctgcccgtt   9180
ttcgctcgtc acatccattt caatcacgtg ctccttattt atcataatgc ttccgtgtag   9240
acacttaagc tcgccttcga tctcagcgca gcggtgcagc cacaacgcgc agcccgtggg   9300
ctcgtgatgc ttgtaggtca cctctgcaaa cgactgcagg tacgcctgca ggaatcgccc   9360
catcatcgtc acaaaggtct tgttgctggt gaaggtcagc tgcaacccgc ggtgctcctc   9420
gttcagccag gtcttgcata cggccgccag agcttccact tggtcaggca gtagtttgaa   9480
gttcgccttt agatcgttat ccacgtggta cttgtccatc agcgcgcgcg cagcctccat   9540
gcccttctcc cacgcagaca cgatcggcac actcagcggg ttcatcaccg taatttcact   9600
ttccgcttcg ctgggctctt cctcttcctc ttgcgtccgc ataccacgcg ccactgggtc   9660
gtcttcattc agccgccgca ctgtgcgctt acctcctttg ccatgcttga ttagcaccgg   9720
tgggttgctg aaacccacca tttgtagcgc cacatcttct cttcttcct cgctgtccac   9780 gattacctct ggtgatggcg ggcgctcggg cttgggagaa gggcgcttct ttttcttctt   9840
gggcgcaatg ccaaatccg ccgccgaggt cgatggccgc gggctgggtg tgcgcggcac   9900
cagcgcgtct tgtgatgagt cttcctcgtc ctcggactcg atacgccgcc tcatccgctt   9960
ttttgggggc gcccggggag gcggcggcga cgggacgg gacgacgt cctccatggt  10020 tgggggacgt cgcgccgcac cgcgtccgcg ctcggggtg gtttcgcgct gctcctcttc  10080
ccgactggcc atttccttct cctataggca gaaaaagatc atggagtcag tcgagaagaa  10140
ggacagccta accgccccct ctgagttcgc caccaccgcc tccaccgatg ccgccaacgc  10200
gcctaccacc ttccccgtcg aggcaccccc gcttgaggag gaggaagtga ttatcgagca  10260
ggacccaggt tttgtaagcg aagacgacga ggaccgctca gtaccaacag aggataaaaa  10320
gcaagaccag gacaacgcag aggcaaacga ggaacaagtc gggcgggggg acgaaaggca  10380
tggcgactac ctagatgtgg gagacgacgt gctgttgaag catctgcagc gccagtgcgc  10440
cattatctgc gacgcgttgc aagagcgcag cgatgtgccc ctcgccatag cggatgtcag  10500
ccttgcctac gaacgccacc tattctcacc gcgcgtaccc cccaaacgcc aagaaaacgg  10560
cacatgcgag cccaacccgc gcctcaactt ctacccgta tttgccgtgc cagaggtgct  10620 tgccaccat cacatctttt tccaaaactg caagataccc ctatcctgcc gtgccaaccg  10680
cagccgagcg gacaagcagc tggccttgcg gcagggcgct gtcatacctg atatcgcctc  10740
gctcaacgaa gtgccaaaaa tctttgaggg tcttggacgc gacgagaagc gcgcggcaaa  10800
cgctctgcaa caggaaaaca gcgaaaatga aagtcactct ggagtgttgg tggaactcga  10860
gggtgacaac gcgcgcctag ccgtactaaa acgcagcatc gaggtcaccc actttgccta  10920
cccggcactt aacctacccc ccaaggtcat gagcacagtc atgagtgagc tgatcgtgcg  10980
ccgtgcgcag cccctggaga gggatgcaaa tttgcaagaa caaacagagg agggcctacc  11040
cgcagttggc gacgagcagc tagcgcgctg gcttcaaacg cgcgagcctg ccgacttgga  11100
ggagcgacgc aaaactaatg atggccgcagt gctcgttacc gtggagcttg agtgcatgca  11160
gcggttcttt gctgacccgg agatgcagcg caagctagag gaaacattgc actacacctt  11220
tcgacagggc tacgtacgcc aggcctgcaa gatctccaac gtggagctct gcaacctggt  11280
```

```
ctcctacctt ggaattttgc acgaaaaccg ccttgggcaa aacgtgcttc attccacgct   11340
caagggcgag gcgcgccgcg actacgtccg cgactgcgtt tacttatttc tatgctacac   11400
ctggcagacg gccatgggcg tttggcagca gtgcttggag gagtgcaacc tcaaggagct   11460
gcagaaactg ctaaagcaaa acttgaagga cctatggacg gccttcaacg agcgctccgt   11520
ggccgcgcac ctggcggaca tcattttccc cgaacgcctg cttaaaaccc tgcaacaggg   11580
tctgccagac ttcaccagtc aaagcatgtt gcagaacttt aggaacttta tcctagagcg   11640
ctcaggaatc ttgcccgcca cctgctgtgc acttcctagc gactttgtgc ccattaagta   11700
ccgcgaatgc cctccgccgc tttggggcca ctgctaccct ctgcagctag ccaactacct   11760
tgcctaccac tctgacataa tggaagacgt gagcggtgac ggtctactgg agtgtcactg   11820
tcgctgcaac ctatgcaccc cgcaccgctc cctggtttgc aattcgcagc tgcttaacga   11880
aagtcaaatt atcggtacct ttgagctgca gggtccctcg cctgacgaaa agtccgcggc   11940
tccggggttg aaactcactc cggggctgtg gacgtcggct taccttcgca aatttgtacc   12000
tgaggactac cacgcccacg agattaggtt ctacgaagac caatcccgcc cgccaaatgc   12060
ggagcttacc gcctgcgtca ttacccaggg ccacattctt ggccaattgc aagccatcaa   12120
caaagcccgc caagagtttc tgctacgaaa gggacggggg gtttacttgg accccagtc    12180 cggcgaggag ctcaacccaa tcccccgcc gccgcagccc tatcagcagc agccgcgggc    12240
ccttgcttcc caggatggca cccaaaaaga agctgcagct gccgccgcca cccacggacg   12300
aggaggaata ctgggacagt caggcagagg aggttttgga cgaggaggag gaggacatga   12360
tggaagactg ggagagccta gacgaggaag cttccgaggt cgaagaggtg tcagacgaaa   12420
caccgtcacc ctcggtcgca ttcccctcgc cggcgcccca gaaatcggca accggttcca   12480
gcatggctac aacctccgct cctcaggcgc cgccggcact gcccgttcgc cgacccaacc   12540
gtagatggga caccactgga accagggccg gtaagtccaa gcagccgccg ccgttagccc   12600
aagagcaaca acagcgccaa ggctaccgct catggcgcgg gcacaagaac gccatagttg   12660
cttgcttgca agactgtggg ggcaacatct ccttcgcccg ccgctttctt ctctaccatc   12720
acggcgtggc cttccccgt aacatcctgc attactaccg tcatctctac agcccatact    12780
gcaccggcgg cagcggcagc ggcagcaaca gcagcggcca cacagaagca aaggcgaccg   12840
gatagcaaga ctctgacaaa gcccaagaaa tccacagcgg cggcagcagc aggaggagga   12900
gcgctgcgtc tggcgcccaa cgaacccgta tcgacccgcg agcttagaaa caggattttt   12960
cccactctgt atgctatatt tcaacagagc aggggccaag aacaagagct gaaaataaaa   13020
aacaggtctc tgcgatccct cacccgcagc tgcctgtatc acaaaagcga agatcagctt   13080
cggcgcacgc tggaagacgc ggaggctctc ttcagtaaat actgcgcgct gactcttaag   13140
gactagtttc gcgccctttc tcaaatttaa gcgcgaaaac tacgtcatct ccagcggcca   13200 caccggcgc cagcacctgt cgtcagcgcc attatgagca aggaaattcc cacgccctac    13260
atgtggagtt accagccaca aatgggactt gcggctggag ctgcccaaga ctactcaacc   13320
cgaataaact acatgagcgc gggaccccac atgatatccc gggtcaacgg aatccgcgcc   13380
caccgaaacc gaattctctt ggaacaggcg gctattacca ccacacctcg taataacctt   13440
aatccccgta gttggcccgc tgccctggtg taccaggaaa gtcccgctcc caccactgtg   13500
gtacttccca gagacgccca ggccgaagtt cagatgacta actcaggggc gcagcttgcg   13560
ggcggctttc gtcacagggt gcggtcgccc gggcagggta taactcacct gacaatcaga   13620
gggcgaggta ttcagctcaa cgacgagtcg gtgagctcct cgcttggtct ccgtccggac   13680
```

```
gggacatttc agatcggcgg cgccggccgc tcttcattca cgcctcgtca ggcaatccta   13740
actctgcaga cctcgtcctc tgagccgcgc tctggaggca ttggaactct gcaatttatt   13800
gaggagtttg tgccatcggt ctactttaac cccttctcgg gacctccggg ccactatccg   13860
gatcaattta ttcctaactt tgacgcggta aaggactcgg cggatggcta cgactgaatg   13920
ttaagtggag aggcagagca actgcgcctg aaacacctgg tccactgtcg ccgccacaag   13980
tgctttgccc gcgactccgg tgagttttgc tactttgaat gcccgagga tcatatcgag    14040
ggcccggcgc acggcgtccg gcttaccgcc cagggagagc ttgcccgtag cctgattcgg   14100
gagtttaccc agcgccccct gctagttgag cgggacaggg gaccctgtgt tctcactgtg   14160
atttgcaact gtcctaaccc tggattacat caagatcttt gttgccatct ctgtgctgag   14220
tataataaat acagaaatta aaatatactg gggctcctat cgccatcctg taaacgccac   14280
cgtcttcacc cgcccaagca aaccaaggcg aaccttacct ggtactttta acatctctcc   14340
ctctgtgatt tacaacagtt tcaacccaga cggagtgagt ctacgagaga acctctccga   14400
gctcagctac tccatcagaa aaaacaccac cctccttacc tgccgggaac gtacgagtgc   14460
gtcaccggcc gctgcaccac acctaccgcc tgaccgtaaa ccagactttt tccggacaga   14520
cctcaataac tctgtttacc agaacaggag gtgagcttag aaaacccta gggtattagg    14580
ccaaaggcgc agctactgtg gggtttatga acaattcaag caactctacg gctattcta    14640
attcaggttt ctctagaaat ggacggaatt attacagagc agcgcctgct agaaagacgc   14700
agggcagcgg ccgagcaaca gcgcatgaat caagagctcc aagacatggt taacttgcac   14760
cagtgcaaaa ggggtatctt ttgtctggta aagcaggcca aagtcaccta cgacagtaat   14820
accaccggac accgccttag ctacaagttg ccaaccaagc gtcagaaatt ggtggtcatg   14880
gtgggagaaa agcccattac cataactcag cactcggtag aaaccgaagg ctgcattcac   14940
tcaccttgtc aaggacctga ggatctctgc acccttatta agaccctgtg cggtctcaaa   15000
gatcttattc cctttaacta ataaaaaaaa ataataaagc atcacttact taaaatcagt   15060
tagcaaattt ctgtccagtt tattcagcag cacctccttg ccctcctccc agctctggta   15120
ttgcagcttc ctcctggctg caaactttct ccacaatcta aatggaatgt cagtttcctc   15180
ctgttcctgt ccatccgcac ccactatctt catgttgttg cagatgaagc gcgcaagacc   15240
gtctgaagat accttcaacc ccgtgtatcc atatgacacg gaaaccggtc tccaactgt    15300
gccttttctt actcctccct ttgtatcccc caatgggttt caagagagtc cccctggggt   15360
actctctttg cgcctatccg aacctctagt tacctccaat ggcatgcttg cgctcaaaat   15420
gggcaacggc ctctctctgg acgaggccgg caaccttacc tcccaaaatg taaccactgt   15480
gagcccacct ctcaaaaaaa ccaagtcaaa cataaacctg gaaatatctg caccccctcac  15540
agttacctca gaagccctaa ctgtggctgc cgccgcacct ctaatggtcg cgggcaacac   15600
actcaccatg caatcacagg ccccgctaac cgtgcacgac tccaaactta gcattgccac   15660
ccaaggaccc ctcacagtgt cagaaggaaa gctagccctg caaacatcag gcccctcac    15720
caccaccgat agcagtaccc ttactatcac tgcctcaccc cctctaacta ctgccactgg   15780
tagcttgggc attgacttga aagagcccat ttatacacaa aatggaaaac taggactaaa   15840
gtacggggct cctttgcatg taacagacga cctaaacact ttgaccgtag caactggtcc   15900
aggtgtgact attaataata cttccttgca aactaaagtt actggagcct tgggttttga   15960
ttcacaaggc aatatgcaac ttaatgtagc aggaggacta aggattgatt ctcaaaacag   16020
```

```
acgccttata cttgatgtta gttatccgtt tgatgctcaa aaccaactaa atctaagact    16080
aggacagggc cctcttttta taaactcagc ccacaacttg gatattaact acaacaaagg    16140
cctttacttg tttacagctt caaacaattc caaaaagctt gaggttaacc taagcactgc    16200
caaggggttg atgtttgacg ctacagccat agccattaat gcaggagatg ggcttgaatt    16260
tggttcacct aatgcaccaa acacaaatcc cctcaaaaca aaaattggcc atggcctaga    16320
atttgattca acaaggctta tggttcctaa actaggaact ggccttagtt ttgacagcac    16380
aggtgccatt acagtaggaa acaaaaataa tgataagcta actttgtgga ccacaccagc    16440
tccatctcct aactgtagac taaatgcaga gaaagatgct aaactcactt tggtcttaac    16500
aaaatgtggc agtcaaatac ttgctacagt ttcagttttg gctgttaaag gcagtttggc    16560
tccaatatct ggaacagttc aaagtgctca tcttattata agatttgacg aaaatggagt    16620
gctactaaac aattccttcc tggacccaga atattggaac tttagaaatg gagatcttac    16680
tgaaggcaca gcctatacaa acgctgttgg atttatgcct aacctatcag cttatccaaa    16740
atctcacggt aaaactgcca aaagtaacat tgtcagtcaa gtttacttaa acggagacaa    16800
aactaaacct gtaacactaa ccattacact aaacggtaca caggaaacag gagacacaac    16860
tccaagtgca tactctatgt cattttcatg ggactggtct ggccacaact acattaatga    16920
aatatttgcc acatcctctt acacttttc atacattgcc caagaataaa gaatcgtttg    16980
tgttatgttt caacgtgttt attttcaat tgcagaaaat ttcaagtcat ttttcattca    17040
gtagtatagc cccaccacca catagcttat acagatcacc gtaccttaat caaactcaca    17100
gaaccctagt attcaacctg ccacctccct cccaacacac agagtacaca gtcctttctc    17160
cccggctggc cttaaaaagc atcatatcat gggtaacaga catattctta ggtgttatat    17220
tccacacggt ttcctgtcga gccaaacgct catcagtgat attaataaac tccccgggca    17280
gctcacttaa gttcatgtcg ctgtccagct gctgagccac aggctgctgt ccaacttgcg    17340
gttgcttaac gggcggcgaa ggagaagtcc acgcctacat gggggtagag tcataatcgt    17400
gcatcaggat agggcggtgg tgctgcagca gcgcgcgaat aaactgctgc cgccgccgct    17460
ccgtcctgca ggaatacaac atggcagtgg tctcctcagc gatgattcgc accgcccgca    17520
gcataaggcg ccttgtcctc cgggcacagc agcgcaccct gatctcactt aaatcagcac    17580
agtaactgca gcacagcacc acaatattgt tcaaaatccc acagtgcaag gcgctgtatc    17640
caaagctcat ggcggggacc acagaaccca cgtggccatc ataccacaag cgcaggtaga    17700
ttaagtggcg accctcata aacacgctgg acataaacat tacctctttt ggcatgttgt    17760
aattccaccac ctcccggtac catataaacc tctgattaaa catggcgcca tccaccacca    17820
tcctaaacca gctggccaaa acctgcccgc cggctataca ctgcagggaa ccgggactgg    17880
aacaatgaca gtggagagcc caggactcgt aaccatggat catcatgctc gtcatgatat    17940
caatgttggc acaacacagg cacacgtgca tacacttcct caggattaca agctcctccc    18000
gcgttagaac catatcccag ggaacaaccc attcctgaat cagcgtaaat cccacactgc    18060
agggaagacc tcgcacgtaa ctcacgttgt gcattgtcaa agtgttacat tcgggcagca    18120
gcggatgatc ctccagtatg gtagcgcggg tttctgtctc aaaaggaggt agacgatccc    18180
tactgtacgg agtgcgccga gacaaccgag atcgtgttgg tcgtagtgtc atgccaaatg    18240
gaacgccgga cgtagtcata tttcctgaag caaaaccagg tgcgggcgtg acaaacagat    18300
ctgcgtctcc ggtctcgccg cttagatcgc tctgtgtagt agttgtagta tatccactct    18360
ctcaaagcat ccaggcgccc cctggcttcg ggttctatgt aaactccttc atgcgccgct    18420
```

```
gccctgataa catccaccac cgcagaataa gccacaccca gccaacctac acattcgttc   18480
tgcgagtcac acacgggagg agcgggaaga gctggaagaa ccatgttttt ttttttattc   18540
caaaagatta tccaaaacct caaaatgaag atctattaag tgaacgcgct ccoctccggt   18600 ggcgtggtca aactctacag ccaaagaaca gataatggca tttgtaagat gttgcacaat   18660
ggcttccaaa aggcaaacgg ccctcacgtc caagtggacg taaaggctaa acccttcagg   18720
gtgaatctcc tctataaaca ttccagcacc ttcaaccatg cccaaataat tctcatctcg   18780
ccaccttctc aatatatctc taagcaaatc ccgaatatta agtccggcca ttgtaaaaat   18840
ctgctccaga gcgccctcca ccttcagcct caagcagcga atcatgattg caaaaattca   18900
ggttcctcac agacctgtat aagattcaaa agcggaacat taacaaaaat accgcgatcc   18960
cgtaggtccc ttcgcagggc cagctgaaca taatcgtgca ggtctgcacg gaccagcgcg   19020
gccacttccc cgccaggaac catgacaaaa gaacccacac tgattatgac acgcatactc   19080
ggagctatgc taaccagcgt agccccgatg taagcttgtt gcatgggcgg cgatataaaa   19140
tgcaaggtgc tgctcaaaaa atcaggcaaa gcctcgcgca aaaagaaag cacatcgtag   19200 tcatgctcat gcagataaag gcaggtaagc tccggaacca ccacagaaaa agacaccatt   19260
tttctctcaa acatgtctgc gggtttctgc ataaacacaa aataaaataa caaaaaaaca   19320
tttaaacatt agaagcctgt cttacaacag gaaaaacaac ccttataagc ataagacgga   19380
ctacggccat gccggcgtga ccgtaaaaaa actggtcacc gtgattaaaa agcaccaccg   19440
acagctcctc ggtcatgtcc ggagtcataa tgtaagactc ggtaaacaca tcaggttgat   19500
tcacatcggt cagtgctaaa aagcgaccga aatagcccgg gggaatacat acccgcaggc   19560
gtagagacaa cattcagcc cccataggag gtataacaaa attaatagga gagaaaaaca   19620
cataaacacc tgaaaaaccc tcctgcctag gcaaaatagc accctcccgc tccagaacaa   19680
catacagcgc ttccacagcg gcagccataa cagtcagcct taccagtaaa aagaaaacc   19740 tattaaaaaa acaccactcg acacggcacc agctcaatca gtcacagtgt aaaaagggc   19800 caagtgcaga gcgagtatat ataggactaa aaaatgacgt aacggttaaa gtccacaaaa   19860
aacacccaga aaaccgcacg cgaacctacg cccagaaacg aaagccaaaa aacccacaac   19920
ttcctcaaat cgtcacttcc gttttcccac gttacgtcac ttcccatttt aagaaaacta   19980
caattcccaa cacatacaag ttactccgcc ctaaaaccta cgtcacccgc cccgttccca   20040
cgccccgcgc cacgtcacaa actccacccc ctcattatca tattggcttc aatccaaaat   20100
aaggtatatt attgatgatg ttaattaaga attcggatct gcgacgcgag gctggatggc   20160
cttccccatt atgattcttc tcgcttccgg cggcatcggg atgcccgcgt tgcaggccat   20220
gctgtccagg caggtagatg acgaccatca gggacagctt caaggccagc aaaaggccag   20280
gaaccgtaaa aaggccgcgt tgctggcgtt tttccatagg ctccgccccc ctgacgagca   20340
tcacaaaaat cgacgctcaa gtcagaggtg gcgaaaccocg acaggactat aaagatacca   20400
ggcgtttccc cctggaagct ccctcgtgcg ctctcctgtt ccgaccctgc cgcttaccgg   20460
atacctgtcc gcctttctcc cttcgggaag cgtggcgctt tctcatagct cacgctgtag   20520
gtatctcagt tcggtgtagg tcgttcgctc caagctgggc tgtgtgcacg aaccccccgt   20580
tcagcccgac cgctgcgcct tatccggtaa ctatcgtctt gagtccaacc cggtaagaca   20640
cgacttatcg ccactggcag cagccactgg taacaggatt agcagagcga ggtatgtagg   20700
cggtgctaca gagttcttga agtggtggcc taactacggc tacactagaa ggacagtatt   20760
```

| | |
|---|---|
| tggtatctgc gctctgctga agccagttac cttcggaaaa agagttggta gctcttgatc | 20820 |
| cggcaaacaa accaccgctg gtagcggtgg ttttttttgtt tgcaagcagc agattacgcg | 20880 |
| cagaaaaaaa ggatctcaag aagatccttt gatcttttct acggggtctg acgctcagtg | 20940 |
| gaacgaaaac tcacgttaag ggattttggt catgagatta tcaaaaagga tcttcaccta | 21000 |
| gatccttttta aatcaatcta agtatatat gagtaaactt ggtctgacag gtttaaactc | 21060 |
| agaagaactc gtcaagaagg cgatagaagg cgatgcgctg cgaatcggga gcggcgatac | 21120 |
| cgtaaagcac gaggaagcgg tcagcccatt cgccgccaag ctcttcagca atatcacggg | 21180 |
| tagccaacgc tatgtcctga tagcggtccg ccacacccag ccggccacag tcgatgaatc | 21240 |
| cagaaaagcg gccattttcc accatgatat tcggcaagca ggcatcgcca tgggtcacga | 21300 |
| cgagatcctc gccgtcgggc atgctcgcct tgagcctggc gaacagttcg gctggcgcga | 21360 |
| gcccctgatg ctcttcgtcc agatcatcct gatcgacaag accggcttcc atccgagtac | 21420 |
| gtgctcgctc gatgcgatgt ttcgcttggt ggtcgaatgg gcaggtagcc ggatcaagcg | 21480 |
| tatgcagccg ccgcattgca tcagccatga tggatacttt ctcggcagga gcaaggtgag | 21540 |
| atgacaggag atcctgcccc ggcacttcgc ccaatagcag ccagtcccctt cccgcttcag | 21600 |
| tgacaacgtc gagcacagct gcgcaaggaa cgcccgtcgt ggccagccac gatagccgcg | 21660 |
| ctgcctcgtc ttgcagttca ttcagggcac cggacaggtc ggtcttgaca aaaagaaccg | 21720 |
| ggcgcccctg cgctgacagc cggaacacgg cggcatcaga gcagccgatt gtctgttgtg | 21780 |
| cccagtcata gccgaatagc ctctccaccc aagcggccgg agaacctgcg tgcaatccat | 21840 |
| cttgttcaat cataacgtta ctcttccttt ttcaatatta ttgaagcatt tatcagggtt | 21900 |
| attgtctcat gagcggatac atatttgaat gtatttagaa aaataaacaa ataggggttc | 21960 |
| cgcgcacatt tccccgaaaa gtgccacctg acgtctaaga aaccattatt atcatgacat | 22020 |
| taacctataa aaataggcgt atcacgaggc cctttcgtct tcaa | 22064 |

<210> SEQ ID NO 7
<211> LENGTH: 21708
<212> TYPE: DNA
<213> ORGANISM: Artificial Sequence
<220> FEATURE:
<223> OTHER INFORMATION: SYNTHETIC POLYNUCLEOTIDE

<400> SEQUENCE: 7

| | |
|---|---|
| gaattggatc cgaattctta attaacatca tcaataatat accttatttt ggattgaagc | 60 |
| caatatgata atgaggggt ggagtttgtg acgtggcgcg gggcgtggga acggggcggg | 120 |
| tgacgtagta gtgtggcgga agtgtgatgt tgcaagtgtg gcggaacaca tgtaagcgac | 180 |
| ggatgtggca aaagtgacgt ttttggtgtg cgccggtgta cacaggaagt gacaattttc | 240 |
| gcgcggtttt aggcggatgt tgtagtaaat ttgggcgtaa ccgagtaaga tttggccatt | 300 |
| ttcgcgggaa aactgaataa gaggaagtga atctgaata attttgtgtt actcatagcg | 360 |
| cgtaatattt gtctagggcc gcggggactt tgaccgtttta cgtggagact cgcccaggtg | 420 |
| tttttctcag gtgttttccg cgttccgggt caaagttggc gttttattat tatagtcagg | 480 |
| gggatcctct agaactagtg gatccgtccc tcaggcctag aagtaaaaaa gggaaaaaag | 540 |
| agtgtgtttg tcaaaatagg agacaggtgg tggcaaccaa ggacttatag ggaccttac | 600 |
| atctacagac caacagatgc ccccttacca tatacaggaa gatatgactt aaattgggat | 660 |
| aggtgggtca caatcaacgg ctataaagtg ttatacagat ccctcccctc cccttttcgtg | 720 |
| aaagactcgc cagagctaga cctccttggt gtatgctaac tgagaagaga aagacgacat | 780 |

```
gaaacaacag gtacatgatt atatttatct aggaacagga atgcacttttt ggggaaaggt    840
tttccatacc aaggaagggg cagtggctgg actgatagaa cattattctg caaaaactta    900
tggtatgagt tattatgatt agcctttatt tgcccaacct tgcggttccc agggtttaaa    960
taagtttatg gttacaaact gttcttaaaa cgaggatgtg agacaagtgg tttcctgact   1020
tggtttggta atcaaatgtt ctgatctgag ctcttagtgt tctattttcc tatgttcttt   1080
tggaatctat ccaagtctta tgtaaatgct tatgtaaacc ataatataaa agagtgctga   1140
ttttttgagt aaacttgcaa cagtcctaac attcttctct cgtgtgtttg tgtctgttcg   1200
ccatcccgtc tccgctcgtc acttatcctt cacttttcag agggtccccc cgcagatccc   1260
ggtcaccctc aggtcgggac ctgcagaaga cgcccgagtg agcacgcagg gtctccattt   1320
tgaagcggga ggtttgaacg cgcagccgcc atgccggggt tttacgagat tgtgattaag   1380
gtccccagcg accttgacgg gcatctgccc ggcatttctg acagctttgt gaactgggtg   1440
gccgagaagg aatgggagtt gccgccagat tctgacatgg atctgaatct gattgagcag   1500
gcacccctga ccgtggccga aagctgcag cgcgactttc tgacggaatg gcgccgtgtg   1560
agtaaggccc cggaggccct tttctttgtg caatttgaga agggagagag ctacttccac   1620
atgcacgtgc tcgtggaaac caccggggtg aaatccatgg ttttgggacg tttcctgagt   1680
cagattcgcg aaaaactgat tcagagaatt taccgcggga tcgagccgac tttgccaaac   1740
tggttcgcgg tcacaaagac cagaaatggc gccggaggcg ggaacaaggt ggtggatgag   1800
tgctacatcc ccaattactt gctccccaaa acccagcctg agctccagtg ggcgtggact   1860
aatatggaac agtatttaag cgcctgtttg aatctcacgg agcgtaaacg gttggtggcg   1920
cagcatctga cgcacgtgtc gcagacgcag gagcagaaca aagagaatca gaatcccaat   1980
tctgatgcgc cggtgatcag atcaaaaact tcagccaggt acatggagct ggtcgggtgg   2040
ctcgtggaca aggggattac ctcggagaag cagtggatcc aggaggacca ggcctcatac   2100
atctccttca atgcggcctc caactcgcgg tcccaaatca aggctgcctt ggacaatgcg   2160
ggaaagatta tgagcctgac taaaaccgcc cccgactact ggtgggccag cagcccgtgg   2220
aggacatttc cagcaatcgg atttataaaa ttttggaact aaacgggtac gatccccaat   2280
atgcggcttc cgtcttttctg ggatgggcca cgaaaaagtt cggcaagagg aacaccatct   2340
ggctgttttgg gcctgcaact accgggaaga ccaacatcgc ggaggccata gcccacactg   2400
tgcccttcta cgggtgcgta aactggacca atgagaactt ccccttcaac gactgtgtcg   2460
acaagatggt gatctggtgg gaggagggga agatgaccgc caaggtcgtg gagtcggcca   2520
aagccattct cggaggaagc aaggtgcgcg tggaccagaa atgcaagtcc tcggcccaga   2580
tagacccgac tccgtgatc gtcacctcca acaccaacat gtgcgccgtg attgacggga   2640
actcaacgac cttcgaacac cagcagccgt tgcaagaccg gatgttcaaa tttgaactca   2700
cccgccgtct ggatcatgac tttgggaagg tcaccaagca ggaagtcaaa gacttttttcc   2760
ggtgggcaaa ggatcacgtg gttgaggtgg agcatgaatt ctacgtcaaa aagggtggag   2820
ccaagaaaag acccgccccc agtgacgcag atataagtga gcccaaacgg gtgcgcgagt   2880
cagttgcgca gccatcgacg tcagacgcgg aagcttcgat caactacgca gacaggtacc   2940
aaaacaaatg ttctcgtcac gtgggcatga atctgatgct gtttccctgc agacaatgcg   3000
agagaatgaa tcagaattca aatatctgct tcactcacgg acagaaagac tgttttagagt   3060
gctttcccgt gtcagaatct caacccgttt ctgtcgtcaa aaaggcgtat cagaaactgt   3120
```

```
gctacattca tcatatcatg ggaaaggtgc cagacgcttg cactgcctgc gatctggtca    3180
atgtggattt ggatgactgc atctttgaac aataaatgat ttaaatcagg tatggctgcc    3240
gatggttatc ttccagattg gctcgaggac aacctctctg agggcattcg cgagtggtgg    3300
gacttgaaac ctggagcccc gaagcccaaa gccaaccagc aaaagcagga cgacggccgg    3360
ggtctggtgc ttcctggcta caagtacctc ggacccttca acggactcga caaggggag    3420 cccgtcaacg cggcggacgc agcggccctc gagcacgaca aggcctacga ccagcagctc    3480
aaagcgggtg acaatccgta cctgcggtat aaccacgccg acgccgagtt tcaggagcgt    3540
ctgcaagaag atacgtcttt tggggggcaac ctcgggcgag cagtcttcca ggccaagaag    3600
cgggttctcg aacctctcgg tctggttgag gaaggcgcta agacggctcc tggaaagaaa    3660
cgtccggtag agcagtcgcc acaagagcca gactcctcct cgggcatcgg caagacaggc    3720
cagcagcccg ctaaaaagag actcaattt ggtcagactg gcgactcaga gtcagtcccc    3780
gatccacaac ctctcggaga acctccagca gcccctcag gtctgggacc taatacaatg    3840
gcttcaggcg gtggcgctcc aatggcagac aataacgaag gcgccgacgg agtgggtaat    3900
tcctcgggaa attggcattg cgattccaca tggctggggg acagagtcat caccaccagc    3960
acccgaacct gggccctgcc cacctacaac aaccacctct acaagcaaat ctccaacggc    4020
acctcgggag gaagcaccaa cgacaacacc tattttggct acagcacccc ctgggggtat    4080
tttgacttca acagattcca ctgtcacttt tcaccacgtg actggcaacg actcatcaac    4140
aacaattggg gattccggcc caaaagactc aacttcaagc tgttcaacat ccaggtcaag    4200
gaagtcacga cgaacgaagg caccaagacc atcgccaata tctcaccag caccgtgcag    4260 gtctttacgg actcggagta ccagttaccg tacgtgctag gatccgctca ccagggatgt    4320
ctgcctccgt tccggcgga cgtcttcatg gttcctcagt acggctatt aactttaaac    4380 aatggaagcc aagccctggg acgttcctcc ttctactgtc tggagtattt cccatcgcag    4440
atgctgagaa ccggcaacaa ctttcagttc agctacacct tcgaggacgt gccttttccac    4500 agcagctacg cgcacagcca gagcctggac aggctgatga atccctcat cgaccagtac    4560 ctgtactacc tggtcagaac gcaaacgact ggaactggag ggacgcagac tctggcattc    4620
agccaagcgg gtcctagctc aatggccaac caggctagaa attgggtgcc cggaccttgc    4680
taccggcagc agcgcgtctc cacgacaacc aaccagaaca caacagcaa ctttgcctgg    4740 acgggagctg ccaagttaa gctgaacggc cgagactctc taatgaatcc gggcgtggca    4800
atggcttccc acaaggatga cgacgaccgc ttcttccctt cgagcggggt cctgattttt    4860
ggcaagcaag gagccgggaa cgatggagtg gattacagcc aagtgctgat tacagatgag    4920
gaagaaatca aggctaccaa ccccgtggcc acagaagaat atggagcagt ggccatcaac    4980
aaccaggccg ccaatacgca ggcgcagacc ggactcgtgc acaaccaggg ggtgattccc    5040
ggcatggtgt ggcagaatag agacgtgtac ctgcagggtc ccatctgggc caaaattcct    5100
cacacggacg gcaactttca cccgtctccc ctgatgggcg gctttggact gaagcacccg    5160
cctcctcaaa ttctcatcaa gaacacaccg gttccagcgg acccgccgct taccttcaac    5220
caggccaagc tgaactcttt catcacgcag tacagcaccg gacaggtcag cgtggaaatc    5280
gagtgggagc tgcagaaaga aaacagcaaa cgctggaatc cagagattca atacacttcc    5340
aactactaca aatctacaaa tgtggacttt gctgtcaaca cggaggggt ttatagcgag    5400 cctcgcccca ttggcacccg ttacctcacc cgcaacctgt aaatcgatgc atgtccttgg    5460
gtccggcctg ctgaatgcgc aggcggtcgg ccatgcccca ggcttcgttt tgacatcggc    5520
```

```
gcaggtctttt gtagtagtct tgcatgagcc tttctaccgg cacttcttct tctccttcct    5580
cttgtcctgc atctcttgca tctatcgctg cggcggcggc ggagtttggc cgtaggtggc    5640
gccctcttcc tcccatcgtg tgaccccgaa gcccctcatc ggctgaagca gggctaggtc    5700
ggcgacaacg cgctcggcta atatggcctg ctgcacctgc gtgagggtag actggaagtc    5760
atccatgtcc acaaagcggt ggtatgcgcc cgtgttgatg tgtaagtgc agttggccat    5820 aacgaccag ttaacggtct ggtgacccgg ctgcagagac tcggtgtacc tgagacgcga    5880
gtaagccctc gagtcaaata cgtagtcgtt acaagtccgc accaggtact ggtatcccac    5940
caaaaagtgc ggcggcggct ggcggtagag gggccagcgt agggtggccg gggctccggg    6000
ggcgagatct tccaacataa ggcgatgata tccgtagatg tacctggaca tccaggtgat    6060
gccggcggcg gtggtggagg cgcgcggaaa gtcgcggacg cggttccaga tgttgcgcag    6120
cggcaaaaag tgctccatgg tcgggacgct ctggccggtc aggcgcgcgc aatcgttgac    6180
gctctagacc gtgcaaaagg agagcctgta agcgggcact cttccgtggt ctggtggata    6240
aattcgcaag ggtatcatgg cggacgaccg gggttcgagc cccgtatccg gccgtccgcc    6300
gtgatccatg cggttaccgc ccgcgtgtcg aacccaggtg tgcgacgtca gacaacgggg    6360
gagtgctcct tttggcttcc ttccaggcgc ggcggctgct gcgctagctt ttttggccac    6420
tggccgcgcg cagcgtaagc ggttaggctg gaaagcgaaa gcattaagtg gctcgctccc    6480
tgtagccgga gggttatttt ccaagggttg agtcgcggga ccccggttc gagtctcgga    6540 ccggccggac tgcggcgaac gggggttgt ctccccgtca tgcaagaccc cgcttgcaaa    6600
ttcctccgga aacagggacg agccccttt ttgcttttcc cagatgcatc cggtgctgcg    6660
gcagatgcgc cccctcctc agcagcggca agagcaagag cagcggcaga catgcagggc    6720
accctcccct cctcctaccg cgtcaggagg ggcgacatcc gcggttgacg cggcagcaga    6780
tggtgattac gaaccccgc ggcgccggc ccggcactac ctggacttgg aggagggcga    6840
gggcctggcg cggctaggag cgccctctcc tgagcggcac ccaagggtgc agctgaagcg    6900
tgatacgcgt gaggcgtacg tgccgcggca gaacctgttt cgcgaccgcg agggagagga    6960
gcccgaggag atgcgggatc gaaagttcca cgcagggcgc gagctgcggc atggcctgaa    7020
tcgcgagcgg ttgctgcgcg aggaggactt tgagcccgac gcgcgaaccg ggattagtcc    7080
cgcgcgcgca cacgtggcgg ccgccgacct ggtaaccgca tacgagcaga cggtgaacca    7140
gggcgatcgc accctttggc gcatcccatt ctccagtaac tttatgtcca tgggcgcact    7200
cacagacctg ggccaaaacc ttctctacgc caactccgcc cacgcgctag acatgacttt    7260
tgaggtggat cccatggacg agcccaccct tctttatgtt ttgtttgaag tctttgacgt    7320
ggtccgtgtg caccggccgc accgcggcgt catcgaaacc gtgtacctgc gcacgccctt    7380
ctcggccggc aacgccacaa cataaagaag caagcaacat caacaacagc tgccgccatg    7440
ggctccagtg agcaggaact gaaagccatt gtcaaagatc ttggttgtgg ccatattttt    7500
ttgggcacct atgacaagcg cttttccaggc tttgtttctc cacacaagct cgcctgcgcc    7560
atagtcaata cggccggtcg cgagactggg ggcgtacact ggatggcctt tgcctggaac    7620
ccgcactcaa aaacatgcta cctctttgag cccttttggct tttctgacca gcgactcaag    7680
caggtttacc agtttgagta cgagtcactc ctgcgccgta gcgccattgc ttcttccccc    7740
gaccgctgta taacgctgga aaagtccacc caaagcgtac aggggcccaa ctcggccgcc    7800
tgtggactat tctgctgcat gtttctccac gcctttgcca actggcccca aactcccatg    7860
```

```
gatcacaacc ccaccatgaa ccttattacc ggggtaccca actccatgct caacagtccc    7920
caggtacagc ccaccctgcg tcgcaaccag gaacagctct acagcttcct ggagcgccac    7980
tcgccctact tccgcagcca cagtgcgcag attaggagcg ccacttcttt ttgtcacttg    8040
aaaaacatgt aaaataatg tactagagac actttcaata aaggcaaatg cttttatttg    8100
tacactctcg ggtgattatt tacccccacc cttgccgtct gcgccgttta aaaatcaaag    8160
gggttctgcc gcgcatcgct atgcgccact ggcagggaca cgttgcgata ctggtgttta    8220
gtgctccact taaactcagg cacaaccatc cgcggcagct cggtgaagtt ttcactccac    8280
aggctgcgca ccatcaccaa cgcgtttagc aggtcgggcg ccgatatctt gaagtcgcag    8340
ttggggcctc cgccctgcgc gcgcgagttg cgatacacag ggttgcagca ctggaacact    8400
atcagcgccg ggtggtgcac gctgccagc acgctcttgt cggagatcag atccgcgtcc     8460
aggtcctccg cgttgctcag ggcgaacgga gtcaactttg gtagctgcct tcccaaaaag    8520
ggcgcgtgcc caggctttga gttgcactcg caccgtagtg gcatcaaaag gtgaccgtgc    8580
ccggtctggg cgttaggata cagcgcctgc ataaaagcct tgatctgctt aaaagccacc    8640
tgagcctttg cgccttcaga gaagaacatg ccgcaagact tgccggaaaa ctgattggcc    8700
ggacaggccg cgtcgtgcac gcagcacctt gcgtcggtgt tggagatctg caccacattt    8760
cggccccacc ggttcttcac gatcttggcc ttgctagact gctccttcag cgcgcgctgc    8820
ccgttttcgc tcgtcacatc catttcaatc acgtgctcct tatttatcat aatgcttccg    8880
tgtagacact taagctcgcc ttcgatctca gcgcagcggt gcagccacaa cgcgcagccc    8940
gtgggctcgt gatgcttgta ggtcacctct gcaaacgact gcaggtacgc ctgcaggaat    9000
cgccccatca tcgtcacaaa ggtcttgttg ctggtgaagg tcagctgcaa cccgcggtgc    9060
tcctcgttca gccaggtctt gcatacggcc gccagagctt ccacttggtc aggcagtagt    9120
ttgaagttcg cctttagatc gttatccacg tggtacttgt ccatcagcgc gcgcgcagcc    9180
tccatgccct tctcccacgc agacacgatc ggcacactca gcgggttcat caccgtaatt    9240
tcactttccg cttcgctggg ctcttcctct tcctcttgcg tccgcatacc acgcgccact    9300
gggtcgtctt cattcagccg ccgcactgtg cgcttacctc cttttgccatg cttgattagc    9360
accggtgggt tgctgaaacc caccatttgt agcgccacat cttctctttc ttcctcgctg    9420
tccacgatta cctctggtga tggcgggcgc tcgggcttgg gagaagggcg cttctttttc    9480
ttcttgggcg caatggccaa atccgccgcc gaggtcgatg gccgcgggct gggtgtgcgc    9540
ggcaccagcg cgtcttgtga tgagtcttcc tcgtcctcgg actcgatacg ccgcctcatc    9600
cgcttttttg ggggcgcccg gggaggcggc ggcgacgggg acggggacga cacgtcctcc    9660
atggttgggg gacgtcgcgc cgcaccgcgt ccgcgctcgg gggtggtttc gcgctgctcc    9720
tcttcccgac tggccatttc cttctcctat aggcagaaaa agatcatgga gtcagtcgag    9780
aagaaggaca gcctaaccgc cccctctgag ttcgccacca ccgcctccac cgatgccgcc    9840
aacgcgccta ccaccttccc cgtcgaggca ccccgcttg aggaggagga agtgattatc      9900
gagcaggacc caggttttgt aagcgaagac gacgaggacc gctcagtacc aacagaggat    9960
aaaaagcaag accaggacaa cgcagaggca acgaggaac aagtcgggcg gggggacgaa     10020
aggcatggcg actacctaga tgtgggagac gacgtgctgt tgaagcatct gcagcgccag    10080
tgcgccatta tctgcgacgc gttgcaagag cgcagcgatg tgcccctcgc catagcggat    10140
gtcagccttg cctacgaacg ccacctattc tcaccgcgcg taccccccaa acgccaagaa    10200
aacggcacat gcgagcccaa cccgcgcctc aacttctacc ccgtatttgc cgtgccagag    10260
```

```
gtgcttgcca cctatcacat cttttttccaa aactgcaaga tacccctatc ctgccgtgcc   10320
aaccgcagcc gagcggacaa gcagctggcc ttgcggcagg gcgctgtcat acctgatatc   10380
gcctcgctca acgaagtgcc aaaaatcttt gagggtcttg gacgcgacga aagcgcgcg    10440 gcaaacgctc tgcaacagga aaacagcgaa aatgaaagtc actctggagt gttggtggaa   10500
ctcgagggtg acaacgcgcg cctagccgta ctaaaacgca gcatcgaggt cacccacttt   10560
gcctacccgg cacttaacct acccccccaag gtcatgagca cagtcatgag tgagctgatc  10620
gtgcgccgtg cgcagcccct ggagagggat gcaaatttgc aagaacaaac agaggagggc   10680
ctacccgcag ttggcgacga gcagctagcg cgctggcttc aaacgcgcga gcctgccgac   10740
ttggaggagc gacgcaaact aatgatggcc gcagtgctcg ttaccgtgga gcttgagtgc   10800
atgcagcggt tctttgctga cccggagatg cagcgcaagc tagaggaaac attgcactac   10860
acctttcgac agggctacgt acgccaggcc tgcaagatct ccaacgtgga gctctgcaac   10920
ctggtctcct accttggaat tttgcacgaa aaccgccttg ggcaaaacgt gcttcattcc   10980
acgctcaagg gcgaggcgcg ccgcgactac gtccgcgact gcgtttactt atttctatgc   11040
tacacctggc agacggccat gggcgttttgg cagcagtgct tggaggagtg caacctcaag  11100
gagctgcaga aactgctaaa gcaaaacttg aaggacctat ggacggcctt caacgagcgc   11160
tccgtggccg cgcacctggc ggacatcatt ttccccgaac gcctgcttaa aaccctgcaa   11220
cagggtctgc cagacttcac cagtcaaagc atgttgcaga actttaggaa ctttatccta   11280
gagcgctcag gaatcttgcc cgccaccgtg tgtgcacttc ctagcgactt tgtgcccatt   11340
aagtaccgcg aatgccctcc gccgctttgg ggccactgct accttctgca gctagccaac   11400
taccttgcct accactctga cataatgaaa gacgtgagcg gtgacggtct actggagtgt   11460
cactgtcgct gcaacctatg cacccccgcac cgctccctgg tttgcaattc gcagctgctt  11520
aacgaaagtc aaattatcgg tacctttgag ctgcagggtc cctcgcctga cgaaaagtcc   11580
gcggctccgg ggttgaaact cactccgggg ctgtggacgt cggcttacct tcgcaaattt   11640
gtacctgagg actaccacgc ccacgagatt aggttctacg aagaccaatc ccgcccgcca   11700
aatgcggagc ttaccgcctg cgtcattacc cagggccaca ttcttggcca attgcaagcc   11760
atcaacaaag cccgccaaga gtttctgcta cgaaagggac gggggttta cttggacccc   11820 cagtccggcg aggagctcaa cccaatcccc ccgccgccgc agccctatca gcagcagccg   11880
cgggcccttg cttccaggga tggcacccaa aaagaagctg cagctgccgc cgccacccac   11940
ggacgaggag gaatactggg acagtcaggc agaggaggtt ttggacgagg aggaggagga   12000
catgatggaa gactgggaga gcctagacga ggaagcttcc gaggtcgaag aggtgtcaga   12060
cgaaacaccg tcaccctcgg tcgcattccc ctcgccggcg cccagaaat cggcaaccgg    12120 ttccagcatg gctacaacct ccgctcctca ggcgccgccg gcactgcccg ttcgccgacc   12180
caaccgtaga tgggacacca ctggaaccag ggccggtaag tccaagcagc cgccgccgtt   12240
agcccaagag caacaacagc gccaaggcta ccgctcatgg cgcgggcaca agaacgccat   12300
agttgcttgc ttgcaagact gtgggggcaa catctccttc gcccgccgct tcttctctta   12360
ccatcacggc gtggccttcc cccgtaacat cctgcattac taccgtcatc tctacagccc   12420
atactgcacc ggcggcagcg gcagcggcag caacagcagc ggccacacag aagcaaaggc   12480
gaccggatag caagactctg acaaagccca agaaatccac agcggcggca gcagcaggag   12540
gaggagcgct gcgtctggcg cccaacgaac ccgtatcgac ccgcgagctt agaaacagga   12600
```

```
tttttcccac tctgtatgct atatttcaac agagcagggg ccaagaacaa gagctgaaaa    12660
taaaaaacag gtctctgcga tccctcaccc gcagctgcct gtatcacaaa agcgaagatc    12720
agcttcggcg cacgctggaa gacgcggagg ctctcttcag taaatactgc gcgctgactc    12780
ttaaggacta gtttcgcgcc ctttctcaaa tttaagcgcg aaaactacgt catctccagc    12840
ggccacaccc ggcgccagca cctgtcgtca gcgccattat gagcaaggaa attcccacgc    12900
cctacatgtg gagttaccag ccacaaatgg gacttgcggc tggagctgcc caagactact    12960
caacccgaat aaactacatg agcgcgggac cccacatgat atcccgggtc aacggaatcc    13020
gcgcccaccg aaaccgaatt ctcttggaac aggcggctat taccaccaca cctcgtaata    13080
accttaatcc ccgtagttgg cccgctgccc tggtgtacca ggaaagtccc gctcccacca    13140
ctgtggtact tcccagagac gcccaggccg aagttcagat gactaactca ggggcgcagc    13200
ttgcgggcgg ctttcgtcac agggtgcggt cgcccgggca gggtataact cacctgacaa    13260
tcagagggcg aggtattcag ctcaacgacg agtcggtgag ctcctcgctt ggtctccgtc    13320
cggacgggac atttcagatc ggcggcgccg gccgctcttc attcacgcct cgtcaggcaa    13380
tcctaactct gcagacctcg tcctctgagc cgcgctctgg aggcattgga actctgcaat    13440
tattgaggag tttgtgccat cggtctactt taaccccttc tcgggacctc ccggccacta    13500
tccggatcaa tttattccta actttgacgc ggtaaaggac tcggcggatg gctacgactg    13560
aatgttaagt ggagaggcag agcaactgcg cctgaaacac ctggtccact gtcgccgcca    13620
caagtgcttt gcccgcgact ccggtgagtt ttgctacttt gaattgcccg aggatcatat    13680
cgagggcccg gcgcacggcg tccggcttac cgcccaggga gagcttgccc gtagcctgat    13740
tcggagtttt acccagcgcc ccctgctagt tgagcgggac aggggaccct gtgttctcac    13800
tgtgatttgc aactgtccta accctggatt acatcaagat ctttgttgcc atctctgtgc    13860
tgagtataat aaatacagaa attaaaatat actggggctc ctatcgccat cctgtaaacg    13920
ccaccgtctt cacccgccca agcaaaccaa ggcgaacctt acctggtact tttaacatct    13980
ctccctctgt gatttacaac agtttcaacc cagacggagt gagtctacga gagaacctct    14040
ccgagctcag ctactccatc agaaaaaaca ccaccctcct tacctgccgg gaacgtacga    14100
gtgcgtcacc ggccgctgca ccacacctac cgcctgaccg taaaccagac tttttccgga    14160
cagacctcaa taactctgtt taccagaaca ggaggtgagc ttagaaaacc cttagggtat    14220
taggccaaag gcgcagctac tgtggggttt atgaacaatt caagcaactc tacgggctat    14280
tctaattcag gtttctctag aaatggacgg aattattaca gagcagcgcc tgctagaaag    14340
acgcagggca gcggccgagc aacagcgcat gaatcaagag ctccaagaca tggttaactt    14400
gcaccagtgc aaaagggta tcttttgtct ggtaaagcag gccaaagtca cctacgacag    14460
taataccacc ggacaccgcc ttagctacaa gttgccaacc aagcgtcaga aattggtggt    14520
catggtggga gaaagccca ttaccataac tcagcactcg gtagaaaccg aaggctgcat    14580
tcactcacct tgtcaaggac ctgaggatct ctgcaccctt attaagaccc tgtgcggtct    14640
caaagatctt attcccttta actaataaaa aaaataata aagcatcact tacttaaaat    14700
cagttagcaa atttctgtcc agtttattca gcagcacctc cttgccctcc tcccagctct    14760
ggtattgcag cttcctcctg gctgcaaact ttctccacaa tctaaatgga atgtcagttt    14820
cctcctgttc ctgtccatcc gcacccacta tcttcatgtt gttgcagatg aagcgcgcaa    14880
gaccgtctga agataccttc aaccccgtgt atccatatga cacggaaacc ggtcctccaa    14940
ctgtgccttt tcttactcct cccttttgtat cccccaatgg gtttcaagag agtccccctg    15000
```

```
gggtactctc tttgcgccta tccgaacctc tagttacctc caatggcatg cttgcgctca    15060
aaatgggcaa cggcctctct ctggacgagg ccggcaacct tacctcccaa aatgtaacca    15120
ctgtgagccc acctctcaaa aaaccaagt  caaacataaa cctggaaata tctgcacccc    15180
tcacagttac ctcagaagcc ctaactgtgg ctgccgccgc acctctaatg gtcgcgggca    15240
acacactcac catgcaatca caggccccgc taaccgtgca cgactccaaa cttagcattg    15300
ccacccaagg acccctcaca gtgtcagaag gaaagctagc cctgcaaaca tcaggccccc    15360
tcaccaccac cgatagcagt acccttacta tcactgcctc accccctcta actactgcca    15420
ctggtagctt gggcattgac ttgaaagagc ccatttatac acaaaatgga aaactaggac    15480
taaagtacgg ggctcctttg catgtaacag acgacctaaa cactttgacc gtagcaactg    15540
gtccaggtgt gactattaat aatacttcct tgcaaactaa agttactgga gccttgggtt    15600
ttgattcaca aggcaatatg caacttaatg tagcaggagg actaaggatt gattctcaaa    15660
acagacgcct tatacttgat gttagttatc cgtttgatgc tcaaaaccaa ctaaatctaa    15720
gactaggaca gggccctctt tttataaact cagcccacaa cttggatatt aactacaaca    15780
aaggccttta cttgtttaca gcttcaaaca attccaaaaa gcttgaggtt aacctaagca    15840
ctgccaaggg gttgatgttt gacgctacag ccatagccat taatgcagga gatgggcttg    15900
aatttggttc acctaatgca ccaaacacaa atccccctcaa acaaaaatt  ggccatggcc    15960 tagaatttga ttcaaacaag gctatggttc ctaaactagg aactggcctt agttttgaca    16020
gcacaggtgc cattacagta ggaaacaaaa ataatgataa gctaactttg tggaccacac    16080
cagctccatc tcctaactgt agactaaatg cagagaaaga tgctaaactc actttggtct    16140
taacaaaatg tggcagtcaa atacttgcta cagtttcagt tttggctgtt aaaggcagtt    16200
tggctccaat atctggaaca gttcaaagtg ctcatcttat tataagattt gacgaaaatg    16260
gagtgctact aaacaattcc ttcctggacc cagaatattg gaactttaga aatggagatc    16320
ttactgaagg cacagcctat acaaacgctg ttggatttat gcctaaccta tcagcttatc    16380
caaaatctca cggtaaaact gccaaaagta acattgtcag tcaagtttac ttaaacggag    16440
acaaaactaa acctgtaaca ctaaccatta cactaaacgg tacacaggaa acaggagaca    16500
caactccaag tgcatactct atgtcatttt catgggactg gtctggccac aactacatta    16560
atgaaatatt tgccacatcc tcttacactt tttcatacat tgcccaagaa taagaatcg     16620 tttgtgttat gtttcaacgt gtttattttt caattgcaga aaatttcaag tcattttca     16680 ttcagtagta tagccccacc accacatagc ttatacagat caccgtacct taatcaaact    16740
cacagaaccc tagtattcaa cctgccacct ccctcccaac acacagagta cacagtcctt    16800
tctccccggc tggccttaaa aagcatcata tcatgggtaa cagacatatt cttaggtgtt    16860
atattccaca cggtttcctg tcgagccaaa cgctcatcag tgatattaat aaactcccg     16920 ggcagctcac ttaagttcat gtcgctgtcc agctgctgag ccacaggctg ctgtccaact    16980
tgcggttgct taacgggcgg cgaaggagaa gtccacgcct acatgggggt agagtcataa    17040
tcgtgcatca ggataggggcg gtggtgctgc agcagcgcgc gaataaactg ctgccgccgc    17100
cgctccgtcc tgcaggaata caacatggca gtggtctcct cagcgatgat tcgcaccgcc    17160
cgcagcataa ggcgccttgt cctccgggca cagcagcgca ccctgatctc acttaaatca    17220
gcacagtaac tgcagcacag caccacaata ttgttcaaaa tcccacagtg caaggcgctg    17280
tatccaaagc tcatggcggg gaccacagaa cccacgtggc catcatacca caagcgcagg    17340
```

```
tagattaagt ggcgacccct cataaacacg ctggacataa acattacctc ttttggcatg   17400
ttgtaattca ccacctcccg gtaccatata aacctctgat taaacatggc gccatccacc   17460
accatcctaa accagctggc caaaacctgc ccgccggcta tacactgcag ggaaccggga   17520
ctggaacaat gacagtggag agcccaggac tcgtaaccat ggatcatcat gctcgtcatg   17580
atatcaatgt tggcacaaca caggcacacg tgcatacact tcctcaggat tacaagctcc   17640
tcccgcgtta gaaccatatc ccagggaaca acccattcct gaatcagcgt aaatcccaca   17700
ctgcagggaa gacctcgcac gtaactcacg ttgtgcattg tcaaagtgtt acattcgggc   17760
agcagcggat gatcctccag tatggtagcg cgggtttctg tctcaaaagg aggtagacga   17820
tccctactgt acggagtgcg ccgagacaac cgagatcgtg ttggtcgtag tgtcatgcca   17880
aatggaacgc cggacgtagt catatttcct gaagcaaaac caggtgcggg cgtgacaaac   17940
agatctgcgt ctccggtctc gccgcttaga tcgctctgtg tagtagttgt agtatatcca   18000
ctctctcaaa gcatccaggc gcccctggc ttcgggttct atgtaaactc cttcatgcgc    18060
cgctgccctg ataacatcca ccaccgcaga ataagccaca cccagccaac ctacacattc   18120
gttctgcgag tcacacacgg gaggagcggg aagagctgga agaaccatgt tttttttttt   18180
attccaaaag attatccaaa acctcaaaat gaagatctat taagtgaacg cgctcccctc   18240
cggtggcgtg gtcaaactct acagccaaag aacagataat ggcatttgta agatgttgca   18300
caatggcttc caaaaggcaa acggccctca cgtccaagtg gacgtaaagg ctaaaccctt   18360
cagggtgaat ctcctctata aacattccag caccttcaac catgcccaaa taattctcat   18420
ctcgccacct tctcaatata tctctaagca aatcccgaat attaagtccg gccattgtaa   18480
aaatctgctc cagagcgccc tccaccttca gcctcaagca gcgaatcatg attgcaaaaa   18540
ttcaggttcc tcacagacct gtataagatt caaaagcgga acattaacaa aaataccgcg   18600
atcccgtagg tcccttcgca gggccagctg aacataatcg tgcaggtctg cacggaccag   18660
cgcggccact tccccgccag gaaccatgac aaaagaaccc acactgatta tgacacgcat   18720
actcggagct atgctaacca gcgtagcccc gatgtaagct tgttgcatgg cggcgatat    18780 aaaatgcaag gtgctgctca aaaaatcagg caaagcctcg cgcaaaaaag aaagcacatc   18840
gtagtcatgc tcatgcagat aaaggcaggt aagctccgga accaccacag aaaaagacac   18900
catttttctc tcaaacatgt ctgcgggttt ctgcataaac acaaaataaa ataacaaaaa   18960
aacatttaaa cattagaagc ctgtcttaca acaggaaaaa caacccttat aagcataaga   19020
cggactacgg ccatgccggc gtgaccgtaa aaaaactggt caccgtgatt aaaaagcacc   19080
accgacagct cctcggtcat gtccggagtc ataatgtaag actcggtaaa cacatcaggt   19140
tgattcacat cggtcagtgc taaaaagcga ccgaaatagc ccgggggaat acatacccgc   19200
aggcgtagag acaacattac agcccccata ggaggtataa caaaattaat aggagagaaa   19260
aacacataaa cacctgaaaa accctcctgc ctaggcaaaa tagcaccctc ccgctccaga   19320
acaacataca gcgcttccac agcggcagcc ataacagtca gccttaccag taaaaaagaa   19380
aacctattaa aaaaacacca ctcgacacgg caccagctca atcagtcaca gtgtaaaaaa   19440
gggccaagtg cagagcgagt atatatagga ctaaaaaatg acgtaacggt taaagtccac   19500
aaaaaacacc cagaaaaccg cacgcgaacc tacgcccaga aacgaaagcc aaaaaaccca   19560
caacttcctc aaatcgtcac ttccgttttc ccacgttacg tcacttccca ttttaagaaa   19620
actacaattc ccaacacata caagttactc cgccctaaaa cctacgtcac ccgcccgtt    19680 cccacgcccc gcgccacgtc acaaactcca ccccctcatt atcatattgg cttcaatcca   19740
```

```
aaataaggta tattattgat gatgttaatt aagaattcgg atctgcgacg cgaggctgga   19800
tggccttccc cattatgatt cttctcgctt ccggcggcat cgggatgccc gcgttgcagg   19860
ccatgctgtc caggcaggta gatgacgacc atcagggaca gcttcaaggc cagcaaaagg   19920
ccaggaaccg taaaaaggcc gcgttgctgg cgttttttcca taggctccgc cccctgacg   19980 agcatcacaa aaatcgacgc tcaagtcaga ggtggcgaaa cccgacagga ctataaagat   20040
accaggcgtt tccccctgga agctccctcg tgcgctctcc tgttccgacc ctgccgctta   20100
ccggatacct gtccgccttt ctcccttcgg aagcgtggc gctttctcat agctcacgct   20160
gtaggtatct cagttcggtg taggtcgttc gctccaagct gggctgtgtg cacgaacccc   20220
ccgttcagcc cgaccgctgc gccttatccg gtaactatcg tcttgagtcc aacccggtaa   20280
gacacgactt atcgccactg gcagcagcca ctggtaacag gattagcaga gcgaggtatg   20340
taggcggtgc tacagagttc ttgaagtggt ggcctaacta cggctacact agaaggacag   20400
tatttggtat ctgcgctctg ctgaagccag ttaccttcgg aaaaagagtt ggtagctctt   20460
gatccggcaa acaaaccacc gctggtagcg gtggtttttt tgtttgcaag cagcagatta   20520
cgcgcagaaa aaaaggatct caagaagatc ctttgatctt ttctacgggg tctgacgctc   20580
agtggaacga aaactcacgt taagggattt tggtcatgag attatcaaaa aggatcttca   20640
cctagatcct tttaaatcaa tctaaagtat atatgagtaa acttggtctg acaggtttaa   20700
actcagaaga actcgtcaag aaggcgatag aaggcgatgc gctgcgaatc gggagcggcg   20760
ataccgtaaa gcacgaggaa gcggtcagcc cattcgccgc caagctcttc agcaatatca   20820
cgggtagcca acgctatgtc ctgatagcgg tccgccacac ccagccggcc acagtcgatg   20880
aatccagaaa agcggccatt ttccaccatg atattcggca agcaggcatc gccatgggtc   20940
acgacgagat cctcgccgtc gggcatgctc gccttgagcc tggcgaacag ttcggctggc   21000
gcgagcccct gatgctcttc gtccagatca tcctgatcga caagaccggc ttccatccga   21060
gtacgtgctc gctcgatgcg atgtttcgct tggtggtcga atgggcaggt agccggatca   21120
agcgtatgca gccgccgcat tgcatcagcc atgatggata ctttctcggc aggagcaagg   21180
tgagatgaca ggagatcctg ccccggcact tcgcccaata gcagccagtc ccttcccgct   21240
tcagtgacaa cgtcgagcac agctgcgcaa ggaacgcccg tcgtggccag ccacgatagc   21300
cgcgctgcct cgtcttgcag ttcattcagg gcaccggaca ggtcggtctt gacaaaaaga   21360
accgggcgcc cctgcgctga cagccggaac acgcggcat cagagcagcc gattgtctgt   21420
tgtgcccagt catagccgaa tagcctctcc acccaagcgg ccgagaacc tgcgtgcaat   21480 ccatcttgtt caatcataac gttactcttc cttttttcaat attattgaag catttatcag   21540
ggttattgtc tcatgagcgg atacatattt gaatgtattt agaaaaataa acaaataggg   21600
gttccgcgca catttccccg aaaagtgcca cctgacgtct aagaaaccat tattatcatg   21660
acattaacct ataaaaatag gcgtatcacg aggccctttc gtcttcaa                21708
```

<210> SEQ ID NO 8
<211> LENGTH: 21788
<212> TYPE: DNA
<213> ORGANISM: Artificial Sequence
<220> FEATURE:
<223> OTHER INFORMATION: SYNTHETIC POLYNUCLEOTIDE

<400> SEQUENCE: 8

```
gaattggatc cgaattctta attaacatca tcaataatat accttatttt ggattgaagc      60
caatatgata atgaggggt ggagtttgtg acgtggcgcg gggcgtggga acggggcggg     120
tgacgtagta gtgtggcgga agtgtgatgt tgcaagtgtg gcggaacaca tgtaagcgac     180
ggatgtggca aaagtgacgt ttttggtgtg cgccggtgta cacaggaagt gacaattttc     240
gcgcggtttt aggcggatgt tgtagtaaat ttgggcgtaa ccgagtaaga tttggccatt     300
ttcgcgggaa aactgaataa gaggaagtga atctgaata attttgtgtt actcatagcg     360
cgtaatattt gtctagggcc gcggggactt tgaccgttta cgtggagact cgcccaggtg     420
tttttctcag gtgttttccg cgttccgggt caaagttggc gttttattat tatagtcagg     480
gggatcctct agaactagtg gatccgtccc tcaggcctag aagtaaaaaa gggaaaaaag     540
agtgtgtttg tcaaaatagg agacaggtgg tggcaaccaa ggacttatag gggaccttac     600
atctacagac caacagatgc ccccttacca tatacaggaa gatatgactt aaattgggat     660
aggtgggtca aatcaacgg ctataaagtg ttatacagat ccctcccctc cctttcgtg     720
aaagactcgc cagagctaga cctccttggt gtatgctaac tgagaagaga aagacgacat     780
gaaacaacag gtacatgatt atatttatct aggaacagga atgcactttt ggggaaaggt     840
tttccatacc aaggaagggg cagtggctgg actgatagaa cattattctg caaaaactta     900
tggtatgagt tattatgatt agcctttatt tgcccaacct tgcggttccc agggtttaaa     960
taagtttatg gttacaaact gttcttaaaa cgaggatgtg agacaagtgg tttcctgact    1020
tggtttggta atcaaatgtt ctgatctgag ctcttagtgt tctattttcc tatgttcttt    1080
tggaatctat ccaagtctta tgtaaatgct tatgtaaacc ataatataaa agagtgctga    1140
ttttttgagt aaacttgcaa cagtcctaac attcttctct cgtgtgtttg tgtctgttcg    1200
ccatcccgtc tccgctcgtc acttatcctt cacttttcag agggtccccc cgcagatccc    1260
ggtcaccctc aggtcgggac ctgcagaaga cgcccgagtg agcacgcagg gtctccattt    1320
tgaagcggga ggtttgaacg cgcagccgcc atgccggggt tttacgagat tgtgattaag    1380
gtccccagcg accttgacgg gcatctgccc ggcatttctg acagctttgt gaactgggtg    1440
gccgagaagg aatgggagtt gccgccagat tctgacatgg atctgaatct gattgagcag    1500
gcacccctga ccgtggccga aagctgcag cgcgactttc tgacggaatg gcgccgtgtg    1560
agtaaggccc cggaggccct tttctttgtg caatttgaga agggagagag ctacttccac    1620
atgcacgtgc tcgtggaaac caccggggtg aaatccatgg ttttgggacg tttcctgagt    1680
cagattcgcg aaaaactgat tcagagaatt taccgcggga tcgagccgac tttgccaaac    1740
tggttcgcg tcacaaagac cagaaatggc gccggaggcg ggaacaaggt ggtggatgag    1800
tgctacatcc ccaattactt gctccccaaa acccagcctg agctccagtg ggcgtggact    1860
aatatggaac agtatttaag cgcctgtttg aatctcacgg agcgtaaacg gttggtggcg    1920
cagcatctga cgcacgtgtc gcagacgcag gagcagaaca aagagaatca gaatcccaat    1980
tctgatgcgc cggtgatcag atcaaaaact tcagccaggt acatggagct ggtcgggtgg    2040
ctcgtggaca aggggattac ctcggagaag cagtggatcc aggaggacca ggcctcatac    2100
atctccttca atgcggcctc caactcgcgg tcccaaatca aggctgcctt ggacaatgcg    2160
ggaaagatta tgagcctgac taaaaccgcc ccgactacc tggtgggcca gcagcccgtg    2220
gaggacattt ccagcaatcg gatttataaa attttggaac taaacgggta cgatccccaa    2280
```

```
tatgcggctt ccgtctttct gggatgggcc acgaaaaagt tcggcaagag gaacaccatc    2340
tggctgtttg ggcctgcaac taccgggaag accaacatcg cggaggccat agcccacact    2400
gtgcccttct acgggtgcgt aaactggacc aatgagaact ttcccttcaa cgactgtgtc    2460
gacaagatgg tgatctggtg ggaggagggg aagatgaccg ccaaggtcgt ggagtcggcc    2520
aaagccattc tcggaggaag caaggtgcgc gtggaccaga aatgcaagtc ctcggcccag    2580
atagacccga ctcccgtgat cgtcacctcc aacaccaaca tgtgcgccgt gattgacggg    2640
aactcaacga ccttcgaaca ccagcagccg ttgcaagacc ggatgttcaa atttgaactc    2700
acccgccgtc tggatcatga ctttgggaag gtcaccaagc aggaagtcaa agacttttc    2760 cggtgggcaa aggatcacgt ggttgaggtg gagcatgaat tctacgtcaa aaagggtgga    2820
gccaagaaaa gacccgcccc cagtgacgca gatataagtg agcccaaacg ggtgcgcgag    2880
tcagttgcgc agccatcgac gtcagacgcg gaagcttcga tcaactacgc agacaggtac    2940
caaaacaaat gttctcgtca cgtgggcatg aatctgatgc tgtttccctg cagacaatgc    3000
gagagaatga atcagaattc aaatatctgc ttcactcacg gacagaaaga ctgtttagag    3060
tgctttcccg tgtcagaatc tcaacccgtt tctgtcgtca aaaaggcgta tcagaaactg    3120
tgctacattc atcatatcat gggaaaggtg ccagacgctt gcactgcctg cgatctggtc    3180
aatgtggatt tggatgactg catctttgaa caataaatga tttaaatcag gtatggctgc    3240
cgatggttat cttccagatt ggctcgagga caacctctct gagggcattc gcgagtggtg    3300
ggacttgaaa cctggagccc cgaaacccaa agccaaccag caaaagcagg acgacggccg    3360
gggtctggtg cttcctggct acaagtacct cggacccttc aacggactcg acaaggggga    3420
gcccgtcaac gcggcggacg cagcggccct cgagcacgac aaggcctacg accagcagct    3480
caaagcgggt gacaatccgt acctgcggta taaccacgcc gacgccgagt ttcaggagcg    3540
tctgcaagaa gatacgtctt ttgggggcaa cctcgggcga cagtcttcc aggccaagaa    3600 gcgggttctc gaacctctcg gtctggttga ggaaggcgct aagacggctc ctggaaagaa    3660
gagaccggta gagccatcac cccagcgttc tccagactcc tctacgggca tcggcaagaa    3720
aggccagcag cccgcgaaaa agagactcaa ctttgggcag actggcgact cagagtcagt    3780
gcccgaccct caaccaatcg agaaccccc cgcaggcccc tctggtctgg gatctggtac    3840
aatggctgca ggcggtggcg ctccaatggc agacaataac gaaggcgccg acggagtggg    3900
tagttcctca ggaaattggc attgcgattc cacatggctg ggcgacagag tcatcaccac    3960
cagcacccga acctgggccc tcccaccta caacaaccac ctctacaagc aaatctccaa    4020
cgggacttcg ggaggaagca ccaacgacaa cacctacttc ggctacagca cccctgggg    4080 gtattttgac tttaacagat tccactgcca cttctcacca cgtgactggc agcgactcat    4140
caacaacaac tggggattcc ggcccaagag actcaacttc aagctcttca acatccaggt    4200
caaggaggtc acgcagaatg aaggcaccaa gaccatcgcc aataacctta ccagcacgat    4260
tcaggtcttt acggactcgg aataccagct cccgtacgtc ctcggctctg cgcaccaggg    4320
ctgcctgcct ccgttccgg cggacgtctt catgattcct cagtacgggt acctgactct    4380
gaacaatggc agtcaggccg tgggccgttc ctccttctac tgcctggagt actttccttc    4440
tcaaatgctg agaacgggca acaactttga gttcagctac cagtttgagg acgtgccttt    4500
tcacagcagc tacgcgcaca gccaaagcct ggaccggctg atgaaccccc tcatcgacca    4560
gtacctgtac tacctgtctc ggactcagtc cacgggaggg accgcaggaa ctcagcagtt    4620 gctatttct caggccgggc ctaataacat gtcggctcag gccaaaaact ggctacccgg    4680
```

```
gccctgctac cggcagcaac gcgtctccac gacactgtcg caaaataaca acagcaactt    4740
tgcctggacc ggtgccacca agtatcatct gaatggcaga gactctctgg taaatcccgg    4800
tgtcgctatg caacccaca aggacgacga agagcgattt tttccgtcca gcggagtctt    4860
aatgtttggg aaacagggag ctggaaaaga caacgtggac tatagcagcg ttatgctaac    4920
cagtgaggaa gaaattaaaa ccaccaaccc agtggccaca gaacagtacg gcgtggtggc    4980
cgataacctg caacagcaaa acgccgctcc tattgtaggg gccgtcaaca gtcaaggagc    5040
cttacctggc atggtctggc agaaccggga cgtgtacctg cagggtccta tctgggccaa    5100
gattcctcac acgacggaa actttcatcc ctcgccgctg atgggaggct ttggactgaa    5160
acacccgcct cctcagatcc tgattaagaa tacacctgtt cccgcggatc ctccaactac    5220
cttcagtcaa gctaagctgg cgtcgttcat cacgcagtac agcaccggac aggtcagcgt    5280
ggaaattgaa tgggagctgc agaaagaaaa cagcaaacgc tggaacccag agattcaata    5340
cacttccaac tactacaaat ctacaaatgt ggactttgct gttaacacag atggcactta    5400
ttctgagcct cgccccatcg gcacccgtta cctcacccgt aatctgtaat tgcttgttaa    5460
tcaataaacc ggttgattcg tttcagttga actttggtct ctgcgaaggg cgaattcgtt    5520
tatcgatgca tgtccttggg tccggcctgc tgaatgcgca ggcggtcggc catgccccag    5580
gcttcgtttt gacatcggcg caggtctttg tagtagtctt gcatgagcct ttctaccggc    5640
acttcttctt ctccttcctc ttgtcctgca tctcttgcat ctatcgctgc ggcggcggcg    5700
gagtttggcc gtaggtggcg ccctcttcct cccatcgtgt gacccgaag cccctcatcg    5760 gctgaagcag ggctaggtcg cgacaacgc gctcggctaa tatggcctgc tgcacctgcg    5820
tgagggtaga ctggaagtca tccatgtcca caaagcggtg gtatgcgccc gtgttgatgg    5880
tgtaagtgca gttggccata acggaccagt taacggtctg gtgacccggc tgcgagagct    5940
cggtgtacct gagacgcgag taagccctcg agtcaaatac gtagtcgtta caagtccgca    6000
ccaggtactg gtatcccacc aaaaagtgcg gcggcggctg gcggtagagg ggccagcgta    6060
gggtggccgg ggctccgggg gcgagatctt ccaacataag gcgatgatat ccgtagatgt    6120
acctggacat ccaggtgatg ccggcggcgg tggtggaggc gcgcggaaag tcgcggacgc    6180
ggttccagat gttgcgcagc ggcaaaaagt gctccatggt cgggacgctc tggccggtca    6240
ggcgcgcgca atcgttgacg ctctagaccg tgcaaaagga gagcctgtaa gcgggcactc    6300
ttccgtggtc tggtggataa attcgcaagg gtatcatggc ggacgaccgg ggttcgagcc    6360
ccgtatccgc ccgtccgccg tgatccatgc ggttaccgcc cgcgtgtcga acccaggtgt    6420
gcgacgtcag acaacggggg agtgctcctt ttggcttcct tccaggcgcg gcggctgctg    6480
cgctagcttt tttggccact ggccgcgcgc agcgtaagcg gttaggctgg aaagcgaaag    6540
cattaagtgg ctcgctccct gtagccggag ggttattttc caagggttga gtcgcgggac    6600
ccccggttcg agtctcggac cggcggact gcggcgaacg ggggtttgtc tccccgtcat    6660
gcaagacccc gcttgcaaat tcctccggaa acagggacga gccccttttt tgcttttccc    6720
agatgcatcc ggtgctgcgg cagatgcgcc ccctcctca gcagcggcaa gagcaagagc    6780
agcggcagac atgcagggca ccctccctc tcctaccgc gtcaggaggg gcgacatccg    6840
cggttgacgc ggcagcagat ggtgattacg aaccccgcg gcgccgggcc cggcactacc    6900
tggacttgga ggaggcgag ggcctggcgc ggctaggagc gccctctcct gagcggcacc    6960
caagggtgca gctgaagcgt gatacgcgtg aggcgtacgt gccgcggcag aacctgtttc    7020
```

-continued

```
gcgaccgcga gggagaggag cccgaggaga tgcgggatcg aaagttccac gcagggcgcg    7080
agctgcggca tggcctgaat cgcgagcggt tgctgcgcga ggaggacttt gagcccgacg    7140
cgcgaaccgg gattagtccc gcgcgcgcac acgtggcggc cgccgacctg gtaaccgcat    7200
acgagcagac ggtgaaccag ggcgatcgca cccttggcg catcccattc tccagtaact    7260
ttatgtccat gggcgcactc acagacctgg gccaaaacct tctctacgcc aactccgccc    7320
acgcgctaga catgactttt gaggtggatc ccatggacga gcccacccct ctttatgttt    7380
tgtttgaagt ctttgacgtg gtccgtgtgc accggccgca ccgcggcgtc atcgaaaccg    7440
tgtacctgcg cacgcccttc tcggccggca acgccacaac ataaagaagc aagcaacatc    7500
aacaacagct gccgccatgg gctccagtga gcaggaactg aaagccattg tcaaagatct    7560
tggttgtggg ccatattttt tgggcaccta tgacaagcgc tttccaggct ttgtttctcc    7620
acacaagctc gcctgcgcca tagtcaatac ggccggtcgc gagactgggg gcgtacactg    7680
gatggccttt gcctggaacc cgcactcaaa aacatgctac ctctttgagc cctttggctt    7740
ttctgaccag cgactcaagc aggtttacca gtttgagtac gagtcactcc tgcgccgtag    7800
cgccattgct tcttcccccg accgctgtat aacgctggaa aagtccaccc aaagcgtaca    7860
ggggcccaac tcggccgcct gtggactatt ctgctgcatg tttctccacg cctttgccaa    7920
ctggccccaa actcccatgg atcacaaccc caccatgaac cttattaccg gggtacccaa    7980
ctccatgctc aacagtcccc aggtacagcc cacccctgcgt cgcaaccagg aacagctcta    8040
cagcttcctg gagcgccact cgccctactt ccgcagccac agtgcgcaga ttaggagcgc    8100
cacttctttt tgtcacttga aaacatgta aaataatgt actagagaca ctttcaataa    8160
aggcaaatgc ttttatttgt acactctcgg gtgattattt ccccccaccc ttgccgtctg    8220
cgccgtttaa aaatcaaagg ggttctgccg cgcatcgcta tgcgccactg gcagggacac    8280
gttgcgatac tggtgtttag tgctccactt aaactcaggc acaaccatcc gcggcagctc    8340
ggtgaagttt tcactccaca ggctgcgcac catcaccaac gcgttagca ggtcgggcgc    8400 cgatatcttg aagtcgcagt tggggcctcc gccctgcgcg cgcgagttgc gatacacagg    8460
gttgcagcac tggaacacta tcagcgccgg gtggtgcacg ctggccagca cgctcttgtc    8520
ggagatcaga tccgcgtcca ggtcctccgc gttgctcagg gcgaacggag tcaactttgg    8580
tagctgcctt cccaaaaagg gcgcgtgccc aggctttgag ttgcactcgc accgtagtgg    8640
catcaaaagg tgaccgtgcc cggtctgggc gttaggatac agcgcctgca taaaagcctt    8700
gatctgctta aaagccacct gagcctttgc gccttcagag aagaacatgc cgcaagactt    8760
gccggaaaac tgattggccg gacaggccgc gtcgtgcacg cagcaccttg cgtcggtgtt    8820
ggagatctgc accacatttc ggccccaccg gttcttcacg atcttggcct tgctagactg    8880
ctccttcagc gcgcgctgcc cgttttcgct cgtcacatcc atttcaatca cgtgctcctt    8940
atttatcata atgcttccgt gtagacactt aagctcgcct tcgatctcag cgcagcggtg    9000
cagccacaac gcgcagcccg tgggctcgtg atgcttgtag gtcacctctg caaacgactg    9060
caggtacgcc tgcaggaatc gccccatcat cgtcacaaag gtcttgttgc tggtgaaggt    9120
cagctgcaac ccgcggtgct cctcgttcag ccaggtcttg catacggccg ccagagcttc    9180
cacttggtca ggcagtagtt tgaagttcgc ctttagatcg ttatccacgt ggtacttgtc    9240
catcagcgcg cgcgcagcct ccatgcccctt ctcccacgca gacacgatcg gcacactcag    9300
cgggttcatc accgtaattt cactttccgc ttcgctgggc tcttcctctt cctcttgcgt    9360
ccgcatacca cgcgccactg ggtcgtcttc attcagccgc cgcactgtgc gcttacctcc    9420
```

```
tttgccatgc ttgattagca ccggtgggtt gctgaaaccc accatttgta gcgccacatc   9480
ttctcttttct tcctcgctgt ccacgattac ctctggtgat ggcgggcgct cgggcttggg   9540
agaagggcgc ttcttttttct tcttgggcgc aatggccaaa tccgccgccg aggtcgatgg   9600
ccgcgggctg ggtgtgcgcg gcaccagcgc gtcttgtgat gagtcttcct cgtcctcgga   9660
ctcgatacgc cgcctcatcc gcttttttgg gggcgcccgg ggaggcggcg gcgacgggga   9720
cggggacgac acgtcctcca tggttggggg acgtcgcgcc gcaccgcgtc cgcgctcggg   9780
ggtggtttcg cgctgctcct cttcccgact ggccatttcc ttctcctata ggcagaaaaa   9840
gatcatggag tcagtcgaga agaaggacag cctaaccgcc ccctctgagt tcgccaccac   9900
cgcctccacc gatgccgcca acgcgcctac caccttcccc gtcgaggcac cccgcttga    9960
ggaggaggaa gtgattatcg agcaggaccc aggttttgta agcgaagacg acgaggaccg  10020
ctcagtacca acagaggata aaagcaaga ccaggacaac gcagaggcaa acgaggaaca  10080
agtcgggcgg ggggacgaaa ggcatggcga ctacctagat gtgggagcg acgtgctgtt  10140
gaagcatctg cagcgccagt gcgccattat ctgcgacgcg ttgcaagagc gcagcgatgt  10200
gcccctcgcc atagcggatg tcagccttgc ctacgaacgc cacctattct caccgcgcgt  10260
accccccaaa cgccaagaaa acggcacatg cgagcccaac ccgcgcctca acttctaccc  10320
cgtatttgcc gtgccagagg tgcttgccac ctatcacatc ttttttccaaa actgcaagat  10380
accccctatcc tgccgtgcca accgcagccg agcggacaag cagctggcct gcggcaggg  10440
cgctgtcata cctgatatcg cctcgctcaa cgaagtgcca aaaatctttg agggtcttgg  10500
acgcgacgag aagcgcgcgg caaacgctct gcaacaggaa aacagcgaaa atgaaagtca  10560
ctctggagtt ttggtggaac tcagggtga caacgcgcgc ctagccgtac taaaacgcag  10620
catcgaggtc acccactttg cctacccggc acttaaccta cccccaagg tcatgagcac  10680
agtcatgagt gagctgatcg tgcgccgtgc gcagccctg gagagggatg caaatttgca  10740
agaacaaaca gaggagggcc tacccgcagt tggcgacgag cagctagcgc gctggcttca  10800
aacgcgcgag cctgccgact tggaggagcg acgcaaacta atgatggccg cagtgctcgt  10860
taccgtggag cttgagtgca tgcagcggtt cttttgctgac ccggagatgc agcgcaagct  10920
agaggaaaca ttgcactaca cctttcgaca gggctacgta cgccaggcct gcaagatctc  10980
caacgtggag ctctgcaacc tggtctccta ccttggaatt ttgcacgaaa accgccttgg  11040
gcaaaacgtg cttcattcca cgctcaaggg cgaggcgcgc cgcgactacg tccgcgactg  11100
cgtttactta tttctatgct acacctggca gacggccatg ggcgtttggc agcagtgctt  11160
ggaggagtgc aacctcaagg agctgcagaa actgctaaag caaaacttga aggacctatg  11220
gacgccctctc aacgagcgct ccgtggccgc gcacctggcg gacatcattt tcccgaacg   11280
cctgcttaaaa acctgcaac agggtctgcc agacttcacc agtcaaagca tgttgcagaa  11340
ctttagggac tttatcctag agcgctcagg aatcttgccc gccacctgct gtgcacttcc  11400
tagcgacttt gtgcccatta gtaccgcga atgcctccg ccgctttggg gccactgcta  11460
ccttctgcag ctagccaact accttgccta ccactctgac ataatggaag acgtgagcgg  11520
tgacggtcta ctggagtgtc actgtcgctg caacctatgc accccgcacc gctccctggt  11580
ttgcaattcg cagctgctta acgaaagtca aattatcggt acctttgagc tgcagggtcc  11640
ctcgcctgac gaaaagtccg cggctccggg gttgaaactc actccgggc tgtgacgtc   11700
ggcttacctt cgcaaatttg tacctgagga ctaccacgcc cacgagatta ggttctacga  11760
```

```
agaccaatcc cgcccgccaa atgcggagct taccgcctgc gtcattaccc agggccacat   11820
tcttggccaa ttgcaagcca tcaacaaagc ccgccaagag tttctgctac gaaagggacg   11880
gggggtttac ttggaccccc agtccggcga ggagctcaac ccaatccccc cgccgccgca   11940
gccctatcag cagcagccgc gggcccttgc ttcccaggat ggcacccaaa agaagctgc    12000 agctgccgcc gccacccacg gacgaggagg aatactggga cagtcaggca gaggaggttt   12060
tggacgagga ggaggaggac atgatggaag actgggagag cctagacgag gaagcttccg   12120
aggtcgaaga ggtgtcagac gaaacaccgt caccctcggt cgcattcccc tcgccggcgc   12180
cccagaaatc ggcaaccggt tccagcatgg ctacaacctc cgctcctcag gcgccgccgg   12240
cactgcccgt tcgccgaccc aaccgtagat gggacaccac tggaaccagg gccggtaagt   12300
ccaagcagcc gccgccgtta gcccaagagc aacaacagcg ccaaggctac cgctcatggc   12360
gcgggcacaa gaacgccata gttgcttgct tgcaagactg tgggggcaac atctccttcg   12420
cccgccgctt tcttctctac catcacggcg tggccttccc ccgtaacatc ctgcattact   12480
accgtcatct ctacagccca tactgcaccg gcggcagcgg cagcggcagc aacagcagcg   12540
gccacacaga agcaaaggcg accggatagc aagactctga caaagcccaa gaaatccaca   12600
gcggcggcag cagcaggagg aggagcgctg cgtctggcgc ccaacgaacc cgtatcgacc   12660
cgcgagctta gaaacaggat ttttcccact ctgtatgcta tatttcaaca gagcaggggc   12720
caagaacaag agctgaaaat aaaaaacagg tctctgcgat ccctcacccg cagctgcctg   12780
tatcacaaaa gcgaagatca gcttcggcgc acgctggaag acgcggaggc tctcttcagt   12840
aaatactgcg cgctgactct taaggactag tttcgcgccc tttctcaaat ttaagcgcga   12900
aaactacgtc atctccagcg gccacacccg gcgccagcac ctgtcgtcag cgccattatg   12960
agcaaggaaa ttcccacgcc ctacatgtgg agttaccagc cacaaatggg acttgcggct   13020
ggagctgccc aagactactc aacccgaata aactacatga gcgcgggacc ccacatgata   13080
tcccgggtca acggaatccg cgcccaccga aaccgaattc tcttggaaca gcggctatt    13140 accaccacac ctcgtaataa ccttaatccc cgtagttggc ccgctgccct ggtgtaccag   13200
gaaagtcccg ctcccaccac tgtggtactt cccagagacg cccaggccga agttcagatg   13260
actaactcag gggcgcagct tgcgggcggc tttcgtcaca gggtgcggtc gcccgggcag   13320
ggtataactc acctgacaat cagagggcga ggtattcagc tcaacgacga gtcggtgagc   13380
tcctcgcttg gtctccgtcc ggacgggaca tttcagatcg gcggcgccgg ccgctcttca   13440
ttcacgcctc gtcaggcaat cctaactctg cagacctcgt cctctgagcc gcgctctgga   13500
ggcattggaa ctctgcaatt tattgaggag tttgtgccat cggtctactt taacccctc    13560 tcgggacctc ccgccactca tccgatcaa tttattccta actttgacgc ggtaaaggac    13620
tcggcggatg gctacgactg aatgttaagt ggagaggcag agcaactgcg cctgaaacac   13680
ctggtccact gtcgccgcca caagtgcttt gcccgcgact ccggtgagtt ttgctacttt   13740
gaattgcccg aggatcatat cgagggcccg gcgcacggcg tccggcttac cgcccaggga   13800
gagcttgccc gtagcctgat tcgggagttt acccagcgcc cctgctagt tgagcgggac    13860 aggggaccct gtgttctcac tgtgatttgc aactgtccta accctggatt acatcaagat   13920 cttttgttgcc atctctgtgc tgagtataat aaatacagaa attaaatat actggggctc    13980 ctatcgccat cctgtaaacg ccaccgtctt caccgcccca agcaaaccaa ggcgaacctt   14040
acctggtact tttaacatct ctccctctgt gatttacaac agtttcaacc cagacggagt   14100
gagtctacga gagaacctct ccgagctcag ctactccatc agaaaaaaca ccaccctcct   14160
```

```
tacctgccgg gaacgtacga gtgcgtcacc ggccgctgca ccacacctac cgcctgaccg   14220
taaaccagac ttttccgga cagacctcaa taactctgtt taccagaaca ggaggtgagc   14280
ttagaaaacc cttagggtat taggccaaag gcgcagctac tgtggggttt atgaacaatt   14340
caagcaactc tacgggctat tctaattcag gtttctctag aaatggacgg aattattaca   14400
gagcagcgcc tgctagaaag acgcagggca gcggccgagc aacagcgcat gaatcaagag   14460
ctccaagaca tggttaactt gcaccagtgc aaaaggggta tcttttgtct ggtaaagcag   14520
gccaaagtca cctacgacag taataccacc ggacaccgcc ttagctacaa gttgccaacc   14580
aagcgtcaga aattggtggt catggtggga gaaaagccca ttaccataac tcagcactcg   14640
gtagaaaccg aaggctgcat tcactcacct tgtcaaggac ctgaggatct ctgcacccctt  14700 attaagaccc tgtgcggtct caaagatctt attcccttta actaataaaa aaaaataata   14760
aagcatcact tacttaaaat cagttagcaa atttctgtcc agtttattca gcagcacctc   14820
cttgccctcc tcccagctct ggtattgcag cttcctcctg gctgcaaact ttctccacaa   14880
tctaaatgga atgtcagttt cctcctgttc ctgtccatcc gcacccacta tcttcatgtt   14940
gttgcagatg aagcgcgcaa gaccgtctga agataccttc aacccgtgt atccatatga    15000 cacggaaacc ggtcctccaa ctgtgccttt tcttactcct ccctttgtat cccccaatgg   15060
gtttcaagag agtcccctg gggtactctc tttgcgccta tccgaacctc tagttacctc    15120
caatggcatg cttgcgctca aaatgggcaa cggcctctct ctggacgagg ccggcaacct   15180
tacctcccaa aatgtaacca ctgtgagccc acctctcaaa aaaaccaagt caaacataaa   15240
cctggaaata tctgcacccc tcacagttac ctcagaagcc ctaactgtgg ctgccgccgc   15300
acctctaatg gtcgcgggca acacactcac catgcaatca caggcccgc taaccgtgca   15360 cgactccaaa cttagcattg ccacccaagg accccctcaca gtgtcagaag gaaagctagc  15420
cctgcaaaca tcaggcccc tcaccaccac cgatagcagt acccttacta tcactgcctc    15480
accccctcta actactgcca ctggtagctt gggcattgac ttgaaagagc ccatttatac   15540
acaaaatgga aaactaggac taaagtacgg ggctcctttg catgtaacag acgacctaaa   15600
cactttgacc gtagcaactg gtccaggtgt gactattaat aatacttcct tgcaaactaa   15660
agttactgga gccttgggtt ttgattcaca aggcaatatg caacttaatg tagcaggagg   15720
actaaggatt gattctcaaa acagacgcct tatacttgat gttagttatc cgtttgatgc   15780
tcaaaaccaa ctaaatctaa gactaggaca gggccctctt tttataaact cagcccacaa   15840
cttggatatt aactacaaca aaggcctta cttgtttaca gcttcaaaca attccaaaaa   15900
gcttgaggtt aacctaagca ctgccaaggg gttgatgttt gacgctacag ccatagccat   15960
taatgcagga gatgggcttg aatttggttc acctaatgca ccaaacacaa atcccctcaa   16020
aacaaaaatt ggccatggcc tagaatttga ttcaaacaag gctatggttc ctaaactagg   16080
aactggcctt agttttgaca gcacaggtgc cattacagta ggaaacaaaa ataatgataa   16140
gctaactttg tggaccacac cagctccatc tcctaactgt agactaaatg cagagaaaga   16200
tgctaaactc actttggtct taacaaaatg tggcagtcaa atacttgcta cagtttcagt   16260
tttggctgtt aaaggcagtt tggctccaat atctggaaca gttcaaagtg ctcatcttat   16320
tataagattt gacgaaaatg gagtgctact aaacaattcc ttcctggacc cagaatattg   16380
gaactttaga aatggagatc ttactgaagg cacagcctat acaaacgctg ttggattat    16440 gcctaacctc tcagcttatc caaaatctca cggtaaaact gccaaagta acattgtcag    16500
```

```
tcaagtttac ttaaacggag acaaaactaa acctgtaaca ctaaccatta cactaaacgg   16560
tacacaggaa acaggagaca caactccaag tgcatactct atgtcatttt catgggactg   16620
gtctggccac aactacatta atgaaatatt tgccacatcc tcttacactt tttcatacat   16680
tgcccaagaa taaagaatcg tttgtgttat gtttcaacgt gtttatttt caattgcaga    16740 aaatttcaag tcatttttca ttcagtagta tagccccacc accacatagc ttatacagat   16800
caccgtacct taatcaaact cacagaaccc tagtattcaa cctgccacct ccctcccaac   16860
acacagagta cacagtcctt tctccccggc tggccttaaa aagcatcata tcatgggtaa   16920
cagacatatt cttaggtgtt atattccaca cggtttcctg tcgagccaaa cgctcatcag   16980
tgatattaat aaactccccg gcagctcac ttaagttcat gtcgctgtcc agctgctgag    17040
ccacaggctg ctgtccaact tgcggttgct taacgggcgg cgaaggagaa gtccacgcct   17100 acatggggt agagtcataa tcgtgcatca ggatagggcg gtggtgctgc agcagcgcgc    17160
gaataaactg ctgccgccgc cgctccgtcc tgcaggaata caacatggca gtggtctcct   17220
cagcgatgat tcgcaccgcc cgcagcataa ggcgccttgt cctccgggca cagcagcgca   17280
ccctgatctc acttaaatca gcacagtaac tgcagcacag caccacaata ttgttcaaaa   17340
tcccacagtg caaggcgctg tatccaaagc tcatggcggg gaccacagaa cccacgtggc   17400
catcatacca caagcgcagg tagattaagt ggcgaccct cataaacacg ctggacataa     17460
acattacctc ttttggcatg ttgtaattca ccacctcccg gtaccatata aacctctgat   17520
taaacatggc gccatccacc accatcctaa accagctggc caaaacctgc ccgccggcta   17580
tacactgcag ggaaccggga ctggaacaat gacagtggag agcccaggac tcgtaaccat   17640
ggatcatcat gctcgtcatg atatcaatgt tggcacaaca caggcacacg tgcatacact   17700
tcctcaggat tacaagctcc tcccgcgtta gaaccatatc ccagggaaca acccattcct   17760
gaatcagcgt aaatcccaca ctgcagggaa gacctcgcac gtaactcacg ttgtgcattg   17820
tcaaagtgtt acattcgggc agcagcggat gatcctccag tatggtagcg cgggtttctg   17880
tctcaaaagg aggtagacga tccctactgt acggagtgcg ccgagacaac cgagatcgtg   17940
ttggtcgtag tgtcatgcca aatggaacgc cggacgtagt catatttcct gaagcaaaac   18000
caggtgcggg cgtgacaaac agatctgcgt ctccggtctc gccgcttaga tcgctctgtg   18060
tagtagttgt agtatatcca ctctctcaaa gcatccaggc gcccctggc ttcgggttct     18120 atgtaaactc cttcatgcgc cgctgccctg ataacatcca ccaccgcaga ataagccaca   18180
cccagccaac ctacacattc gttctgcgag tcacacacgg gaggagcggg aagagctgga   18240
agaaccatgt tttttttttt attccaaaag attatccaaa acctcaaaat gaagatctat   18300
taagtgaacg cgctcccctc cggtggcgtg gtcaaactct acagccaaag aacagataat   18360
ggcatttgta agatgttgca caatggcttc caaaaggcaa acggccctca cgtccaagtg   18420
gacgtaaagg ctaaaccctt cagggtgaat ctcctctata acattccag caccttcaac     18480 catgcccaaa taattctcat ctcgccacct tctcaatata tctctaagca aatcccgaat   18540
attaagtccg gccattgtaa aaatctgctc cagagcgccc tccaccttca gcctcaagca   18600
gcgaatcatg attgcaaaaa ttcaggttcc tcacagacct gtataagatt caaaagcgga   18660
acattaacaa aaataccgcg atcccgtagg tcccttcgca gggccagctg aacataatcg   18720
tgcaggtctg cacggaccag cgccggcact tccccgccag gaaccatgac aaaagaaccc   18780
acactgatta tgcacgcat actcggagct atgctaacca gcgtagcccc gatgtaagct     18840
tgttgcatgg gcggcgatat aaaatgcaag gtgctgctca aaaaatcagg caaagcctcg   18900
```

```
cgcaaaaaag aaagcacatc gtagtcatgc tcatgcagat aaaggcaggt aagctccgga   18960
accaccacag aaaaagacac cattttctc tcaaacatgt ctgcgggttt ctgcataaac    19020
acaaaataaa ataacaaaaa aacatttaaa cattagaagc ctgtcttaca acaggaaaaa   19080
caacccttat aagcataaga cggactacgg ccatgccggc gtgaccgtaa aaaaactggt   19140
caccgtgatt aaaaagcacc accgacagct cctcggtcat gtccggagtc ataatgtaag   19200
actcggtaaa cacatcaggt tgattcacat cggtcagtgc taaaaagcga ccgaaatagc   19260 ccggggggaat acatacccgc aggcgtagag acaacattac agcccccata ggaggtataa  19320
caaaattaat aggagagaaa aacacataaa cacctgaaaa accctcctgc ctaggcaaaa   19380
tagcaccctc ccgctccaga acaacataca gcgcttccac agcggcagcc ataacagtca   19440
gccttaccag taaaaaagaa aacctattaa aaaaacacca ctcgacacgg caccagctca   19500
atcagtcaca gtgtaaaaaa gggccaagtg cagagcgagt atatatagga ctaaaaaatg   19560
acgtaacggt taaagtccac aaaaaacacc cagaaaaccg cacgcgaacc tacgcccaga   19620
aacgaaagcc aaaaaaccca caacttcctc aaatcgtcac ttccgttttc ccacgttacg   19680
tcacttccca ttttaagaaa actacaattc ccaacacata caagttactc cgccctaaaa   19740
cctacgtcac ccgccccgtt cccacgcccc gcgccacgtc acaaactcca cccctcatt   19800 atcatattgg cttcaatcca aaataaggta tattattgat gatgttaatt aagaattcgg   19860
atctgcgacg cgaggctgga tggccttccc cattatgatt cttctcgctt ccggcggcat   19920
cgggatgccc gcgttgcagg ccatgctgtc caggcaggta gatgacgacc atcagggaca   19980
gcttcaaggc cagcaaaagg ccaggaaccg taaaaaggcc gcgttgctgg cgttttttcca  20040 taggctccgc cccctgacg agcatcacaa aaatcgacgc tcaagtcaga ggtggcgaaa    20100
cccgacagga ctataaagat accaggcgtt tccccctgga agctccctcg tgcgctctcc   20160
tgttccgacc ctgccgctta ccggatacct gtccgccttt ctcccttcgg gaagcgtggc   20220
gctttctcat agctcacgct gtaggtatct cagttcggtg taggtcgttc gctccaagct   20280
gggctgtgtg cacgaacccc ccgttcagcc cgaccgctgc gccttatccg gtaactatcg   20340
tcttgagtcc aacccggtaa gacacgactt atcgccactg gcagcagcca ctggtaacag   20400
gattagcaga gcgaggtatg taggcggtgc tacagagttc ttgaagtggt ggcctaacta   20460
cggctacact agaaggacag tatttggtat ctgcgctctg ctgaagccag ttaccttcgg   20520
aaaaagagtt ggtagctctt gatccggcaa acaaaccacc gctggtagcg gtggtttttt   20580
tgtttgcaag cagcagatta cgcgcagaaa aaaaggatct caagaagatc ctttgatctt   20640
ttctacgggg tctgacgctc agtggaacga aaactcacgt taagggattt tggtcatgag   20700
attatcaaaa aggatcttca cctagatcct tttaaatcaa tctaaagtat atatgagtaa   20760
acttggtctg acaggtttaa actcagaaga actcgtcaag aaggcgatag aaggcgatgc   20820
gctgcgaatc gggagcggcg ataccgtaaa gcacgaggaa gcggtcagcc cattcgccgc   20880
caagctcttc agcaatatca cgggtagcca acgctatgtc ctgatagcgg tccgccacac   20940
ccagccggcc acagtcgatg aatccagaaa agcggccatt ttccaccatg atattcggca   21000
agcaggcatc gccatgggtc acgacgagat cctcgccgtc gggcatgctc gccttgagcc   21060
tggcgaacag ttcggctggc gcgagcccct gatgctcttc gtccagatca tcctgatcga   21120
caagaccggc ttccatccga gtacgtgctc gctcgatgcg atgtttcgct tggtggtcga   21180
atgggcaggt agccggatca agcgtatgca gccgccgcat tgcatcagcc atgatggata   21240
```

| | |
|---|---|
| ctttctcggc aggagcaagg tgagatgaca ggagatcctg ccccggcact tcgcccaata | 21300 |
| gcagccagtc ccttcccgct tcagtgacaa cgtcgagcac agctgcgcaa ggaacgcccg | 21360 |
| tcgtggccag ccacgatagc cgcgctgcct cgtcttgcag ttcattcagg gcaccggaca | 21420 |
| ggtcggtctt gacaaaaaga accgggcgcc cctgcgctga cagccggaac acggcggcat | 21480 |
| cagagcagcc gattgtctgt tgtgcccagt catagccgaa tagcctctcc acccaagcgg | 21540 |
| ccggagaacc tcgtgcaat ccatcttgtt caatcataac gttactcttc cttttcaat | 21600 |
| attattgaag catttatcag ggttattgtc tcatgagcgg atacatattt gaatgtattt | 21660 |
| agaaaaataa acaaataggg gttccgcgca catttccccg aaaagtgcca cctgacgtct | 21720 |
| aagaaaccat tattatcatg acattaacct ataaaaatag gcgtatcacg aggccctttc | 21780 |
| gtcttcaa | 21788 |

<210> SEQ ID NO 9
<211> LENGTH: 21722
<212> TYPE: DNA
<213> ORGANISM: Artificial Sequence
<220> FEATURE:
<223> OTHER INFORMATION: SYNTHETIC POLYNUCLEOTIDE

<400> SEQUENCE: 9

| | |
|---|---|
| gaattggatc cgaattctta attaacatca tcaataatat accttatttt ggattgaagc | 60 |
| caatatgata atgaggggt ggagtttgtg acgtggcgcg gggcgtggga acggggcggg | 120 |
| tgacgtagta gtgtggcgga agtgtgatgt tgcaagtgtg gcggaacaca tgtaagcgac | 180 |
| ggatgtggca aaagtgacgt ttttggtgtg cgccggtgta cacaggaagt gacaattttc | 240 |
| gcgcggtttt aggcggatgt tgtagtaaat ttgggcgtaa ccgagtaaga tttggccatt | 300 |
| ttcgcgggaa aactgaataa gaggaagtga atctgaata attttgtgtt actcatagcg | 360 |
| cgtaatattt gtctagggcc gcggggactt tgaccgttta cgtggagact cgcccaggtg | 420 |
| tttttctcag gtgttttccg cgttccgggt caaagttggc gttttattat tatagtcagg | 480 |
| gggatcctct agaactagtg gatccgtccc tcaggcctag aagtaaaaaa gggaaaaaag | 540 |
| agtgtgtttg tcaaaatagg agacaggtgg tggcaaccaa ggactatag gggaccttac | 600 |
| atctacagac caacagatgc ccccttacca tatacaggaa gatatgactt aaattgggat | 660 |
| aggtgggtca caatcaacgg ctataaagtg ttatacagat ccctcccctc cccttttcgtg | 720 |
| aaagactcgc cagagctaga cctccttggt gtatgctaac tgagaagaga aagacgacat | 780 |
| gaaacaacag gtacatgatt atatttatct aggaacagga atgcacttt ggggaaaggt | 840 |
| tttccatacc aaggaagggg cagtggctgg actgatagaa cattattctg caaaaactta | 900 |
| tggtatgagt tattatgatt agcctttatt tgcccaacct tgcggttccc agggtttaaa | 960 |
| taagtttatg gttacaaact gttcttaaaa cgaggatgtg agacaagtgg tttcctgact | 1020 |
| tggtttggta atcaaatgtt ctgatctgag ctcttagtgt tctatttcc tatgttctt | 1080 |
| tggaatctat ccaagtctta tgtaaatgct tatgtaaacc ataatataaa agagtgctga | 1140 |
| ttttttgagt aaacttgcaa cagtcctaac attcttctcc gtgtgtttgt gtctgttcgc | 1200 |
| catcccgtct ccgctcgtca cttatccttc acttttcaga gggtccccc gcagatcccg | 1260 |
| gtcaccctca ggtcgggacc tgcagaagac gcccgagtga gcacgcaggg tctccatttt | 1320 |
| gaagcgggag gtttgaacgc gcagccgcca tgcggggtt ttacgagatt gtgattaagg | 1380 |
| tccccagcga ccttgacggg catctgcccg gcatttctga cagctttgtg aactgggtgg | 1440 |
| ccgagaagga atgggagttg ccgccagatt ctgacatgga tctgaatctg attgagcagg | 1500 |

| | |
|---|---|
| caccccctgac cgtggccgag aagctgcagc gcgactttct gacggaatgg cgccgtgtga | 1560 |
| gtaaggcccc ggaggcccct tctttgtgc aatttgagaa gggagagagc tacttccaca | 1620 |
| tgcacgtgct cgtggaaacc accggggtga atccatggt tttgggacgt ttcctgagtc | 1680 |
| agattcgcga aaaactgatt cagagaattt accgcgggat cgagccgact ttgccaaact | 1740 |
| ggttcgcggt cacaaagacc agaaatggcg ccggaggcgg aacaaggtg gtggatgagt | 1800 |
| gctacatccc caattacttg ctccccaaaa cccagcctga gctccagtgg gcgtggacta | 1860 |
| atatggaaca gtatttaagc gcctgtttga atctcacgga gcgtaaacgg ttggtggcgc | 1920 |
| agcatctgac gcacgtgtcg cagacgcagg agcagaacaa agagaatcag aatcccaatt | 1980 |
| ctgatgcgcc ggtgatcaga tcaaaaactt cagccaggta catggagctg gtcgggtggc | 2040 |
| tcgtggacaa ggggattacc tcggagaagc agtggatcca ggaggaccag gcctcataca | 2100 |
| tctccttcaa tgcggcctcc aactcgcggt cccaaatcaa ggctgccttg acaatgcgg | 2160 |
| gaaagattat gagcctgact aaaaccgccc ccgactacct ggtgggccag cagcccgtgg | 2220 |
| aggacatttc cagcaatcgg atttataaaa ttttggaact aaacgggtac gatccccaat | 2280 |
| atgcggcttc cgtcttttctg ggatgggcca cgaaaaagtt cggcaagagg aacaccatct | 2340 |
| ggctgtttgg gcctgcaact accgggaaga ccaacatcgc ggaggccata gcccacactg | 2400 |
| tgcccttcta cgggtgcgta aactggacca atgagaactt tcccttcaac gactgtgtcg | 2460 |
| acaagatggt gatctggtgg gaggagggga agatgaccgc caaggtcgtg gagtcggcca | 2520 |
| aagccattct cggaggaagc aaggtgcgcg tggaccagaa atgcaagtcc tcggcccaga | 2580 |
| tagacccgac tcccgtgatc gtcacctcca acaccaacat gtgcgccgtg attgacggga | 2640 |
| actcaacgac cttcgaacac cagcagccgt tgcaagaccg gatgttcaaa tttgaactca | 2700 |
| cccgccgtct ggatcatgac tttgggaagg tcaccaagca ggaagtcaaa gactttttcc | 2760 |
| ggtgggcaaa ggatcacgtg gttgaggtgg agcatgaatt ctacgtcaaa aagggtggag | 2820 |
| ccaagaaaag acccgccccc agtgacgcag atataagtga gcccaaacgg gtgcgcgagt | 2880 |
| cagttgcgca gccatcgacg tcagacgcgg aagcttcgat caactacgca gacaggtacc | 2940 |
| aaaacaaatg ttctcgtcac gtgggcatga atctgatgct gtttccctgc agacaatgcg | 3000 |
| agagaatgaa tcagaattca aatatctgct tcactcacgg acagaaagac tgtttagagt | 3060 |
| gctttcccgt gtcagaatct caacccgttt ctgtcgtcaa aaaggcgtat cagaaactgt | 3120 |
| gctacattca tcatatcatg ggaaaggtgc cagacgcttg cactgcctgc gatctggtca | 3180 |
| atgtggattt ggatgactgc atctttgaac aataaatgat ttaaatatgg ctgccgatgg | 3240 |
| ttatcttcca gattggctcg aggacaacct tagtgaagga attcgcgagt ggtgggcttt | 3300 |
| gaaacctgga gcccctcaac ccaaggcaaa tcaacaacat caagacaacg ctcgaggtct | 3360 |
| tgtgcttccg ggttacaaat accttggacc cggcaacgga ctcgacaagg gggagccggt | 3420 |
| caacgcagca gacgcggcgg ccctcgagca cgacaaggcc tacgaccagc agctcaaggc | 3480 |
| cggagacaac ccgtacctca gtacaaccac cgccgacgcc gagttccagg agcggctcaa | 3540 |
| agaagatacg tcttttgggg gcaacctcgg cgcagcagtc ttccaggcca aaaagaggct | 3600 |
| tcttgaacct cttggtctgg ttgaggaagc ggctaagacg gctcctggaa agaagaggcc | 3660 |
| tgtagagcag tctcctcagg aaccggactc ctccgcgggt attggcaaat cgggtgcaca | 3720 |
| gcccgctaaa aagagactca atttcggtca gactggcgac acagagtcag tcccagaccc | 3780 |
| tcaaccaatc ggagaacctc ccgcagcccc ctcaggtgtg ggatctctta caatggcttc | 3840 |

```
aggtggtggc gcaccagtgg cagacaataa cgaaggtgcc gatggagtgg gtagttcctc    3900
gggaaattgg cattgcgatt cccaatggct gggggacaga gtcatcacca ccagcacccg    3960
aacctgggcc ctgcccacct acaacaatca cctctacaag caaatctcca acagcacatc    4020
tggaggatct tcaaatgaca acgcctactt cggctacagc acccccctggg ggtatttga    4080 cttcaacaga ttccactgcc acttctcacc acgtgactgg cagcgactca tcaacaacaa    4140
ctggggattc cggcctaagc gactcaactt caagctcttc aacattcagg tcaaagaggt    4200
tacggacaac aatggagtca agaccatcgc caataacctt accagcacgg tccaggtctt    4260
cacggactca gactatcagc tcccgtacgt gctcgggtcg gctcacgagg gctgcctccc    4320
gccgttccca gcggacgttt tcatgattcc tcagtacggg tatctgacgc ttaatgatgg    4380
aagccaggcc gtgggtcgtt cgtccttta ctgcctggaa tatttcccgt cgcaaatgct    4440
aagaacgggt aacaacttcc agttcagcta cgagtttgag aacgtacctt tccatagcag    4500
ctacgctcac agccaaagcc tggaccgact aatgaatcca ctcatcgacc aatacttgta    4560
ctatctctca agaactatta acggttctgg acagaatcaa caaacgctaa aattcagtgt    4620
ggccggaccc agcaacatgg ctgtccaggg aagaaactac ataccctggac ccagctaccg    4680 acaacaacgt gtctcaacca ctgtgactca aaacaacaac agcgaatttg cttggcctgg    4740
agcttcttct tgggctctca atggacgtaa tagcttgatg aatcctggac ctgctatggc    4800
cagccacaaa gaaggagagg accgtttctt tcctttgtct ggatctttaa tttttggcaa    4860
acaaggaact ggaagagaca acgtggatgc ggacaaagtc atgataacca acgaagaaga    4920
aattaaaact actaacccgg tagcaacgga gtcctatgga caagtggcca caaaccacca    4980
gagtgcccaa actttggcgg tgcctttaa ggcacaggcg cagaccggct gggttcaaaa    5040
ccaaggaata cttccgggta tggtttggca ggacagagat gtgtacctgc aaggacccat    5100
ttgggccaaa attcctcaca cggacggcaa ctttcaccct tctccgctga tgggagggtt    5160
tggaatgaag caccccgcctc ctcagatcct catcaaaaac acacctgtac ctgcggatcc    5220
tccaacggcc ttcaacaagg acaagctgaa ctctttcatc acccagtatt ctactggcca    5280
agtcagcgtg gagatcgagt gggagctgca gaaggaaaac agcaagcgct ggaacccgga    5340
gatccagtac acttccaact attacaagtc taataatgtt gaatttgctg ttaatactga    5400
aggtgtatat agtgaacccc gccccattgg caccagatac ctgactcgta atctgtaaat    5460
cgatgcatgt ccttgggtcc ggcctgctga atgcgcaggc ggtcggccat gccccaggct    5520
tcgttttgac atcggcgcag gtctttgtag tagtcttgca tgagcctttc taccggcact    5580
tcttcttctc cttcctcttg tcctgcatct cttgcatcta tcgctgcggg gcggcggagt    5640
ttggccgtag gtggcgccct cttcctccca tcgtgtgacc ccgaagcccc tcatcggctg    5700
aagcagggct aggtcggcga caacgcgctc ggctaatatg gcctgctgca cctgcgtgag    5760
ggtagactgg aagtcatcca tgtccacaaa gcggtggtat gcgcccgtgt tgatggtgta    5820
agtgcagttg gccataacgg accagttaac ggtctggtga cccggctgcg agagctcggt    5880
gtacctgaga cgcgagtaag ccctcgagtc aaatacgtag tcgttacaag tccgcaccag    5940
gtactggtat cccaccaaaa agtgcggcgg cggctggcgg tagagggggcc agcgtagggt    6000 ggccggggct ccgggggcga gatcttccaa cataaggcga tgatatccgt agatgtacct    6060
ggacatccag gtgatgccgg cggcggtggt ggaggcgcgc ggaaagtcgc ggacgcggtt    6120
ccagatgttg cgcagcggca aaagtgctc catggtcggg acgctctggc cggtcaggcg    6180
cgcgcaatcg ttgacgctct agaccgtgca aaaggagagc ctgtaagcgg gcactcttcc    6240
```

```
gtggtctggt ggataaattc gcaagggtat catggcggac gaccggggtt cgagcccgt    6300
atccggccgt ccgccgtgat ccatgcggtt accgcccgcg tgtcgaaccc aggtgtgcga    6360
cgtcagacaa cgggggagtg ctccttttgg cttccttcca ggcgcggcgg ctgctgcgct    6420
agcttttttg gccactggcc gcgcgcagcg taagcggtta ggctggaaag cgaaagcatt    6480
aagtggctcg ctccctgtag ccggagggtt attttccaag ggttgagtcg cgggaccccc    6540
ggttcgagtc tcggaccggc cggactgcgg cgaacggggg tttgtctccc cgtcatgcaa    6600
gaccccgctt gcaaattcct ccggaaacag ggacgagccc cttttttgct tttcccagat    6660
gcatccggtg ctgcggcaga tgcgcccccc tcctcagcag cggcaagagc aagagcagcg    6720
gcagacatgc agggcaccct cccctcctcc taccgcgtca ggaggggcga catccgcggt    6780
tgacgcggca gcagatggtg attacgaacc ccgcggcgc cgggccggc actacctgga     6840
cttggaggag ggcgagggcc tggcgcggct aggagcgccc tctcctgagc ggcacccaag    6900
ggtgcagctg aagcgtgata cgcgtgaggc gtacgtgccg cggcagaacc tgtttcgcga    6960
ccgcgaggga gaggagcccg aggagatgcg ggatcgaaag ttccacgcag ggcgcgagct    7020
gcggcatggc ctgaatcgcg agcggttgct gcgcgaggag gactttgagc ccgacgcgcg    7080
aaccgggatt agtcccgcgc gcgcacacgt ggcggccgcc gacctggtaa ccgcatacga    7140
gcagacggtg aaccagggcg atcgcaccct ttggcgcatc ccattctcca gtaactttat    7200
gtccatgggc gcactcacag acctgggcca aaaccttctc tacgccaact ccgcccacgc    7260
gctagacatg acttttgagg tggatcccat ggacgagccc acccttcttt atgttttgtt    7320
tgaagtcttt gacgtggtcc gtgtgcaccg gccgcaccgc ggcgtcatcg aaaccgtgta    7380
cctgcgcacg cccttctcgg ccggcaacgc acaacataa agaagcaagc aacatcaaca     7440
acagctgccg ccatgggctc cagtgagcag gaactgaaag ccattgtcaa agatcttggt    7500
tgtgggccat attttttggg cacctatgac aagcgctttc caggctttgt ttctccacac    7560
aagctcgcct gcgccatagt caatacggcc ggtcgcgaga ctgggggcgt acactggatg    7620
gcctttgcct ggaacccgca ctcaaaaaca tgctacctct ttgagccctt tggcttttct    7680
gaccagcgac tcaagcaggt ttaccagttt gagtacgagt cactcctgcg ccgtagcgcc    7740
attgcttctt cccccgaccg ctgtataacg ctggaaaagt ccacccaaag cgtacagggg    7800
cccaactcgg ccgcctgtgg actattctgc tgcatgtttc tccacgcctt tgccaactgg    7860
ccccaaactc ccatggatca aaccccacc atgaaccta ttaccggggt acccaactcc      7920
atgctcaaca gtccccaggt acagccacc ctgcgtcgca accaggaaca gctctacagc     7980
ttcctggagc gccactcgcc ctacttccgc agccacagtg cgcagattag gagcgccact    8040
tcttttttgtc acttgaaaaa catgtaaaaa taatgtacta gagacacttt caataaaggc    8100
aaatgctttt atttgtacac tctcgggtga ttatttaccc ccacccttgc cgtctgcgcc    8160
gtttaaaaat caaggggtt ctgccgcgca tcgctatgcg ccactggcag ggacacgttg      8220
cgatactggt gtttagtgct ccacttaaac tcaggcacaa ccatccgcgg cagctcggtg    8280
aagttttcac tccacaggct gcgcaccatc accaacgcgt ttagcaggtc gggcgccgat    8340
atcttgaagt cgcagttggg gcctccgccc tgcgcgcgcg agttgcgata cacagggttg    8400
cagcactgga acactatcag cgccgggtgg tgcacgctgg ccagcacgct cttgtcggag    8460
atcagatccg cgtccaggtc ctccgcgttg ctcaggcga acggagtcaa ctttggtagc      8520
tgccttccca aaaagggcgc gtgcccaggc tttgagttgc actcgcaccg tagtggcatc    8580
```

```
aaaaggtgac cgtgcccggt ctgggcgtta ggatacagcg cctgcataaa agccttgatc    8640
tgcttaaaag ccacctgagc ctttgcgcct tcagagaaga acatgccgca agacttgccg    8700
gaaaactgat tggccggaca ggccgcgtcg tgcacgcagc accttgcgtc ggtgttggag    8760
atctgcacca catttcggcc ccaccggttc ttcacgatct tggccttgct agactgctcc    8820
ttcagcgcgc gctgcccgtt ttcgctcgtc acatccattt caatcacgtg ctccttattt    8880
atcataatgc ttccgtgtag acacttaagc tcgccttcga tctcagcgca gcggtgcagc    8940
cacaacgcgc agcccgtggg ctcgtgatgc ttgtaggtca cctctgcaaa cgactgcagg    9000
tacgcctgca ggaatcgccc catcatcgtc acaaaggtct tgttgctggt gaaggtcagc    9060
tgcaacccgc ggtgctcctc gttcagccag gtcttgcata cggccgccag agcttccact    9120
tggtcaggca gtagtttgaa gttcgccttt agatcgttat ccacgtggta cttgtccatc    9180
agcgcgcgcg cagcctccat gcccttctcc cacgcagaca cgatcggcac actcagcggg    9240
ttcatcaccg taatttcact ttccgcttcg ctgggctctt cctcttcctc ttgcgtccgc    9300
ataccacgcg ccactgggtc gtcttcattc agccgccgca ctgtgcgctt acctcctttg    9360
ccatgcttga ttagcaccgg tgggttgctg aaacccacca tttgtagcgc cacatcttct    9420
ctttcttcct cgctgtccac gattacctct ggtgatggcg ggcgctcggg cttgggagaa    9480
gggcgcttct ttttcttctt gggcgcaatg ccaaatccg ccgccgaggt cgatggccgc     9540
gggctgggtg tgcgcggcac cagcgcgtct tgtgatgagt cttcctcgtc ctcggactcg    9600
atacgccgcc tcatccgctt ttttgggggc gcccggggag gcggcggcga cggggacggg    9660
gacgacacgt cctccatggt tgggggacgt cgcgccgcac cgcgtccgcg ctcggggtg    9720
gtttcgcgct gctcctcttc ccgactggcc atttccttct cctataggca gaaaaagatc    9780
atggagtcag tcgagaagaa ggacagccta accgccccct ctgagttcgc caccaccgcc    9840
tccaccgatg ccgccaacgc gcctaccacc ttccccgtcg aggcaccccc gcttgaggag    9900
gaggaagtga ttatcgagca ggacccaggt tttgtaagcg aagacgacga ggaccgctca    9960
gtaccaacag aggataaaaa gcaagaccag gacaacgcag aggcaaacga ggaacaagtc   10020
gggcggggg acgaaaggca tggcgactac ctagatgtgg gagacgacgt gctgttgaag    10080
catctgcagc gccagtgcgc cattatctgc gacgcgttgc aagagcgcag cgatgtgccc   10140
ctcgccatag cggatgtcag ccttgcctac gaacgccacc tattctcacc gcgcgtaccc   10200
cccaaacgcc aagaaaacgg cacatgcgag cccaacccgc gcctcaactt ctaccccgta   10260
tttgccgtgc cagaggtgct tgccacctat cacatctttt tccaaaactg caagataccc   10320
ctatcctgcc gtgccaaccg cagccgagcg acaagcagc tggccttgcg gcagggcgct     10380
gtcatacctg atatcgcctc gctcaacgaa gtgccaaaaa tctttgaggg tcttggacgc   10440
gacgagaagc gcgcggcaaa cgctctgcaa caggaaaaca gcgaaaatga aagtcactct   10500
ggagtgttgg tggaactcga gggtgacaac gcgcgcctag ccgtactaaa acgcagcatc   10560
gaggtcaccc actttgccta cccggcactt aacctacccc ccaaggtcat gagcacagtc   10620
atgagtgagc tgatcgtgcg ccgtgcgcag cccctggaga gggatgcaaa tttgcaagaa   10680
caaacagagg agggcctacc cgcagttggc gacgagcagc tagcgcgctg gcttcaaacg   10740
cgcgagcctg ccgacttgga ggagcgacgc aaactaatga tggccgcagt gctcgttacc   10800
gtggagcttg agtgcatgca gcggttcttt gctgacccgg agatgcagcg caagctagag   10860
gaaacattgc actacacctt tcgacagggc tacgtacgcc aggcctgcaa gatctccaac   10920
gtggagctct gcaacctggt ctcctacctt ggaattttgc acgaaaaccg ccttgggcaa   10980
```

```
aacgtgcttc attccacgct caagggcgag gcgcgccgcg actacgtccg cgactgcgtt    11040
tacttatttc tatgctacac ctggcagacg gccatgggcg tttggcagca gtgcttggag    11100
gagtgcaacc tcaaggagct gcagaaactg ctaaagcaaa acttgaagga cctatggacg    11160
gccttcaacg agcgctccgt ggccgcgcac ctggcggaca tcatttttccc cgaacgcctg    11220 cttaaaaccc tgcaacaggg tctgccagac ttcaccagtc aaagcatgtt gcagaacttt    11280
aggaacttta tcctagagcg ctcaggaatc ttgcccgcca cctgctgtgc acttcctagc    11340
gactttgtgc ccattaagta ccgcgaatgc cctccgccgc tttggggcca ctgctacctt    11400
ctgcagctag ccaactacct tgcctaccac tctgacataa tggaagacgt gagcggtgac    11460
ggtctactgg agtgtcactg tcgctgcaac ctatgcaccc cgcaccgctc cctggtttgc    11520
aattcgcagc tgcttaacga aagtcaaatt atcggtacct ttgagctgca gggtccctcg    11580
cctgacgaaa agtccgcggc tccggggttg aaactcactc cggggctgtg gacgtcggct    11640
taccttcgca aatttgtacc tgaggactac cacgcccacg agattaggtt ctacgaagac    11700
caatcccgcc cgccaaatgc ggagcttacc gcctgcgtca ttacccaggg ccacattctt    11760
ggccaattgc aagccatcaa caaagcccgc caagagtttc tgctacgaaa gggacgggg    11820 gtttacttgg acccccagtc cggcgaggag ctcaacccaa tccccccgcc gccgcagccc    11880
tatcagcagc agccgcgggc ccttgcttcc caggatggca cccaaaaaga agctgcagct    11940
gccgccgcca cccacggacg aggaggaata ctgggacagt caggcagagg aggttttgga    12000
cgaggaggag gaggacatga tggaagactg ggagagccta gacgaggaag cttccgaggt    12060
cgaagaggtg tcagacgaaa caccgtcacc ctcggtcgca ttcccctcgc cggcgcccca    12120
gaaatcggca accggttcca gcatggctac aacctccgct cctcaggcgc cgccggcact    12180
gcccgttcgc cgacccaacc gtagatggga caccactgga accagggccg gtaagtccaa    12240
gcagccgccg ccgttagccc aagagcaaca acagcgccaa ggctaccgct catggcgcgg    12300
gcacaagaac gccatagttg cttgcttgca agactgtggg ggcaacatct ccttcgcccg    12360
ccgctttctt ctctaccatc acggcgtggc cttcccccgt aacatcctgc attactaccg    12420
tcatctctac agcccatact gcaccggcgg cagcggcagc ggcagcaaca gcagcggcca    12480
cacagaagca aaggcgaccg gatagcaaga ctctgacaaa gcccaagaaa tccacagcgg    12540
cggcagcagc aggaggagga gcgctgcgtc tggcgcccaa cgaacccgta tcgacccgcg    12600
agcttagaaa caggattttt cccactctgt atgctatatt tcaacagagc aggggccaag    12660
aacaagagct gaaaataaaa aacaggtctc tgcgatccct cacccgcagc tgcctgtatc    12720
acaaaagcga agatcagctt cggcgcacgc tggaagacgc ggaggctctc ttcagtaaat    12780
actgcgcgct gactcttaag gactagtttc gcgccctttc tcaaatttaa gcgcgaaaac    12840
tacgtcatct ccagcggcca cacccggcgc cagcacctgt cgtcagcgcc attatgagca    12900
aggaaattcc cacgccctac atgtggagtt accagccaca aatgggactt gcggctggag    12960
ctgcccaaga ctactcaacc cgaataaact acatgagcgc gggaccccac atgatatccc    13020
gggtcaacgg aatccgcgcc caccgaaacc gaattctctt ggaacaggcg gctattacca    13080
ccacacctcg taataacctt aatccccgta gttggcccgc tgccctggtg taccaggaaa    13140
gtcccgctcc caccactgtg gtacttccca gagacgccca ggccgaagtt cagatgacta    13200 actcagggc gcagcttgcg gcggcttttc gtcacagggt gcggtcgccc gggcagggta    13260
taactcacct gacaatcaga gggcgaggta ttcagctcaa cgacgagtcg gtgagctcct    13320
```

```
cgcttggtct ccgtccggac gggacatttc agatcggcgg cgccggccgc tcttcattca    13380
cgcctcgtca ggcaatccta actctgcaga cctcgtcctc tgagccgcgc tctggaggca    13440
ttggaactct gcaatttatt gaggagtttg tgccatcggt ctactttaac cccttctcgg    13500
gacctcccgg ccactatccg gatcaattta ttcctaactt tgacgcggta aaggactcgg    13560
cggatggcta cgactgaatg ttaagtggag aggcagagca actgcgcctg aaacacctgg    13620
tccactgtcg ccgccacaag tgctttgccc gcgactccgg tgagttttgc tactttgaat    13680
tgcccgagga tcatatcgag ggcccggcgc acggcgtccg gcttaccgcc cagggagagc    13740
ttgcccgtag cctgattcgg gagtttaccc agcgcccct gctagttgag cgggacaggg    13800
gaccctgtgt tctcactgtg atttgcaact gtcctaaccc tggattacat caagatcttt    13860
gttgccatct ctgtgctgag tataataaat acagaaatta aaatatactg gggctcctat    13920
cgccatcctg taaacgccac cgtcttcacc cgcccaagca aaccaaggcg aaccttacct    13980
ggtactttta acatctctcc ctctgtgatt tacaacagtt tcaacccaga cggagtgagt    14040
ctacgagaga acctctccga gctcagctac tccatcagaa aaaacaccac cctccttacc    14100
tgccgggaac gtacgagtgc gtcaccggcc gctgcaccac acctaccgcc tgaccgtaaa    14160
ccagactttt tccggacaga cctcaataac tctgtttacc agaacaggag gtgagcttag    14220 aaaacccta gggtattagg ccaaaggcgc agctactgtg gggtttatga acaattcaag    14280
caactctacg ggctattcta attcaggttt ctctagaaat ggacggaatt attacagagc    14340
agcgcctgct agaaagacgc agggcagcgg ccgagcaaca gcgcatgaat caagagctcc    14400
aagacatggt taacttgcac cagtgcaaaa ggggtatctt ttgtctggta aagcaggcca    14460
aagtcaccta cgacagtaat accaccggac accgcttag ctacaagttg ccaaccaagc    14520
gtcagaaatt ggtggtcatg gtgggagaaa agcccattac cataactcag cactcggtag    14580
aaaccgaagg ctgcattcac tcaccttgtc aaggacctga ggatctctgc acccttatta    14640
agaccctgtg cggtctcaaa gatcttattc cctttaacta ataaaaaaaa ataataaagc    14700
atcacttact taaaatcagt tagcaaattt ctgtccagtt tattcagcag cacctccttg    14760
ccctcctccc agctctggta ttgcagcttc tccctggctg caaactttct ccacaatcta    14820
aatggaatgt cagtttcctc ctgttcctgt ccatccgcac ccactatctt catgttgttg    14880
cagatgaagc gcgcaagacc gtctgaagat accttcaacc ccgtgtatcc atatgacacg    14940
gaaaccggtc ctccaactgt gccttttctt actcctccct ttgtatcccc caatgggttt    15000
caagagagtc cccctggggt actctctttg cgcctatccg aacctctagt tacctccaat    15060
ggcatgcttg cgctcaaaat gggcaacggc ctctctctgg acgaggccgg caaccttacc    15120
tcccaaaatg taaccactgt gagcccacct ctcaaaaaaa ccaagtcaaa cataaacctg    15180
gaaatatctg caccccctcac agttacctca gaagccctaa ctgtggctgc cgccgcacct    15240
ctaatggtcg cgggcaacac actcaccatg caatcacagg cccgctaac cgtgcacgac    15300 tccaaactta gcattgccac ccaaggaccc ctcacagtgt cagaaggaaa gctagccctg    15360
caaacatcag gccccctcac caccaccgat agcagtaccc ttactatcac tgcctcaccc    15420
cctctaacta ctgccactgg tagcttgggc attgacttga agagcccat ttatacacaa    15480 aatggaaaac taggactaaa gtacggggct cctttgcatg taacagacga cctaaacact    15540
ttgaccgtag caactggtcc aggtgtgact attaataata cttccttgca aactaaagtt    15600
actggagcct gggttttga ttcacaaggc aatatgcaac ttaatgtagc aggaggacta    15660
aggattgatt ctcaaaacag acgccttata cttgatgtta gttatccgtt tgatgctcaa    15720
```

```
aaccaactaa atctaagact aggacagggc cctcttttta taaactcagc ccacaacttg    15780
gatattaact acaacaaagg cctttacttg tttacagctt caaacaattc caaaaagctt    15840
gaggttaacc taagcactgc caaggggttg atgtttgacg ctacagccat agccattaat    15900
gcaggagatg ggcttgaatt tggttcacct aatgcaccaa acacaaatcc cctcaaaaca    15960
aaaattggcc atggcctaga atttgattca acaaggcta tggttcctaa actaggaact     16020
ggccttagtt ttgacagcac aggtgccatt acagtaggaa acaaaaataa tgataagcta    16080
actttgtgga ccacaccagc tccatctcct aactgtagac taaatgcaga gaaagatgct    16140
aaactcactt tggtcttaac aaaatgtggc agtcaaatac ttgctacagt ttcagttttg    16200
gctgttaaag gcagtttggc tccaatatct ggaacagttc aaagtgctca tcttattata    16260
agatttgacg aaaatggagt gctactaaac aattccttcc tggacccaga atattggaac    16320
tttagaaatg gagatcttac tgaaggcaca gcctatacaa acgctgttgg atttatgcct    16380
aacctatcag cttatccaaa atctcacggt aaaactgcca aaagtaacat tgtcagtcaa    16440
gtttacttaa acggagacaa aactaaacct gtaacactaa ccattacact aaacggtaca    16500
caggaaacag gagacacaac tccaagtgca tactctatgt cattttcatg ggactggtct    16560
ggccacaact acattaatga aatatttgcc acatcctctt cacttttttc atacattgcc    16620
caagaataaa gaatcgtttg tgttatgttt caacgtgttt attttcaat tgcagaaaat     16680 ttcaagtcat ttttcattca gtagtatagc cccaccacca catagcttat acagatcacc    16740
gtaccttaat caaactcaca gaaccctagt attcaacctg ccacctccct cccaacacac    16800
agagtacaca gtcctttctc cccggctggc cttaaaaagc atcatatcat gggtaacaga    16860
catattctta ggtgttatat tccacacggt ttcctgtcga gccaaacgct catcagtgat    16920
attaataaac tccccgggca gctcacttaa gttcatgtcg ctgtccagct gctgagccac    16980
aggctgctgt ccaacttgcg gttgcttaac gggcggcgaa ggagaagtcc acgcctacat    17040
gggggtagag tcataatcgt gcatcaggat agggcggtgg tgctgcagca gcgcgcgaat    17100
aaactgctgc cgccgccgct ccgtcctgca ggaatacaac atggcagtgg tctcctcagc    17160
gatgattcgc accgcccgca gcataaggcg ccttgtcctc cgggcacagc agcgcaccct    17220
gatctcactt aaatcagcac agtaactgca gcacagcacc acaatattgt tcaaaatccc    17280
acagtgcaag gcgctgtatc caaagctcat ggcgggacc acagaaccca cgtggccatc     17340
ataccacaag cgcaggtaga ttaagtggcg acccctcata aacacgctgg acataaacat    17400
tacctctttt ggcatgttgt aattcaccac ctcccggtac catataaacc tctgattaaa    17460
catggcgcca tccaccacca tcctaaacca gctggccaaa acctgccgc cggctataca     17520 ctgcagggaa ccgggactgg aacaatgaca gtggagagcc caggactcgt aaccatggat    17580
catcatgctc gtcatgatat caatgttggc acaacacagg cacacgtgca tacattcct    17640 caggattaca agctcctccc gcgttagaac catatcccag ggaacaaccc attcctgaat    17700
cagcgtaaat cccacactgc agggaagacc tcgcacgtaa ctcacgttgt gcattgtcaa    17760
agtgttacat tcgggcagca gcggatgatc ctccagtatg gtagcgcggg tttctgtctc    17820
aaaaggaggt agacgatccc tactgtacgg agtgcgccga acaaccgag atcgtgttgg     17880 tcgtagtgtc atgccaaatg gaacgccgga cgtagtcata tttcctgaag caaaaccagg    17940
tgcgggcgtg acaaacagat ctgcgtctcc ggtctcgccg cttagatcgc tctgtgtagt    18000
agttgtagta tatccactct ctcaaagcat ccaggcgccc cctggcttcg ggttctatgt    18060
```

```
aaactccttc atgcgccgct gccctgataa catccaccac cgcagaataa gccacaccca  18120
gccaacctac acattcgttc tgcgagtcac acacgggagg agcgggaaga gctggaagaa  18180
ccatgttttt tttttattc caaaagatta tccaaaacct caaaatgaag atctattaag   18240
tgaacgcgct cccctccggt ggcgtggtca aactctacag ccaagaaaca gataatggca  18300
tttgtaagat gttgcacaat ggcttccaaa aggcaaacgg ccctcacgtc caagtggacg  18360
taaaggctaa acccttcagg gtgaatctcc tctataaaca ttccagcacc ttcaaccatg  18420
cccaaataat tctcatctcg ccaccttctc aatatatctc taagcaaatc ccgaatatta  18480
agtccggcca ttgtaaaaat ctgctccaga gcgccctcca ccttcagcct caagcagcga  18540
atcatgattg caaaaattca ggttcctcac agacctgtat aagattcaaa agcggaacat  18600
taacaaaaat accgcgatcc cgtaggtccc ttcgcagggc cagctgaaca taatcgtgca  18660
ggtctgcacg gaccagcgcg gccacttccc cgccaggaac catgacaaaa gaacccacac  18720
tgattatgac acgcatactc ggagctatgc taaccagcgt agccccgatg taagcttgtt  18780
gcatgggcgg cgatataaaa tgcaaggtgc tgctcaaaaa atcaggcaaa gcctcgcgca  18840
aaaaagaaag cacatcgtag tcatgctcat gcagataaag gcaggtaagc tccggaacca  18900
ccacagaaaa agacaccatt tttctctcaa acatgtctgc gggtttctgc ataaacacaa  18960
aataaaataa caaaaaaaca tttaaacatt agaagcctgt cttacaacag gaaaaacaac  19020
ccttataagc ataagacgga ctacggccat gccggcgtga ccgtaaaaaa actggtcacc  19080
gtgattaaaa agcaccaccg acagctcctc ggtcatgtcc ggagtcataa tgtaagactc  19140
ggtaaacaca tcaggttgat tcacatcggt cagtgctaaa aagcgaccga aatagcccgg  19200
gggaatacat acccgcaggc gtagagacaa cattacagcc cccataggag gtataacaaa  19260
attaatagga gagaaaaaca cataaacacc tgaaaaaccc tcctgcctag gcaaaatagc  19320
accctcccgc tccagaacaa catacagcgc ttccacagcg gcagccataa cagtcagcct  19380
taccagtaaa aaagaaaacc tattaaaaaa acaccactcg acacggcacc agctcaatca  19440
gtcacagtgt aaaaagggc caagtgcaga gcgagtatat ataggactaa aaaatgacgt    19500
aacggttaaa gtccacaaaa aacacccaga aaaccgcacg cgaacctacg cccagaaacg  19560
aaagccaaaa aacccacaac ttcctcaaat cgtcacttcc gttttcccac gttacgtcac   19620
ttcccatttt aagaaaacta caattcccaa cacatacaag ttactccgcc ctaaaaccta  19680
cgtcacccgc cccgttccca cgccccgcgc cacgtcacaa actccacccc ctcattatca  19740
tattggcttc aatccaaaat aaggtatatt attgatgatg ttaattaaga attcggatct  19800
gcgacgcgag gctggatggc cttccccatt atgattcttc tcgcttccgg cggcatcggg  19860
atgcccgcgt tgcaggccat gctgtccagg caggtagatg acgaccatca gggacagctt   19920
caaggccagc aaaaggccag gaaccgtaaa aaggccgcgt tgctggcgtt tttccatagg   19980
ctccgccccc ctgacgagca tcacaaaaat cgacgctcaa gtcagaggtg gcgaaacccg  20040
acaggactat aaagatacca ggcgtttccc cctggaagct ccctcgtgcg ctctcctgtt  20100
ccgaccctgc cgcttaccgg atacctgtcc gcctttctcc cttcgggaag cgtggcgctt  20160
tctcatagct cacgctgtag gtatctcagt tcggtgtagg tcgttcgctc caagctgggc  20220
tgtgtgcacg aaccccccgt tcagcccgac cgctgcgcct tatccggtaa ctatcgtctt  20280
gagtccaacc cggtaagaca cgacttatcg ccactggcag cagccactgg taacaggatt  20340
agcagagcga ggtatgtagg cggtgctaca gagttcttga agtggtggcc taactacggc  20400
tacactagaa ggacagtatt tggtatctgc gctctgctga agccagttac cttcggaaaa   20460
```

```
agagttggta gctcttgatc cggcaaacaa accaccgctg gtagcggtgg ttttttttgtt  20520 tgcaagcagc agattacgcg cagaaaaaaa ggatctcaag aagatccttt gatcttttct  20580
acggggtctg acgctcagtg gaacgaaaac tcacgttaag ggattttggt catgagatta  20640
tcaaaaagga tcttcaccta gatccttta aatcaatcta aagtatatat gagtaaactt  20700
ggtctgacag gtttaaactc agaagaactc gtcaagaagg cgatagaagg cgatgcgctg  20760
cgaatcggga gcggcgatac cgtaaagcac gaggaagcgg tcagcccatt cgccgccaag  20820
ctcttcagca atatcacggg tagccaacgc tatgtcctga tagcggtccg ccacacccag  20880
ccggccacag tcgatgaatc cagaaaagcg gccattttcc accatgatat tcggcaagca  20940
ggcatcgcca tgggtcacga cgagatcctc gccgtcgggc atgctcgcct tgagcctggc  21000
gaacagttcg gctggcgcga gcccctgatg ctcttcgtcc agatcatcct gatcgacaag  21060
accggcttcc atccgagtac gtgctcgctc gatgcgatgt ttcgcttggt ggtcgaatgg  21120
gcaggtagcc ggatcaagcg tatgcagccg ccgcattgca tcagccatga tggatacttt  21180
ctcggcagga gcaaggtgag atgacaggag atcctgcccc ggcacttcgc ccaatagcag  21240
ccagtccctt cccgcttcag tgacaacgtc gagcacagct gcgcaaggaa cgcccgtcgt  21300
ggccagccac gatagccgcg ctgcctcgtc ttgcagttca ttcagggcac cggacaggtc  21360
ggtcttgaca aaaagaaccg ggcgcccctg cgctgacagc cggaacacgg cggcatcaga  21420
gcagccgatt gtctgttgtg cccagtcata gccgaatagc ctctccaccc aagcggccgg  21480
agaacctgcg tgcaatccat cttgttcaat cataacgtta ctcttccttt ttcaatatta  21540
ttgaagcatt tatcagggtt attgtctcat gagcggatac atatttgaat gtatttagaa  21600
aaataaacaa ataggggttc cgcgcacatt tccccgaaaa gtgccacctg acgtctaaga  21660
aaccattatt atcatgacat taacctataa aaataggcgt atcacgaggc cctttcgtct  21720
tc                                                                 21722
```